(12) United States Patent
Wang et al.

(10) Patent No.: US 10,363,239 B2
(45) Date of Patent: Jul. 30, 2019

(54) METHOD FOR INHIBITING GROWTH OF CANCER CELLS

(71) Applicant: Pain Therapeutics, Inc., Austin, TX (US)

(72) Inventors: Hoau-Yan Wang, Philadelphia, PA (US); Lindsay Burns Barbier, Austin, TX (US)

(73) Assignee: Pain Therapeutics, Austin, TX (US)

( * ) Notice: Subject to any disclaimer, the term of this patent is extended or adjusted under 35 U.S.C. 154(b) by 0 days.

(21) Appl. No.: 15/221,311

(22) Filed: Jul. 27, 2016

(65) Prior Publication Data

US 2018/0311210 A1    Nov. 1, 2018

Related U.S. Application Data

(63) Continuation of application No. 14/497,816, filed on Sep. 26, 2014, now Pat. No. 9,433,604.

(60) Provisional application No. 61/888,350, filed on Oct. 8, 2013.

(51) Int. Cl.

| | | |
|---|---|---|
| A61K 31/395 | (2006.01) | |
| A61K 31/47 | (2006.01) | |
| A61K 31/5375 | (2006.01) | |
| A61K 31/40 | (2006.01) | |
| A61K 31/426 | (2006.01) | |
| A61K 31/435 | (2006.01) | |
| A61K 31/445 | (2006.01) | |
| A61K 31/472 | (2006.01) | |
| A61K 31/4741 | (2006.01) | |
| A61K 31/485 | (2006.01) | |
| A61K 31/495 | (2006.01) | |
| A61K 31/5377 | (2006.01) | |
| A61K 31/54 | (2006.01) | |
| A61K 31/551 | (2006.01) | |
| A61K 31/625 | (2006.01) | |
| A61K 31/438 | (2006.01) | |
| A61K 31/444 | (2006.01) | |

(52) U.S. Cl.
CPC .......... *A61K 31/395* (2013.01); *A61K 31/40* (2013.01); *A61K 31/426* (2013.01); *A61K 31/435* (2013.01); *A61K 31/438* (2013.01); *A61K 31/444* (2013.01); *A61K 31/445* (2013.01); *A61K 31/47* (2013.01); *A61K 31/472* (2013.01); *A61K 31/4741* (2013.01); *A61K 31/485* (2013.01); *A61K 31/495* (2013.01); *A61K 31/5375* (2013.01); *A61K 31/5377* (2013.01); *A61K 31/54* (2013.01); *A61K 31/551* (2013.01); *A61K 31/625* (2013.01)

(58) Field of Classification Search
CPC .. A61K 31/395; A61K 31/444; A61K 31/438; A61K 31/625; A61K 31/426; A61K 31/551; A61K 31/5377; A61K 31/40; A61K 31/54; A61K 31/435; A61K 31/445; A61K 31/472; A61K 31/4741; A61K 31/485; A61K 31/495; A61K 31/5375; A61K 31/47
See application file for complete search history.

(56) References Cited

U.S. PATENT DOCUMENTS

| | | |
|---|---|---|
| 3,723,442 A | 3/1973 | Nakanishi et al. |
| 4,981,858 A | 1/1991 | Fisher et al. |
| 4,996,210 A | 2/1991 | Tsukamoto et al. |
| 5,534,520 A | 7/1996 | Fisher et al. |
| 5,852,029 A | 12/1998 | Fisher et al. |
| 5,869,496 A | 2/1999 | Hale et al. |
| 6,060,469 A | 5/2000 | Baker et al. |
| 7,049,321 B2 | 5/2006 | Fisher et al. |
| 7,192,964 B2 | 3/2007 | Hashimoto et al. |
| 7,544,695 B2 | 6/2009 | Berk et al. |
| 7,557,117 B2 | 7/2009 | Hashimoto et al. |
| 7,560,468 B2 | 7/2009 | Sundermann et al. |
| 7,951,815 B2 | 5/2011 | Sundermann et al. |
| 8,048,890 B2 | 11/2011 | Buschmann et al. |
| 8,153,795 B2 | 4/2012 | Sundermann et al. |
| 8,492,349 B2 | 7/2013 | Wang et al. |
| 8,580,808 B2 | 11/2013 | Barbier et al. |
| 8,580,809 B2 | 11/2013 | Barbier et al. |
| 8,614,324 B2 | 12/2013 | Barbier et al. |
| 8,653,068 B2 | 2/2014 | Barbier et al. |
| 8,722,851 B2 | 5/2014 | Wang et al. |
| 10,017,736 B2 | 7/2018 | Wang |
| 2004/0192916 A1 | 9/2004 | Buschmann et al. |

(Continued)

FOREIGN PATENT DOCUMENTS

WO    WO 2010/051476 A1    5/2010

OTHER PUBLICATIONS

Wang et al., *Neurobiol Aging* 55:99-114 (2017).

(Continued)

*Primary Examiner* — John M Mauro
(74) *Attorney, Agent, or Firm* — Husch Blackwell LLP

(57) ABSTRACT

A method of inhibiting the growth of cancer cells is disclosed in which cancer cells that contain an enhanced amount relative to non-cancerous cells of one or more of phosphorylated mTOR, Akt1, ERK2 and serine2152-phosphorylated filamin A are contacted with an FLNA-binding effective amount of a compound or a pharmaceutically acceptable salt thereof that binds to the pentapeptide of filamin A (FLNA) of SEQ ID NO: 1 and exhibits at least about 60 percent of the FITC-labeled naloxone binding amount when present at a 10 μM concentration and using unlabeled naloxone as the control inhibitor at the same concentration. A compound that binds to the FLNA pentapeptide preferably also contains at least four of the six pharmacophores of FIGS. 19-24.

22 Claims, 90 Drawing Sheets

Specification includes a Sequence Listing.

(56) References Cited

U.S. PATENT DOCUMENTS

| | | |
|---|---|---|
| 2007/0015783 A1 | 1/2007 | Sundermann et al. |
| 2007/0117824 A1 | 5/2007 | Berk et al. |
| 2011/0105487 A1 | 5/2011 | Barbier et al. |
| 2012/0083476 A1 | 4/2012 | Breitenbucher et al. |

OTHER PUBLICATIONS

Declaration of Lindsay Burns Barbier filed in U.S. Appl. No. 13/940,016 dated Nov. 8, 2017.
Nakamura et al., *Cell Adh Migr.* 5(2):160-169 (2011).
ZINC12342403 Compound Summary—NCBI PubChem Chemical Database, (Nov. 2007).
Written Opinion and Preliminary Report for PCT/US2009/062823.
Written Opinion and Preliminary Report for PCT/US2009/062860.
Restriction dated Mar. 31, 2011.
Office Action dated Jul. 20, 2011 in U.S. Appl. No. 12/610,091.
Final Office Action dated Jan. 11, 2012.
29665 Caplus; Doc. No. 62:29665.
Advisory Action dated Mar. 8, 2012.
Office Action dated May 22, 2012.
Art CAS RN 10708056-65-0.
Noller, *Chemistry of Organic Compounds*, .W.B. Saunders Co., Philadelphia, 1951, p. 35.
Anderson, *Chem and Biol* 10:787-797 (2003).
Thiel, *Nature Biotechnol* 2:513-519, (2004).
STN Search Report (Accession No. 2007:564923).
Eliel et al., Stereochemistry of Organic Compounds, John Wiley & Sons, New York, (1994) pp. 11-15.
J. McMurry, Organic Chemistry, 6.sup.th ed., Brooks/Cole-Thomson Learning, Belmont, CA, (2004) pp. 75-77.
Action in U.S. Appl. No. 12/609,518 dated Dec. 20, 2012.
U.S. Appl. No. 12/609,518 Notice of Allowance, dated Aug. 6, 2013.
Woo et al., *Mol Cell Biol* 24(7):3025-3035 (2004).
Wang et al., *PLoS One* 3(2):e1554 (2008).
CAS RN 1070805-65-0 Nov. 4, 2008.
Ravid et al., *Exp Cell Res* 314(15):2762-2773 (2008).
Wang et al., *PLoS One* 4(1):e4282 (2009).
Xu et al., *J Exp Med* 207(11):2421-2437 (2010).
Burns et al., *Recent Pat CNS Drug Discov* 5:210-220 (2010).
Wang et al., *J Neurosci* 32(29):9773-9784 (Jul. 18, 2012).
WO 2015/054027 A1 Search Report.
Li et al., *Oncogene* 29:5329-5345 (2010).
Savoy et al., *Endocr Relat Cancer.* 20(6):R341-R356 (Dec. 2013).
Chapter 16 of the *Molecular Probes Handbook*, 11$^{th}$ ed., Invitrogen 741-772 (2010).
Setareth Biotech, LLC of Eugene, OR (2016) on line catalogue page for FITC-NLX.
Setareth Biotech, LLC MSDS sheet for FITC-NLX.
Farooqui, M. "Naloxone acts as an antagonist of estrogen receptor activity in MCF-7 cells." Molecular cancer therapeutics 5.3 (2006):611-620.
Lin, H.J., "Elevated phosphorylation and activation of PDK-1/AKT pathway in human breast cancer." British journal of cancer 93.12 (2005): 1372-1381.

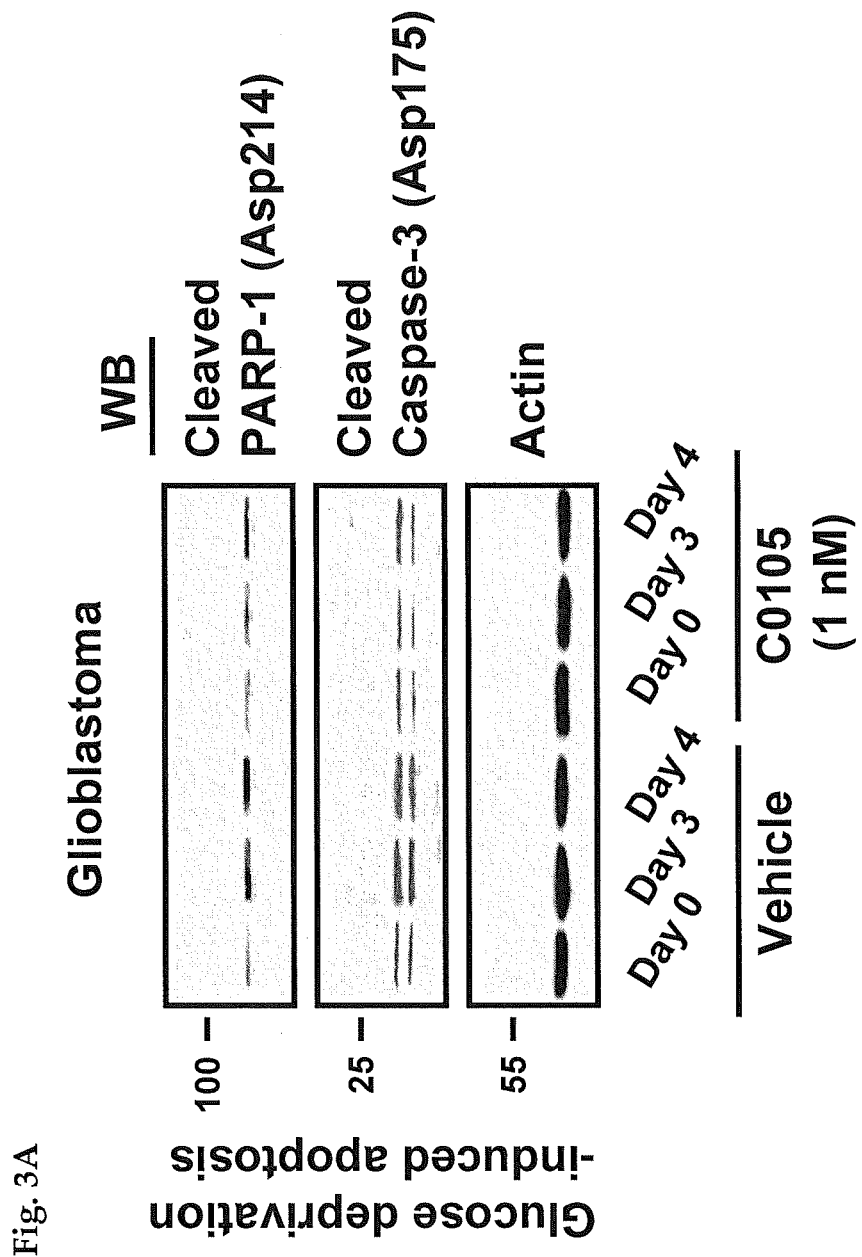

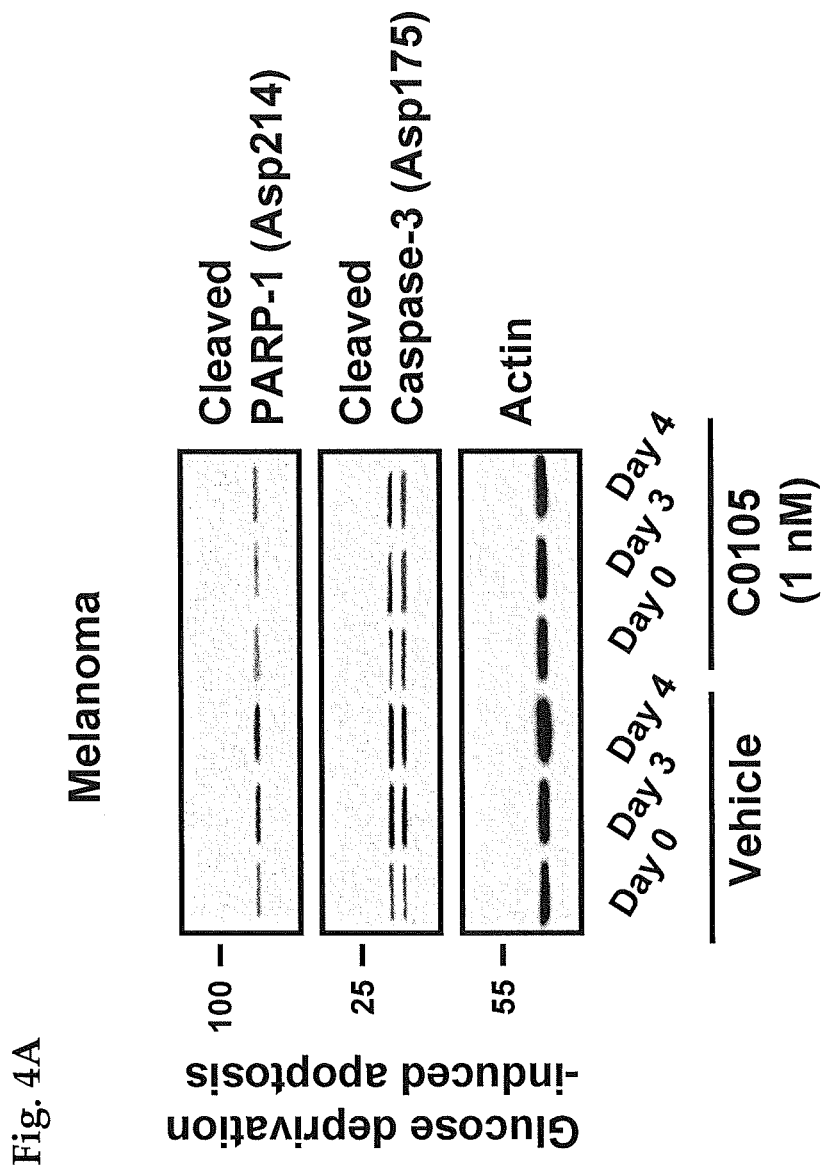

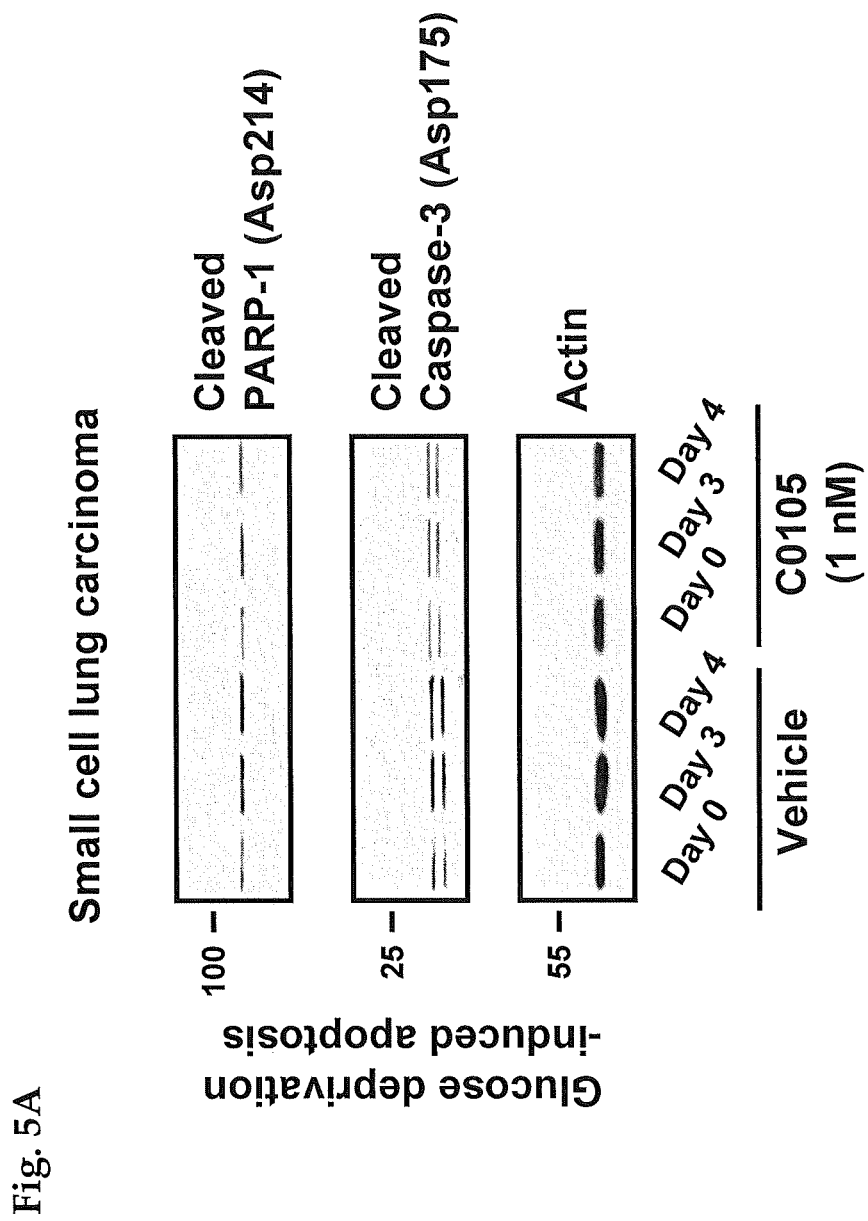

Lung fibroblast
Fig. 12E
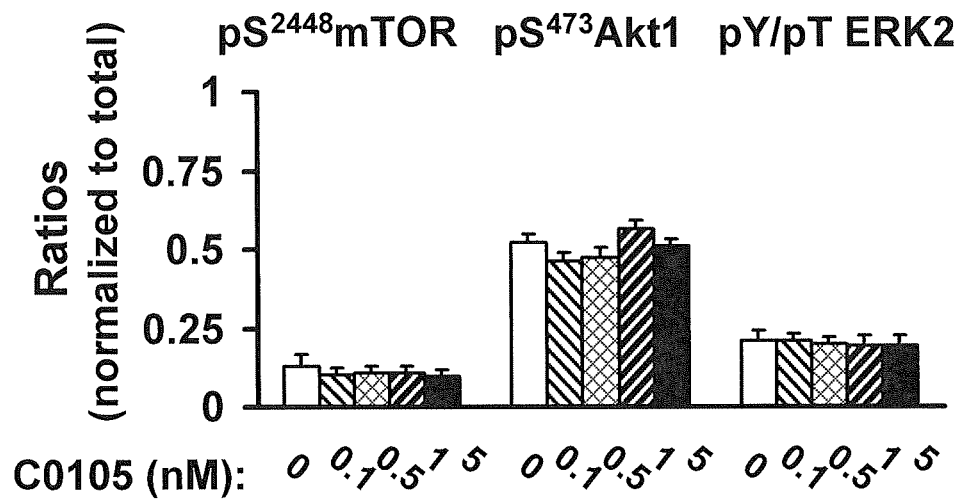
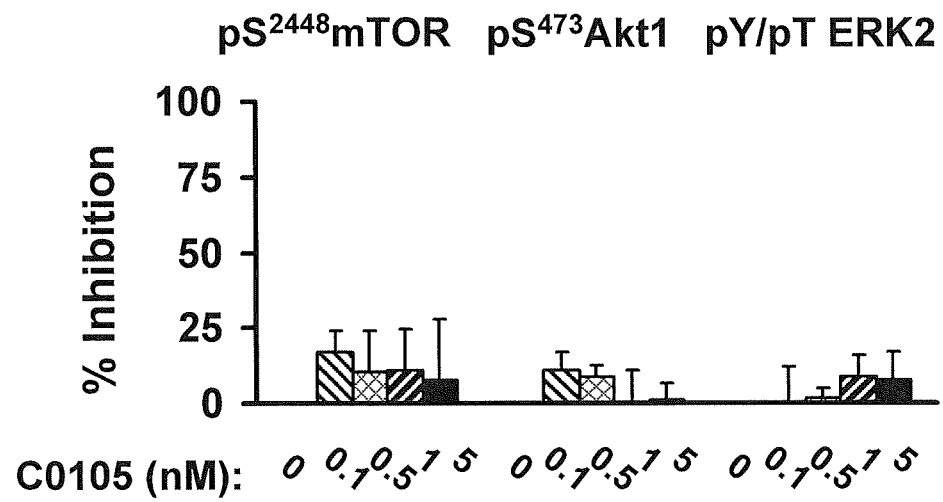
Fig. 12F

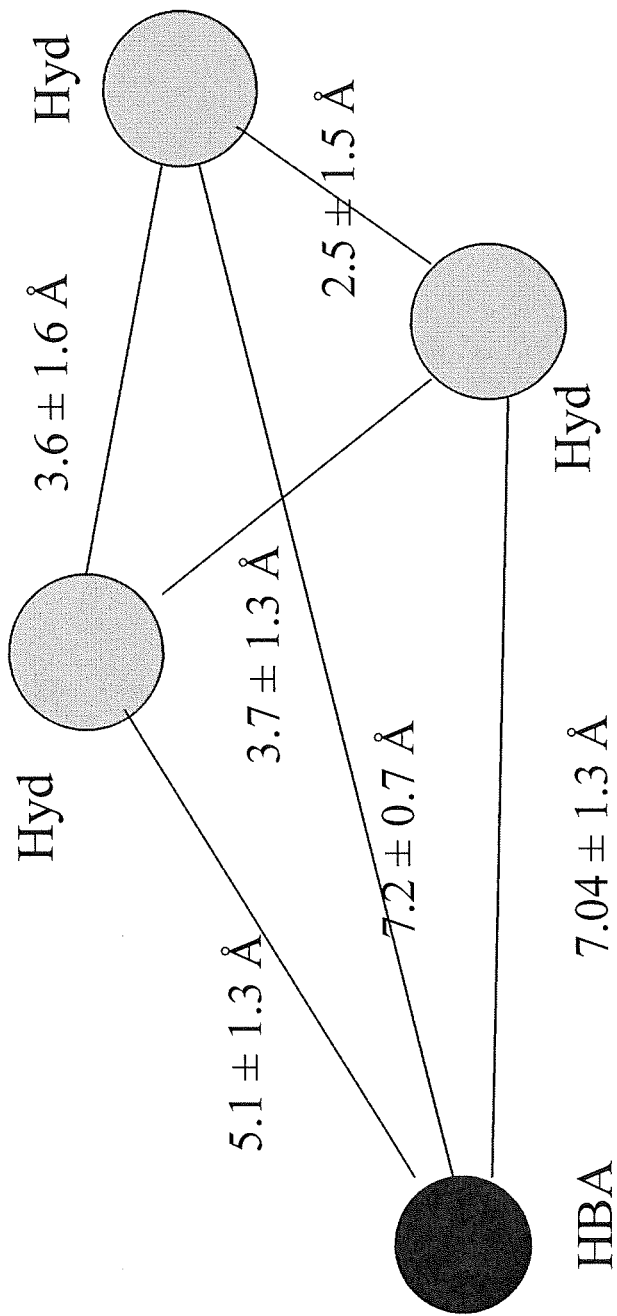
Fig. 19 Pharmacophore 1

Fig. 21 Pharmacophore 3

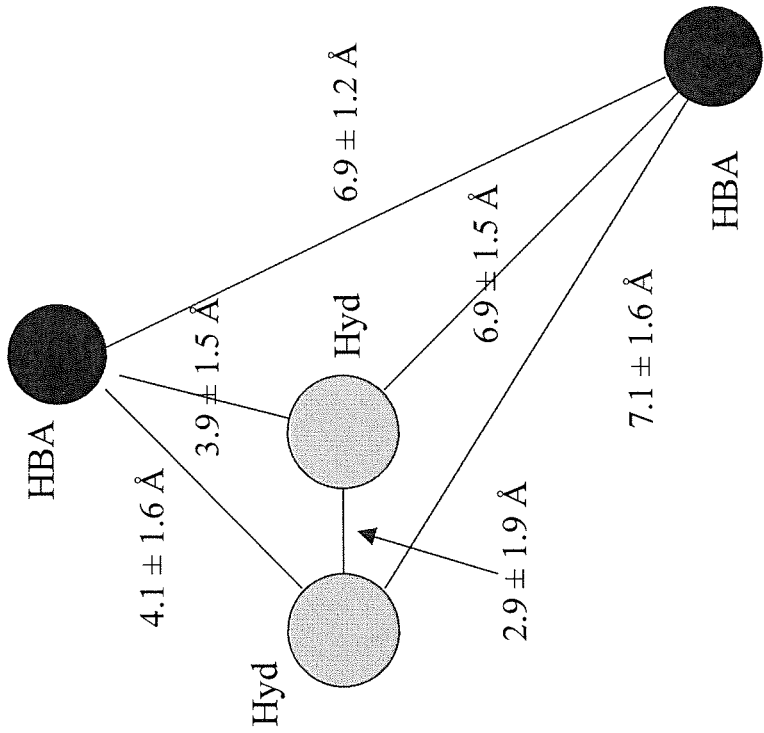
Fig. 23 Pharmacophore 5

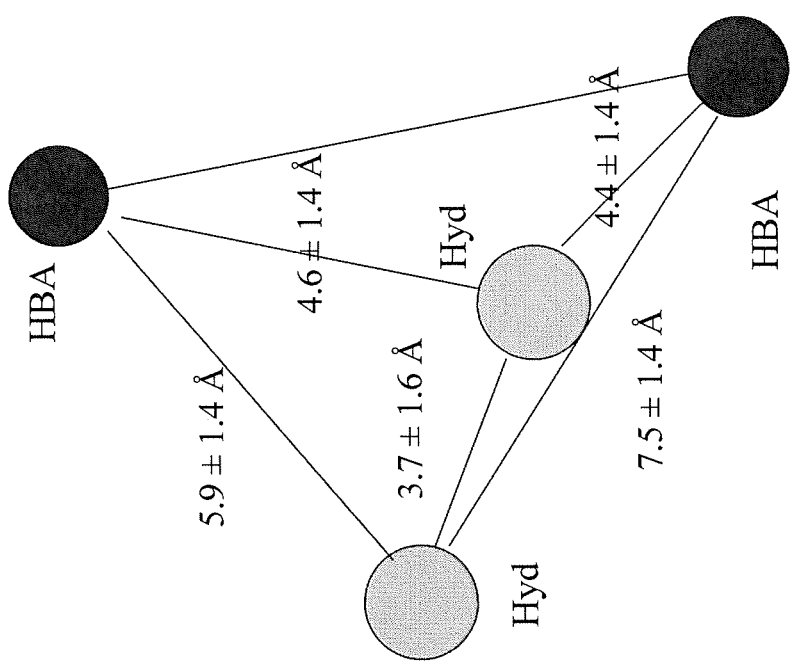

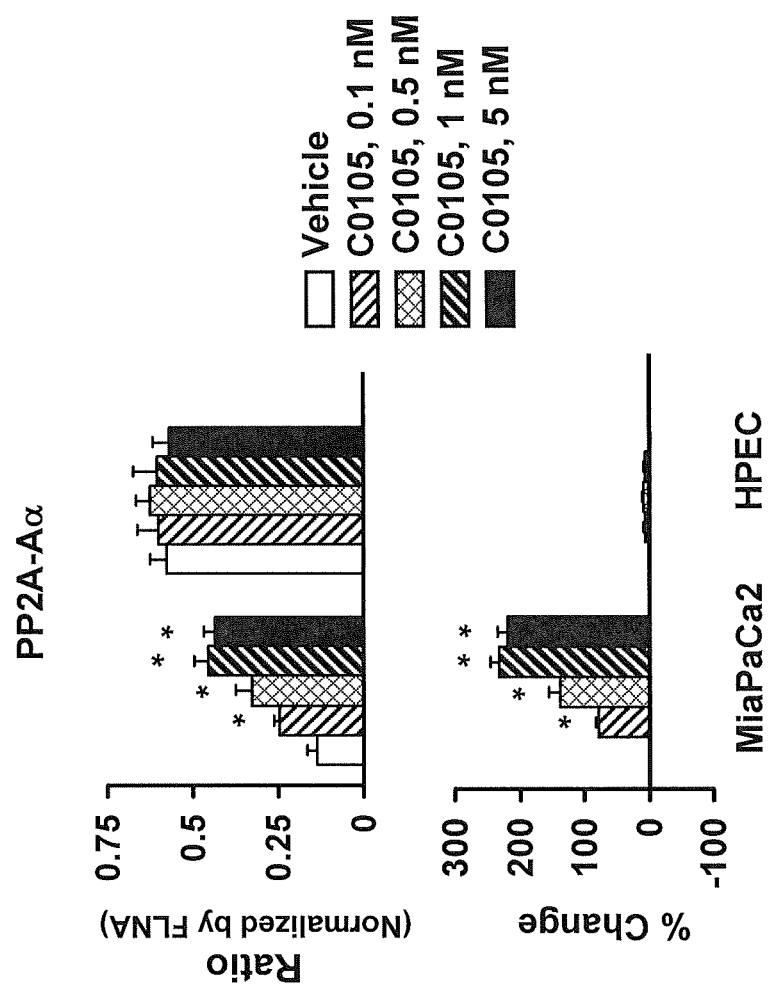

Glioblastoma (U87)
Fig. 30A
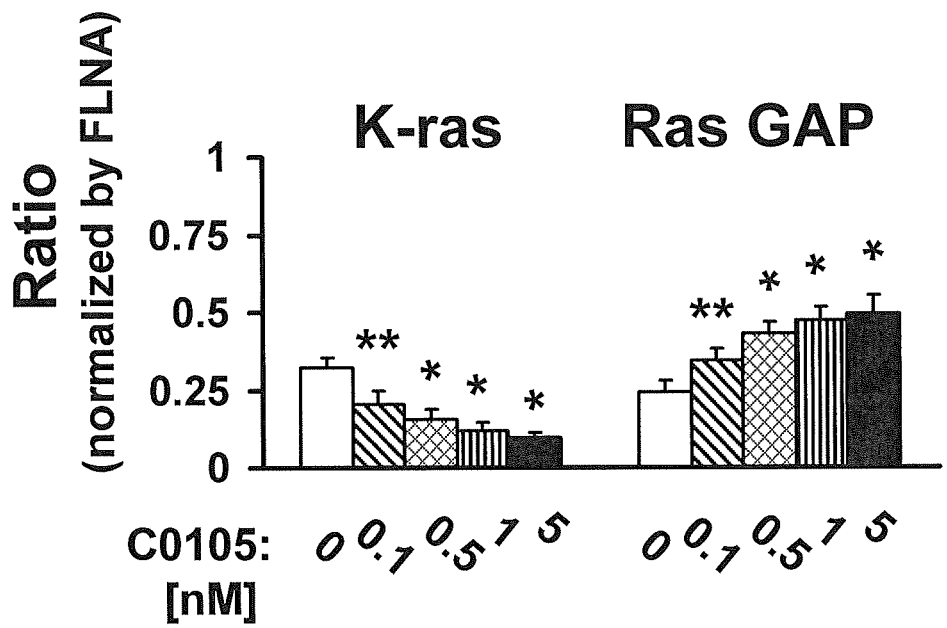
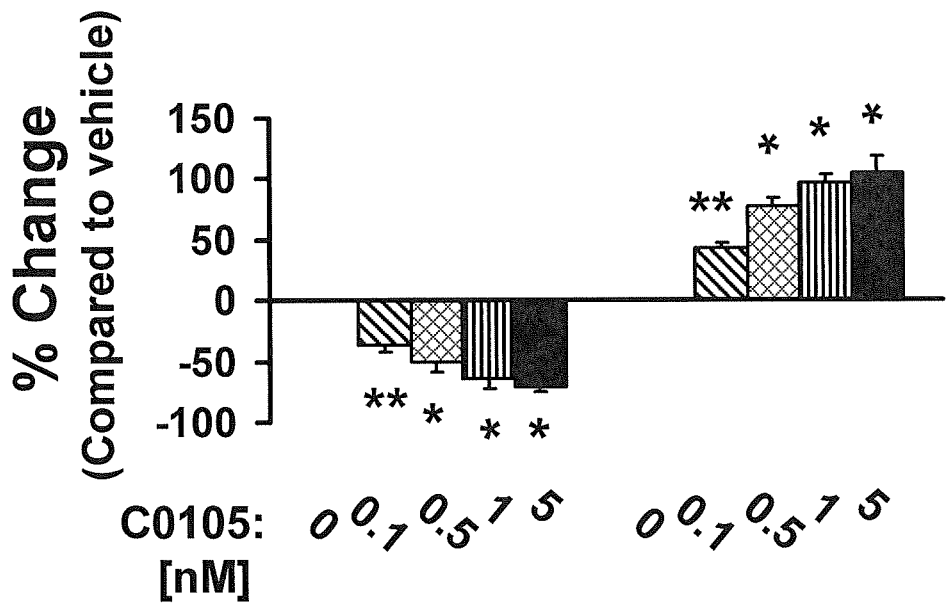
Fig. 30B

Small-cell lung carcinoma

Primary lung fibroblast

MiaPaCa2

Human pancreatic epithelial cells

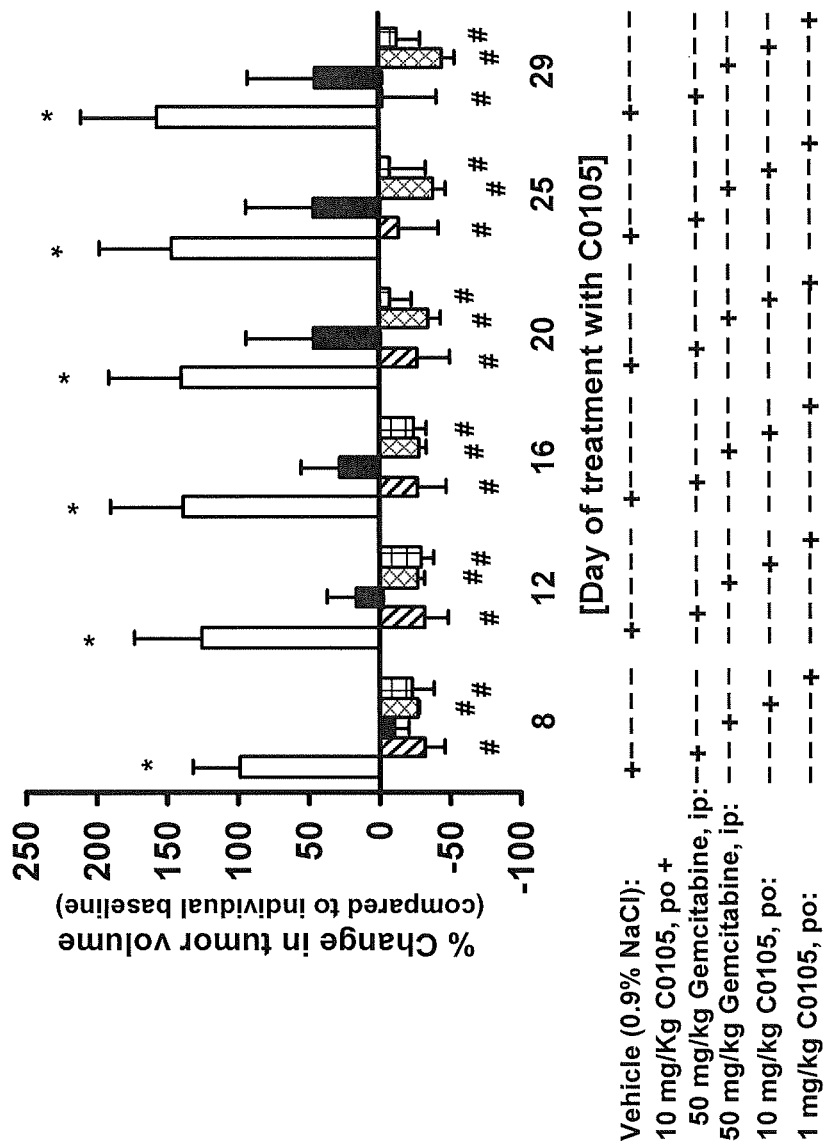

METHOD FOR INHIBITING GROWTH OF CANCER CELLS

CROSS-REFERENCE TO RELATED APPLICATION

This application is a division of application Ser. No. 14/497,816, now U.S. Pat. No. 9,433,604, that was filed Sep. 26, 2014, and claims priority to U.S. application Ser. No. 61/888,350, filed on Oct. 8, 2013, whose disclosures are incorporated herein by reference.

TECHNICAL FIELD

The present invention relates to a method of inhibiting the growth of cancer cells, and particularly to the growth of cancer cells in which the serine residue at amino acid residue position 2152 of the filamin A (FLNA) of those cancer cells is phosphorylated to a greater extent than in non-cancerous cells.

BACKGROUND ART

Phosphorylation has come to be recognized as a global regulator of cellular activity, and abnormal phosphorylation is implicated in a host of human diseases, particularly cancers. Phosphorylation of a protein involves the enzymatically mediated addition of a phosphate group ($-OPO_3^{-2}$) to its amino acid side chains of one or more serine, threonine or tyrosine residues.

Phosphorylation and the reverse reaction, dephosphorylation, occur via the actions of two key enzymes. Protein kinases phosphorylate proteins by transferring a phosphate group from a nucleotide triphosphate such as adenosine triphosphate (ATP) to their target protein. This process is balanced by the action of protein phosphatases, which can subsequently remove the phosphate group. The amount of phosphate that is associated with a protein at a particular time is therefore determined by the relative activities of the associated kinase and phosphatase.

If the protein is an enzyme, phosphorylation and dephosphorylation can impact its enzymatic activity, essentially acting like a switch, turning it on and off in a regulated manner. Phosphorylation can regulate protein-protein interactions by facilitation of binding to a partner protein.

Protein phosphorylation also has a vital role in intracellular signal transduction. Many of the proteins that make up a signaling pathway are kinases, from the tyrosine kinase receptors at the cell surface to downstream effector proteins, many of which are serine/threonine kinases.

Not all targets of phosphorylation are proteins. Other kinds of molecules can also be phosphorylated. In particular, the phosphorylation of phosphoinositide lipids, such as phosphatidylinositol-4,5-bisphosphate (PIP2), at various positions on their inositol ring, also plays a key role in signal transduction.

Thus, ligand binding at the cell surface can establish a phosphorylation cascade, with the phosphorylation and activation of one protein stimulating the phosphorylation of another, subsequently amplifying a signal and transmitting that signal through the cell. The signal continues to propagate until it is switched off by the action of a phosphatase.

Recent research activity has successfully developed drugs that interact with kinase and phosphatase activities. Illustrative of approved drugs and their target proteins are Herceptin® that blocks the function of the HER2-receptor (used in breast cancer treatment), Tarceva® that inhibits the epidermal growth factor receptor (EGFR) that is a tyrosine kinase (used in non-small cell lung cancer treatment), Afinitor® and Torisel® target the mammalian target of rapamycin (mTOR) (used in renal carcinoma treatment). Drugs in the pipeline to approval include Keryx™ that is an inhibitor of Akt [also known as protein kinase B (PKB)], selumetinib that targets MEK (also known as MAPKK), and alvocidib that targets cyclin-dependent kinases.

Human phosphatase and tensin homolog deleted on chromosome ten (PTEN; EC 3.1.3.16; UniProt Accession P60484) is a protein enzyme that, in humans, is encoded by the PTEN gene. [Steck et al., *Nat. Genet.* 15(4):356-362 (1997).] The corresponding PTEN protein is found in almost all tissues in the body in both the cytoplasm and the nucleus and acts as a phosphatidylinositol-3,4,5-trisphosphate 3-phosphatase.

As a lipid phosphatase, PTEN dephosphorylates phosphatidylinositol (3,4,5)triphosphate [PtdIns (3,4,5)$P_3$ or PIP3] to form the corresponding diphosphate, phosphatidylinositol-4,5-bisphosphate [PtdIns(4,5)P2 or PIP2). PTEN is a lipid-second messenger and a regulator of the PI3K/Akt pathway [Wu al., *Oncogene* 22:3113-3122 (2003)] thereby playing a central role in controlling many important cellular activities regulated by this pathway, including cell division, cell growth, cell survival, and DNA damage.

The dephosphorylation of PIP3 is important because it leads to decreased phosphorylated-Akt (P-Akt) levels resulting in inhibition of the AKt signaling pathway; i.e., inhibition of Akt phosphorylation. PTEN's protein phosphatase activity (PPA) is also known to regulate cyclin D1 protein levels and those activities appear to be regulated by nuclear PTEN [Chung et al., *Cancer Res.* 65:8096-8100 (2005)].

The PTEN gene acts as a tumor suppressor gene through the action of its phosphatase protein product that dephosphorylates both protein and lipid substrates. This phosphatase is involved in the regulation of the cell cycle, preventing cells from growing and dividing too rapidly. [Chu et al., *Med. Sci. Monit.* 10 (10): RA235-241 (2004).] It is one of the targets of an oncomiR, miRN21, a microRNA.

The PTEN gene is mutated at high frequency in a large number of cancers. Thus, loss of functionally active PTEN, as demonstrated by genetic inactivation in human cancer or mouse knockout (KO) models, causes constitutive activation of Akt in cells, resulting in dysregulated cell proliferation, growth, and survival, which are hallmarks of tumorigenesis.

The structure of PTEN [solved by X-ray crystallography; Lee et al., *Cell* 99(3):323-334 (1999)]reveals that it consists of a phosphatase domain, and a C2, tensin-like, domain, providing a structural similarity to the dual specificity protein tyrosine phosphatases. The phosphatase domain contains the active site, which carries out the enzymatic function of the protein, whereas the C2 domain binds the phospholipid membrane. Thus, PTEN binds the membrane through its C2 domain, bringing the active site to the membrane-bound PIP3 to de-phosphorylate it.

Unlike most of the protein tyrosine phosphatases, this protein preferentially dephosphorylates phosphoinositide substrates. PTEN protein negatively regulates phosphatidylinositol-3,4,5-trisphosphate (PIP3) in cells and functions as a tumor suppressor by negatively regulating the Akt/PKB signaling pathway. PTEN negatively regulates phosphorylation of phosphatidylinositol 4,5-bisphosphate by phosphoinositide 3-kinase (PI3K), a main regulator of cell growth, metabolism and survival. PI3K-mediated PIP(3) production leads to the activation of the canonical Akt-mTORC1 pathway.

Akt is activated by PDK1-mediated phosphorylation at Thr308 and by phosphorylation at Ser473 via mTOR complex 2 [mTORC2; composed of mTOR, DEP domain-containing mTOR-interacting protein (DEPTOR), mammalian lethal with SEC13 protein 8 (mLST8), stress-activated MAP kinase-interacting protein 1 (mSIN1), Pro-rich protein 5 (PRR5; also known as PROTOR) and rapamycin insensitive companion of mTOR (RICTOR)]. Active Akt drives cell survival, proliferation and cellular metabolism through inhibiting phosphorylation of downstream proteins, including glycogen synthase kinase 3 (GSK3), forkhead box O (FOXO), peroxisome proliferator-activated receptor-γ (PPARγ) co-activator 1α (PGC1) and p27, and through activatory phosphorylation of ectonucleoside triphosphate diphosphohydrolase 5 (ENTPD5), sterol-responsive element-binding protein 1C (SREBP1C), AS160 and S phase kinase-associated protein 2 (SKP2). Akt can also activate mTORC1 [composed of mTOR, DEPTOR, mLST8, 40 kDa Pro-rich Akt1 substrate 1 (PRAS40) and regulatory associated protein of mTOR (RAPTOR)] by mediating the inhibitory phosphorylation of its negative regulators tuberous sclerosis protein 2 (TSC2) and PRAS40.

When the PTEN enzyme is functioning properly, it acts as part of a chemical pathway that signals cells to stop dividing and can cause cells to undergo programmed cell death (apoptosis) when necessary. These functions prevent uncontrolled cell growth that can lead to the formation of tumors. There is also evidence that the protein made by the PTEN gene may play a role in cell movement (migration) and adhesion of cells to surrounding tissues.

PTEN is one of the most commonly lost tumor suppressors in human cancers. During tumor development, mutations and deletions of PTEN occur that inactivate its enzymatic activity leading to increased cell proliferation and reduced cell death.

Frequent genetic inactivation of PTEN occurs in glioblastoma, endometrial cancer, melanoma, small cell lung cancer and prostate cancer; and reduced expression is found in many other tumor types such as lung and breast cancer. "Up to 70 percent of men with prostate cancer have lost one copy of the PTEN gene at the time of diagnosis". [Chen et al., *Nature* 436 (7051):725-730 (2005).]

PTEN mutations have also been found in non-cancerous syndromes. For example, researchers have found more than 70 mutations in the PTEN gene in people with Cowden syndrome. These mutations can be changes in a small number of base pairs or, in some cases, deletions of a large number of base pairs. Most of these mutations cause the PTEN gene to make a protein that does not function properly or does not work at all. The defective protein is unable to stop cell division or signal abnormal cells to die, which can lead to tumor growth, particularly in the breast, thyroid, or uterus.

Mutations in the PTEN gene cause several other disorders that, like Cowden syndrome, are characterized by the development of noncancerous tumors called hamartomas. These disorders include Bannayan-Riley-Ruvalcaba syndrome, and Proteus-like syndrome. Together, the disorders caused by PTEN mutations are called PTEN hamartoma tumor syndromes, or PHTS. Mutations responsible for these syndromes cause the resulting protein to be nonfunctional or absent. The defective protein allows the cell to divide in an uncontrolled way and prevents damaged cells from dying, which can lead to the growth of tumors.

Defects of the PTEN gene have been cited to be a potential cause of Autism Spectrum Disorders. [Napoli et al., *PLoS One* 7(8):e42504 (2012).] When defective, PTEN protein interacts with the protein of a second gene known as p53 to dampen energy production in neurons. This severe stress leads to a spike in harmful mitochondrial DNA changes and abnormal levels of energy production in the cerebellum and hippocampus—brain regions critical for social behavior and cognition. When PTEN protein was insufficient, its interaction with p53 has been shown to trigger deficiencies and defects in other proteins that also have been found in patients with learning disabilities including autism. [Napoli et al., *PLoS One* 7(8):e42504 (2012).]

The RAS proteins are members of a large superfamily of low molecular-weight GTP-binding proteins, which can be divided into several families according to the degree of sequence conservation. Different families are important for different cellular processes—the RAS family controls cell growth and the RHO family controls the actin cytoskeleton. Three members of the RAS family—HRAS, KRAS and NRAS—are found to be activated by mutation in human tumors [Lowy et al., *Annu. Rev. Biochem.* 62:851-891 (1993)]. These three members are very closely related, having 85 percent amino acid residue sequence identity, and although they function in very similar ways, some indications of subtle differences between them have recently come to light.

The HRAS, KRAS and NRAS proteins are widely expressed, with KRAS being expressed in almost all cell types. Knockout studies have shown that Hras and Nras, either alone or in combination, are not required for normal development in the mouse, whereas Kras is essential [Johnson et al., *Genes Dev.* 11:2468-2481 (1997)]. The normal function of RAS proteins requires them to be post-translationally modified.

RAS proteins have essential roles in controlling the activity of several crucial signaling pathways that regulate normal cellular proliferation. Ras mediates downstream signaling by interacting with effector proteins, including Raf and PI3 kinase.

Raf1 is a serine/threonine protein kinase that is part of the MAP kinase signaling pathway that leads to the activation of ERK and p38, which influences proliferation and survival. Signaling by PI3 kinase activates AKT and mTOR, which are central for cell growth and survival. Ras is also integral for cellular differentiation and development, including immune cell development and function.

Human tumors very frequently express RAS proteins that have been activated by point mutation—about 20 percent of all tumors have undergone an activating mutation in one of the RAS genes [Bos, *Cancer Res.* 49:4682-4689 (1989)]. In these tumors, the activated RAS protein contributes significantly to several aspects of the malignant phenotype, including the deregulation of tumor-cell growth, programmed cell death (apoptosis) and invasiveness, and the ability to induce new blood-vessel formation [Shields et al., *Trends Cell Biol.* 10:147-154 (2000)].

The activation state of RAS proteins depends on whether they are bound to GTP (in which case, they are active and are able to engage downstream target enzyme) or GDP (in which case, they are inactive and fail to interact with these effectors). In normal, non-cancerous cells, the activity of RAS proteins is controlled by the ratio of bound GTP to GDP [Campbell et al., *Oncogene* 17:1395-1413 (1998)]. In vitro, purified RAS possesses a low level of intrinsic GTPase activity; i.e., bound GTP is slowly converted to GDP. It also has a slow rate of nucleotide exchange with the surrounding medium; i.e., bound GDP is gradually replaced by GTP. However, these processes are catalyzed within the cell by guanine nucleotide exchange factors (GEFs) and the nucleotide hydrolysis by GTPase activating proteins (GAPs). Both of these activities involve large, considerably divergent families of proteins. It is the balance between these proteins that determines the activation state of RAS and its downstream target pathways. [Downward, *Nature Reviews Cancer* 3:11-22 (2003).]

In addition to PTEN and Kras, a growing body of research is revealing a complex role of filamin A (FLNA) in cancer. [Yue et al., *Cell & Bioscience* 3:7 (2013).] Best known for cross-linking cytoplasmic actin into dynamic scaffolds to control cell motility, filamins are large cytoplasmic proteins increasingly found to regulate cell signaling by interacting with over 30 different receptors and signaling molecules [Feng et al., *Nat Cell Biol* 6:1034-1038 (2004); Stossel et al., *Nature Rev. Mol. Cell Biol.* 2:138-145 (2001)], including the mu opioid receptor (MOR) [Onoprishvili et al., *Mol Pharmacol* 64:1092-1100 (2003)]. Filamins are dimerized through the last carboxy-terminal repeat near the transmembrane regions, allowing an intracellular V-shaped structure that is critical for function. There are three mammalian isoforms: filamin A (FLNA), B and C. As a key regulator of the cytoskeleton network, FLNA interacts with many proteins involved in cancer metastasis, [Yue et al., *Cell & Bioscience* 3:7 (2013)] and its knockdown or inhibition has been shown to reduce cancer metastasis potential. [Xi et al., *Int J Biol Sci* 9:67-77 (2013).]

Human FLNA is given the identifier P21333 in the UniProtKB/Swiss-Prot data base, and contains a sequence of 2647 amino acid residues. This protein is also sometimes referred to in the art as actin-binding protein (ABP-280). [Gorlin et al., *J Cell Biol* 111:1089-1105 (1990).] Nakamura et al., *Cell Adh Migr.* 5(2):160-169 (2011) discuss the history of research concerning FLNA and notes that the protein serves as a scaffold for over 90 binding partners including channels, receptors, intracellular signaling molecules and transcription factors.

FLNA also has been implicated in tumor progression. FLNA knockout mice show reduced oncogenic properties of K-RAS, including the downstream activation of ERK and Akt. [Nallapalli et al., *Mol Cancer* 11:50 (2012).] Many different cancers show high levels of FLNA expression in contrast to low FLNA levels in corresponding normal tissue, including colorectal and pancreatic cancer, [Uhlen et al., *Mol Cell Proteomics* 4:1920-1932 (2005)] and glioblastoma [Sun et al., *Cancer Cell* 9:287-300 (2006)]. Inhibition of FLNA also sensitizes cancer cells to both cisplatin and radiation [Sun et al., *Cancer Cell* 9:287-300 (2006)], and FLNA deficiency in cancer cells similarly sensitizes them to chemotherapeutic agents [Yue et al., *DNA Repair (Amst)* 11:192-200 (2012)] and radiation [Yue et al., *Cancer Res* 69:7978-7985 (2009); Yuan et al., *J Biol Chem* 276:48318-48324 (2001)]. On the other hand, Jiang et al., *Int. J. Biol. Sci.* 9:67-77 (2013) report that inhibition of filamin A expression leads to reduced metastasis in nude mice implanted with melanoma and breast cancer cells.

Additionally, FLNA is phosphorylated at a number of positions in its protein sequence in both normal and in cancer cells. For example, FLNA is phosphorylated at position 2152 by PAK1 as is required for PAK1-mediated actin cytoskeleton reorganization and for PAK1-mediated membrane ruffling. [Vadlamudi et al., *Nat. Cell Biol.* 4:681-690 (2002); Woo et al., *Mol Cell Biol.* 24(7):3025-3035 (2004).] Cyclin B1/Cdk1 phosphorylates serine 1436 in vitro in FLNA-dependent actin remodeling. [Cukier et al., *FEBS Letters* 581(8):1661-1672 (2007).]

The UniProtKB/Swiss-Prot data base entry for human FLNA (P21333) lists published reports of the following amino acid residue positions as being phosphorylated under different circumstances: 11, 1081, 1084, 1089, 1286, 1338, 1459, 1533, 1630, 1734, 2053, 2152, 2158, 2284, 2327, 2336, 2414, and 2510. Further, polyclonal and monoclonal antibodies are commercially available from one or more of Abgent, Inc. (San Diego, Calif.), Abcam, Inc. (Beverly, Mass.), Bioss, Inc. (Woburn, Mass.), and GeneTex, Inc. (Irvine, Calif.) that immunoreact with FLNA that is phosphorylated (phospho-FLNA) at serine-1083, tyrosine-1046, serine-1458, serine-2152, and serine-2522.

Inflammation is implicated in tumorgenesis, metastasis and angiogenesis [Coussens et al., *Nature* 420:860-867 (2002)], and FLNA can regulate inflammation via its recruitment to toll-like receptor 4 (TLR-4) that is required for signaling and subsequent release of inflammatory cytokines IL-6, IL-1β and TNFα [Wang et al., *J Neurosci* 32:9773-9784 (2012)]. Activation of TLRs on cancer cells promotes chronic inflammation which stimulates cancer cell proliferation, migration, tumor angiogenesis, and creates a tumor microenvironment that impairs the antitumor function of the immune system, allowing tumors to develop and survive [McCall et al., "Toll-Like Receptors as Novel Therapeutic Targets for the Treatment of Pancreatic Cancer" (Chapter 20), *Pancreatic Cancer—Molecular Mechanism and Targets*, Srivastava Ed., InTech, Rieka, Croatia, 361-398 (2012)].

In particular, the inflammatory cytokines TNFα, IL-6 and IL-1β have been implicated in tumor growth and angiogenesis [Leibovich et al., *Nature* 329:630-632 (1987); Waters et al., *J Pathol* 230:241-248 (2013); Wei et al., *Oncogene* 22:1517-1527 (2003); Voronov et al., *Proc Natl Acad Sci, USA* 100:2645-2650 (2003); Carmi et al., *J Immunol* 190: 3500-3509 (2013); Naldini and Carraro In: *Current Drug Targets—Inflammation & Allergy*, 4:3-8 (2005); Shchors et al., *Genes Dev* 20:2527-2538 (2006)]. Because the release of these inflammatory cytokines is controlled predominantly by TLR4 and TLR2, disrupting the required association of FLNA with these receptors can suppress angiogenesis and tumor growth.

The role of FLNA and phospho-FLNA in cellular biology of both normal, disease-free states and in cancerous states is seen to be quite complex and not yet definitively worked out. The present invention and its underlying biochemical bases disclosed hereinafter help to further delineate some of the biochemical pathways involved in the cancerous condition of some cells and assist in treating that condition to inhibit the progression of the cancerous state.

BRIEF DESCRIPTION OF THE INVENTION

The present invention contemplates a method of inhibiting the growth of cancerous cells that comprises the step of contacting cancer cells that contain a significantly enhanced amount of one or more of phosphorylated-mTOR, phosphorylated-Akt1, phosphorylated-ERK2 and serine2152-phosphorylated filamin A (pS$^{2152}$FLNA) compared to the amount present in a non-cancerous cell of the same type with an FLNA-binding effective amount of a compound or a pharmaceutically acceptable salt thereof that binds to the pentapeptide of FLNA of SEQ ID NO: 1 and exhibits at least about 60 percent of the FITC-labeled naloxone binding amount when present at a 10 μM concentration, using unlabeled naloxone as the control inhibitor at the same concentration. The enhanced amount of one or more of phosphorylated-mTOR, phosphorylated-Akt1, phosphorylated-ERK2 and serine2152-phosphorylated filamin A is an amount that is significantly greater than the amount of that phosphorylated protein in a non-cancerous cell of the same type. ERK2 is also known in the art as MAPK1 (mitogen-activated protein kinase 1). Each of mTOR, Akt1 and ERK2 is a threonine or serine/threonine kinase.

A contemplated method comprises the steps of contacting cancer cells having a significantly enhanced amount of one or more of activated (phosphorylated) mTOR, Akt1, ERK2 and phosphorylated serine2152 of FLNA with an FLNA-binding effective amount of a compound or a pharmaceutically acceptable salt thereof that binds to the pentapeptide of FLNA of SEQ ID NO: 1, exhibiting at least about 60 percent of the FITC-labeled naloxone binding amount when present at a 10 μM concentration and using unlabeled naloxone as the control inhibitor at the same concentration.

One of the underlying aspects of the present invention is the targeting of a scaffolding protein, FLNA, in what is understood to be a means to regulate PTEN (and PP2A) and its (their) effects on cancerous cells. The targeting of a scaffolding protein that appears to regulate PTEN, which in turn controls PI3K and downstream signaling partners Akt and mTOR, is a highly innovative approach to cancer therapy.

One aspect of the invention contemplates a method of inhibiting the growth of cancer cells in vivo or in vitro by contacting those cells whose growth is to be inhibited with a FLNA-binding effective amount of a FLNA-binding compound or a pharmaceutically acceptable salt thereof. The FLNA-binding compound is preferably of Series A, B, C-1, C-2, D, E or a benzazocine-ring compound as described hereinafter, and preferably also contains at least four of the six pharmacophores of FIGS. 19-24.

The cancer cells whose growth is inhibited can be solid or liquid tumor cells. Presently, solid tumors of epithelial origin appear to be particularly susceptible to growth inhibition by a contemplated method. In one preferred embodiment, the cancer cells are one or more of melanoma cells, glioblastoma cells, small cell lung carcinoma cells, breast cancer cell, prostate cancer and pancreatic cancer cells. More preferably, a cancer cell that is treated (whose proliferation is to be inhibited) exhibits an increased level of $pS^{2152}$FLNA, and also exhibits a significantly enhanced amount of one or more of phosphorylated-mTOR, phosphorylated-Akt1, and phosphorylated-ERK2 relative to a non-cancerous cell of the same type.

In a further embodiment of the invention, the cells are contacted by administration of a pharmaceutical composition that contains an FLNA-binding effective amount of a hereinafter-discussed FLNA-binding compound or a pharmaceutically acceptable salt thereof dissolved or dispersed in a pharmaceutically acceptable diluent. This contacting, particularly when carried out in vivo, is typically carried out a plurality of times. The in vivo or in vitro contacting can be continued until the cancer cell growth has diminished to a desired extent, until a tumor size has shrunken to a desired size, or can be continued through the remainder of the life of the subject receiving the administration.

BRIEF DESCRIPTION OF THE DRAWINGS

In the drawings forming a portion of this disclosure,
FIG. 1A shows that Compound C0105 induced a dose-dependent inhibition of basal glucose uptake in glioblastoma and melanoma cells.
FIG. 1B illustrates that the amounts of [$^3$H]glucose in DPM in glioblastoma and melanoma cells are decreased by contact with Compound C0105.
FIG. 1C shows that Compound C0105 has no effect on [$^3$H]glucose content in primary human lung fibroblasts.
FIG. 1D shows percentage inhibition in glucose uptake in glioblastoma cells induced by various FLNA-binding compounds at 1 or 5 nM concentration (A0033, A0053, B0055, C0108, C0124, C0134M and C0139M whose structures are shown elsewhere herein).
FIG. 1E shows that the amounts of [$^3$H]glucose in glioblastoma cells are reduced by FLNA-binding compounds.
FIG. 1F shows percentage inhibition of glucose uptake in melanoma cells induced by the FIG. 1D FLNA-binding compounds at 1 or 5 nM concentration.
FIG. 1G shows the amounts of [$^3$H]glucose in melanoma cells are reduced by FLNA-binding compounds.
FIG. 1H shows that no significant inhibition in glucose content was induced by the FIG. 1D FLNA-binding compounds at 1 or 5 nM concentration in primary lung fibroblasts.
FIG. 1I illustrates that those FLNA-binding compounds had no effect on amounts of [$^3$H]glucose in primary lung fibroblasts.
FIG. 1J illustrates that Compound C0105 induced a dose-dependent inhibition of basal glucose uptake in breast cancer HTB-22 cells, but not in human mammalian epithelial cells (HMEC).
FIG. 1K shows a dose—dependent inhibition of glucose uptake by contact with varying concentrations of Compound C0105 in HTB-22 cells, and no change in HMECs over the same concentration range.
FIG. 1L shows that Compound C0105 induced a dose-dependent inhibition of basal glucose uptake in pancreatic cancer MiaPaCa2 cancer cells but showed no effect in primary human pancreatic epithelial cells.
FIG. 1M shows that contact with Compound C0105 reduced the amounts of [$^3$H]glucose in pancreatic cancer MiaPaCa2 but not in primary human pancreatic epithelial cells.

FIG. 2A shows the percentage cell death in vehicle- and Compound C0105-treated glioblastoma cells over 4 days. FIG. 2B shows percentage cell death in vehicle- and in Compound C0105-treated melanoma cells over 4 days.

FIG. 3A through FIG. 3C illustrate that apoptosis markers show that contact with Compound C0105 attenuates glucose deprivation-induced cell death in glioblastoma cells. The effect of Compound C0105 on cell death induced by glucose withdrawal was assessed in glioblastoma cells on Day 3 and 4 by the levels of apoptosis markers: cleaved poly [ADP-ribose]polymerase 1 (PARP-1) and caspase-3 (19- and 17-KDa). Cells were grown to >90 percentage confluence, washed and incubated in 0.1% FBS-containing medium and incubated in glucose-free 0.1% FBS-containing medium without or with 1 nM Compound C0105 for 3 or 4 days, collected, washed and lysed. The resultant cell lysates were size-fractionated on SDS-PAGE and Western blotting with antibodies specific for Cleaved PCNA (Asp214) and caspase-3 (Asp175). The protein bands were quantified by densitometric scanning. FIG. 3A shows representative blots of the cleaved PARP (Asp214) and 19- and 17-KDa cleaved caspase-3 (Asp175) isoforms. FIG. 3B shows ratios of cleaved PARP (Asp214) and 19- and 17-KDa cleaved caspase-3 (Asp175) isoform levels normalized by actin. FIG. 3C shows densitometric inhibition on normalized cleaved PARP (Asp214) and 19- and 17-KDa cleaved caspase-3 (Asp175) isoform levels by 1 nM Compound C0105. Data are mean±S.E.M. of ratios (FIG. 3B) and % inhibition (FIG. 3C). Statistical significance was determined by ANOVA followed by Newman-Keuls test for multiple comparisons. N=5. *p<0.01 compared to Day 0. #p<0.01 compared to vehicle (open bars).

FIG. 4A through 4C illustrate via apoptosis markers that contact with Compound C0105 reduces glucose deprivation-induced cell death in melanoma cells in a manner similar to that in FIGS. 3A-3C. The effect of Compound C0105 on cell death induced by the glucose withdrawal was assessed in melanoma cells on the Day 3 and 4 by the levels of apoptosis markers cleaved PARP-1 and caspase-3 (19- and 17-KDa). Cells were grown to >90% confluence, washed and incubated in 0.1% FBS-containing medium and incubated in glucose-free 0.1% FBS-containing medium without or with 1 nM C0105 for up to 4 days. Cell density was assessed at day 3 and 4. FIG. 4A shows representative blots of the cleaved PARP (Asp214) and 19- and 17-KDa cleaved caspase-3 (Asp175) isoforms. FIG. 4B shows ratios of cleaved PARP (Asp214) and 19- and 17-KDa cleaved caspase-3 (Asp175) isoform levels normalized by actin. FIG. 4C shows % inhibition on normalized cleaved PARP (Asp214) and 19- and 17-KDa cleaved caspase-3 (Asp175) isoform levels by 1 nM C0105. Data are mean±S.E.M. of ratios (FIG. 4B) and % inhibition (FIG. 4C). Statistical significance was determined by ANOVA followed by Newman-Keuls test for multiple comparisons. N=5. *p<0.01 compared to Day 0. #p<0.01 compared to vehicle (open bars).

FIG. 5A through FIG. 5C illustrate via apoptosis markers that contact with Compound C0105 reduces glucose deprivation-induced cell death in small-cell lung carcinoma cells. The effect of Compound C0105 on cell death induced by the glucose withdrawal was assessed in small-cell lung carcinoma cells on the Day 3 and 4 by the levels of apoptosis markers cleaved PARP-1 and caspase-3 (19- and 17-KDa). Cells were grown to >90% confluence, washed and incubated in 0.1% FBS-containing medium and incubated in glucose-free 0.1% FBS-containing medium without or with 1 nM Compound C0105 for up to 4 days. Cells were washed, solubilized and the levels of apoptotic markers PARP-1 and caspase-3 (19- and 17-KDa) in the obtained cell lysates were determined by Western blotting. The density of protein bands was quantified by densitometric scanning. FIG. 5A shows representative blots of the cleaved PARP (Asp214) and 19- and 17-KDa cleaved caspase-3 (Asp175) isoforms. FIG. 5B shows ratios of cleaved PARP (Asp214) and 19- and 17-KDa cleaved caspase-3 (Asp175) isoform levels normalized by actin. Data are mean±S.E.M. FIG. 5C shows % inhibition on normalized cleaved PARP (Asp214) and 19- and 17-KDa cleaved caspase-3 (Asp175) isoform levels by 1 nM Compound C0105. Statistical significance was determined by ANOVA followed by Newman-Keuls test for multiple comparisons. N=5. *p<0.01 compared to Day 0. #p<0.01 compared to vehicle (open bars).

FIG. 6A shows levels of [$^3$H] thymidine incorporation, expressed as mean±S.E.M. FIG. 6B shows % inhibition by varying concentrations of Compound C0105. Statistical significance was determined by ANOVA followed by Newman-Keuls test for multiple comparisons. N=4. **p<0.05, *p<0.01 compared to vehicle (open bars).

FIG. 7A shows representative blots of the pS$^{2152}$FLNA, PTEN, PP2A-Aα and PP2A-Aβ. FIG. 7B shows ratios of pS$^{2152}$FLNA, PTEN, PP2A-Aα and PP2A-Aβ levels normalized by the amounts of FLNA immunoprecipitated. Data are means of ratios ±S.E.M. FIG. 7C shows densitometric change induced by contact with Compound C0105 in normalized pS$^{2152}$FLNA, PTEN, PP2A-Aα and PP2A-Aβ levels. Statistical significance was determined by ANOVA followed by Newman-Keuls test for multiple comparisons. N=4. **p<0.05, *p<0.01 compared to vehicle (open bars).

FIG. 8A shows representative blots of the pS$^{2152}$FLNA, PTEN, PP2A-Aα and PP2A-Aβ. FIG. 8B shows ratios of pS$^{2152}$FLNA, PTEN, PP2A-Aα and PP2A-Aβ levels normalized by the amounts of FLNA immunoprecipitated. Data are means of ratios ±S.E.M. FIG. 8C shows % change induced by contact with Compound C0105 in normalized pS$^{2152}$FLNA, PTEN, PP2A-Aα and PP2A-Aβ levels. Statistical significance was determined by ANOVA followed by Newman-Keuls test for multiple comparisons. N=4. **p<0.05, *p<0.01 compared to vehicle (open bars).

FIG. 9A shows representative blots of the $pS^{2152}$FLNA, PTEN, PP2A-Aα and PP2A-Aβ. FIG. 9B shows ratios of $pS^{2152}$FLNA, PTEN, PP2A-Aα and PP2A-Aβ levels normalized by the amounts of FLNA immunoprecipitated. Data are mean±S.E.M. FIG. 9C shows % change induced by C0105 in normalized $pS^{2152}$FLNA, PTEN, PP2A-Aα and PP2A-Aβ levels. Statistical significance was determined by ANOVA followed by Newman-Keuls test for multiple comparisons. N=4. **p<0.05, *p<0.01 compared to vehicle (open bars).

FIG. 10A shows representative blots of the $pS^{2448}$mTOR, $pS^{473}$Akt, pY/pTERK2 as well as their respective controls independent of their phosphorylation status: mTOR, Akt and ERK2. FIG. 10B shows $pS^{2448}$mTOR, $pS^{473}$Akt, pY/pTERK2 levels normalized by the amounts of mTOR, Akt and ERK2 immunoprecipitated. Data are means of ratios ±S.E.M. FIG. 10C shows % inhibition induced by C0105 in normalized $pS^{2448}$mTOR, $pS^{473}$Akt, pY/pTERK2 levels. Statistical significance was determined by ANOVA followed by Newman-Keuls test for multiple comparisons. N=4. *p<0.01 compared to vehicle (open bars).

FIG. 11A shows representative blots of the $pS^{2448}$mTOR, $pS^{473}$Akt, pY/pTERK2 as well as their respective controls independent of their phosphorylation status—mTOR, Akt and ERK2. FIG. 11B shows $pS^{2448}$mTOR, $pS^{473}$Akt, pY/pTERK2 levels normalized by the amounts of mTOR, Akt and ERK2 immunoprecipitated. Data are means of ratios ±S.E.M. FIG. 11C shows % inhibition induced by C0105 in normalized $pS^{2448}$mTOR, $pS^{473}$Akt, pY/pTERK2 levels. Statistical significance was determined by ANOVA followed by Newman-Keuls test for multiple comparisons. N=4. *p<0.01 compared to vehicle (open bars).

FIG. 12A through FIG. 12F (two sets of three panels) show that contact with Compound C0105 robustly reduces mTOR, Akt and ERK activation (phosphorylated mTOR, Akt and ERK) in small-cell lung carcinoma cells (FIGS. 12A-12C), and little effect on mTOR, Akt and ERK activation (phosphorylated mTOR, Akt and ERK) in primary lung fibroblast cells (FIGS. 12D-12F). Cells were treated with vehicle and 0.1-5 nM C0105 for 4 days. Cells were washed, solubilized and the resultant cell lysate was immunoprecipitated with anti-mTOR, -Akt or -ERK2. The levels of $pS^{2448}$mTOR, $pS^{473}$Akt, pY/pTERK2 in the respective anti-mTOR, -Akt, and -ERK2 immunoprecipitates were determined by Western blotting. FIG. 12A shows representative blots of the $pS^{2448}$mTOR, $pS^{473}$Akt, pY/pTERK2 as well as their respective controls mTOR, Akt and ERK2 in small-cell lung carcinoma cells, whereas FIG. 12D shows similar blots obtained using lung fibroblast cells. The density of protein bands was measured by densitometric scanning. FIG. 12E shows $pS^{2448}$mTOR, $pS^{473}$Akt, pY/pTERK2 levels normalized by the amounts of mTOR, Akt and ERK2 immunoprecipitated in lung fibroblast cells. FIG. 12F shows % inhibition in normalized $pS^{2448}$mTOR, $pS^{473}$Akt, pY/pTERK2 levels compared to vehicle-treated cells following C0105 treatment in lung carcinoma. Data are expressed as mean±S.E.M. of ratios (FIGS. 12B and 12E) and % inhibition (FIGS. 12C and 12F). Statistical significance was determined by ANOVA followed by Newman-Keuls test for multiple comparisons. N=4. *p<0.01 compared to vehicle (open bars).

FIGS. 13A, 13B, 13E and 13F), and two non-cancerous cell types from analogous epithelial tissues (HMEC and HPEC; FIGS. 13C, 13D, and 13G and 13H). Cells were treated with vehicle and 0.1-5 nM C0105 for 4 days. Cells were washed, solubilized and the resultant cell lysate was immunoprecipitated with anti-mTOR, -Akt or -ERK2. The levels of $pS^{2448}$mTOR, $pS^{473}$Akt, pY/pTERK2 in the respective anti-mTOR, -Akt, and -ERK2 immunoprecipitates were determined by Western blotting (not shown). The density of protein bands was measured by densitometric scanning. FIGS. 13A and 13E show $pS^{2448}$mTOR, $pS^{473}$Akt, pY/pTERK2 levels normalized by the amounts of mTOR, Akt and ERK2 immunoprecipitated in HTB-22 and MiaPaCa2, respectively, those cells, whereas FIGS. 13B and 13F show % inhibition in normalized $pS^{2448}$mTOR, $pS^{473}$Akt, pY/pTERK2 levels compared to vehicle-treated cells that resulted from C0105 treatment in those same cells. FIGS. 13C and 13G and FIGS. 13D and 13H show similarly obtained data for immunoprecipitates from HMEC and HPEC cells, respectively. Cell treatments and data handling were as discussed in FIG. 12.

using Western blots in human melanoma cells. Cells treated with vehicle and 0.1-5 nM C0105 for 4 days were collected, washed and solubilized (lysed). The resultant cell lysates were size-fractionated on SDS-PAGE and Western blotting to determine the levels of Ki67, PCNA and actin (loading control). The protein bands were quantified using densitometric scanning. FIG. 14A shows representative blots of the Ki67 and PCNA in melanoma cells without and with contacting by Compound C0105. FIG. 14B shows ratios of Ki67 and PCNA normalized by levels of actin, the loading control, in melanoma cells. Data are means of ratios ±S.E.M. FIG. 14C shows % inhibition in normalized Ki67 and PCNA levels by Compound C0105 in melanoma cells. Statistical significance was determined by ANOVA followed by Newman-Keuls test for multiple comparisons. N=4. *p<0.01 compared to vehicle (open bars).

FIG. 15A shows representative blots of the Ki67 and PCNA in lung carcinoma cells without and with contact by Compound C0105. FIG. 15B shows ratios of Ki67 and PCNA normalized by levels of actin, the loading control, in lung carcinoma cells. Data are means of ratios ±S.E.M. FIG. 15C shows saturable inhibition in normalized Ki67 and PCNA levels by C0105 in lung carcinoma cells. Statistical significance was determined by ANOVA followed by Newman-Keuls test for multiple comparisons. N=4. *p<0.01 compared to vehicle (open bars).

FIG. 16A shows representative blots of the Ki67 and PCNA in glioblastoma cells without and with Compound C0105 contact. FIG. 16B shows ratios of Ki67 and PCNA normalized by actin levels in glioblastoma cells. Data are means of ratios ±S.E.M. FIG. 16C shows % inhibition in normalized Ki67 and PCNA levels by C0105 in glioblastoma cells. Statistical significance was determined by ANOVA followed by Newman-Keuls test for multiple comparisons. N=4. *p<0.01 compared to vehicle (open bars).

FIG. 17A shows representative blots of the Ki67 and PCNA in HTB-22 cells without and with contact with Compound C0105. FIG. 17B shows representative blots of the Ki67 and PCNA in control HMECs without and with contact with Compound C0105. FIG. 17C shows ratios of Ki67 normalized by actin levels in HTB-22 and HMECs. FIG. 17D shows % inhibition in normalized Ki67 levels by Compound C0105 in HTB-22 and HMECs. FIG. 17E shows ratios of PCNA normalized by actin levels in HTB-22 and HMECs. FIG. 17F shows % inhibition in normalized PCNA levels by C0105 in HTB-22 and HMECs. Data are expressed as mean±S.E.M. of ratios (FIGS. 17C and 17E) and % inhibition (FIGS. 17D and 17F). Statistical significance was determined by ANOVA followed by Newman-Keuls test for multiple comparisons. N=4. *p<0.01 compared to vehicle-treated group (open bars).

FIG. 18A shows a competition (displacement) curve for the inhibition of [$^3$H]NLX binding by naltrexone to membranes from FLNA-expressing A7 cells shows two affinity states with $IC_{50}$-H of 3.94 picomolar and $IC_{50}$-L of 834 picomolar as taken from Wang et al., PLoS One. 3(2):e1554 (2008), FIG. 3. A nonlinear curve-fit analysis was performed using a competition equation that assumed two saturable sites for the naltrexone curve comprising of 16 concentrations ranging from 0.1 pM to 1 µM. Data are derived from 6 studies, each using a different set of A7 cells. FIG. 18B is a competition (displacement) curve for the inhibition of FITC-conjugated NLX binding by naltrexone to membranes from FLNA-expressing A7 cells that shows two affinity states with $IC_{50}$-H of 1.63 picomolar (pM) and $IC_{50}$-L of 18.8 nanomolar (nM). A nonlinear curve-fit analysis was performed using a competition equation that assumed two saturable sites for the naltrexone curve comprising of 16 concentrations ranging from 0.1 pM to 1 µM. FIG. 18C is a competition (displacement) curve for the inhibition of [$^3$H]NLX binding by naltrexone to biotinylated pentapeptide (Bn-VAKGL) of SEQ ID NO: 1, that shows a single affinity state with $IC_{50}$ of 42.99 picomolar. A nonlinear curve-fit analysis was performed using a competition equation that assumed a single saturable site for the naltrexone curve comprising of 16 concentrations ranging from 0.1 pM to 1 µM.

FIG. 19 through FIG. 24 represent schematic pharmacophores (Pharmacophores 1-6, respectively) showing relative locations of chemical features such as a hydrogen bond acceptor (HBA), an aromatic/hydrophobe (ARO/HYD) center, and the intramolecular distances there between in Angstroms for a compound that binds to the pentameric peptide of FLNA of SEQ ID NO: 1.

FIG. 25A shows representative blots of the Ki67, PCNA and the loading control, actin, in MiaPaCa2 cells without and with contacting by Compound C0105. FIG. 25B shows similar blots of Ki67, PCNA and actin, in HPECs without and with contacting by Compound C0105. FIG. 25C shows ratios of Ki67 normalized by actin in MiaPaCa2 cells and in HPECs. FIG. 25D shows percentage inhibition in normalized Ki67 levels by Compound C0105 in MiaPaCa2 cells and in HPECs. Data are means of ratios ±S.E.M. Statistical significance was determined by ANOVA followed by Newman-Keuls test for multiple comparisons. N=4. *p<0.01 compared to vehicle (open bars).

FIG. 26A shows tumor volumes in $mm^3$ measured using a digital external caliper, expressed as mean±S.E.M. FIG. 26B shows percentage change in tumor volumes compared to individual baseline (Day 0) at Days 3, 10, 14, and 20 following initiation of treatments. Statistical significance was determined by ANOVA followed by post-hoc two-tailed Student's t test. N=5 (controls) or 6 (treated). **p<0.05, *p<0.01 compared to baseline tumor volumes. ++p<0.05, +p<0.01 compared to vehicle-treated group (open bars).

FIGS. 27A through 27J illustrate that contact with Compound C0105 reduces $pS^{2152}$FLNA but increases FLNA-associated PTEN and PP2A levels in pancreatic cancer MiaPaCa2 cells but not in control primary human pancreatic epithelial cells (HPEC). The effect of contact with Compound C0105 on the levels of $pS^{2152}$FLNA and FLNA-associated phosphatases, PTEN and PP2A subclasses was determined in MiaPaCa2 and HPECs. Cells were contacted with vehicle and 0.1-5 nM Compound C0105 for 4 days. Cells were washed, solubilized and the cell lysate derived was immunoprecipitated with anti-FLNA. The levels of $pS^{21}$2FLNA and FLNA-associated phosphatases, PTEN and PP2A subclasses in the anti-FLNA immunoprecipitate were determined by Western blotting. The density of protein bands was quantified by densitometric scan. FIG. 27A shows representative blots of the $pS^{2152}$FLNA, PTEN, PP2A-Aα and PP2A-Aβ in MiaPaCa2 cells. FIG. 27B shows representative blots of the $pS^{2152}$FLNA, PTEN, PP2A-Aα and PP2A-Aβ in HPECs. FIG. 27C shows ratios of $pS^{2152}$FLNA levels normalized by the amounts of FLNA immunoprecipitated in MiaPaCa2 and HPECs. FIG. 27D shows percentage change in normalized $pS^{2152}$FLNA levels compared to vehicle-treated cells resulted by C0105 treatment in MiaPaCa2 and HPECs. FIG. 27E shows ratios of PTEN to FLNA levels in MiaPaCa2 and HPECs. FIG. 27F shows percentage change in normalized PTEN levels compared to vehicle-treated cells following C0105 treatment in MiaPaCa2 and HPECs. FIG. 27G shows ratios of PP2A-Aα to FLNA levels in MiaPaCa2 and HPECs. FIG. 27H shows % change in normalized PP2A-Aα levels compared to vehicle-treated cells following C0105 treatment in MiaPaCa2 and HPECs. FIG. 27I shows ratios of PP2A-Aβ to FLNA levels in MiaPaCa2 and HPECs. FIG. 27J shows percentage change in normalized PP2A-Aβ levels compared to vehicle-treated cells due to contact with Compound C0105 in MiaPaCa2 and HPECs. Data are expressed as mean±S.E.M. of ratios (FIGS. 27C, 27E and 27G) and percentage inhibition (FIGS. 27D, 27F and 27H). Statistical significance was determined by ANOVA followed by Newman-Keuls test for multiple comparisons. N=4. **p<0.05, *p<0.01 compared to vehicle (open bars).

FIG. 29A shows representative blots of the Ki67, PCNA and actin in HTB-22 cells without and with Compound C0105 treatments. FIG. 29B shows representative blots of the Ki67, PCNA and actin in control HMECs without and with C0105 treatments. FIG. 29C shows ratios of Ki67 to actin levels in HTB-22 cells and HMECs. FIG. 29D shows % inhibition in normalized Ki67 levels by C0105 in HTB-22 cells and in HMECs. FIG. 29E shows PCNA levels normalized by the loading control, actin in HTB-22 cells and HMECs. FIG. 29F shows % inhibition in normalized PCNA levels by Compound C0105 in HTB-22 cells and in HMECs. Data are expressed as mean±S.E.M. of ratios (FIGS. 29C and 29E) and % inhibition (FIGS. 29D and 29F). Statistical significance was determined by ANOVA followed by Newman-Keuls test for multiple comparisons. N=4. *p<0.01 compared to vehicle (open bars).

FIGS. 30A through 30L illustrate that Compound C0105 reduces K-ras and increases Ras-GAP on administration to cancer cells in a dose-dependent manner and has little effect on normal primary epithelial cells from similar tissues. Thus, melanoma, two different pancreatic cancerous cell lines (MiaPaCa2 and BxPc3) and a glioblastoma cell line (U87) were treated with zero (vehicle), 0.1, 0.5, 1 and 5 nM Compound C0105 as previously discussed, and FLNA-bound K-ras and ras-GAP were immunoprecipitated, separated by Western blotting and the blot densities determined as discussed previously.

FIG. 33B shows the quantification of those results using Densitometric scanning to illustrate the relative amounts of the FLNA protein isolated from each cell type having one pI value or the other. N=4, *p<0.01.

FIG. 34B illustrates average tumor volumes (mm3) in mice treated with vehicle alone (black diamonds), gemcitabine (open squares), Compound C0105 at 10 mg/kg (black triangles) and Compound C0105 at 100 mg/kg (open diamonds).

FIG. 35 illustrates percentage change data for tumor size from a xenograft study of Nu/Nu mice implanted with cells of pancreatic cancer cell line, BxPC3, and using the pancreatic cancer standard of care gemcitabine (50 mg/kg i.p. bi-weekly; black bars) as an additional control. Compound C0105 was administered alone by oral gavage twice daily at each of the two concentrations [10 mg/kg (diagonal hatching) and 1 mg/kg (vertical-horizontal cross-hatching)]. Gemcitabine (50 mg/kg twice weekly intraperitoneally) was used alone or in combination with 10 mg/kg Compound C0105 (diagonal cross-hatching). *p<0.01 compared to individual baseline. +p<0.01 compared to vehicle control group (open bars).

FIG. 36A shows Western blots prepared from each cell type in the absence and presence of 1 nM Compound C0105 in the growth medium. Cells were plated, treated for 4 days with vehicle or 1 nM C0105, washed and solubilized, and the resultant cell lysate was immunoprecipitated with anti-FLNA. The levels of $pS^{2152}$FLNA and FLNA-associated phosphatases, PTEN, PP2A subclasses, Ras-GAP and K-Ras in the anti-FLNA immunoprecipitate were determined by Western blotting. The density of protein bands was quantified by densitometric scan. FIG. 36A shows representative blots of the $pS^{2152}$FLNA, PTEN, PP2A-A$\alpha$, PP2A-A$\beta$. FIG. 36B show ratios of $pS^{2152}$FLNA, PTEN, PP2A-A$\alpha$/$\beta$ and Ras-GAP and K-Ras levels normalized by the amounts of FLNA immunoprecipitated and FIG. 36C show the percentage change for each induced by administration of Compound C0105 for the primary tumor cells (FIG. 36B) and the metastatic tumor cells (FIG. 36C), respectively. Statistical data were obtained using a two-tailed Student's t-test, with p<0.02 for all comparisons between treatment and control showing a *.

ABBREVIATIONS AND SHORT FORMS

Figures 1A, 1B:
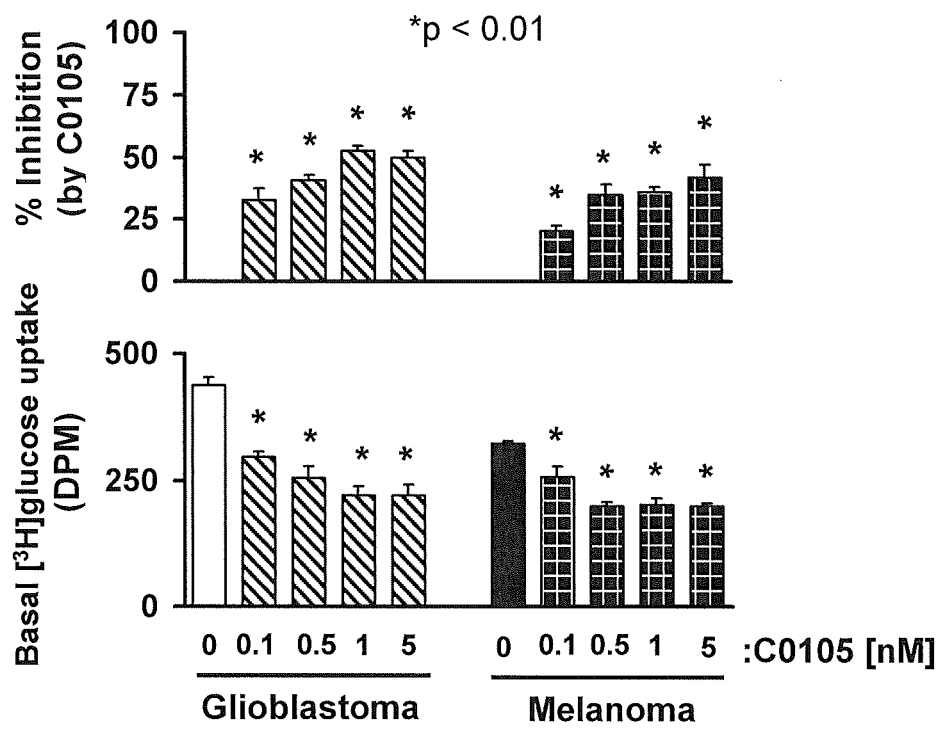
FIG. 1A through FIG. 1M illustrate the effects of various FLNA-binding compounds on glucose uptake in glioblastoma, melanoma, breast and pancreatic cancer cell lines, along with appropriate non-cancerous primary cell controls. Cells were grown in the absence or presence of 0.1-5 nM indicated compounds for 4 days. Following brief washes with PBS, cells were serum-deprived for 4 hours and then incubated in oxygenated Kreb's Ringer containing 0.1 μCi [$^3$H]glucose for 2 hours under constant oxygenation. The reaction was terminated by removal of the incubation medium, and cells were washed and scraped off to determine the amounts of [$^3$H]glucose in cells by scintillation spectrometry. Data are expressed as mean±S.E.M. Statistical significance was determined by ANOVA followed by Newman-Keuls test for multiple comparisons. **$p<0.05$, *$p<0.01$ compared to vehicle-treated group in each cell type (open bars). N=5-6.

The following abbreviations and short forms are used in this specification.

"DAMGO" means [D-Ala2, N-MePhe4, Gly-ol]-enkephalin

"ERK2" means extracellular signal-regulated kinase 2

"FLNA" means filamin A

"FITC" means fluorescein isothiocyanate

"Gs" means G protein stimulatory subtype, stimulates adenylyl cyclase

"MOR" means µ (mu) opioid receptor

"NLX" means naloxone

"NTX" means naltrexone

"pERK2" means phosphorylated ERK2

"PARP-1" means poly[ADP-ribose]polymerase 1

"PTEN" means phosphatase and tensin homolog

"mTOR $pS^{2448}$" means mTOR phosphorylated at serine-2448

"Akt1-3 $pS^{473}$" means Akt1-3 phosphorylated at serine-473

"ERK2 $pT^{183}$/$pY^{185}$" means ERK2 phosphorylated at one or both of threonine-183 and tyrosine-185

"$pS^{2152}$FLNA" means filamin A phosphorylated at serine-2152

DEFINITIONS

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

As used herein, the term "hydrocarbyl" is a short hand term for a non-aromatic group that includes straight and branched chain aliphatic as well as alicyclic groups or radicals that contain only carbon and hydrogen. Inasmuch as alicyclic groups are cyclic aliphatic groups, such substituents are deemed hereinafter to be subsumed within the aliphatic groups. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups, substituents, moieties or radicals, as discussed hereinafter. An aralkyl substituent group such as benzyl is deemed an aromatic group as being an aromatic ring bonded to an X group, where X is $CH_2$. A substituent group containing both an aliphatic ring and an aromatic ring portion such as tetralin (tetrahydronaphthalene) that is linked directly through the aliphatic portion to the depicted ring containing the W group is deemed a non-aromatic, hydrocarbyl group. On the other hand, a similar group bonded directly via the aromatic portion, is deemed to be a substituted aromatic group. Where a specific aliphatic hydrocarbyl substituent group is intended, that group is recited; i.e., $C_1$-$C_4$ alkyl, methyl or dodecenyl. Exemplary hydrocarbyl groups contain a chain of 1 to about 12 carbon atoms, and preferably 1 to about 8 carbon atoms, and more preferably 1 to 6 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl, octyl, decyl, dodecyl and the like. Cyclic alkyl radicals such as cyclo propyl, cyclobutyl, cyclopentyl, cyclohexyl and cycloheptyl are also contemplated, as are their corresponding alkenyl and alkynyl radicals. Examples of suitable straight and branched chain alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of straight and branched chain alkynyl radicals include ethynyl, 2-propynyl, 3-propynyl, decynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, and cyclohexenyloxy groups. On the other hand, a hydrocarbyl group containing a —C(O)— functionality is referred to as a hydrocarboyl (acyl) and that containing a —C(O)O— is a hydrocarboyloxy group inasmuch as there is no ambiguity. Exemplary hydrocarboyl and hydrocarboyloxy groups include acyl and acyloxy groups, respectively, such as acetyl and acetoxy, acryloyl and acryloyloxy.

Carboxyl-related linking groups between the central spiro ring system and an aromatic or heteroaromatic ring system, circle A, include several types of ester and amide bonds. Illustrative of such bonds are sulfonamide, sulfonate and thiosulfonate esters that can be formed between a $SO_2$-containing group [also sometimes shown as a $S(=O)_2$ group] and an amine, oxygen or sulfur atom, respectively. Amide, ester and thioester links can be formed between an aromatic or heteroaromatic ring containing a C(O) [also sometimes shown as (C=O)] group and a nitrogen, oxygen or sulfur atom, respectively. Similarly, a guanidino linker can be formed between an aromatic or heteroaromatic ring containing a NHC(NH) [NHC(=NH)] group and a nitrogen, a urethane, carbonate or thiocarbonate can be formed between an aromatic or heteroaromatic ring containing a OC(O) [or OC(=O)] group and a nitrogen, oxygen or sulfur, respectively. A compound containing a urea linker, urethane linker or isothiourea linker [NHC(O)S] {or [NHC(=O)S]} can be formed between an aromatic or heteroaromatic ring containing a NHC(O) group and a nitrogen, oxygen or sulfur, respectively. A thiourea linkage is also contemplated.

A "carboxyl" substituent is a —C(O)OH group. A $C_1$-$C_6$ hydrocarbyl carboxylate is a $C_1$-$C_6$ hydrocarbyl ester of a carboxyl group. A carboxamide is a —C(O)$NR^3R^4$ substituent, where the R groups are defined elsewhere and are numbered here as 3 and 4 for ease in further discussion, but need not be so numbered in the following chemical formulas. Similarly, a sulfonamide is a —S(O)$_2NR^3R^4$ substituent, where the R groups are defined hereinafter. Illustrative $R^3$ and $R^4$ groups that together with the depicted nitrogen of a carboxamide form a 5-7-membered ring that optionally contains 1 or 2 additional hetero atoms that independently are nitrogen, oxygen or sulfur, include morpholinyl, piperazinyl, oxathiazolyl, 1,2,3-triazolyl, 1,2,4-triazolyl, pyrazolyl, 1,2,4-oxadiazinyl and azepinyl groups.

As a skilled worker will understand, a substituent that cannot exist such as a $C_1$ alkenyl or alkynyl group is not intended to be encompassed by the word "hydrocarbyl", although such substituents with two or more carbon atoms are intended.

The term "aryl", alone or in combination, means a phenyl, naphthyl or other radical as recited hereinafter that optionally carries one or more substituents selected from hydrocarbyl, hydrocarbyloxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, and the like. The term "arylhydrocarbyl", alone or in combination, means a hydrocarbyl radical as defined above in which one hydrogen atom is replaced by an aryl radical as defined above, such as benzyl, 2-phenylethyl and the like. The term "arylhydrocarbyloxycarbonyl", alone or in combination, means a radical of the formula —C(O)—O—arylhydrocarbyl in which the term "arylhydrocarbyl" has the significance given above. An example of an arylhydrocarbyloxycarbonyl radical is benzyloxycarbonyl. The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

As used herein, the term "binds" refers to the adherence of molecules to one another, such as, but not limited to, the interaction of a ligand with its receptor, or a polypeptide of SEQ ID NO: 1 with a small molecule such as the compounds disclosed herein.

The word "activation" used connection with a discussed protein such as an enzyme, receptor or G protein, is well known in biochemistry and is intended to be understood in its usually used manner. Most simply, "activation" is used to describe one of two functionally distinct states: the inactive (R) and the active (R*) state. When activated, the protein is primed to carry out a function, such as a signaling function, whereas when not activated or inactive, the protein does not carry out that function, or does so more slowly. That activation can occur by many routes including the making or breaking of a covalent bond, the binding or release of a non-covalently bound ligand, an allosteric change in structure caused by bond formation or cleavage of one or more molecules associated with the protein of interest, and many other routes as are known in the art. Many of the activation steps involved with the proteins discussed herein occur via phosphorylation and the changes in charge and shape caused thereby. "Activation" and "phosphorylation" are therefore often used synonymously.

As used herein, the term "FLNA-binding compound" refers to a compound that binds to the scaffolding protein filamin A, or more preferably to a polypeptide comprising residues -Val-Ala-Lys-Gly-Leu-(SEQ ID NO: 1) of the FLNA sequence that correspond to amino acid residue positions 2561-2565 of the FLNA protein sequence as noted in the sequence provided at the web address: UniProtKB/Swiss-Prot entry P21333, FLNA-HUMAN, Filamin-A protein sequence. A FLNA-binding compound can inhibit the MOR-Gs coupling caused by agonist stimulation of the p opioid receptor via interactions with filamin A, preferably in the 24$^{th}$ repeat region.

As used herein, the term "opioid receptor" refers to a G protein-coupled receptor located in the CNS that interacts with opioids. More specifically, the p opioid receptor is activated by morphine causing analgesia, sedation, nausea, and many other side effects known to one of ordinary skill in the art. The other two major receptors, δ (delta) and κ (kappa) are activated by other ligands.

As used herein, the term "opioid agonist" refers to a substance that upon binding to an opioid receptor can stimulate the receptor, induce G protein coupling and trigger a physiological response. More specifically, an opioid agonist is a morphine-like substance that interacts with MOR to produce analgesia.

As used herein, the term "opioid antagonist" refers to a substance that upon binding to an opioid receptor inhibits the function of an opioid agonist by interfering with the binding of the opioid agonist to the receptor.

As used herein the term "ultra-low-dose" or "ultra-low amount" refers to an amount of compound that when given in combination with an opioid agonist is sufficient to enhance the analgesic potency of the opioid agonist. More specifically, the ultra-low-dose of an opioid antagonist is admixed with an opioid agonist in an amount about 1000- to about 10,000,000-fold less, and preferably about 10,000- to about 1,000,000-fold less than the amount of opioid agonist.

As used herein an "FLNA-binding effective amount" or more simply an "effective amount" refers to an amount of a contemplated compound sufficient to bind to the FLNA pentapeptide of SEQ ID NO: 1 and perform the functions described herein, such as inhibiting at least about 60 percent, and preferably about 70 percent, of the FITC-labeled naloxone binding amount when present at a 10 μM concentration and using unlabeled naloxone as the control inhibitor at the same concentration. An effective amount of a contemplated compound is most easily determined using the in vitro assay of Example 1. Using that definition, an effective amount of a contemplated compound binds to a pentapeptide of SEQ ID NO: 1 with at least about 60 percent of the value obtained when using naloxone as the control inhibitor at the same concentration as the contemplated compound, and up to about twice (200 percent) the value obtained with naloxone as control.

As used herein the term "pharmacophore" is not meant to imply any pharmacological activity. Rather, a pharmacophore is defined as the relevant groups on a molecule that interact with a receptor and are responsible for the activity of the compound. [R. B. Silverman, *The Organic Chemistry of Drug Design and Drug Action*, 2$^{nd}$ ed., Elsevier Academic Press, Amsterdam, (2004), p. 17.] The term refers to chemical features and their distribution in three-dimensional space that constitutes the preferred requirements for molecular interaction with a receptor (See, U.S. Pat. No. 6,034,066). A pharmacophore is calculated by determining the shared aromatic/hydrophobic and hydrogen bond acceptor functions and the distances there between of a group of compounds that bind similarly to a particular receptor, here, pentapeptide of SEQ ID NO: 1.

As used herein, the term "receptor" is broadly used to refer to an entity with which another entity, a ligand, specifically binds. A receptor is generally a macromolecule and a ligand is generally a smaller, lower molecular weight molecule, but that distinction is not required. Some receptors discussed herein are specific proteins such as MOR, and those receptors can themselves be ligands for other receptors such as antibodies. Other receptors include whole antibodies and antibody combining site portions (paratopes) that immunoreact with specific epitope ligands, as well as proteins such as Staphylococcal and Streptococcal proteins A and G, respectively, that bind to Fab and Fc antibody portions. Biotin and avidin (streptavidin) can also be viewed as a ligand-receptor pair, as can aptamers.

As used herein, the phrase "significantly different", "significant difference", "significantly greater extent", "significantly greater amount", "significantly enhanced quantity", "significantly enhanced amount" and like terms and phrases, including lessened or decreased amounts, mean that when the amount of a cancer-related phosphorylated protein present in a cancer cell is enhanced relative to the amount present in an appropriate non-cancerous cell, the compared results differ by greater than one standard deviation of either measurement, preferably by greater than two standard deviations, and more preferably by three standard deviations if an assay is repeated. An "appropriate non-cancerous cell" is also referred to herein as a "non-cancerous cell of the same type". Illustrative appropriate cell pairs (cells of the same type) include HTB-22 vs. human mammary epithelial cells (HMEC), small cell lung carcinoma DMS 114 cells vs. human lung epithelial cells, and human pancreatic cancer MiaPaCa2 cells vs. human pancreatic epithelial cells (HPEC).

DETAILED DESCRIPTION OF THE INVENTION

In normal, non-cancerous cells, filamin A (FLNA) is phosphorylated and dephosphorylated at the serine residue of sequence position 2152 ($S^{2152}$FLNA) such that there is a relatively small amount of that phosphorylated protein ($pS^{2152}$FLNA) present at any time. It has been found that many cancer cells have (exhibit) elevated levels of $pS^{2152}$FLNA, which suggests a reduced phosphatase level or phosphatase activity in that cancerous state. Contacting such cancerous cells with a FLNA-binding compound as discussed hereinafter, such as illustrative Compound C0105, reduces the level of $pS^{2152}$FLNA and returns the amount of $pS^{2152}$FLNA to or toward the normal level (normalizes) as is seen from the data of FIGS. 7A-7C, 8A-8C and 27C. On the other hand, as is seen in FIGS. 9A-9C and 27D, normal, non-cancerous cells (lung fibroblasts and pancreatic epithelial cells, respectively) begin with little $pS^{2152}$FLNA and contacting those cells with illustrative Compound C0105 causes little change in the amount of $pS^{2152}$FLNA present.

In investigating the mechanism of the interaction of PTEN and FLNA, it has been found that PTEN is normally physically associated with FLNA, but appears to be released from FLNA in cancer cell lines. PTEN, via the enzyme PPA2 (inorganic pyrophosphatase 2, mitochondrial; EC 3.6.1.1; UniProt Accession Q9H2U2; a serine/threonine protein phosphatase), inhibits mTOR activation when tethered to FLNA but loses this ability when dissociated, as noted in the cancer-diseased states. In some cancer cells, the dissociation of PTEN and FNLA leads to the phosphorylation of the serine 2152 residue in FLNA, thereby providing an enhanced amount of phosphorylated FLNA serine2152 [often referred to herein as ($pS^{2152}$FLNA)] relative to the same cell type in a non-cancerous state.

The present invention contemplates inhibiting the growth (proliferation) of cancer cells by contacting those cells in vivo or in vitro that exhibit (contain) an enhanced amount of one or more of phosphorylated mTOR (as mTOR $pS^{2448}$), Akt1 (as Akt1-3 pS$^{473}$), ERK2 (as ERK2 pT$^{183}$/pY$^{185}$) or the persistently enhanced amount serine2152-phosphorylated filamin A (pS$^{2152}$FLNA) with a filamin A- (FLNA-) binding effective amount of a FLNA-binding compound discussed hereinafter or a pharmaceutically acceptable salt thereof. An enhanced amount of an above phosphorylated protein is an amount that is significantly greater than the amount of that phosphorylated protein present in a non-cancerous cell of the same type. The above contacting is typically carried out a plurality of times.

For ease of discussion hereinafter, activated, phosphorylated mTOR (often referred to as mTOR pS$^{2448}$), Akt1 (often referred to as Akt1-3 pS$^{473}$) ERK2 (often referred to as ERK2 pT$^{183}$/pY$^{185}$) and serine2152-phosphorylated filamin A (often referred to as pS$^{2152}$FLNA) are sometimes referred to herein as phosphorylated-mTOR, phosphorylated-Akt1, phosphorylated-ERK2 and phosphorylated-FLNA or serine2152-phosphorylated-FLNA.

An enhanced amount of one or more of phosphorylated-mTOR, phosphorylated-Akt1, phosphorylated-ERK2 and serine2152-phosphorylated-FLNA can be readily determined from cancerous cell lines as is shown herein. A biopsied body sample from a living host animal can be used for a quantitative determination of an in vivo inhibition of cancer cell growth following usually utilized techniques.

A significantly decreased amount of one or more of those enumerated phosphorylated proteins is used as a surrogate for inhibition of cancer cell growth inasmuch as an enhanced amount of one or more of those phosphorylated proteins is an indicator of cellular growth.

Thus, the present invention contemplates a method of inhibiting the significantly enhanced amount of one or more of phosphorylated mTOR (as mTOR pS$^{2448}$), Akt1 (as Akt1-3 pS$^{473}$), ERK2 (as ERK2 pT$^{183}$/pY$^{185}$) and filamin A (FLNA) phosphorylated at serine2152 (pS$^{2152}$FLNA) in a cancerous cell. Three of those phosphorylated species are the active forms of the mTOR, Akt1 and ERK2 proteins (enzymes). The presence of each of those active enzyme forms correlates with higher growth and survival (Akt—reflects PI3k and mTOR) and oncogenic activity (ERK)—primary characteristic of the cancers. FLNA is a scaffold protein and is not "activated" by phosphorylation as are the enzymes, but phosphorylation at serine2152 changes a function of the protein that also associates with cancer cell growth. Thus, the presence in a cancerous cell of a significantly enhanced quantity of one or more of those proteins enhances cancerous growth, whereas inhibition of such a significantly enhanced quantity of one or more of those proteins; i.e., effecting an significant decrease in one or more of the four enumerated phosphorylated proteins, indicates an inhibition of cancerous cell growth (proliferation).

For pS2152-FLNA, a greater amount pS2152-FLNA indicates two (possibly more) functional consequences that favor the growth and survival of cancerous cells. First, an enhanced amount of pS2152-FLNA correlates with lower levels of FLNA-tethered PTEN and PP2A. Both PTEN and PP2A keep growth signals in check when associated with FLNA because they are then in the vicinity of their substrates in the membrane (they both are protein phosphatases). A contemplated method that is capable of reducing pS2152-FLNA leads to increased FLNA-linked PTEN and PP2A that help in reducing phosphorylated Akt, mTOR (by keeping PI3K in check) and ERK. Second, the increased amount of pS2152-FLNA may alter (increase or decrease) FLNA binding to partners and promote cancer metastasis.

Similarly to pS$^{2152}$FLNA, each of activated mTOR, activated Akt1 and activated ERK2 is phosphorylated at one or more particular residues in the protein sequence that is known to have a relation to enhancement of cancerous growth [cancer-related phosphorylated residue(s)]. For mTOR, the cancer-related phosphorylated residue is serine 2448 (mTOR pS$^{2448}$). For Akt1, the cancer-related phosphorylated residue is serine 473 (Akt1-3 pS$^{473}$). For ERK2, there are two cancer-related phosphorylated residues, threonine 183 and tyrosine 185 (ERK2 pT$^{183}$/pY$^{185}$) Normal (cancer-free) cells use these proteins (enzymes) to perform the same functions—growth and survival. The difference is that the activation of these enzymes in normal cells is driven and under strict control of growth/survival signals such as trophic factors, whereas in cancer cells these enzymes are "constitutively active" meaning that they are always active even without trophic factors.

In one preferred embodiment, the cancer cells are solid tumor cells. Those solid tumor cancer cells are one or more of sarcoma cells, carcinoma cells, and lymphoma cells that are exemplified by osteosarcoma cells, Kaposi's sarcoma cells, melanoma cells, glioblastoma cells, small cell lung carcinoma cells, breast cancer cells, neuroblastoma cells, pancreatic cancer cells, and Hodgkin's lymphoma cells. Preferably, the solid tumor cancer cells are one or more of melanoma cells, glioblastoma cells, small cell lung carcinoma cells, breast cancer cells and pancreatic cancer cells. A solid tumor cell is preferably of epithelial cell origin.

In another embodiment, the cancer cells are liquid or blood tumor cells such as leukemia cells like acute lymphoblastic, chronic lymphoblastic, acute myelogenous, chronic myelogenous and hairy cell leukemias that are contacted in vivo or in vitro as discussed above.

Together with the increased amounts of one or more of ERK2, Akt and mTOR in these diseases, an elevated pS$^{2152}$FLNA was often noted. Consequently, it is more preferred that a cancer cell that is contacted (treated) exhibit a "significantly greater amount" of pS$^{2152}$FLNA relative to a non-cancerous cell from the same tissue as the cancerous cell, as well as enhanced amount of one or more of phosphorylated mTOR (as mTOR pS$^{2448}$), Akt1 (as Akt1-3 pS$^{473}$), ERK2 (as ERK2 pT$^{183}$/pY$^{185}$).

As noted above, a non-cancerous cell typically exhibits a relatively small amount of pS$^{2152}$FLNA compared to a cancerous cell. That "relatively small amount" is about 20 to about 30 percent of the total amount of FLNA present in the cell. A preferred cancerous cell utilized in a contemplated cell growth inhibition method typically contains about 50 to about 60 percent pS$^{2152}$FLNA of the total amount of FLNA present in the cell. In an in vitro cell culture assay, cancer cells contacted in accordance with a contemplated method with an FLNA-binding effective amount of a compound or a pharmaceutically acceptable salt thereof that binds to the pentapeptide of FLNA of SEQ ID NO: 1 as discussed elsewhere herein, exhibit a significant lessening in the amount of pS$^{2152}$FLNA after being contacted with a FLNA-binding compound when assayed 4 days after the contacting (see, FIGS. 7A-8C).

The data provided herein show that contact with illustrative Compound C0105 and other FLNA-binding compounds normalize the originally elevated FLNA phosphorylation at serine$^{2152}$ (pS$^{2152}$FLNA) in cancer cell lines. Contacting cancer cells with a FLNA-binding compound such as Compound C0105 increases associations of the phosphatases PTEN and PPA2 with FLNA, which are reduced in cancer cell lines.

Functionally, FLNA-binding compound treatment (contacting) of melanoma, glioblastoma, neuroblastoma, small cell lung cancer, pancreatic cancer, prostate cancer and breast cancer cells greatly reduces their proliferation but has no effect on non-cancerous cells of similar origin such as primary fibroblasts, or astrocytes or pancreatic epithelial cells. Contact with a FLNA-binding compound such as illustrative Compound C0105 also reduces the typical glucose dependence of these cell lines and restores resistance to glucose deprivation.

Illustrative Compound C0105 robustly reduces the heightened active mTOR, Akt1 and ERK2 levels in those cancer cell lines examined, possibly as a result of keeping PTEN and PPA2 associated with FLNA.

A dysregulated PTEN/PI3K/Akt pathway, one of the primary cell growth/survival regulators, is a prominent feature in liquid tumors µMin et al., *Leukemia* 17:995-997 (2003); Chang et al., *Leukemia* 17:590-603 (2003); Steelman et al., *Leukemia* 22:686-707 (2008); and Lee Jr. et al., *Leukemia* 16: 486-507 (2002)]. That Compound C0105 robustly decreases activated (phosphorylated) Akt1 in cancer cells indicates that Compound C0105 and other FLNA-binding compounds can effectively suppress abnormal cell proliferation in liquid tumors. Aberrant activation of the Raf/MEK/ERK cascade that regulates cell growth and survival has been noted in the liquid tumors [Steelman et al., *Leukemia* 22:686-707 (2008); and Lee Jr. et al., *Leukemia* 16: 486-507 (2002)]. That activation indicates that illustrative Compound C0105's ability to normalize ERK activation is useful in the treatment of liquid tumors.

Robust increase in mTOR signaling has been shown in liquid tumors [Steelman et al., *Leukemia* 22:686-707 (2008); Teachey et al., *Br J Haematol* 145:569-580 (2009); Nemes et al., *PLOS ONE* 8:e59335 (2013); and Mark et al., *BMC Cancer* 13:250 (2013)]. Normalization of mTOR signaling by contact with illustrative Compound C0105 can be similarly used in the treatment of liquid tumors.

FLNA Binding Assay

Figure 18A:
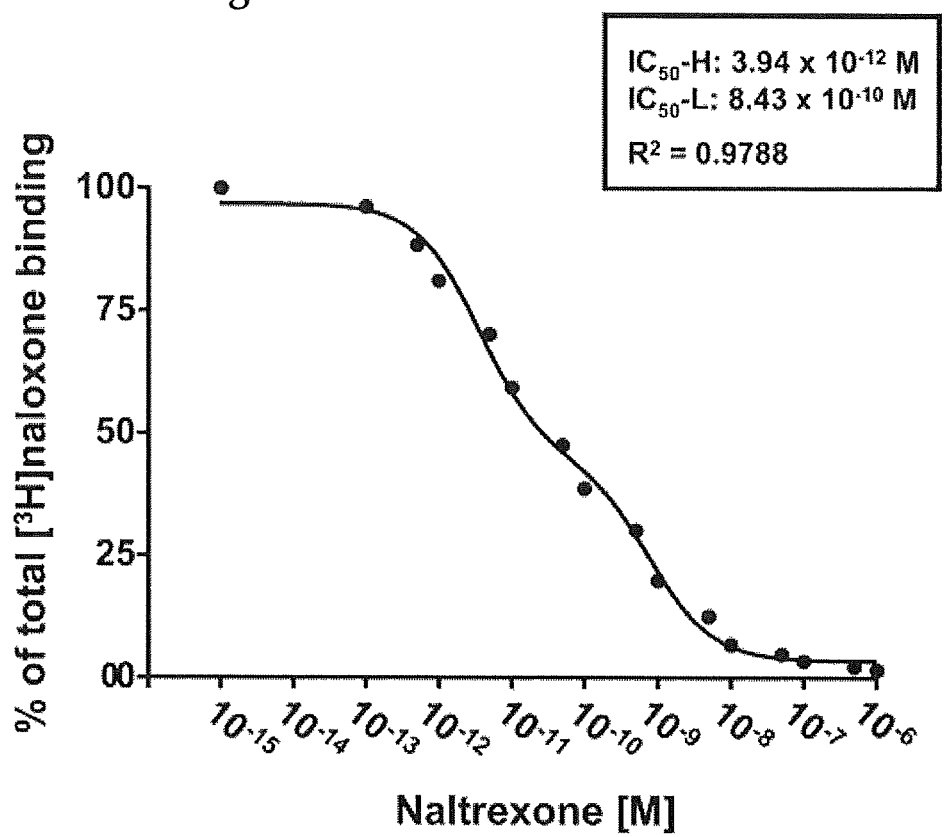
FIG. 18A through FIG. 18C illustrate that NLX (naloxone) binds FLNA with picomolar affinity.
Figure 18B:
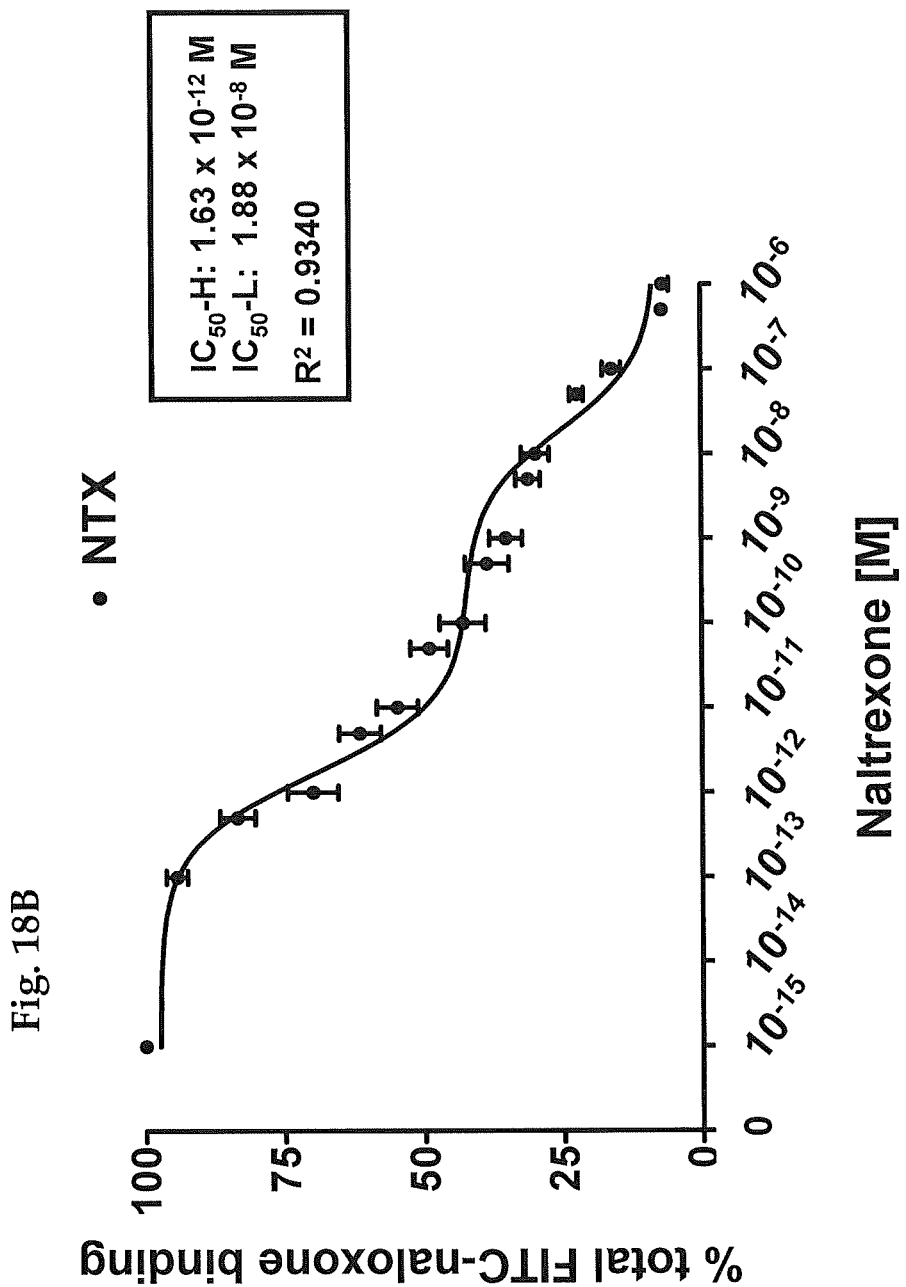
Figure 18C:
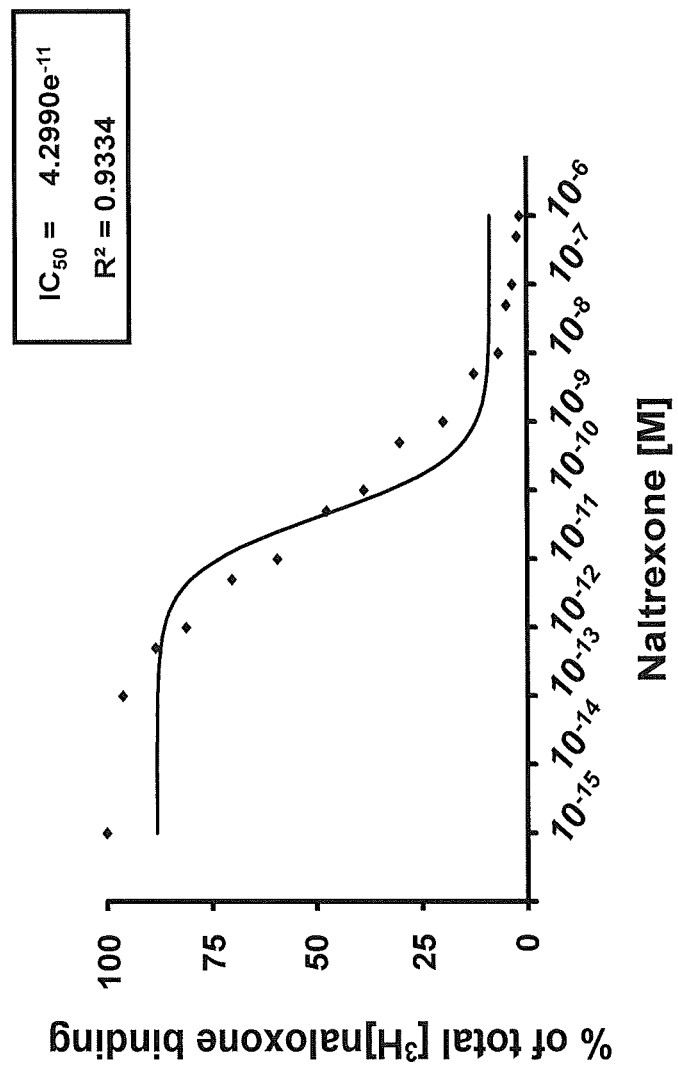
Figure 20:
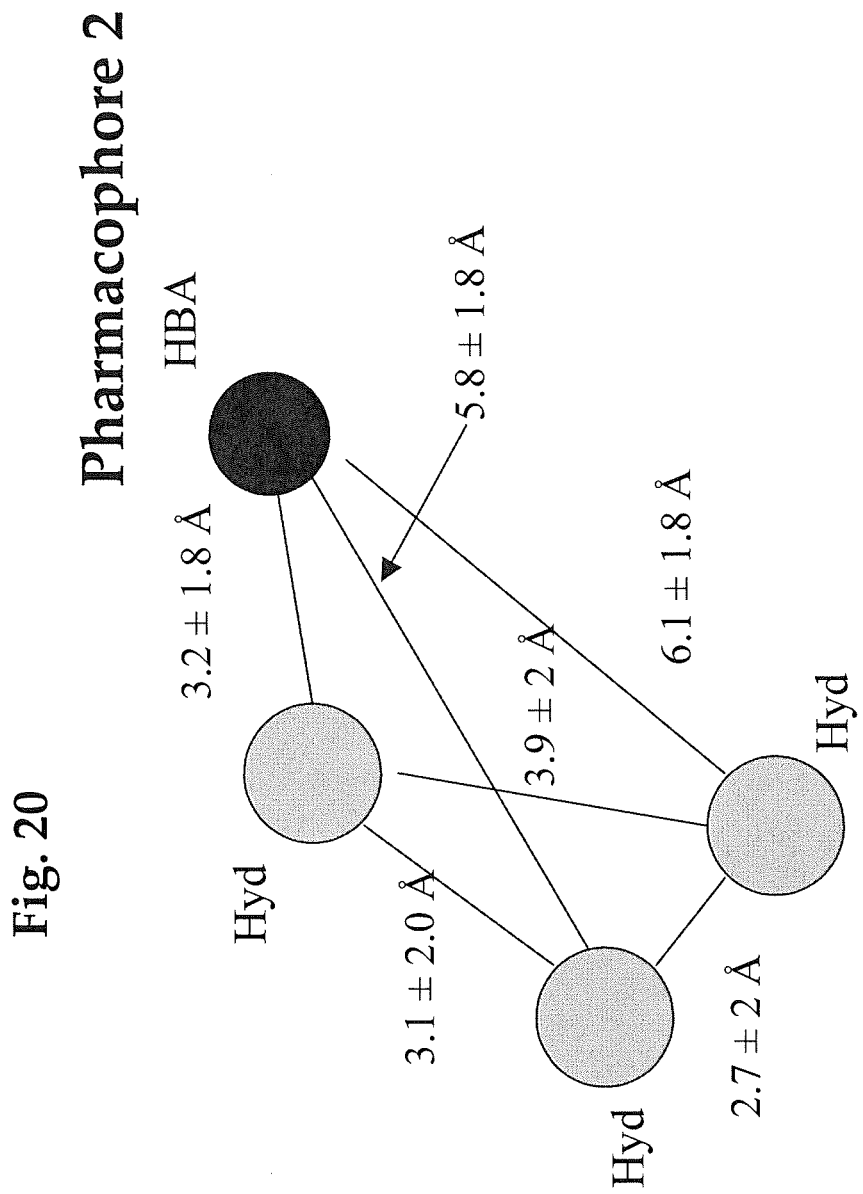
Figure 21:
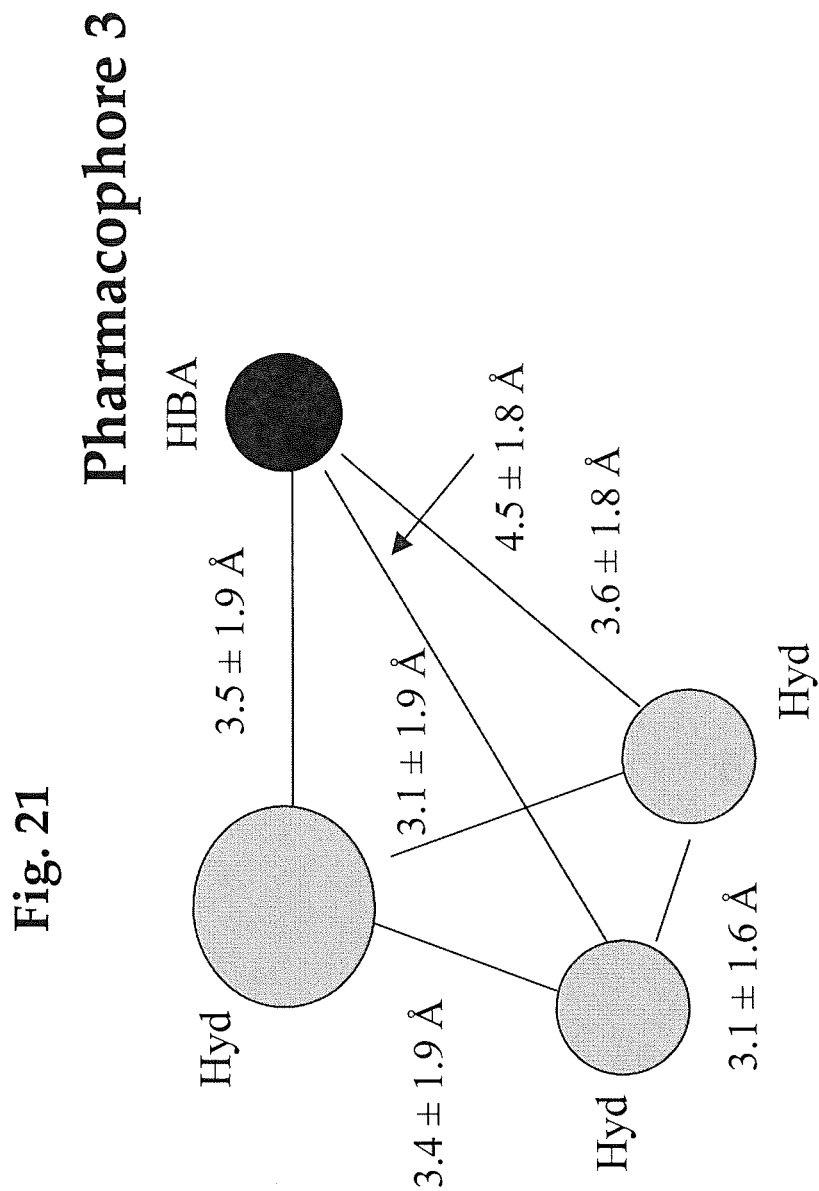
Figure 22:
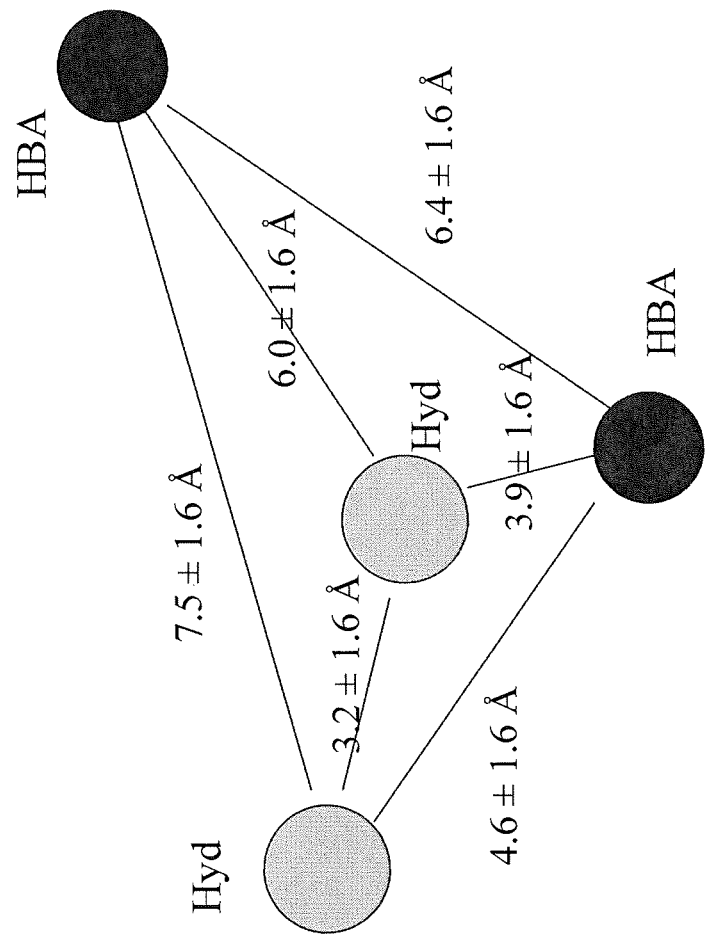
Figures 25A, 25B:
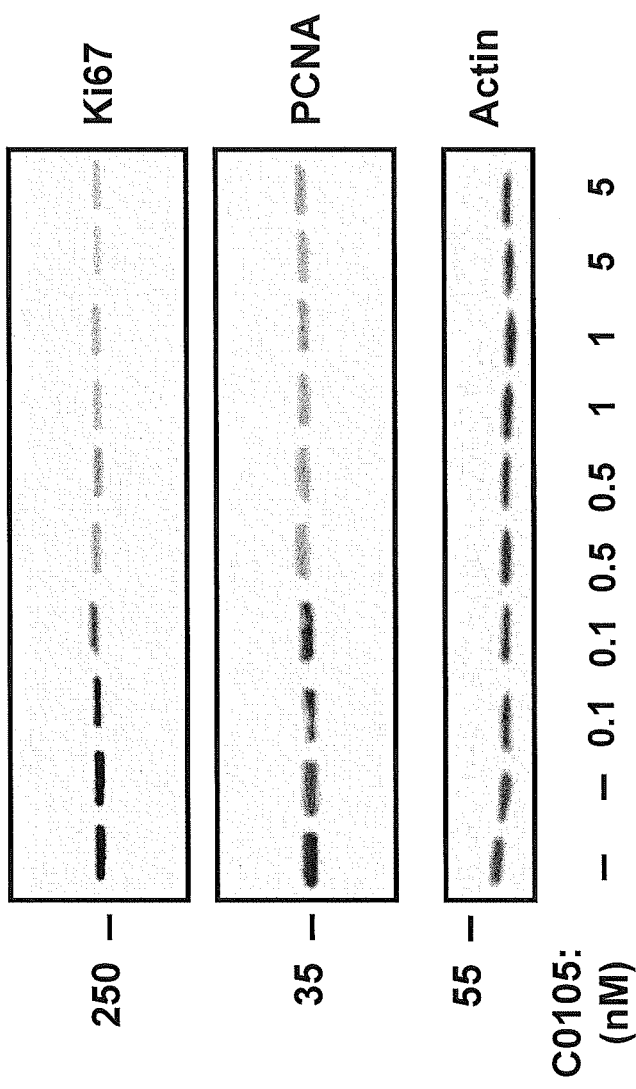
FIG. 25A through FIG. 25D illustrate that contact with Compound C0105 reduces cell proliferation in MiaPaCa2 cells but not in control human pancreatic epithelial cells (HPECs). The effect of contact with Compound C0105 on cell proliferation was determined by the levels of cell-cycling markers Ki67 and PCNA using Western blots. Cells treated with vehicle and 0.1-5 nM C0105 for 4 days were collected, washed and solubilized (lysed). The resultant cell lysates were size-fractionated on SDS-PAGE and Western blotting to determine the levels of Ki67, PCNA and actin (loading control). The protein bands were quantified using densitometric scanning.
Figure 25C:
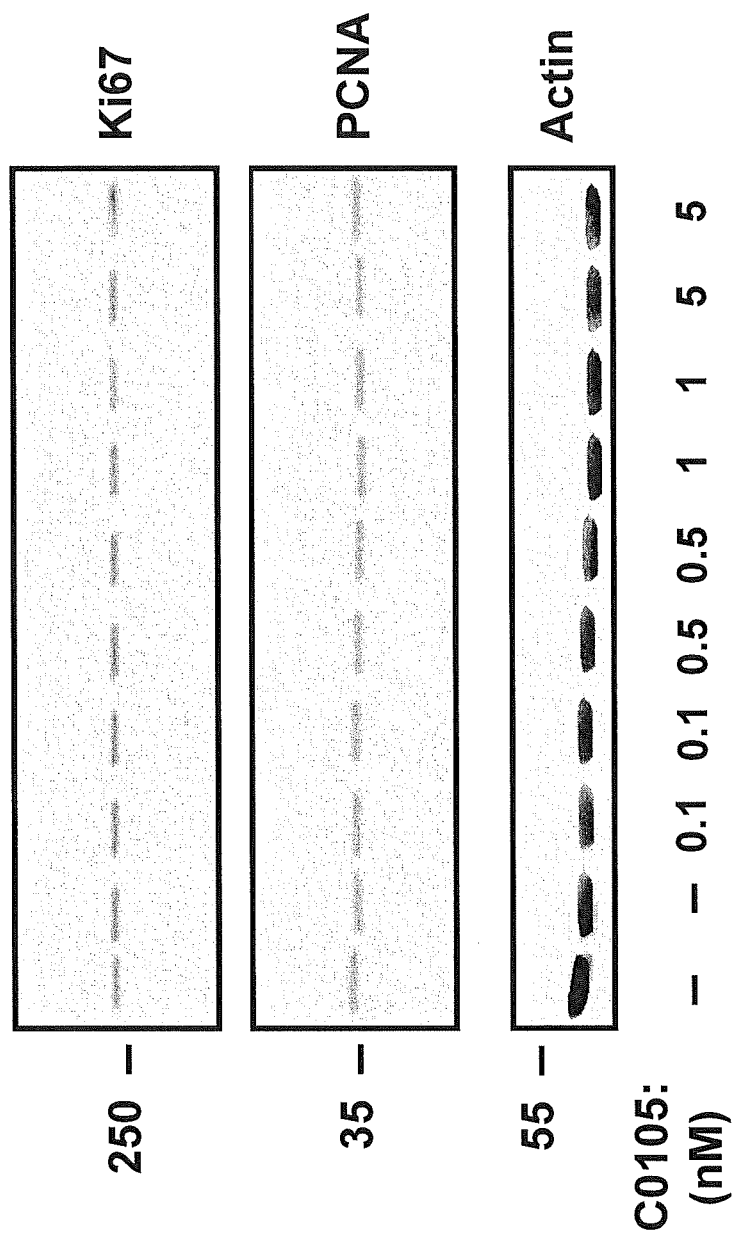
Figure 25D:
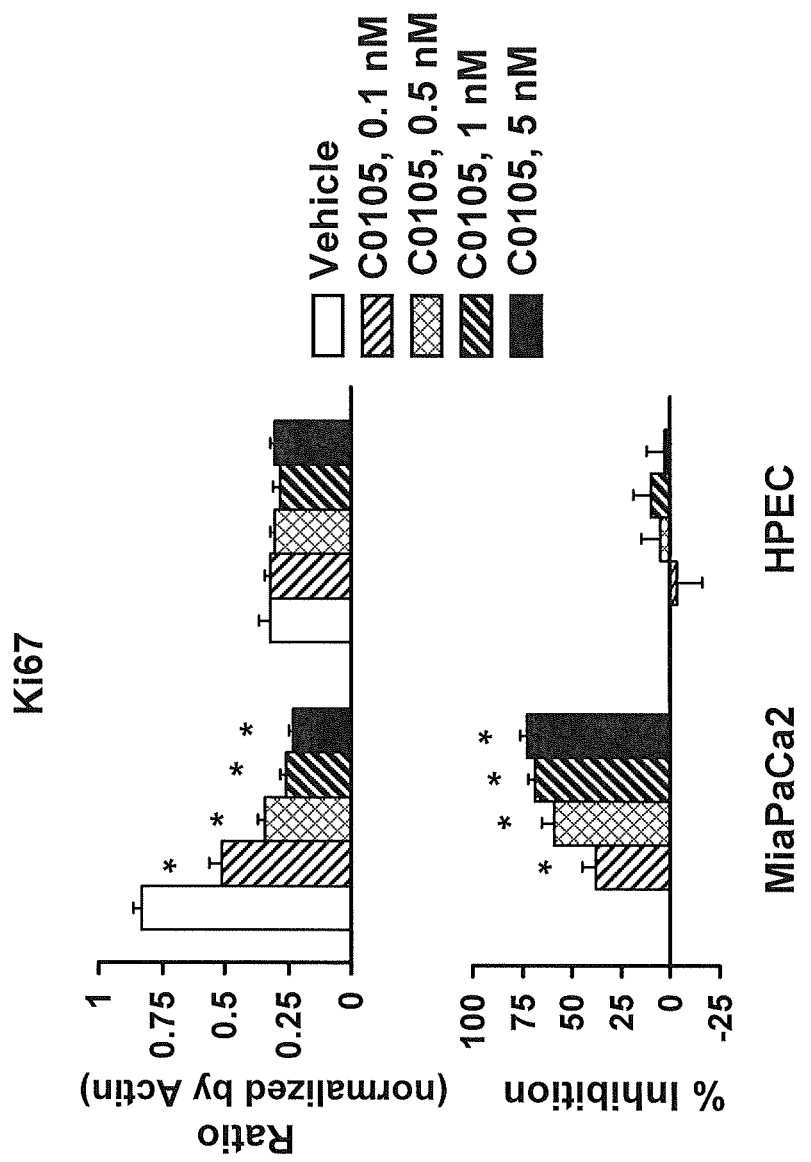

A contemplated FLNA-binding compound binds to the scaffolding FLNA protein (FIGS. 18A and 18B), and particularly to a five residue portion of the FLNA protein sequence—Val-Ala-Lys-Gly-Leu (SEQ ID NO: 1) (FIG. 18C)—in an in vitro assay that is discussed hereinafter in Example 1, and briefly below. A contemplated FLNA-binding compound binds only to a single site on FLNA and that site contains the amino acid residue sequence of the SEQ ID NO: 1 pentapeptide.

Studies of the naltrexone inhibition of tritiated-naloxone, [$^3$H]NLX, binding to membranes from FLNA-expressing A7 cells has shown the existence of two affinity sites on FLNA; a high affinity site (H) with an $IC_{50}$—H of 3.94 picomolar and a lower affinity site (L) $IC_{50}$-L of 834 picomolar. [Wang et al., *PLoS One* 3(2):e1554 (2008); Wang et al., *PLoS One.* 4(1):e4282 (2009).] The high affinity site was subsequently identified as the FLNA pentapeptide of SEQ ID NO: 1 (U.S. Pat. No. 8,722,851 and its predecessor application Ser. No. 60/985,086 that was filed on Nov. 2, 2007), whereas the lower affinity site has not yet been identified.

A FLNA-binding compound contemplated for use in the present invention inhibits the binding of fluorescein isothiocyanate-labeled naloxone (FITC-NLX) or tritiated-naloxone ([H$^3$]NLX) to biotin-linked SEQ ID NO: 1 (Bn-VAKGL) bound to coated streptavidin plates under conditions described hereinafter in Example 1 to an extent that is at least about 60 percent and more preferably at least about 70 percent of the value obtained of the value obtained when present at a 10 µM concentration and using naloxone as the control inhibitor at the same concentration as the contemplated FLNA-binding compound, and up to about twice the value obtained with naloxone as control.

Naltrexone (NTX) can also be used as a control inhibitor. Average inhibition values obtained using NTX rather than NLX tend to be 1 or 2 percentage digits lower in absolute value than those with NLX. Thus, for example, where an average inhibition value at a particular concentration of NLX is 40 percent, one can expect values obtained with NTX to be about 38 or 39 percent. The binding inhibition values for a contemplated FLNA-binding benzazocine-ring compound are determined taking the expected NLX/NTX value difference into account.

Pharmacophore Determinations

One aspect of the invention is the use of a compound that binds to the pentapeptide of SEQ ID NO: 1 that is present in FLNA to inhibit formation of an assayed complex as a control. In this aspect, the structure of a compound that effectively binds to a pentapeptide of SEQ ID NO: 1 is quite varied but can be unified through the calculation of a group of pharmacophores shared by those compounds that so bind.

A contemplated compound useful in this aspect of a method of the invention preferably contains at least four of the six pharmacophores of FIGS. 19-24. In more preferred practice, a contemplated compound contains five of the six pharmacophores of those figures, and more preferably still, a contemplated compound contains all six of the pharmacophores.

An ensemble pharmacophore model was prepared using the three-dimensional conformations of compounds in the training sets. Using 0.1 µM data from Example 1 as a starting point, 153 compounds out of the list of compounds in the tables of Example 1 have a binding activity to the FLNA pentapeptide that is less than the mean value of 45.54 percent. A "poor binding" compound or "poor binder" is defined as a compound whose binding inhibition is equal to or less than the mean value of 45.54 percent in an assay as conducted in Example 1, whose results are shown in the tables of Example 1. The training set consists of ten compounds known to bind to the FLNA pentapeptide, the above poor binding 153 compounds and also about 1000 random compounds selected from ZINC database at zinc.docking.org.

The selection of pharmacophores involves in the following steps: 1) Three-dimensional conformations of all compounds were first prepared. 2) A set of 4-point pharmacophores present in most of known active compounds was derived. 3) Using known inactive and random selected compounds as reference compounds, only those pharmacophores that were not present in the most of the reference compounds were identified as relevant to FLNA binding activity. 4) Six 4-point pharmacophores were finally identified from those determined above to best represent the 10 active compounds.

An untested compound not having a structure of one of the compound structural formulas shown hereinafter, that contains four out of the six pharmacophores has about a 20 percent chance to be an active binder in FLNA pentapeptide. A compound containing five of the six pharmacophores has about a 32 percent chance to be an active binder in FLNA pentapeptide, and about a 60 percent chance when containing six of the six pharmacophores.

A computer running the Molecular Operating Environment (MOE) software from Chemical Computing Group, Montreal, Quebec, Canada, was used to generate three-dimensional conformations, to derive 4-point pharmacophores from active compounds, and to test these pharmacophores against known inactive compounds and random selected compounds. Pharmacophore modeling as used herein is carried out as discussed and explained in Penzotti et al., *J. Med. Chem.*, 2002, 45(9):1737-1740 (2002); Siew et al., *Bioorganic & Medicinal Chemistry Letters*, 21(10): 2898-2905 (15 May 2011); Leong, *Chem. Res. Toxicol.*, 20(2):217-226 (2007); and Lin, chemcomp.com/journal/ph4.htm, and the citations therein.

The ten known FLNA pentapeptide-binding training set compounds are shown below along with their alpha-numeric designations used herein. Of the

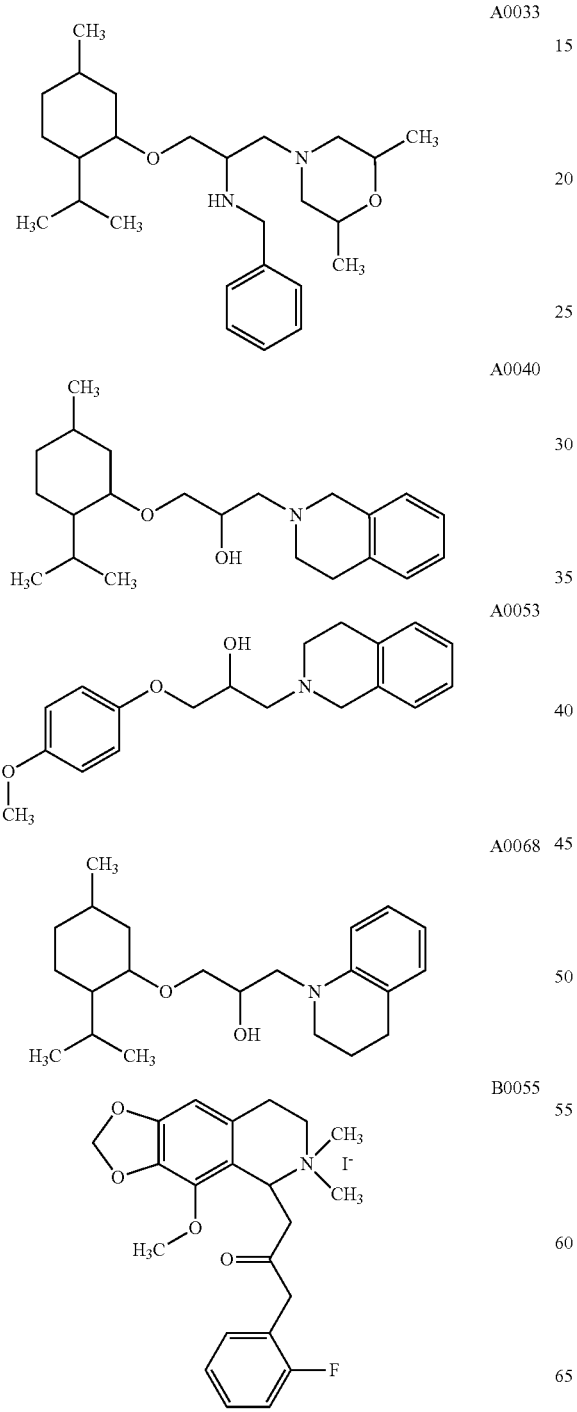

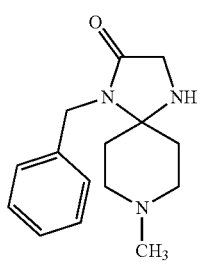

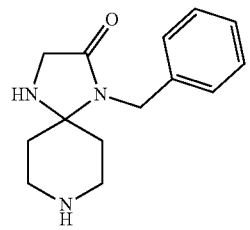

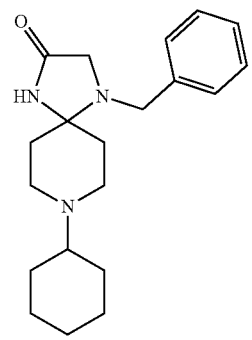

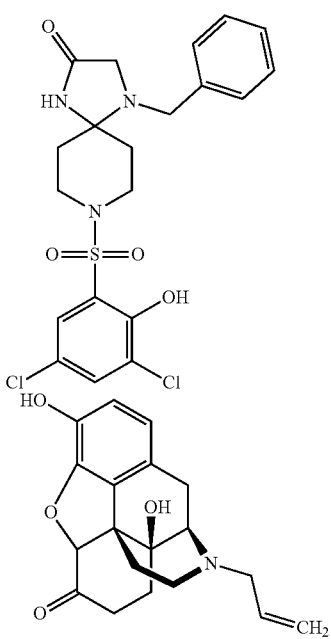

above ten compounds used in the training set for determining the pharmacophores, nine contained all six pharmacophores. Naloxone, a benzazocine-ring compound, contained five of the six. Examining several more of the structures of the four groups of compounds (Series A, Series B, Series C-1 and Series C-2) shown in the tables and assayed in Example 1 hereinafter, twenty further compounds contained five of the six pharmacophores, and another twenty contained four of the six.

Specific Contemplated FLNA-Binding Compounds

A FLNA-binding compound contemplated for use in a contemplated method can have a varied structure as noted before. Regardless of that structural variance, a contemplated FLNA-binding compound binds to filamin A or binds to a biotin-linked pentapeptide of filamin A (FLNA) of SEQ ID NO: 1 (Bn-VAKGL) bound to coated streptavidin plates as described in Example 1, and inhibits at least about 60 percent, and more preferably about 70 percent, of the fluorescein isothiocyanate-labeled naloxone (FITC-NLX) binding to FLNA or to that FLNA pentapeptide of SEQ ID NO: 1 when present at a 10 µM concentration and using unlabeled naloxone as the control inhibitor at the same concentration. A preferred contemplated compound can bind to the FLNA pentapeptide of SEQ ID NO: 1 at a 100 femtomolar concentration, as well as at picomolar to micromolar concentrations.

Particularly preferred compounds not only bind to FLNA as discussed above, but furthermore bind poorly if at all to receptors. Those compounds that bind to one or more receptors are preferably antagonists rather than agonists. Thus, for example, illustrative Compounds A0049, C0027, C0105 and C0139 were assayed for binding to more than 65 receptors in a standard binding assay. At a 10 µM concentration, Compounds C0105 and C0139 exhibited no significant binding to any of the assayed receptors, whereas compound A0049 was an antagonist for the sigma $\sigma_1$ receptor and Compound C0027 was an antagonist for both the sigma $\sigma_1$ and adrenergic $\alpha_1$ receptors.

Compounds having five exemplary structures have been found to bind well to the pentapeptide of SEQ ID NO: 1. Those compounds are referred to herein as Series A, Series B, Series C-1, Series C-2, Series D, Series E and a benzazocine-ring compound. Inhibition of cancer cell growth by Compounds A, B and C and Series D are illustrated herein and those compounds are representative of those structural series. Compounds of Series E overlap with those of Series C-1 and -2 and are therefore also included herein. The general structures of the compounds of each series are shown below, followed by more specific disclosures. A 2,6-methano-3-benzazocine ring structure present in a benzazocine-ring compound is shown below as a secondary amine without substituents.

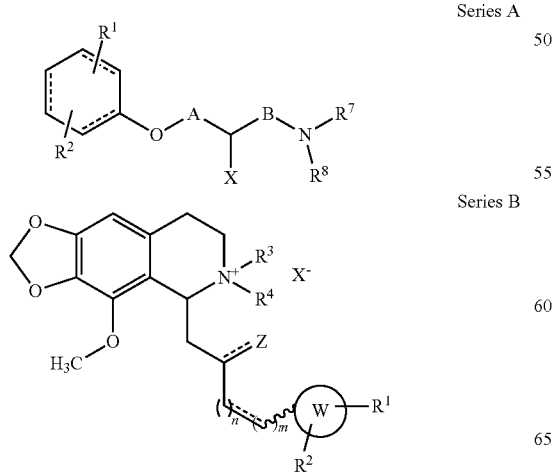

Series A

Series B

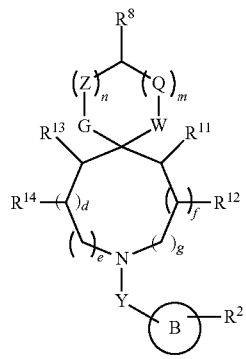

Series C-1

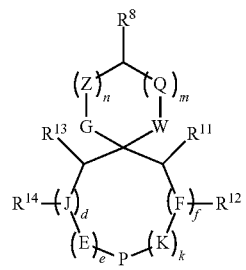

Series C-2

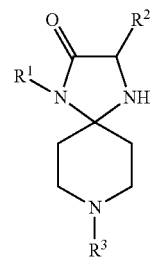

Series D

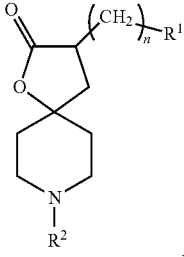

Series E

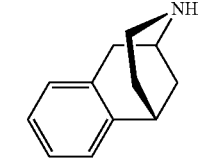

2,6-methano-3-benzazocine ring structure

A pharmaceutically acceptable salt of a compound of each of the above Formulas is also contemplated. A compound having an asymmetrical (chiral) carbon or a salt of such a compound can exist in the form of stereoisomers that are two enantiomers. The invention relates both to each enantiomer separately, and to their mixture; i.e., to both enantiomeric forms (d and l, or R and S) and to their mixture. Additionally, where two or more chiral centers are present, stereoisomers called diastereomers can form, and diastereomers are also contemplated.

As will be seen from the following definitions, a contemplated compound can contain one or more deuterated carbon atoms, in which deuterium is designated by its usual chemical designation, D. Deuterated compounds can be useful in studying the mechanism of drug interactions with living organisms for the elucidation of metabolic and biosynthetic pathways. Deuteration can also extend the half-life of a contemplated compound in vivo because a carbon-deuterium (C-D) bond is stronger than a Carbon-hydrogen (C—H) bond thereby requiring more energy input for bond cleavage. See, Blake et al., 1975 *J. Pharm. Sci.* 64(3):367-391; and Nelson et al., 2003 *Drug Metab. Dispos.* 31(12): 1481-1498, and the citations therein. Contemplated deuterated compounds are prepared using well-known reactions.

Benzazocine-Ring Compounds

A benzazocine ring compound contains 6-membered phenyl ring fused to an 8-membered azocine ring that contains seven carbon atoms and one nitrogen atom in the 8-membered ring. Structural formulas for the 3-, 4- and 5-benzazocines are shown below.

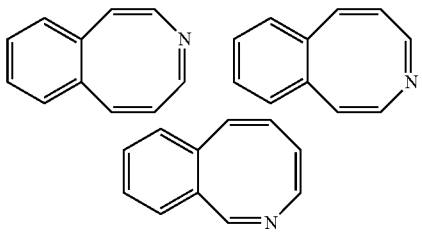

Saturated and partially saturated azocine rings form the core structure of a group of opioid compounds. A contemplated benzazocine-ring compound preferably contains at least a 2,6-methano-3-benzazocine ring structure whose azocine ring is at least partially saturated (shown before) and is typically a) an opioid receptor antagonist, b) a mixed opioid receptor agonist/antagonist compound, c) an opioid receptor agonist compound or d) an enantiomer of an opioid receptor interacting compound.

A contemplated FLNA-binding benzazocine-ring compound binds to a FLNA pentapeptide of SEQ ID NO: 1 as described in Example 1, and preferably contains four, five or six of the pharmacophores of FIGS. 19-24, and is preferably a reversible antagonist at an opioid receptor.

One group of preferred FLNA-binding benzazocine-ring compounds is a morphinan or 4,5-epoxymorphinan ring compound. Morphinan ring compounds are analogs of morphine. The structural formulas of morphine and typical morphinan and 4,5-epoxymorphinan ring compounds are shown below, where $R^1$ and $R^2$ are substituent groups.

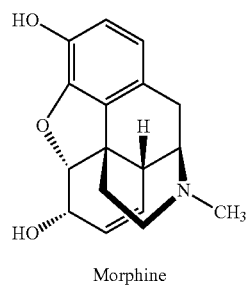

Morphine

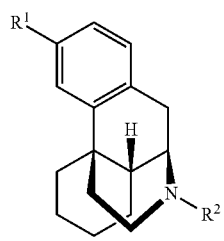

Morphinan

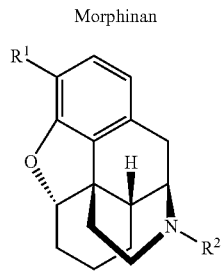

4,5-Epoxy-Morphinan

Preferably, the opioid receptor antagonized is at least the mu opioid receptor (MOR). Many of the morphinan or 4,5-epoxymorphinan ring compounds are analgesics that bind to the mu opioid receptor (MOR). The table below lists several benzazocine-ring compounds, the opioid receptor that they antagonize, and the relative potency of the antagonism or agonism as reported in *Goodman & Gilman's The Pharmaceutical Basis of Therapeutics*, 12th ed., Brunton ed., McGraw-Hill Medical Publishing Division, New York, Table 18-1-3, pages 483-484 (2011). A morphinan or 4,5-epoxymorphinan ring compound is particularly preferred for use in a contemplated method. Of this group of particularly preferred compounds, a morphinan and 4,5-epoxymorphinan ring compound that is an opioid receptor antagonist is usually more particularly preferred.

| | OPIOID RECEPTOR* | | |
|---|---|---|---|
| OPIOID LIGAND | MU | DELTA | KAPPA |
| Naloxone | --- | - | -- |
| Naltrexone | --- | - | --- |
| Diprenorphine | --- | -- | --- |
| Naloxonazine | --- | - | - |
| nor-Binaltrophimine | - | - | --- |
| Binaltrophimine# | | | - |
| Naltrindole | - | --- | - |
| Naloxone benzoylhydrazone | --- | - | - |
| Nalbuphine | -- | NR | ++ |
| Buprenorphine | P | NR | -- |
| Butorphanol | P | NR | +++ |
| Ethyl Ketocyclazcine | P | + | +++ |
| Nalorphine | --- | NR | + |
| Cyprodime# | - | | |

*"-" = antagonist; "+" = agonist; "NR" = not reported in the published table; P = partial agonist; The number of symbols in an indication of relative potency; "#" = not reported in the published table, but reported to have specific antagonist activities.

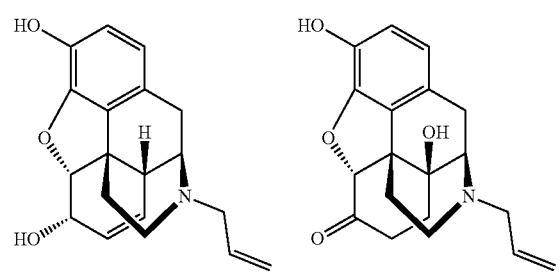
Nalorphine
Naloxone
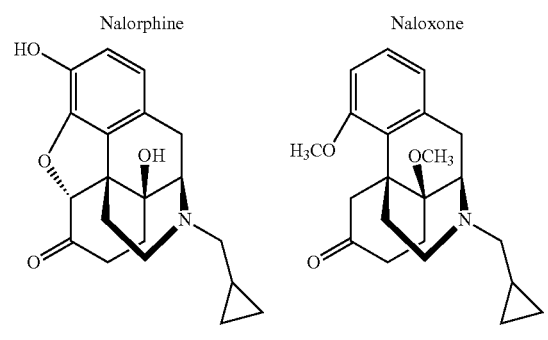
Naltrexone
Cyprodime
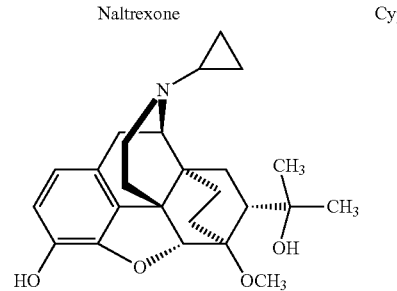
Diprenorphine
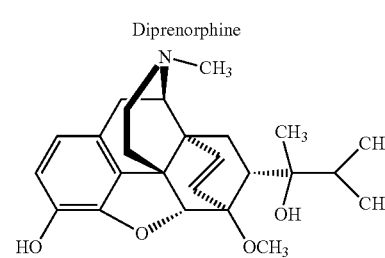
Etorphine
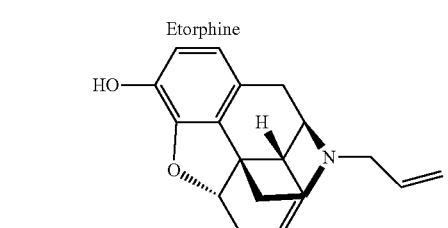
Naloxnazine
-continued
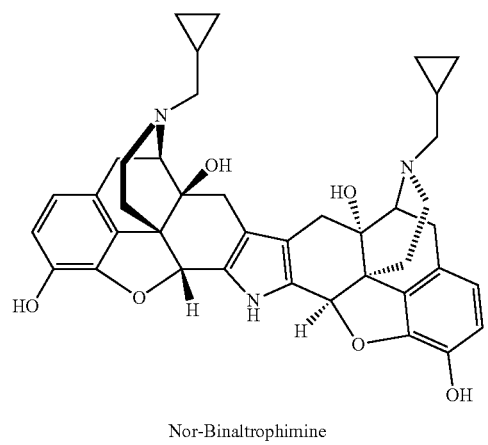
Nor-Binaltrophimine
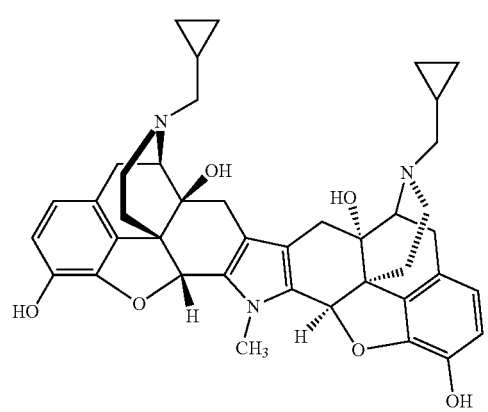
Binaltrophimine
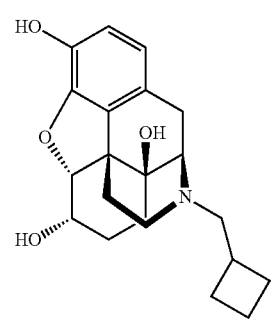
Nalbuphine
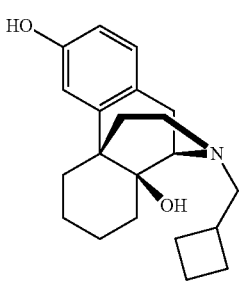
Butorphanol
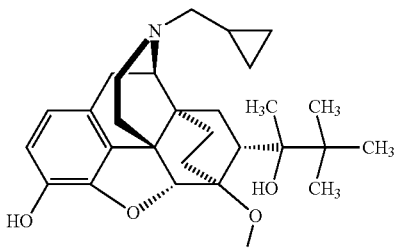
Buprenorphine

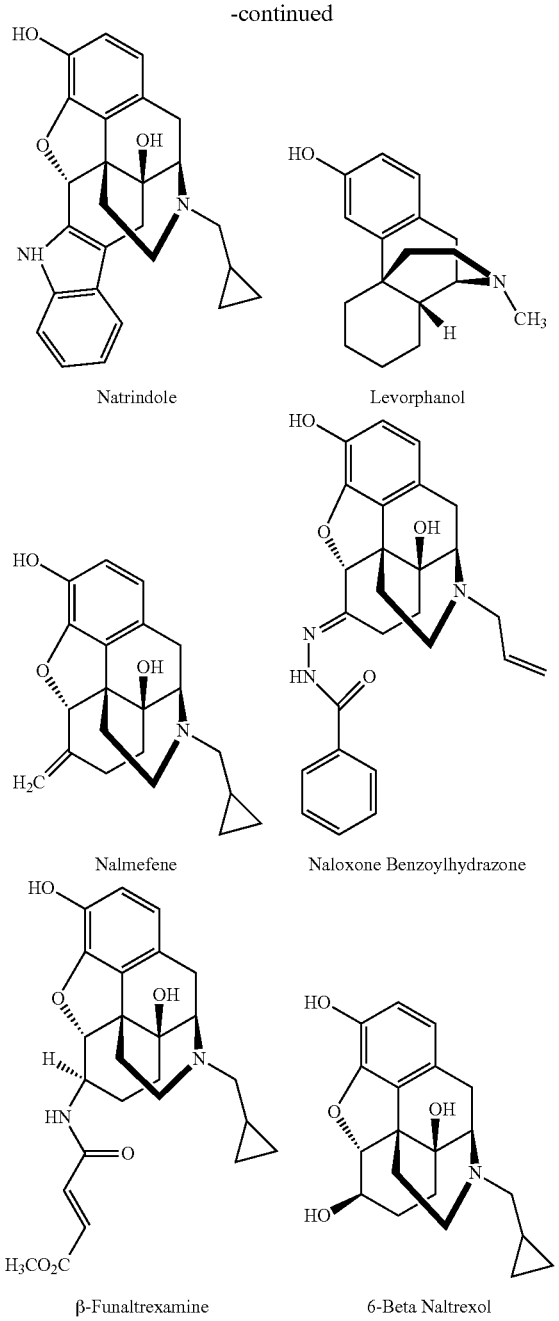

Natrindole  
Levorphanol  
Nalmefene  
Naloxone Benzoylhydrazone  
β-Funaltrexamine  
6-Beta Naltrexol Many morphinan and 4,5-epoxymorphinan ring compounds such as naloxone (NLX), naltrexone (NTX), nalorphine, nalbuphine and buprenorphine are commercially available products and bind well to the high affinity FLNA pentapeptide of SEQ ID NO: 1 (VAKGL). However, when used at a dosage recited on the product labels, those compounds also bind to the lower affinity site on FLNA, and typically also bind to MOR. Some of the compounds are MOR antagonists such as naloxone, naltrexone, nalbuphine, whereas others such as buprenorphine and etorphine are full or partial agonists of MOR.

Binding to that lower affinity FLNA site impairs the activity of the FLNA protein to exhibit its activities as discussed, utilized and illustrated herein. As a consequence, a FLNA-binding benzazocine-ring compound such as nalox- one, naltrexone, nalorphine, nalbuphine, buprenorphine and similar compounds that also bind to the lower affinity site on the FLNA protein are utilized in an amount that is about $1000^{th}$ to about $1,000,000^{th}$ less than that amount normally used or suggested for use, and more preferably at a level that is about $10,000^{th}$ to about $100,000^{th}$ the minimal dosage listed on the product labels, as noted previously.

Figure 28:
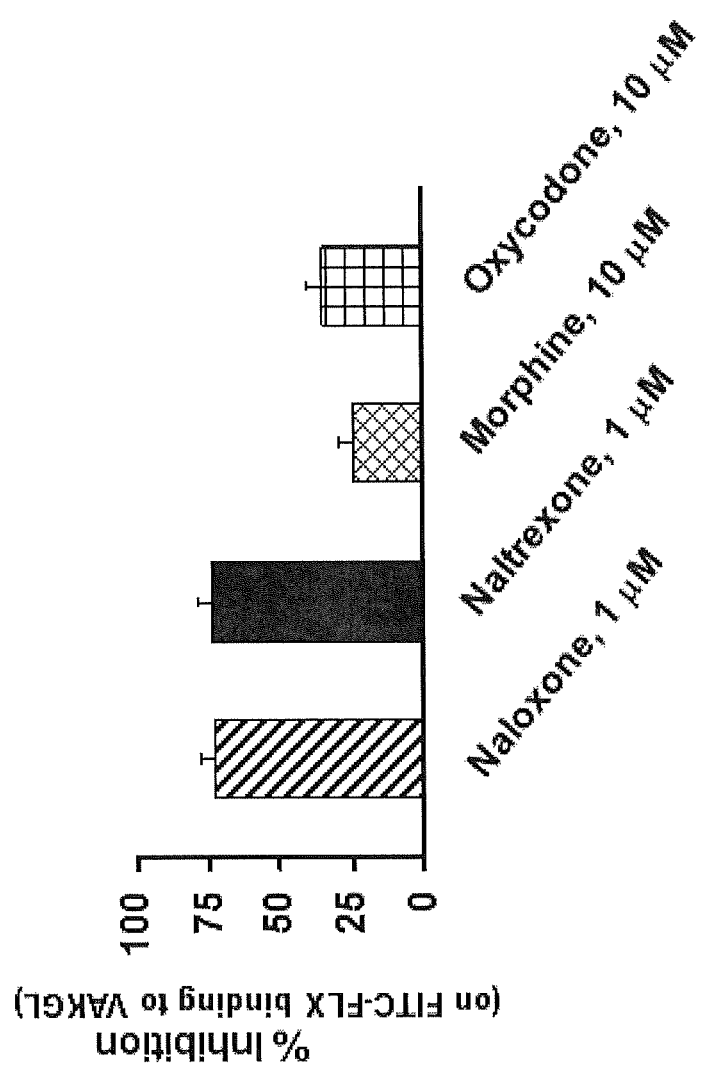
FIG. 28 is a graph that compares the inhibition of 10 nM FITC-conjugated NLX binding to the biotinylated FLNA pentapeptide of SEQ ID NO: 1 using NLX, NTX, morphine and oxycodone at the indicated concentrations.
Figure 29A:
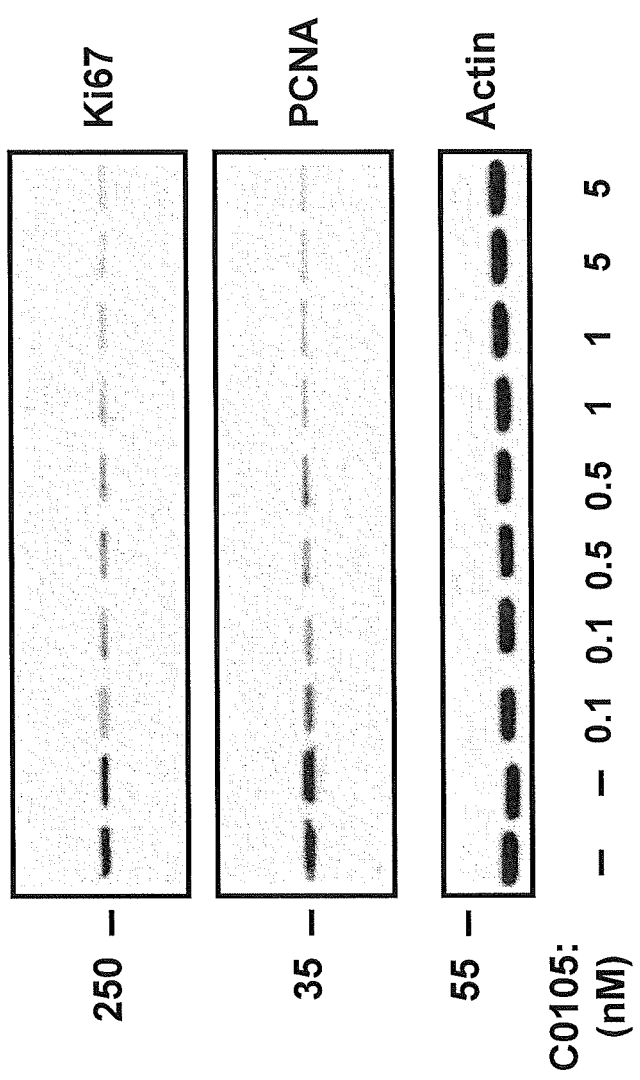
FIG. 29A through 29F illustrate that contact with Compound C0105 reduces cell proliferation in breast cancer HTB-22 cells but had no effect in primary human mammary epithelial cells (HMECs). The effect of C0105 on cell proliferation was determined by the levels of cell-cycling markers Ki67 and PCNA using Western blots in HTB-22 and control HMECs. Cells contacted with vehicle and 0.1-5 nM Compound C0105 for 4 days were collected, washed and solubilized. The resultant cell lysates were size-fractionated on SDS-PAGE and Western blotting to determine the levels of Ki67, PCNA and actin (loading control). The protein bands were quantified using densitometric scanning.
Figure 29B:
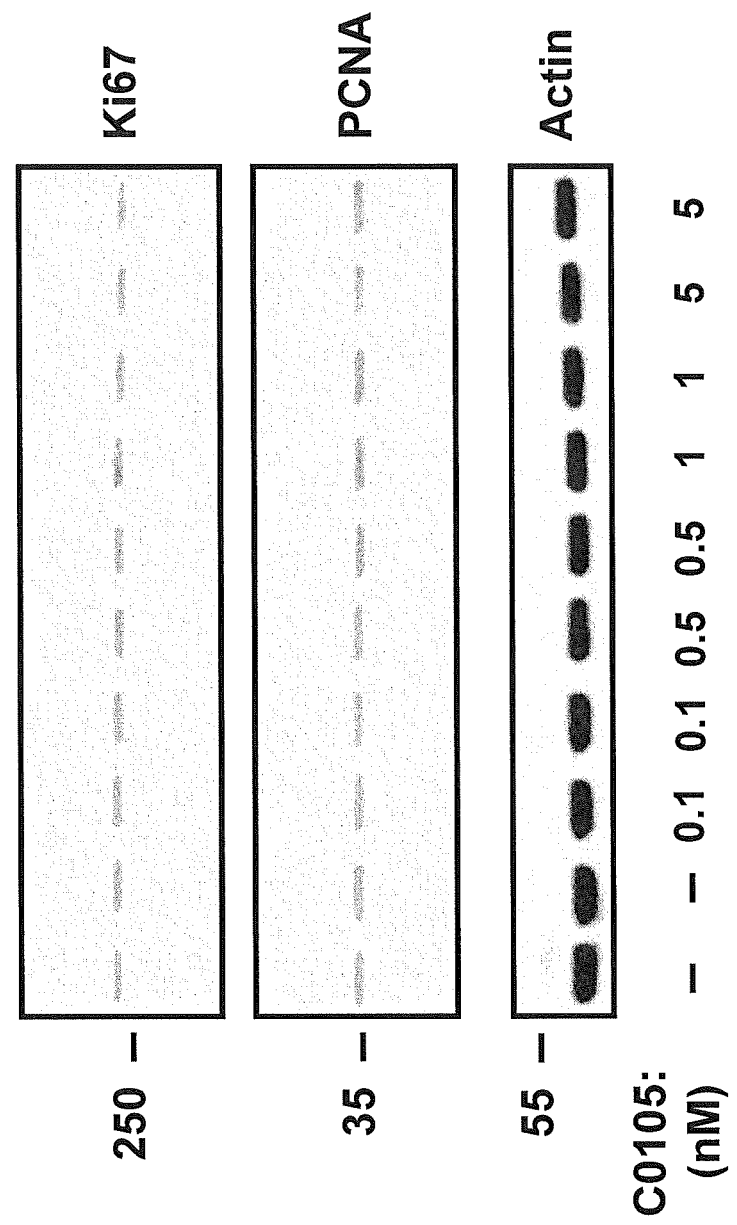
Figures 29C, 29D:
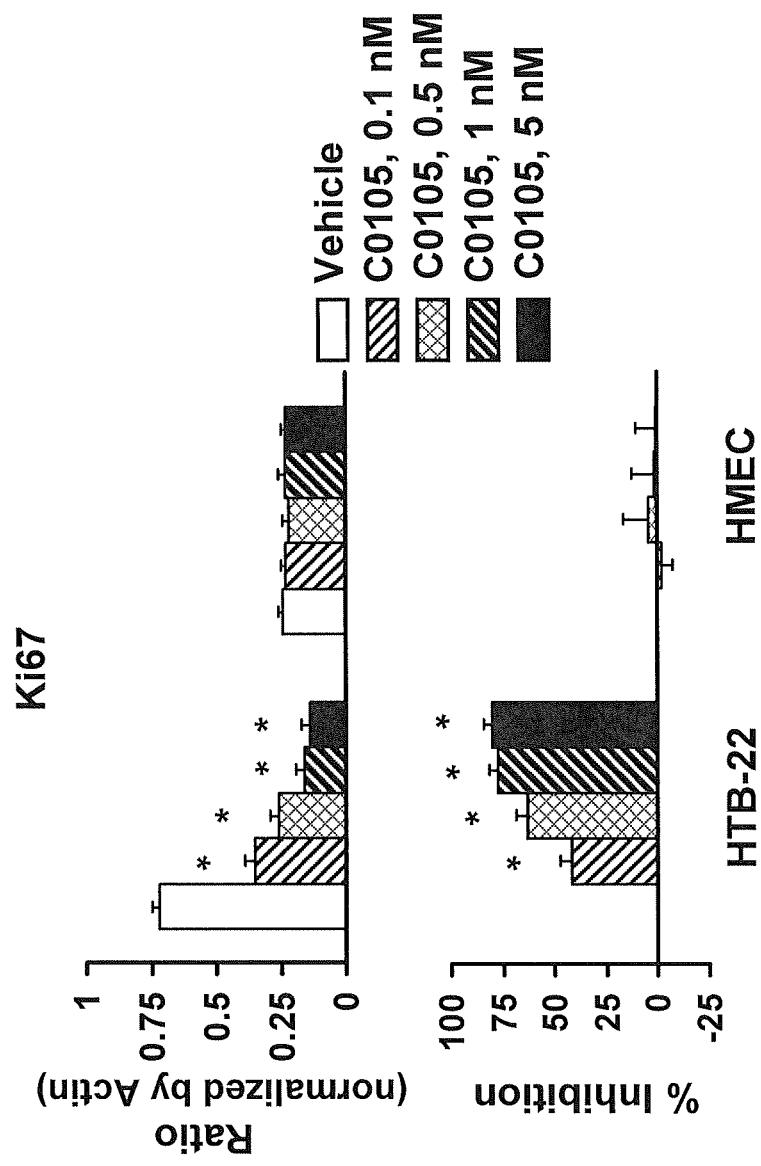
Figures 29E, 29F:
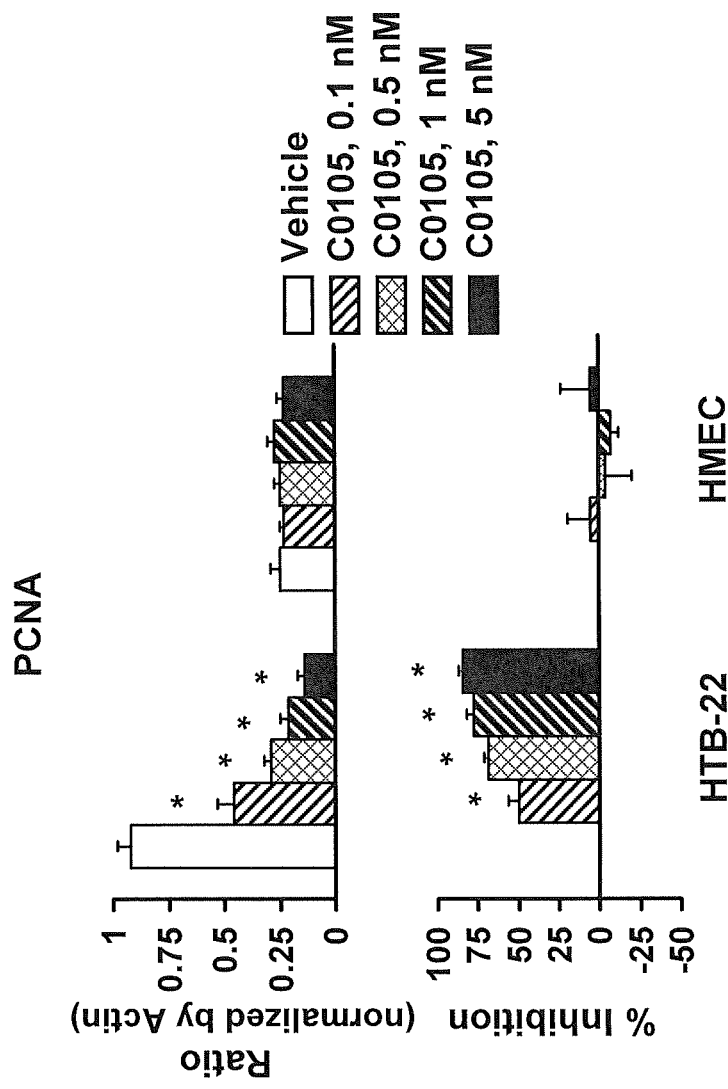
Figures 30C, 30D:
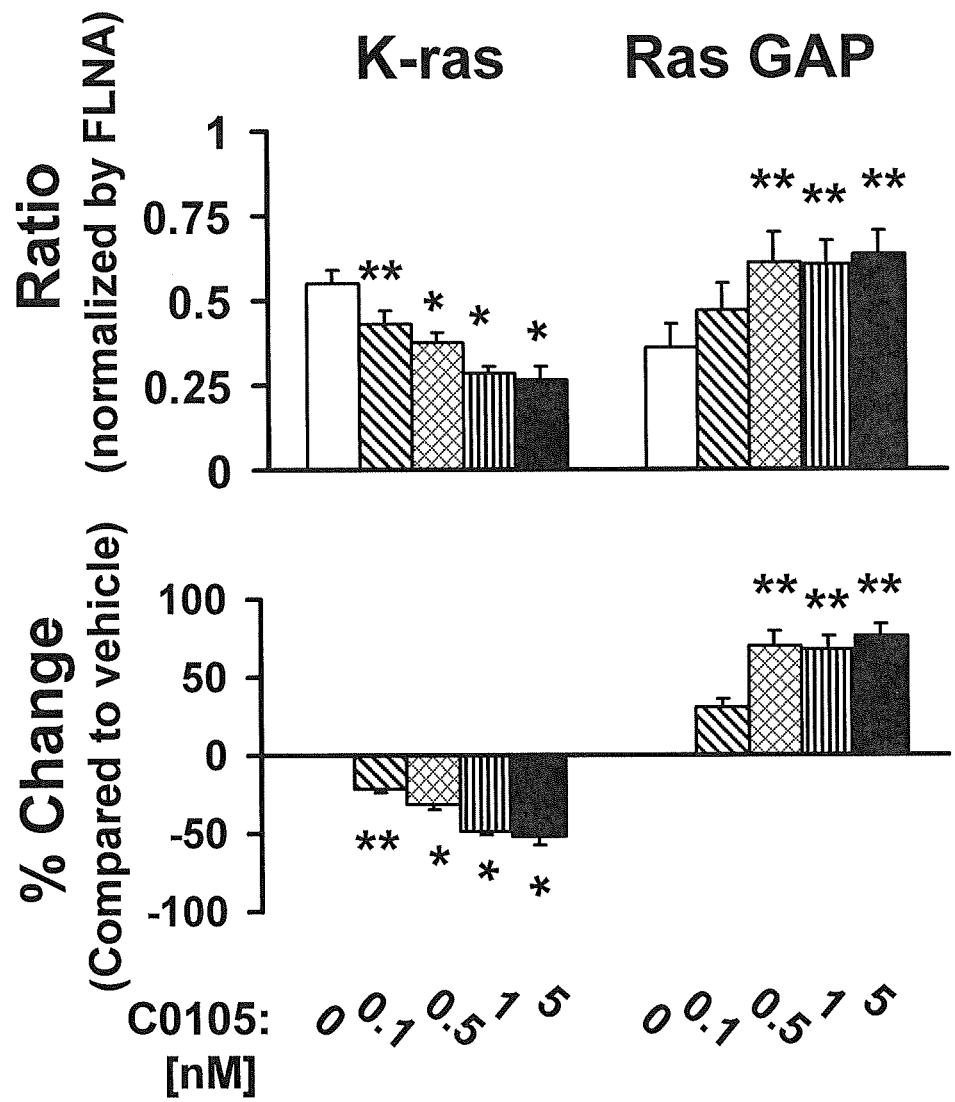
Figures 30E, 30F:
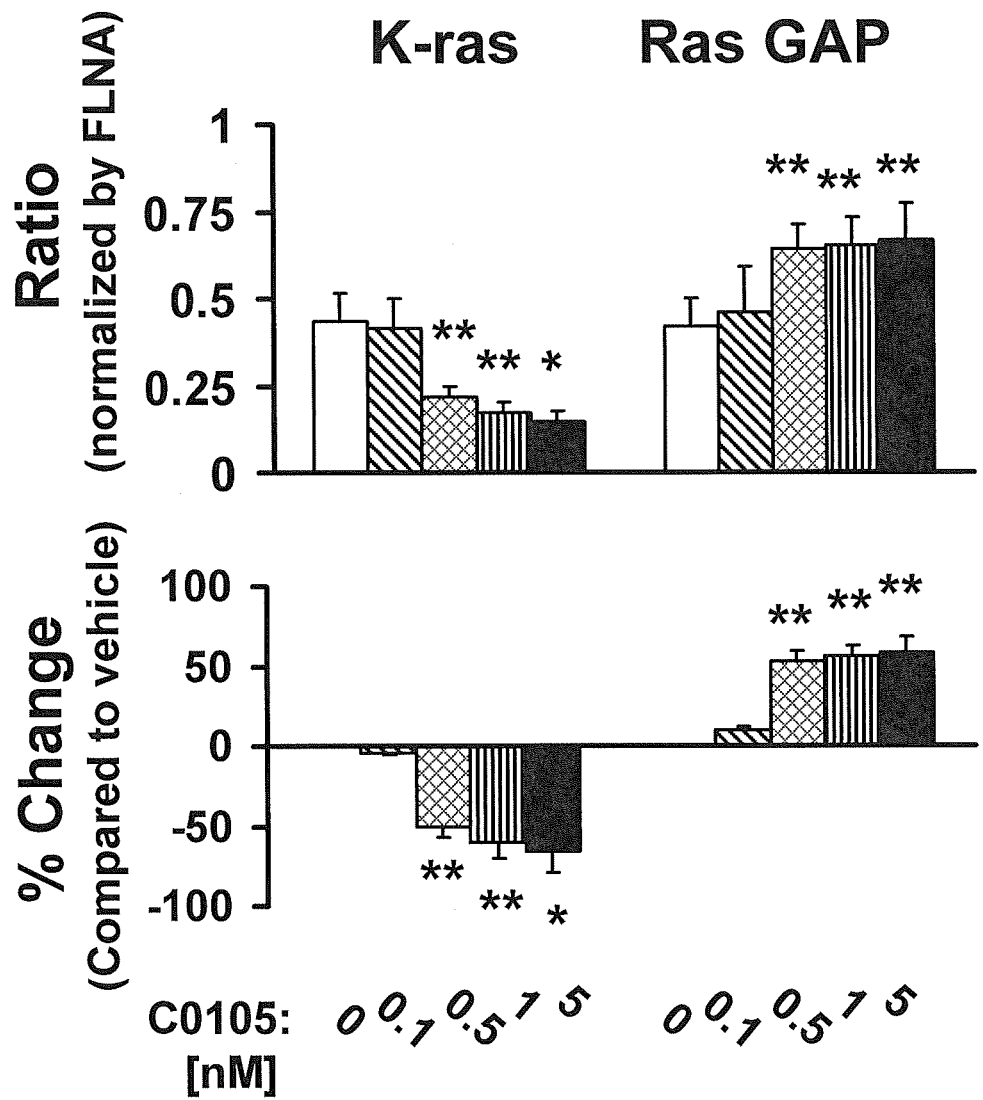
Figures 30G, 30H:
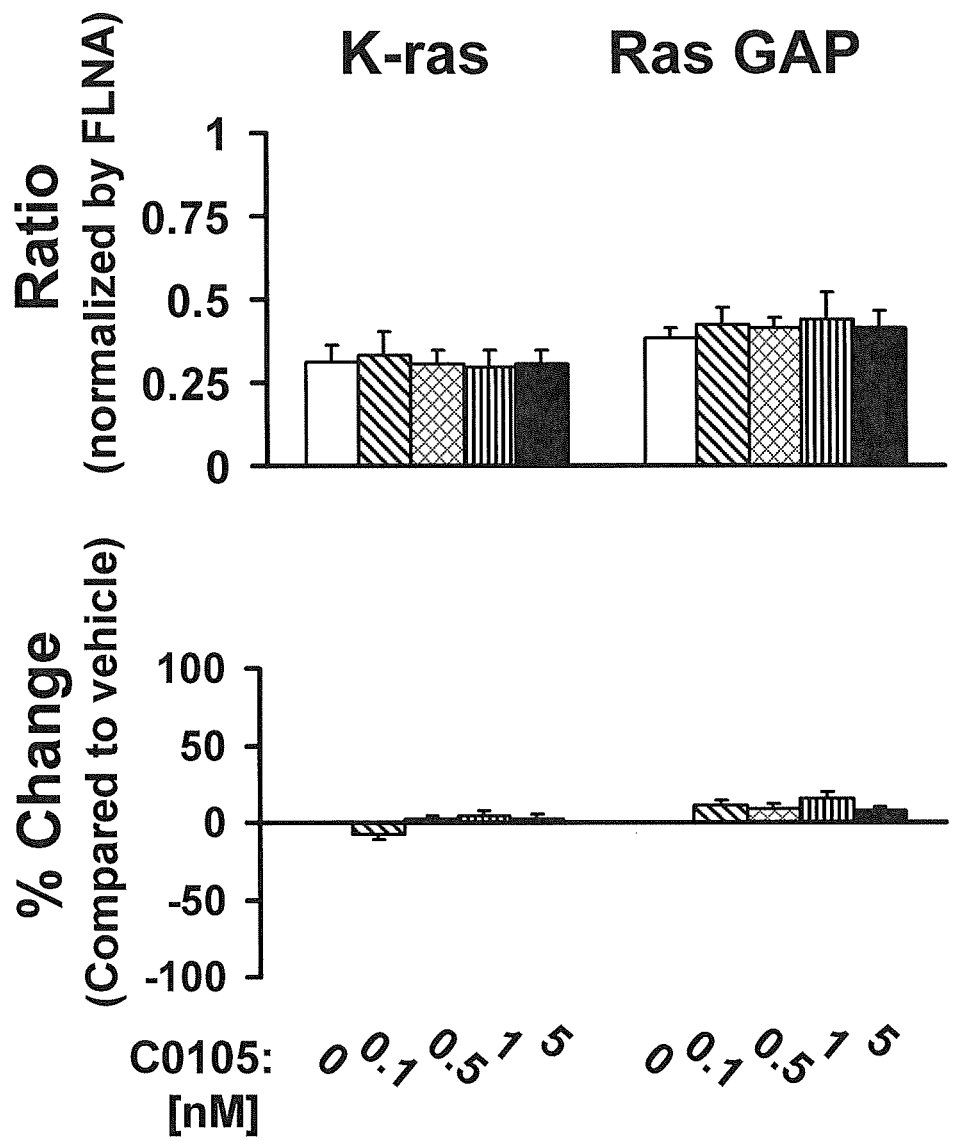
Figure 30I:
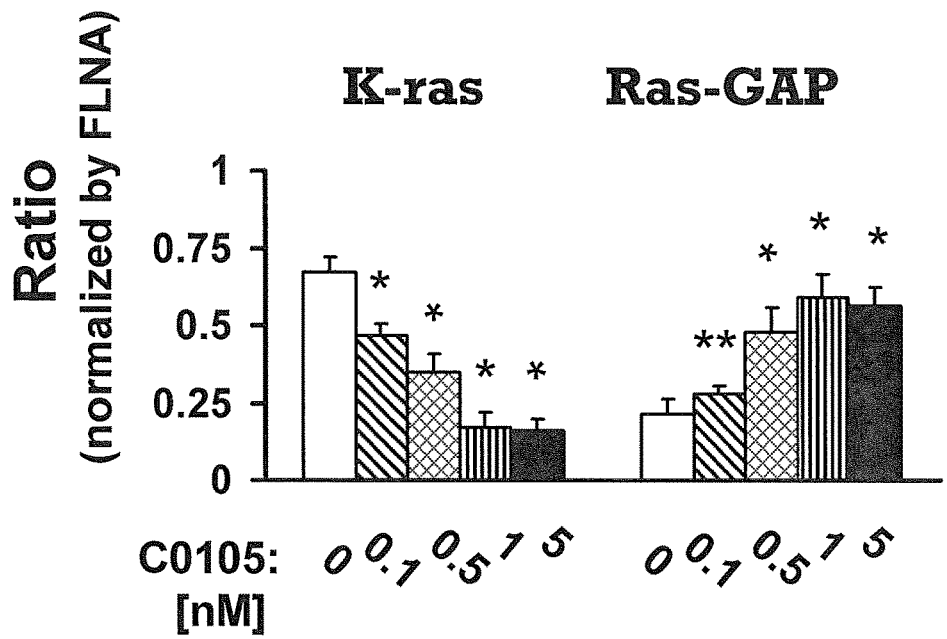
Figure 30J:
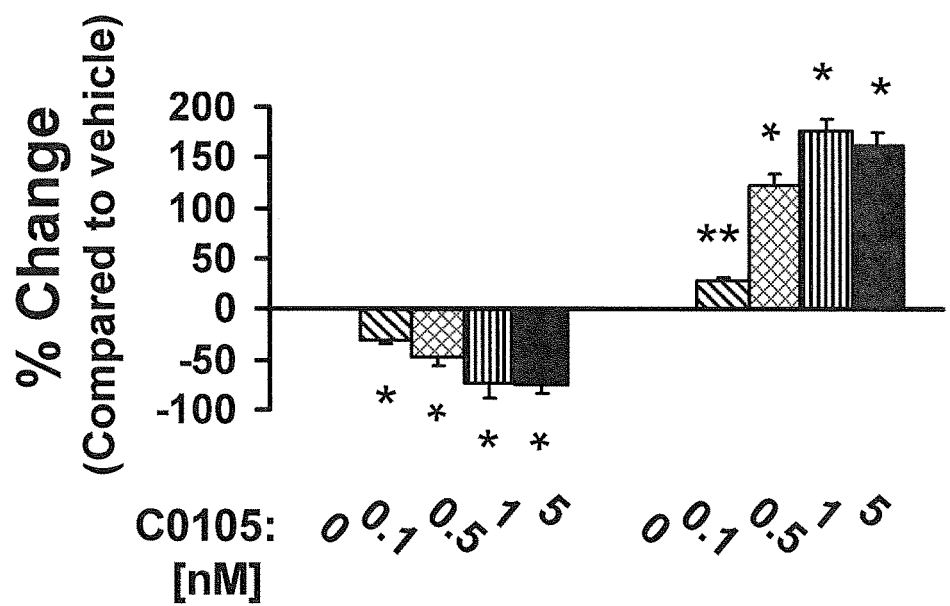
Figures 30K, 30L:
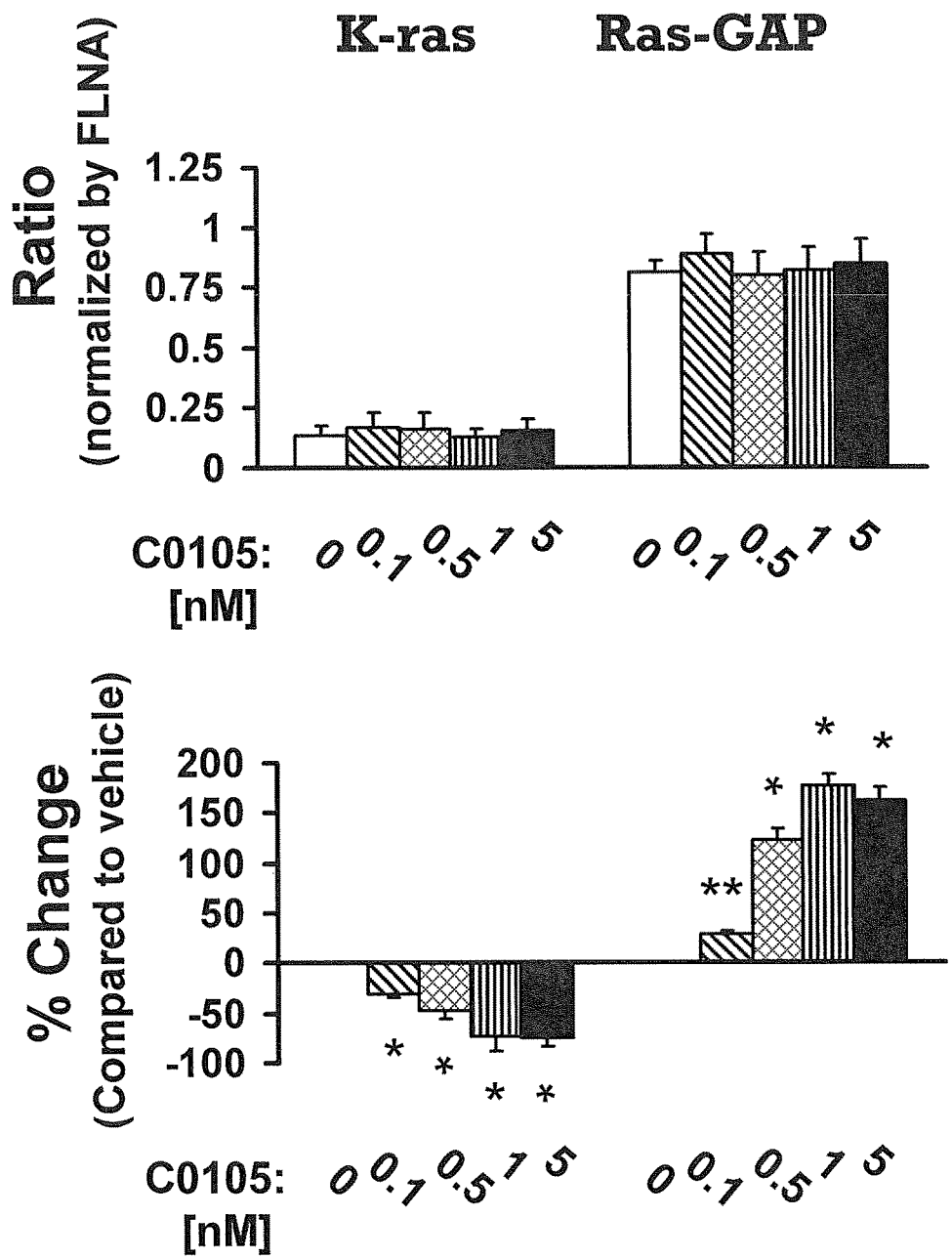

In addition, opioid agonists such as morphine itself and oxycodone do not bind well to the FLNA pentapeptide as is seen from the data of FIG. 28. As is seen, NLX and NTX both inhibit well at 1 µM, whereas each of morphine and oxycodone exhibited minimal binding inhibition when each was present at 10 µM.

Most of the FLNA-binding benzazocine-ring compounds are chiral and can exist as enantiomers of each other. It is presently preferred to utilize an enantiomeric compound that exhibits the lesser analgesic activity over the enantiomer that is more analgesically potent for the present method. It is further preferred to utilize an enantiomeric compound that exhibits lesser opioid agonist/antagonist activity over the enantiomer that exhibits the greater opioid agonist/antagonist activity.

Another related class of useful FLNA-binding benzazocine-ring compounds that share the 2,6-methano-3-benzazocine ring structure shown are the benzomorphan ring compounds that include zenazocine, volazocine, tonazocine, quadazocine, phenazocine, pentazocine, moxazocine, metazocine, ketazocine, ibazocine, gemazocine, fluorophen, eptazocine, cogazocine, cyclazocine, brenazocine, anazocine and alazocine.

These compounds are typically partial agonists of opioid receptors and are less preferred than are the morphinan or 4,5-epoxymorphinan ring compounds noted in the table above. The structures of some of these benzomorphans are illustrated below.

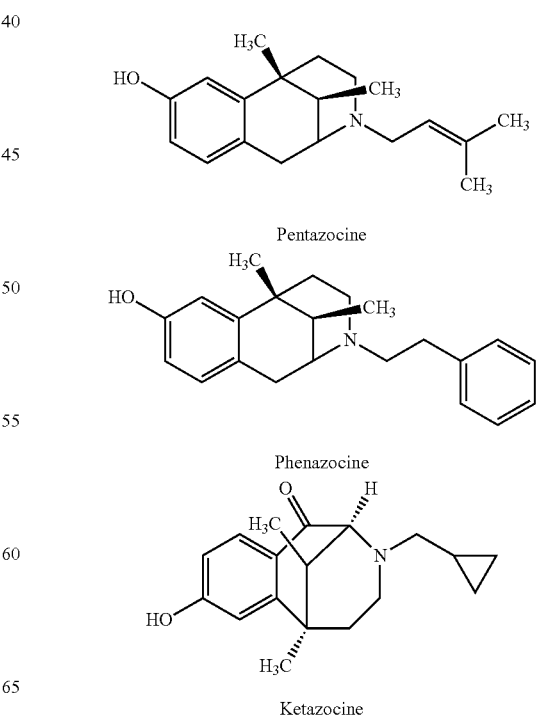

Pentazocine  
Phenazocine  
Ketazocine

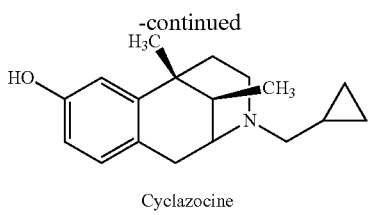

Cyclazocine

Further FLNA-Binding Compounds

Additionally, further compounds having four exemplary structures have been found to bind well to the FLNA pentapeptide of SEQ ID NO: 1. Compounds representative of those structural series are shown herein to inhibit the uptake of tritiated glucose by three cancer cell lines, while having no effect on a non-cancerous primary cells (see, FIG. 1A-1F). Those compounds are referred to herein as Series A, Series B, Series C-1, Series C-2, Series D and Series E. Compounds of Series D and E overlap with those of Series C-1 and C-2 and are therefore also included herein.

The general structures of the compounds of each series are shown below, followed by more specific disclosures. The chemical formulas shown below and hereinafter often contain atoms, subscripted letters, substituent R-groups or other indicia that have the same number or designation. It is to be understood that the definitions of those atoms subscripted letters, R-groups or other indicia are meant to apply only to a particular compound structural series being discussed and do not apply across compound structural series except atoms given their usual chemical definitions such as C for carbon, N for nitrogen, O for oxygen, S for sulfur and D for deuterium.

Series A

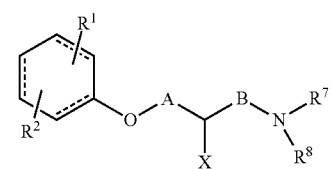

Series B

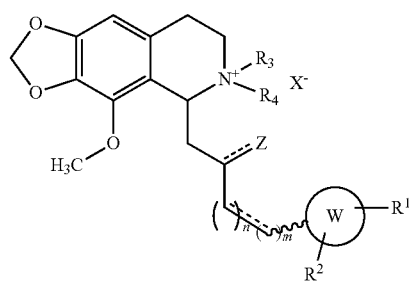

Series C-1

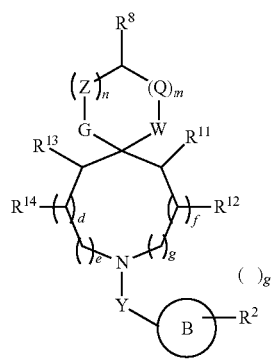

Series C-2

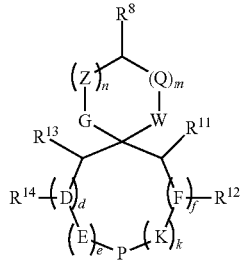

Series D

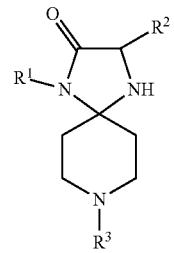

Series E

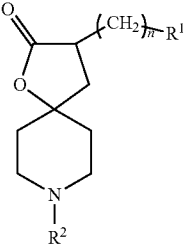

A pharmaceutically acceptable salt of a compound of each of the above Formulas is also contemplated. A compound having an asymmetrical (chiral) carbon or a salt of such a compound can exist in the form of stereoisomers that are two enantiomers. The invention relates both to each enantiomer separately, and to their mixture; i.e., to both enantiomeric forms (d and l, or R and S) and to their mixture. Additionally, where two or more chiral centers are present, stereoisomers called diastereomers can form, and diastereomers are also contemplated.

As will be seen from the following definitions, a contemplated compound can contain one or more deuterated carbon, in which deuterium is designated by its usual chemical designation, D. Deuterated compounds can be useful in studying the mechanism of drug interactions with living organisms for the elucidation of metabolic and biosynthetic pathways. Deuteration can also extend the half-life of a contemplated compound in vivo because a carbon-deuterium (C-D) bond is stronger than a carbon-hydrogen (C—H) bond thereby requiring more energy input for bond cleavage. See, Blake et al., 1975 *J. Pharm. Sci.* 64(3):367-391; and Nelson et al., 2003 *Drug Metab. Dispos.* 31(12):1481-1498, and the citations therein. Contemplated deuterated compounds are prepared using well-known reactions.

Series a Compounds

More particularly, a compound of Series A corresponds in structure to Formula A, below,

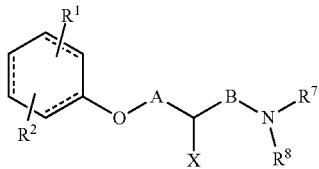

wherein $R^1$ and $R^2$ are the same or different and are independently H, halogen, $C_1$-$C_{12}$ hydrocarbyl, $C_1$-$C_6$ acyl, $C_1$-$C_6$ hydrocarbyloxy, $CF_3$ and $NR^3R^4$, wherein $R^3$ and $R^4$ are the same or different and are H, $C_1$-$C_4$ hydrocarbyl, $C_1$-$C_4$ acyl, $C_1$-$C_4$ hydrocarbylsulfonyl, or $R^3$ and $R^4$ together with the depicted nitrogen form a 5-7-membered ring that optionally contains 1 or 2 additional hetero atoms that independently are nitrogen, oxygen or sulfur;

A and B are the same or different and are $CH_2$, CDH or $CD_2$ (where D is deuterium);

X is OH or $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur;

$NR^7R^8$, $R^7$ and $R^8$ are the same or different and are H, $C_1$-$C_6$ hydrocarbyl, $C_1$-$C_6$ acyl, $C_1$-$C_6$ hydrocarbylsulfonyl, or $R^7$ and $R^8$ together with the depicted nitrogen form a ring structure W;

W contains 5 to 14 atoms in the ring structure including the depicted nitrogen, and preferably up to 12 atoms. W can optionally contain:

a) 1 or 2 further hetero atoms that are independently oxygen, nitrogen or sulfur, and b) one or more substituent groups bonded to one or more ring atoms, in which the one or more substituents contain a total of up to 8 atoms, and preferably up to 6 atoms, selected from the group consisting of carbon, nitrogen, oxygen and sulfur, and mixtures thereof.

A dashed line (----) represents an optional double bond.

In regard to a contemplated compound, $R^1$ and $R^2$ are preferably other than methyl and isopropyl, respectively, when W is N-morpholinyl or dimethyl-N-morpholinyl and the optional double bonds are absent.

A preferred compound of Formula A is a compound of Formula I, below, in which A, B, X, W and $R^1$ and $R^2$ are as defined above.

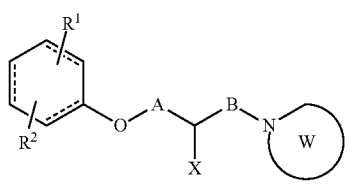

In one preferred embodiment, a contemplated compound corresponds in structure to Formula Ia

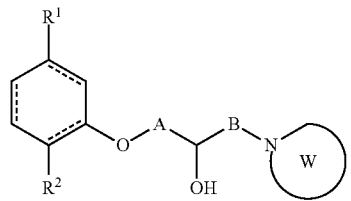

Here, $R^1$ and $R^2$ are the same or different and are independently H, or $C_1$-$C_6$ hydrocarbyl; A and B are the same or different and are $CH_2$, CDH or $CD_2$; W is a ring structure that contains 5 to 14 atoms in the ring structure including the depicted nitrogen, and can optionally contain: a) 1, 2 or 3 further hetero atoms that are independently oxygen, nitrogen or sulfur, and b) one or more substituent groups bonded to one or more ring atoms, in which the one or more substituent contain a total of up to 14 atoms, preferably up to 12 atoms and more preferably up to 8 atoms selected from the group consisting of carbon, nitrogen, oxygen and sulfur, and mixtures thereof. The dashed line (----) represents 1, 2, or 3 optional double bonds. Preferably, $R^1$ and $R^2$ are other than methyl and isopropyl, respectively, when W is N-morpholinyl or dimethyl-N-morpholinyl, and the optional double bonds are absent.

In preferred practice for some embodiments of a compound of either Formula I or Formula Ia, W further includes one or more substituent groups bonded to one or more ring atoms, in which those one or more substituents contain a total of up to 8 atoms selected from the group consisting of carbon, nitrogen, oxygen and sulfur, and mixtures thereof. Hydrogen atoms bonded to those atoms are not counted.

In one preferred embodiment, a compound of Formulas I and Ia has the structure of Formula II, whereas in another preferred embodiment, a compound of Formulas I and Ia has the structure of a compound of Formula III.

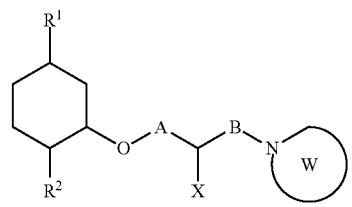

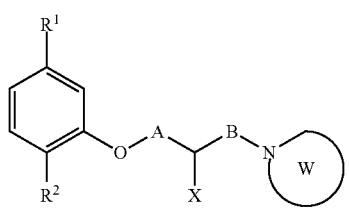

In a compound of both of Formulas II and III, A, B, W and X are as previously defined for a compound of Formulas I and Ia, above. $R^1$ and $R^2$ for a compound of Formula II are defined as $R^1$ and $R^2$ for a compound of Formula Ia, whereas $R^1$ and $R^2$ for a compound of Formula III are defined as $R^1$ and $R^2$ for a compound of Formula I.

More preferably, the $R^1$ and $R^2$ groups of a compound of Formula II contain 3 to 5 carbon atoms. For some compounds of Formula III, $R^1$ is H and $R^2$ is halogen, $C_1$-$C_6$ hydrocarbyl, $C_1$-$C_6$ acyl, $C_1$-$C_6$ hydrocarbyloxy or $NR^3R^4$, whereas for others, both R groups are other than H, but chosen as defined above.

In a compound of either Formula II or Formula III, W can optionally contain 1 or 2 further hetero atoms that are independently oxygen, nitrogen or sulfur, and more preferably still, contains at least one such hetero atom. It is also preferred that W further includes one or more substituent groups bonded to one or more ring atoms, in which the one or more substituents contain a total of up to 8 atoms selected from the group consisting of carbon, nitrogen, oxygen and sulfur, and mixtures thereof, and hydrogens bonded to those atoms are not counted.

A particularly preferred compound of Formulas II and III has a structure of Formulas IIa and IIIa, wherein the other groups A, B, W, $R^1$ and $R^2$ are as defined above.

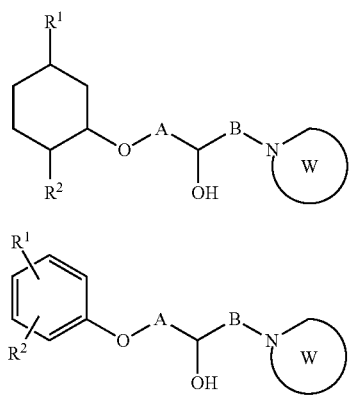

IIa

IIIa

Series B Compounds

A compound of Series B corresponds generally to the Formula I, below

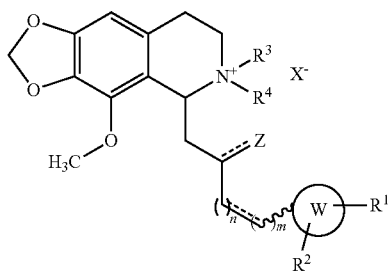

I wherein
  n=0 or 1;
  m=0 or 1;
  m+n=0, 1 or 2;

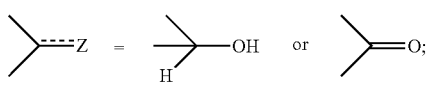

W is an aromatic ring containing 0, 1 or 2 hetero atoms that can be nitrogen, oxygen or sulfur, or mixtures thereof in the ring;

$R^1$ is selected from the group consisting of H, $C_1$-$C_6$ hydrocarbyl, $C_1$-$C_6$ hydrocarbyloxy, halogen, cyano, $C_1$-$C_6$ hydrocarbyloxyhydrocarboxylene, trifluoromethyl, and hydroxyl;

$R^2$ is selected from the group consisting of H, $C_1$-$C_6$ hydrocarbyl, $C_1$-$C_6$ hydrocarbyloxy, $C_1$-$C_6$ hydrocarbyloxyhydrocarboxylene and halogen;

$R^3$ is absent or $C_1$-$C_6$ hydrocarbyl;

$R^4$ is $C_1$-$C_6$ hydrocarbyl;

$X^-$=an anion or is absent when $R^3$ is absent;

the dashed line indicates an optional double bond between the depicted carbon atoms; and the wavy line indicates that the depicted phenyl substituent can be in the Z or E configuration when the optional double bond is present.

Illustrative anions can be monovalent or polyvalent. A contemplated anion is pharmaceutically acceptable and includes phosphate, hydrogen phosphate, dihydrogenphosphate, sulfate, bisulfate, chloride, bromide, iodide, acetate, formate, benzenesulfonate, methanesulfonate, toluenesulfonate and the like as are well known. These and other anions are listed in Berge et al., 1977 *J. Pharm Sci.* 68(1): 1-19.

It is preferred that m+n=1 or 2, and the optional double bond is absent, and is rather a saturated, single bond.

In preferred practice, W is a six-membered ring, although five membered rings are also contemplated. Thus, a contemplated aromatic ring that can include zero, one or two hetero atoms that are nitrogen, oxygen or sulfur or mixtures thereof include phenyl, pyridyl, furanyl, imidazyl, oxazolyl and the like. In some preferred embodiments, W is free of (has zero) ring nitrogen atoms. In other embodiments, preferred compounds have W groups that are free of ring hetero atoms, having only ring carbon atoms.

W preferably further includes one or more substituent groups ($R^1$ and $R^2$) to one or more ring atoms, in which those one or more substituents contain a total of up to 12 atoms selected from the group consisting of carbon, nitrogen, oxygen and sulfur, and mixtures thereof, with hydrogen atoms not being counted. Preferred substituent groups on ring W have an oxygen atom bonded to the W ring. Such compounds are preferably $C_1$-$C_6$ hydrocarbyloxy groups such as methoxy groups.

The Z-containing group can be a keto group or can be reduced to a hydroxyl group. Both groups are preferred.

In some embodiments, both $R^3$ and $R^4$ are $C_1$-$C_6$ hydrocarbyl groups that are both methyl. In other embodiments, one is an ethyl group and the other is methyl or absent. When $R^3$ is absent, a Series B compound is a tertiary amine.

In one preferred embodiment, a Series B compound of Formula I has the structure of Formula II,

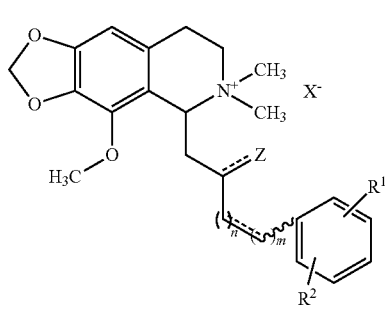

II wherein
n=0 or 1;
m=0 or 1;
m+n=0, 1 or 2;

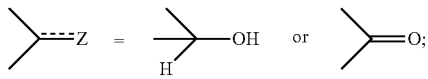

X⁻=an anion;

$R^1$ is selected from the group consisting of H, $C_1$-$C_6$ hydrocarbyl, $C_1$-$C_6$ hydrocarbyloxy, halogen, cyano, $C_1$-$C_6$ hydrocarbyloxyhydrocarboxylene, trifluoromethyl, and hydroxyl;

$R^2$ is selected from the group consisting of H, $C_1$-$C_6$ hydrocarbyl, $C_1$-$C_6$ hydrocarbyloxy, $C_1$-$C_6$ hydrocarbyloxyhydrocarboxylene and halogen;

the dashed line indicates an optional double bond between the depicted carbon atoms; and the wavy line indicates that the depicted phenyl substituent can be in the Z or E configuration when the optional double bond is present.

In some preferred embodiments, $R^2$=H. In some such embodiments, $R^1$ includes an oxygen atom bonded to the depicted phenyl ring, and that oxygen is preferably part of a $C_1$-$C_6$ hydrocarbyloxy group. For many compounds, it is preferred that

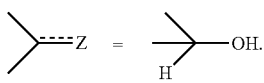

In yet other preferred embodiments, a contemplated Series B compound of has a structure that corresponds to Formula III, below

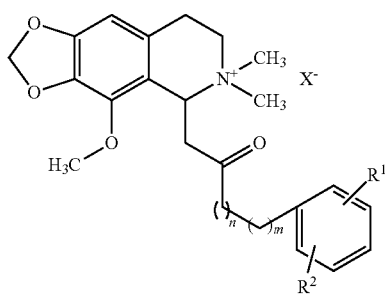

here,
n=0 or 1;
m=0 or 1;
m+n=0, 1 or 2;
X⁻=an anion;

$R^1$ is selected from the group consisting of H, $C_1$-$C_6$ hydrocarbyl, $C_1$-$C_6$ hydrocarbyloxy, halogen, cyano, $C_1$-$C_6$ hydrocarbyloxyhydrocarboxylene, trifluoromethyl, and hydroxyl; and $R^2$ is selected from the group consisting of H, $C_1$-$C_6$ hydrocarbyl, $C_1$-$C_6$ hydrocarbyloxy, $C_1$-$C_6$ hydrocarbyloxyhydrocarboxylene and halogen.

As was the case for other Series B compound embodiments, $R^2$ is sometimes H, and one or both of $R^1$ and $R^2$ are $C_1$-$C_6$ hydrocarbyloxy groups such as methoxy. A pharmaceutically acceptable salt of a compound of Formula I, II and III and all of the remaining Series B formulas disclosed herein is also contemplated.

Series C-1 Compounds

A compound of Series C-1 corresponds generally to the Formula A, below

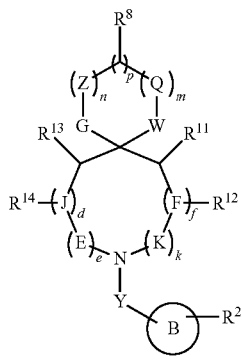

In Formula Series C-1 Formula A, G and W are selected from the group consisting of $NR^{20}$, $NR^7$, $CH_2$, S and O, where $R^7$ is H, $C(H)_v(D)_h$ where each of v and h is 0, 1, 2 or 3 and v+h=3, $C(H)_q(D)_r$-$C_1$-$C_{11}$ hydrocarbyl where each of q and r is 0, 1, or 2 and q+r=0, 1 or 2, $C_1$-$C_{12}$ hydrocarbyl sulfonyl or $C_1$-$C_{12}$ hydrocarboyl (acyl) and $R^{20}$ is a group X-circle A-$R^1$ as defined hereinafter, with the provisos that only one of G and W is $NR^{20}$ and that one of G and W must be $NR^{20}$, and G and W are preferably $NR^{20}$ and $NR^7$. In one preferred embodiment, only one of G and W is $NR^7$ and one of G and W must be $NR^7$ or $NR^{20}$;

X and Y are the same or different and are $SO_2$, C(O), $CH_2$, $CD_2$ (where D is deuterium), OC(O), NHC(NH), NHC(S) or NHC(O);

Q is $CHR^9$ or C(O); Z is $CHR^{10}$ or C(O);

each of d, e, f and k is either zero or one and the sum of (d+e+f+k)=2. In some embodiments, e is zero when d is zero, and g is zero when f is zero. In other embodiments, d is zero when f is zero, or e is zero when g is zero.

J and F are the same or different and are CH or CD;

E and K are the same or different and are $CH_2$, CHD or $CD_2$;

Each of m, n and p is zero or one and the sum of m+n+p is 2 or 3 for all embodiments. Each of m and n is preferably 1, and p is preferably zero so that the sum of m+n+p is preferably 2.

The circles A and B are the same or different aromatic or heteroaromatic ring systems. Groups $R^1$ and $R^2$ are the same or different and each can be hydrogen or represent up to three substituents other than hydrogen that themselves can be the same or different; i.e., $R^{1a}$, $R^{1b}$, and $R^{1c}$, and $R^{2a}$, $R^{2b}$, and $R^{2c}$. Each of those six groups, $R^{1a-c}$ and $R^{2a-c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl (acyl), hydroxy-, trifluoromethyl- (—$CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen, nitro, phenyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [S(O)$_2NR^3R^4$]

wherein the amido nitrogen in either group has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N=N— and Ar is a single-ringed aryl group as described previously, and $NR^5R^6$, wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur;

$R^8$, $R^9$, and $R^{10}$ are each H, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms;

$R^{11}$, $R^{12}$, $R^{13}$ and $R^{14}$ are all H, or one of the pair $R^{11}$ and $R^{12}$ or the pair $R^{13}$ and $R^{14}$ together with the depicted ring form a saturated or unsaturated 6-membered ring, and the other pair are each H, or they are H and D as recited herein (in this subparagraph).

Also in the above preferred embodiment, $R^1$ and $R^2$ are not both methoxy when X and Y are both $SO_2$, W is O and p is zero.

In another preferred embodiment,
i) only one of G and W is $NR^{20}$,
ii) one of G and W must be $NR^{20}$,
iii) one of G and W is other than $NR^7$ in which $R^7$ is H or an aliphatic $C_1$ hydrocarbyl; i.e., methyl, when (a) the sum of m+n+p is 2, and (b) the other of G and W is $NR^{20}$ bonded to a Z or Q, respectively, that is C(O), and
iv) when X and Y are both $SO_2$, W is O, Q is $CH_2$, p is zero, and d and f are both 1, $R^1$ and $R^2$ are other than (a) both H, methoxy, or $C_1$-$C_3$-hydrocarbyl, (b) H, halogen and $C_1$-$C_3$-hydrocarbyl, (c) H and $C_1$-$C_3$-hydrocarbyl, (d) halogen and $C_1$-$C_3$-hydrocarbyl, or (e) H and halogen.

$R^1$ and $R^2$ are preferably also not both methoxy when X and Y are both $SO_2$, W is O and p is zero in the above-preferred embodiment.

A pharmaceutically acceptable salt of a compound of Series C-1 Formula A and all of the remaining Series C-1 formulas disclosed herein is also contemplated.

In one preferred Series C-1 embodiment, e and g are both zero and a compound of Series C-1 Formula A becomes a compound of Series C-1 Formula B, below.

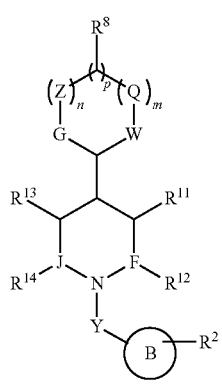

B

In Formula B, the letters of the formula G, J, F, W, Q, Z, d, e, f, k, n, m, p, X, Y, circle A and circle B and all R groups are as previously defined for a compound of Formula A of Series C-1.

In all of the following sub-generic formulas of a compound of Series C-1, the formula letters of G, J, E, F, K, W, Q, Z, d, e, f, k, n, m, p, X, Y, circle A and circle B and all R groups are as previously defined for a compound of Formula A of Series C-1, unless otherwise defined. Additionally, the previously stated preferences also apply unless a depicted structural formula precludes such a preference.

More preferably, a compound of Series C-1 Formula B corresponds in structure to Series C-1 Formula I, below

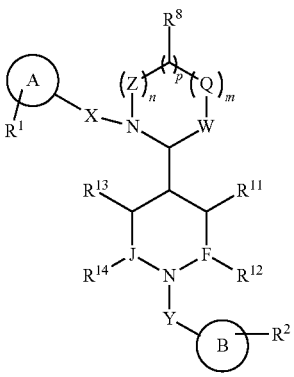

I

In Series C-1 Formula I, X and Y are the same or different and are $SO_2$, C(O), $CH_2$, $CD_2$, NHC(NH), OC(O), NHC(S) or NHC(O);

W is $NR^7$, $CH_2$, S or O, where $R^7$ is H, where $R^7$ is H, $C(H)_v(D)_h$ where each of v and h is 0, 1, 2 or 3 and v+h=3, $C(H)_q(D)_r$-$C_1$-$C_{11}$ hydrocarbyl where each of q and r is 0, 1, or 2 and q+r=0, 1 or 2, or $C_1$-$C_{12}$ hydrocarboyl (acyl), and is preferably $NR^7$;

Q is $CHR^9$ or C(O);
Z is $CHR^{10}$ or C(O);
J and F are the same or different and are CH or CD (where D is deuterium);
each of m, n and p is zero or one and the sum of m+n+p is 2 or 3, preferably 2; and
the circles A and B are the same or different aromatic or heteroaromatic ring systems that contain one ring or two fused rings. Groups $R^1$ and $R^2$ are the same or different and each can be hydrogen or represent up to three substituents other than hydrogen that themselves can be the same or different; i.e., $R^{1a}$, $R^{1b}$, and $R^{1c}$, and $R^{2a}$, $R^{2b}$, and $R^{2c}$. Each of those six groups, $R^{1a-c}$ and $R^{2a-c}$, is separately selected from the group consisting of H, $C_1$-$C_6$ hydrocarbyl, $C_1$-$C_6$ hydrocarbyloxy, trifluoromethyl, trifluoromethoxy, $C_1$-$C_7$ hydrocarboyl (acyl), hydroxy-, trifluoromethyl-(—$CF_3$) or halogen-substituted $C_1$-$C_7$ hydrocarboyl, $C_1$-$C_6$ hydrocarbylsulfonyl, halogen (F, Cl or Br, and preferably Cl), nitro, phenyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [$SO_2NR^3R^4$] wherein the amido nitrogen of either group (the carboxamide or sulfonamide) has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is where M is —CH$_2$—, —O— or —N=N— and Ar is a single-ringed aryl group, and NR$^5$R$^6$ wherein R$^5$ and R$^6$ are the same or different and are H, C$_1$-C$_4$ hydrocarbyl, C$_1$-C$_4$ acyl, C$_1$-C$_4$ hydrocarbylsulfonyl, or R$^5$ and R$^6$ together with the depicted nitrogen form a 5-7-membered ring that optionally contains 1 or 2 additional hetero atoms that independently are nitrogen, oxygen or sulfur;

R$^8$, R$^9$, and R$^{10}$ are each H, or two of R$^8$, R$^9$, and R$^{10}$ are H and one is a C$_1$-C$_8$ hydrocarbyl group that is unsubstituted or is substituted with up to three atoms that are the same or different and are oxygen or nitrogen atoms; and R$^{11}$, R$^{12}$, R$^{13}$ and R$^{14}$ are all H, or R$^{11}$ and R$^{13}$ are H and R$^{12}$ and R$^{14}$ are H or D, or one of the pair R$^{11}$ and R$^{12}$ or the pair R$^{13}$ and R$^{14}$ together with the depicted ring form a saturated or unsaturated 6-membered ring, and the other pair are each H or they are H and D as recited herein (in this subparagraph).

Preferably, R$^1$ and R$^2$ are not both methoxy when X and Y are both SO$_2$, W is O and p is zero.

In other preferred embodiments, X and Y are the same. X and Y are preferably both C(O) or both SO$_2$, and more preferably are both SO$_2$. In further preferred embodiments, X and Y are different and are C(O) and CH$_2$. In those and other embodiments, W is preferably O or NR$^7$. It is also preferred that p be zero.

A contemplated aromatic or heteroaromatic ring system of circle A or circle B can contain one ring or two fused rings, and preferably contains a single aromatic ring. An illustrative aromatic or heteroaromatic ring system is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl, isothiazolyl, naphthyl, benzofuranyl, isobenzofuranyl, benzothiophenyl, isobenzothiophenyl, benzoxazolyl, benzisoxazole, quinolyl, isoquinolyl, quinazolyl, cinnolinyl, quinoxalinyl, naphthyridinyl, benzopyrimidinyl, and mixtures thereof. The mixtures of the previous sentence occur when circle A and circle B aromatic or heteroaromatic ring systems are different.

An illustrative single-ringed aryl group of substituent MAr is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl and isothiazolyl.

Phenyl is a preferred aromatic or heteroaromatic ring system of circle A and circle B. Phenyl, pyridinyl and furanyl are preferred single-ringed aryl groups, Ar, of a MAr substituent, with phenyl being particularly preferred.

There are several independent and separate preferences regarding the substituent R groups. Thus, R$^1$ and R$^2$ are preferably the same single substituent other than hydrogen, so that circle A and circle B both contain a single substituent other than hydrogen. The single substituent of R$^1$ and R$^2$ is preferably located at the same relative position in their respective ring systems.

Thus, X and Y can form a sulfonamido, a carboxamido, a urea, a thiourea, a guanidino or methylene linkage from the circle A or circle B ring system to a depicted nitrogen atom of the central spiro ring. A compound having a central ring that is a spiro 6,6-ring system or a spiro 5,6-ring system, along with one nitrogen and one oxygen or two nitrogen atoms is contemplated. Illustrative central spiro rings are shown below where wavy lines are used to indicate the presence of covalent bonds to other entities, and where R$^7$ is defined above and R$^8$ is H.

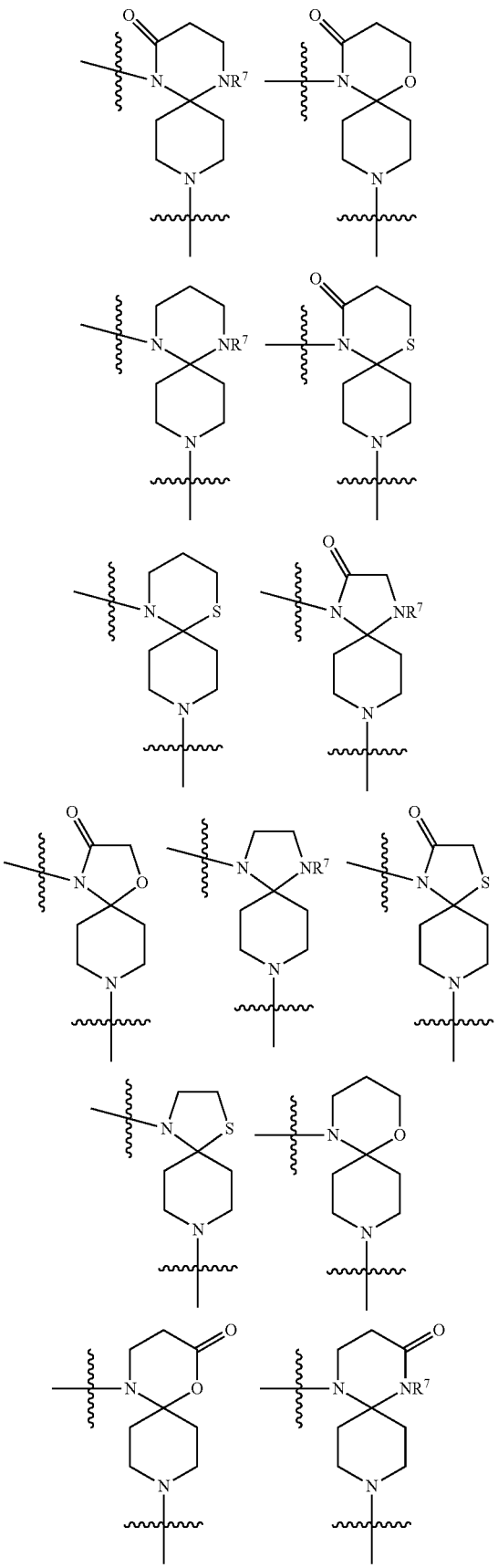

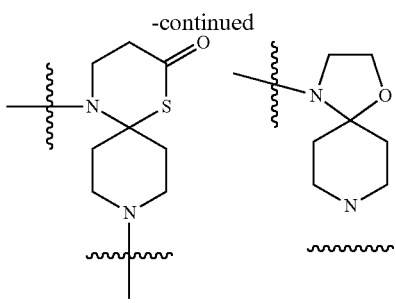
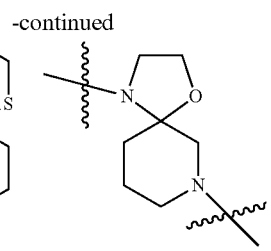
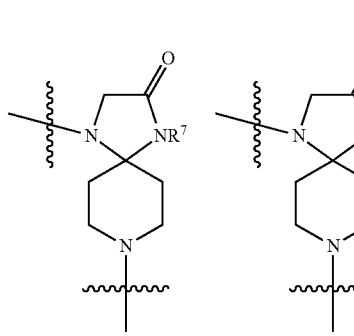
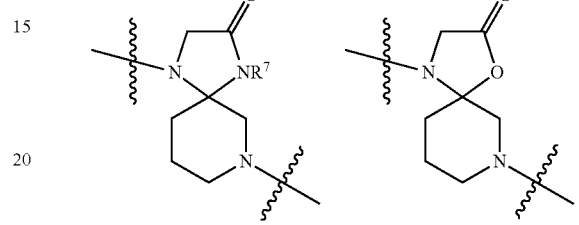
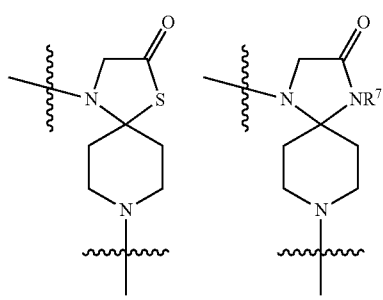
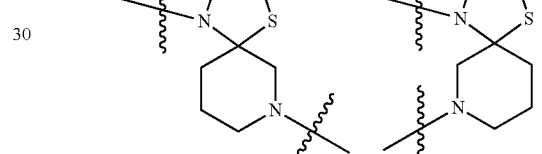

Illustrative compounds of Formula A in which d and e are each zero and $R^{11}$, $R^{12}$ and $R^{13}$ are each H have asymmetric spiro ring structures a few of which are shown below with wavy lines indicating the presence of covalent bonds to other entities, and $R^7$ is defined above and $R^8$ is H.

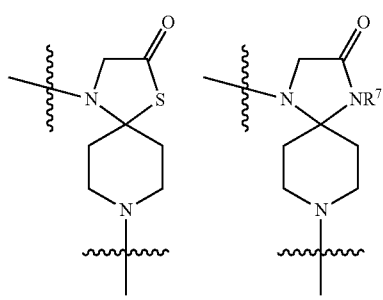
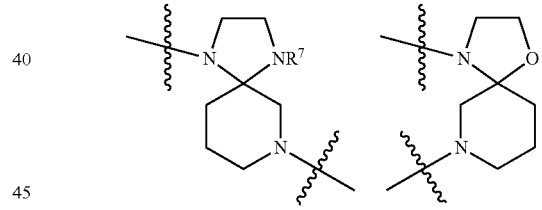
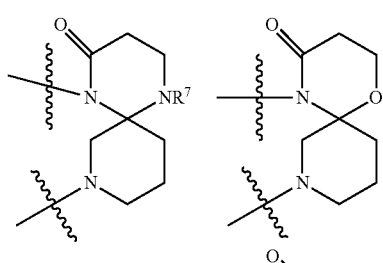
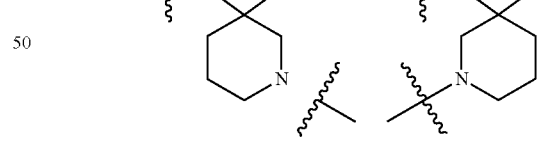
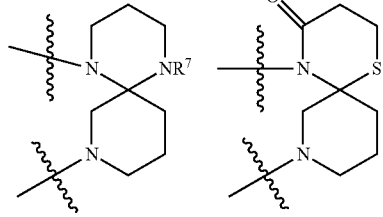

In preferred practice, p is zero, e and g are both zero and $R^{11}$, $R^{12}$ and $R^{13}$ are all H, so the central ring is a spiro 5,6-ring system whose 6-membered ring is unsubstituted and in which the spiro bonds are in the 4-position relative to the nitrogen of the 6-membered ring. It is separately preferred that W be O. A compound in which X and Y are the same is preferred. It is also separately preferred that X and Y both be $SO_2$ (sulfonyl).

A particularly preferred compound of Series C-1 Formula A that embodies the above separate preferences is a compound of Series C-1 Formula II

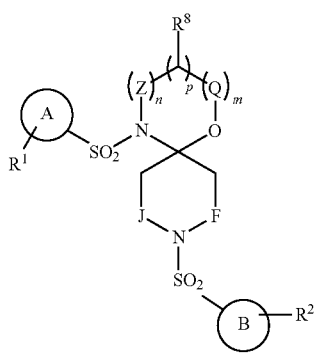

II wherein circle A and circle B, Z, Q, m, n, p, $R^1$, $R^2$ and $R^8$ are as described above for a compound of Series C-1, unless the formula as shown precludes a definition provided for a compound of Formula A; and J and F are the same or different and are $CH_2$, CHD or $CD_2$ (where D is deuterium).

It is more preferred that circle A and circle B are each phenyl, furanyl or pyridyl and $R^1$ and $R^2$ is each a single substituent. There are several independent and separate preferences regarding the substituent R groups. Thus, $R^1$ and $R^2$ are preferably the same. $R^1$ and $R^2$ are also preferably located at the same relative position in their respective rings. Thus, if $R^1$ is 4-cyano, $R^2$ is also 4-cyano. It is also preferred that the sum of m+n+p=2 so that the upper depicted ring contains 5-ring atoms.

Preferred $R^1$ and $R^2$ substituent groups do not themselves provide a positive or negative charge to a compound at a pH value of about 7.2-7.4.

In other embodiments, a particularly preferred compound of Series C-1 Formula A is a compound of Series C-1 Formula III

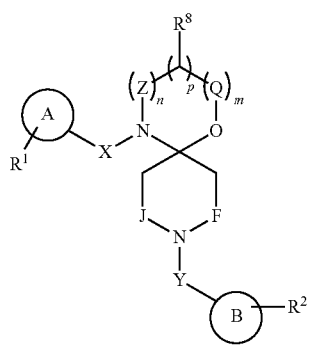

III wherein circle A and circle B, Z, Q, m, n, p, $R^1$, $R^2$ and $R^8$ are as described previously for a compound of Series C-1 unless the formula as shown precludes a prior definition; J and F are the same or different and are $CH_2$, CHD or $CD_2$ (where D is deuterium); and X and Y are both CO, or X and Y are different and are $SO_2$, C(O), $CH_2$, $CD_2$ (where D is deuterium), OC(O), NHC(NH), NHC(S) or NHC(O). Previous preferences are also applicable unless precluded by the above structural formula.

More preferably, circle A and circle B are each phenyl, furanyl or pyridyl. $R^1$ and $R^2$ are the same and are selected from the group consisting of trifluoromethyl, $C_1$-$C_6$ acyl, $C_1$-$C_4$ alkylsulfonyl, halogen, nitro, cyano, carboxyl, $C_1$-$C_4$ alkyl carboxylate, carboxamide wherein the amido nitrogen has the formula $NR^3R^4$ wherein $R^3$ and $R^4$ are the same or different and are H, $C_1$-$C_4$ alkyl, and $NR^5R^6$ wherein $R^5$ and $R^6$ are the same or different and are H, $C_1$-$C_4$ alkyl, $C_1$-$C_4$ acyl, $C_1$-$C_4$ alkylsulfonyl.

It is still more preferred that $R^1$ and $R^2$ each be a single substituent. There are several independent and separate preferences regarding the substituent R groups. $R^1$ and $R^2$ are preferably the same. $R^1$ and $R^2$ are also preferably located at the same relative position in their respective rings. Thus, if $R^1$ is 4-cyano, $R^2$ is also 4-cyano. It is also preferred that p=0, and that the sum of m+n+p=2, so that the upper depicted ring contains 5-ring atoms.

In still further embodiments, a particularly preferred compound of Series C-1 Formula A is a compound of Series C-1 Formula IV

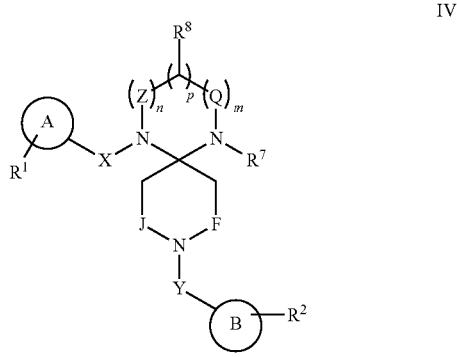

IV wherein circle A and circle B, Z, Q, m, n, p, $R^1$, $R^2$, $R^7$ and $R^8$ are as described previously for a compound of Series C-1 unless the formula as shown precludes such a prior definition; J and F are the same or different and are $CH_2$, CHD or $CD_2$ (where D is deuterium); and X and Y are the same or different and are $SO_2$, C(O), $CH_2$, $CD_2$ (where D is deuterium), OC(O), NHC(NH), NHC(S) or NHC(O). In some preferred embodiments, it is preferred that X and Y are different and are C(O) and $CH_2$. Previous preferences are also applicable unless precluded by the above structural formula.

More preferably, circle A and circle B are each phenyl, furanyl or pyridyl. $R^1$ and $R^2$ are the same and are selected from the group consisting of trifluoromethyl, $C_1$-$C_6$ acyl, $C_1$-$C_4$ alkylsulfonyl, halogen, nitro, cyano, carboxyl, $C_1$-$C_4$ alkyl carboxylate, carboxamide wherein the amido nitrogen has the formula $NR^3R^4$ wherein $R^3$ and $R^4$ are the same or different and are H, $C_1$-$C_4$ alkyl, and $NR^5R^6$ wherein $R^5$ and $R^6$ are the same or different and are H, $C_1$-$C_4$ alkyl, $C_1$-$C_4$ acyl, $C_1$-$C_4$ alkylsulfonyl.

It is still more preferred that $R^1$ and $R^2$ each be a single substituent. There are several independent and separate preferences regarding the substituent R groups. $R^1$ and $R^2$ are preferably the same. $R^1$ and $R^2$ are also preferably located at the same relative position in their respective rings. Thus, if $R^1$ is 4-cyano, $R^2$ is also 4-cyano. It is also preferred that the sum of m+n=1, so that the upper depicted ring contains 5-ring atoms.

It is noted that the previously mentioned preferences regarding E, J, F, G, K, Q, W, X, Y, Z, d, e, f, k, n, m, p, circle A and circle B, and all of the R groups as are appropriate for a particular formula apply to a compound of Series C-1 Formulas A, B, and I-IV.

Series C-2 Compounds

A compound of Series C-2 corresponds generally to the Formula A, below

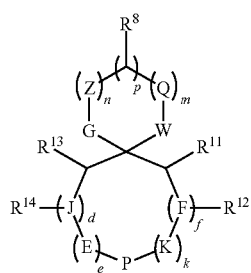

In Series C-2 Formula A,

Q is $CHR^9$ or C(O), Z is $CHR^{10}$ or C(O), and only one of Q and Z is C(O);

each of m and n and p is zero or one and the sum of m+n+p is 2 or 3, preferably 2;

each of G, P and W is selected from the group consisting of $NR^{20}$, $NR^2$, $NR^7$, S and O, where $R^7$ and $R^2$ are the same or different and are H, $C(H)_v(D)_h$ where each of v and h is 0, 1, 2 or 3 and v+h=3, $C(H)_q(D)_r$-$C_1$-$C_{11}$ hydrocarbyl where each of q and r is 0, 1, or 2 and q+r=0, 1 or 2, (including $C_1$-$C_{12}$ hydrocarbyl when q+r=0), $C_1$-$C_{12}$ hydrocarbyl sulfonyl or $C_1$-$C_{12}$ hydrocarboyl (acyl), and $R^{20}$ is X-circle A-$R^1$ as defined hereinafter.

Preferably, in one embodiment,
 i) only one of G, P and W is $NR^{20}$,
 ii) one of G, P and W must be $NR^{20}$,
 iii) P is $NR^2$ when other than $NR^{20}$,
 iv) one of G and W is other than $NR^2$ or $NR^7$ in which $R^2$ and $R^7$ is H or a $C_1$ hydrocarbyl when (a) the sum of m+n+p is 2 and (b) the other of G and W is $NR^{20}$, $NR^2$, or $NR^7$ bonded to a Z or Q, respectively, that is C(O), and
 v) P is $NR^2$ in which $R^2$ is other than —$S(O)_2C_1$-$C_3$-hydrocarbyl when (a) the sum of m+n+p is 2 and the Q or Z present is $CH_2$, (b) the G or W that is not $NR^{20}$ is O, and (c) $R^{20}$ is —$S(O)_2$phenyl-$R^1$, where $R^1$ is H, $C_1$-$C_3$-hydrocarbyl or halogen.

Each of d, e, f and k is either zero or one and the sum of (d+e+f+k)=2. In some embodiments, e is zero when d is zero, and k is zero when f is zero. In other embodiments, e is zero when k is zero, and f is zero when d is zero.

J and F are the same or different and are CH or CD (where D is deuterium).

E and K are the same or different and are $CH_2$, CHD or $CD_2$ (where D is deuterium).

X is $SO_2$, C(O), $CH_2$, $CD_2$, OC(O), NHC(NH), NHC(S) or NHC(O), preferably $SO_2$, C(O) or $CH_2$. In some embodiments, X is more preferably $CH_2$ or $SO_2$. In other embodiments, X is preferably $SO_2$, NHC(NH), NHC(S) or NHC(O).

Circle A is an aromatic or heteroaromatic ring system that preferably contains a single ring, but can also contain two fused rings. $R^1$ is H or represents up to three substituents, $R^{1a}$, $R^{1b}$, and $R^{1c}$, that themselves can be the same or different, wherein each of those three groups, $R^{1a-c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl, hydroxy-, trifluoromethyl- (—$CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen (F, Cl, or Br, and preferably Cl) nitro, phenyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [S(O)$_2NR^3R^4$], wherein the amido nitrogen in either amide group has the formula $NR^3R^4$ in which $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N=N— and Ar is a single-ringed aryl or heteroaryl group and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur.

$R^8$, $R^9$, and $R^{10}$ are each H, which is preferred, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms (including hydrogens as appropriate).

$R^{11}$, $R^{12}$, $R^{13}$ and $R^{14}$ are all H, or $R^{11}$ and $R^{13}$ are H and $R^{12}$ and $R^{14}$ are H or D, or one of the pair $R^{11}$ and $R^{12}$ or the pair $R^{13}$ and $R^{14}$ together with the depicted ring form a saturated or unsaturated 6-membered ring, and the other pair are each H or they are H and D as recited herein (in this subparagraph).

In another preferred embodiment of a compound of Formula A, above,
 i) only one of G, P and W is $NR^{20}$,
 ii) one of G, P and W must be $NR^{20}$, and
 iii) P is $NR^2$ when other than $NR^{20}$.

Additionally, Q is $CHR^9$ or C(O); and

Z is $CHR^{10}$ or C(O), with the other of J, E, F, K, X, Z, d, e, f, k, n, m, p, circle A, and all of the R groups being defined as discussed above unless precluded by the structural formula.

A pharmaceutically acceptable salt of a compound of Series C-2 Formula A and all of the remaining formulas disclosed herein is also contemplated.

In preferred embodiments, a compound of Series C-2 Formula A corresponds in structure to either Formula B or Formula C, can be present as a pharmaceutically acceptable salt, and can optionally be present including both individual enantiomeric forms, a racemate, diastereomers and mixtures thereof.

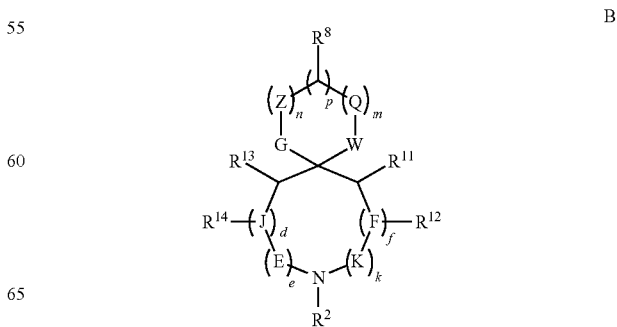

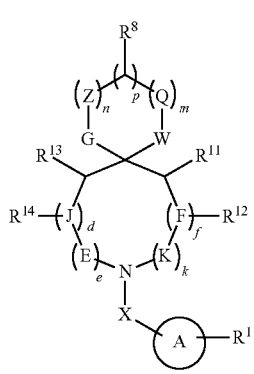

In a compound of Series C-2 that corresponds in structure to Series C-2 Formula B, G and W are selected from the group consisting of $NR^{20}$, $NR^7$, S and O, where $R^2$ and $R^7$ are the same or different and are $C(H)_v(D)_h$ (where D is deuterium) and where each of v and h is 0, 1, 2 or 3 and v+h=3, $C(H)_q(D)_r$-aliphatic $C_1$-$C_{11}$ hydrocarbyl (where D is deuterium) where each of q and r is 0, 1, or 2 and q+r=0, 1 or 2, aliphatic $C_1$-$C_{12}$ hydrocarbyl sulfonyl or aliphatic $C_1$-$C_{12}$ hydrocarboyl, or $R^2$ and $R^{20}$ are the same or different, and $R^{20}$ is X-circle A-$R^1$.

Preferably in one embodiment,
i) only one of G and W is $NR^{20}$,
ii) one of G and W must be $NR^{20}$,
iii) the G or W that is not $NR^{20}$ is other than $NR^2$ or $NR^7$ in which $R^2$ or $R^7$ is H or an aliphatic $C_1$ hydrocarbyl when (a) the sum of m+n+p is 2 and (b) the G or W that is $NR^{20}$ is bonded to a Z or Q, respectively, that is C(O), and
iv) $R^2$ of the depicted $NR^2$ is other than —$S(O)_2C_1$-$C_3$-hydrocarbyl when (a) the sum of m+n+p is 2 and the Q or Z that is present is $CH_2$, (b) the G or W that is not $NR^{20}$ is O, and (c) $R^{20}$ is —$S(O)_2$phenyl-$R^1$, where $R^1$ is H, $C_1$-$C_3$-hydrocarbyl or halogen.

In another preferred embodiment:
i) only one of G and W is $NR^{20}$,
ii) one of G and W must be $NR^{20}$,
iii) the G or W that is not $NR^{20}$ is $NR^2$ or $NR^7$ in which $R^2$ or $R^7$ is H or an aliphatic $C_1$ hydrocarbyl,
(iv) the sum of m+n+p is 2, and
(v) the G or W that is $NR^{20}$ is bonded to a Z or Q, respectively, that is C(O).

In yet another preferred embodiment:
i) only one of G and W is $NR^{20}$,
ii) one of G and W must be $NR^{20}$,
iii) the G or W that is not $NR^{20}$ is $NR^7$ that is H or an aliphatic $C_1$ hydrocarbyl,
(iv) the sum of m+n+p is 2,
(v) the G or W that is $NR^{20}$ is bonded to a Z or Q, respectively, that is C(O),
(vi) $R^2$ of the depicted $NR^2$ is the same or different $R^{20}$, and
(vii) $R^{20}$ is X-circle A-$R^1$.

For a compound of Formula C, G and W are selected from the group consisting of $NR^2$, $NR^7$, S and O, where $R^2$ and $R^7$ are the same or different and are H, $C(H)_v(D)_h$ (where D is deuterium) and where each of v and h is 0, 1, 2 or 3 and v+h=3, $C(H)_q(D)_r$-aliphatic $C_1$-$C_{11}$ hydrocarbyl where each of q and r is 0, 1, or 2 and q+r=0, 1 or 2, aliphatic $C_1$-$C_{12}$ hydrocarbyl sulfonyl or aliphatic $C_1$-$C_{12}$ hydrocarboyl.

Preferably, in another embodiment:
i) one of G and W must be $NR^2$ or $NR^7$, and
ii) one of G and W is other than $NR^2$ or $NR^7$ in which $R^2$ or $R^7$ is H or an aliphatic $C_1$ hydrocarbyl when (a) the sum of m+n+p is 2 and (b) the other of G and W is $NR^2$ or $NR^7$ bonded to a Z or Q, respectively, that is C(O).

In both of Series C-2 Formulas B and C, the symbols X, Z, Q, d, e, f, g, n, m, circle A, and all of the R groups not otherwise defined in the paragraphs following their structural formulas are as defined previously for a compound of Series C-2 Formula A unless the formula as shown precludes a prior definition. The previously noted preferences are also as discussed before unless the formula as shown precludes a prior preference.

In one embodiment, a preferred compound of Series C-2 Formulas A and B has the structure of Formula I

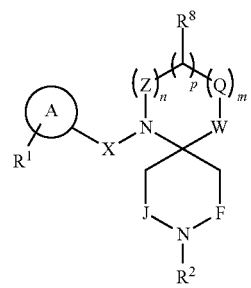

wherein J and F are the same or different and are $CH_2$, CHD or $CD_2$ (where D is deuterium); and W, X, Z, Q, n, m, p, circle A, $R^1$, $R^2$, $R^8$ and the R groups therein defined are as described previously for a compound of Series C-2 Formula A, unless the formula as shown precludes a prior definition. Preferably, i) $R^2$ of the depicted $NR^2$ is other than —$S(O)_2C_1$-$C_3$-hydrocarbyl when (a) the sum of m+n+p is 2 and the Q or Z present is $CH_2$, (b) the G or W that is not $NR^{20}$ is O, and (c) $R^{20}$ is —$S(O)_2$phenyl-$R^1$, where $R^1$ is H, $C_1$-$C_3$-hydrocarbyl or halogen, and ii) W is other than $NR^2$ or $NR^7$ in which $R^2$ or $R^7$ is H or an aliphatic $C_1$ hydrocarbyl when (a) the sum of m+n+p is 2 and (b) Z is C(O).

In another preferred embodiment where $R^8$ is H, one of n and m is zero and the remaining Z or Q is $CH_2$, a compound of Series C-2 Formulas A, B and I has the structure of Series C-2 Formula II

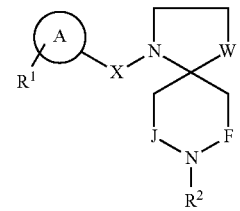

wherein J and F are the same or different and are $CH_2$, CHD or $CD_2$ (where D is deuterium); and X, W, circle A, $R^1$, $R^2$ and the R groups therein defined are as described previously for a compound of Series C-2 Formula A, unless the formula as shown precludes a prior definition. Preferably, $R^2$ of the depicted $NR^2$ is other than —$S(O)_2C_1$-$C_3$-hydrocarbyl when W is O, and X-circle A-$R^1$ is —$S(O)_2$phenyl-$R^1$, where $R^1$ is H, $C_1$-$C_3$-hydrocarbyl or halogen.

In a further preferred embodiment, where $R^8$ is H, a compound of Series C-2 Formulas A, B and I has the structure of Series C-2 Formula III

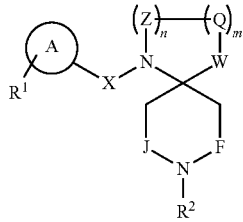

III wherein J and F are the same or different and are $CH_2$, CHD or $CD_2$ (where D is deuterium);

each of m and n is one; and

W, X, Z, Q, circle A, $R^1$, $R^2$ and the R groups therein defined are as described previously for a compound of Series C-2 Formula A, unless the formula as shown precludes a prior definition.

In one preferred embodiment, i) Z is C(O), ii) Q is $CH_2$, iii) W is NH, and $R^2$ is H or $C_1$-$C_{12}$ aliphatic straight, branched or cyclic hydrocarbyl, iv) X is preferably $CH_2$, $SO_2$, NHC(NH), NHC(S) or NHC(O), and more preferably $CH_2$. In another preferred embodiment, i) one of Z and Q is C(O), and ii) W is other than $NR^2$ or $NR^7$ in which $R^2$ and $R^7$ is H or an aliphatic $C_1$ hydrocarbyl when Z is C(O), and iii) X is preferably $CH_2$, $SO_2$, NHC(NH), NHC(S) or NHC(O).

In a still further preferred embodiment, i) Z is C(O), ii) Q is $CH_2$, iii) W is NH, (vi) $R^2$ is the same or different $R^{20}$, and (vii) $R^{20}$ is X-circle A-$R^1$. In this embodiment, X is preferably $CH_2$, $SO_2$, NHC(NH), NHC(S) or NHC(O), more preferably $CH_2$.

A presently most preferred compound for carrying out a contemplated method corresponds in structure to Formula III, above, in which i) Z is C(O), ii) Q is $CH_2$, iii) W is NH, and $R^2$ is H or a $C_1$-$C_{12}$, preferably $C_1$-$C_8$, and more preferably a $C_1$-$C_6$ aliphatic straight, branched or cyclic hydrocarbyl group, iv) X is $CH_2$, and circle A-$R^1$ is unsubstituted phenyl so that the substituent X-circle A-$R^1$ is a benzyl group. Illustrative presently most preferred compounds include Compounds C0105M, C0115M and C0124M, whose structural formulas are shown below.

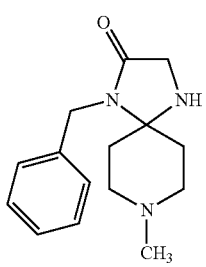

C0105 M

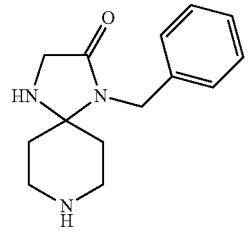

C0114M

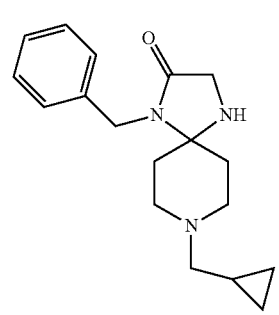

C0124M

In a still further preferred embodiment, a compound of Series C-2 Formulas A and C has the structure of Series C-2 Formula IV

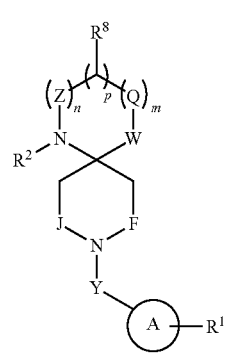

IV wherein J and F are the same or different and are $CH_2$, CHD or $CD_2$ (where D is deuterium); and W, X, Z, Q, circle A, $R^1$, $R^2$, $R^8$ and the R groups therein defined are as described previously for a compound of Series C-2 Formula A, unless the formula as shown precludes a prior definition.

In one preferred embodiment, i) W is other than $NR^2$ or $NR^7$ in which $R^2$ or $R^7$ is H or an aliphatic $C_1$ hydrocarbyl, when p is zero and the sum of m+n+p is 2 and Z is C(O), and ii) $R^2$ of the depicted $NR^2$ group is other than H or an aliphatic $C_1$ hydrocarbyl, when p is zero and the sum of m+n+p is 2, W is $NR^2$ or $NR^7$, and Q is C(O).

In yet another preferred embodiment where $R^8$ is H, one of n and m is zero and the remaining Z or Q is $CH_2$, a compound of Formulas A, C and IV has the structure of Series C-2 Formula V

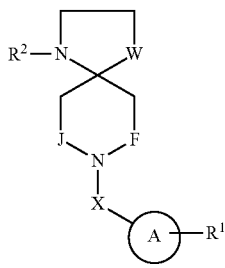

wherein J and F are the same or different and are CH$_2$, CHD or CD$_2$ (where D is deuterium); and X, W, circle A, R$^1$, R$^2$ and the R groups therein defined are as described previously for a compound of Series C-2, unless the formula as shown precludes a prior definition.

In still another preferred embodiment, where R$^8$ is H, a compound of Series C-2 Formulas A, C and I has the structure of Series C-2 Formula VI

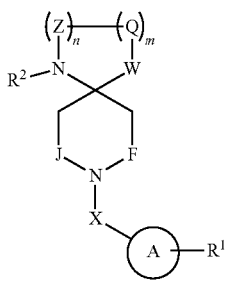

wherein J and F are the same or different and are CH$_2$, CHD or CD$_2$ (where D is deuterium); and each of m and n is one; W, X, Z, Q, circle A, R$^1$, R$^2$ and the R groups therein defined are as described previously for a compound of Series C-2, unless the formula as shown precludes a prior definition.

Preferably, i) one of Z and Q is C(O), ii) W is other than NR$^2$ or NR$^7$ in which R$^2$ or R$^7$ is H or an aliphatic C$_1$ hydrocarbyl when Z is C(O), and iii) R$^2$ of the depicted NR$^2$ group is other than H or an aliphatic C$_1$ hydrocarbyl when W is NR$^2$ or NR$^7$, and Q is C(O). In a compound of the above formula, X is preferably SO$_2$, NHC(NH), NHC(S) or NHC(O).

It is also noted that the previously mentioned preferences regarding apply to X, W, Z, Q, d, e, f, k, n, m, circle A, and all of the R groups apply to a compound of Series C-2 Formulas A, B, C, and I-VI, unless the formula as shown precludes a prior definition.

A contemplated aromatic ring (aryl) system of circle A of one of the contemplated compounds preferably contains a single aromatic ring, but can also contain two fused aromatic rings. An illustrative circle A aromatic ring system is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl, isothiazolyl, naphthyl, benzofuranyl, isobenzofuranyl, benzothiophenyl, isobenzothiophenyl, benzoxazolyl, benzisoxazole, quinolyl, isoquinolyl, quinazolyl, cinnolinyl, quinoxalinyl, naphthyridinyl, and benzopyrimidinyl.

An illustrative single-ringed aryl or heteroaryl group of a circle A group or of a substituent of circle A, MAr, is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl and isothiazolyl groups.

Phenyl, pyridinyl and furanyl are a preferred aromatic or heteroaromatic ring system of circle A, with phenyl being more preferred. Phenyl, pyridinyl and furanyl are also preferred single-ringed aryl or heteroaryl groups, Ar, of a MAr substituent, with phenyl being particularly preferred.

From a depicted nitrogen atom of the central spiro rings to the circle A ring system, X and Y can form a sulfonamido (N—SO$_2$-circle A), a carboxamido [N—C(=O)-circle A), a urea [carbonyldiimino; N—C(=O)—NH-circle A], a thiourea [thiocarbonyldiimino; N—C(=S)—NH-circle A], a guanidino [N—C(=NH)—NH-circle A] or aminomethylene (N—CH$_2$-circle A) linkage.

Examining a compound of the above Series C-2 formulas more closely, it is seen that that formula defines a double ringed, substituted spiro compound that can have two six-membered rings or one six- and one five-membered ring, as when one of "m" and "n" is one and the other zero. One of those rings (the lower ring in the formulas) contains one nitrogen atom in the 6-membered ring and the remaining ring atoms are carbons. The ring that can contain 5- or 6-ring atoms (upper ring in the formulas) can contain one ring nitrogen and four or five carbons, or two nitrogens, a nitrogen and a sulfur or a nitrogen and an oxygen atom along with three or four ring carbons. Illustrative central spiro rings are shown below where wavy lines are used to indicate the presence of covalent bonds to other entities, and where R$^7$ is defined above and R$^8$ is H for clarity.

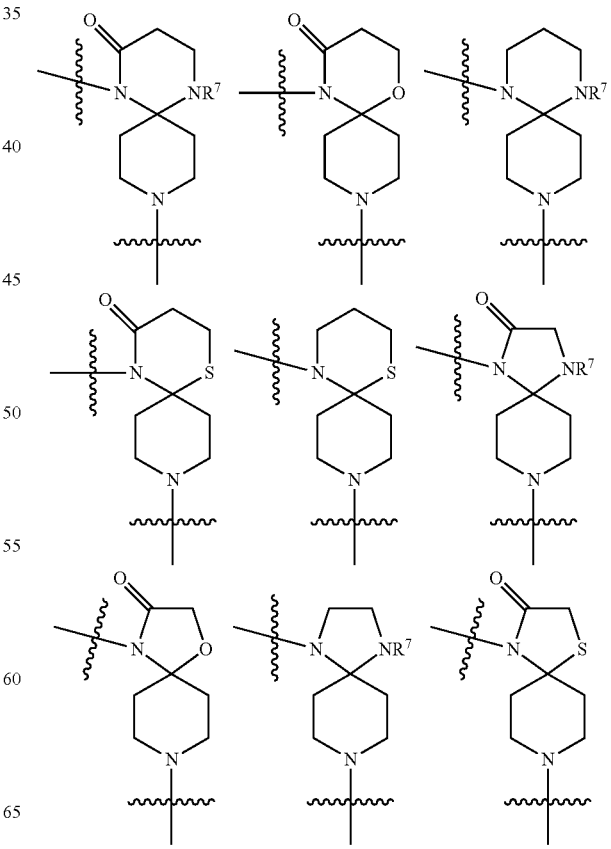

-continued

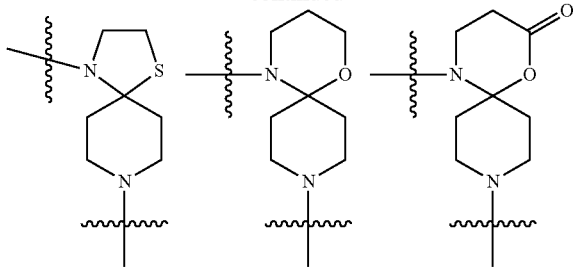

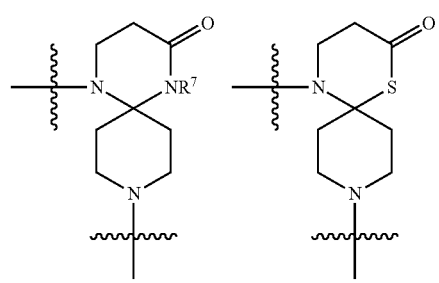

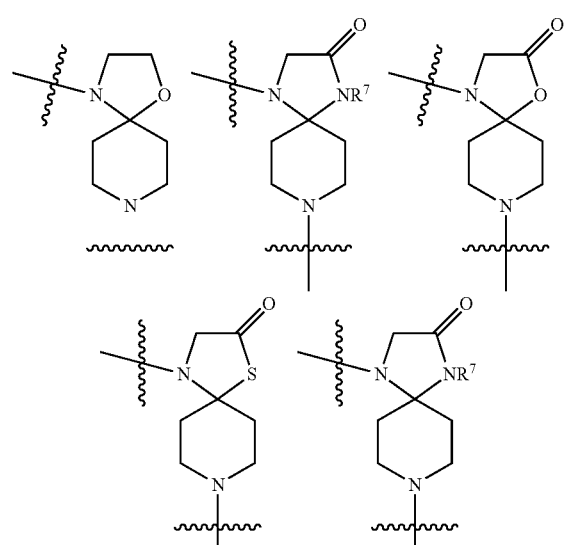

-continued

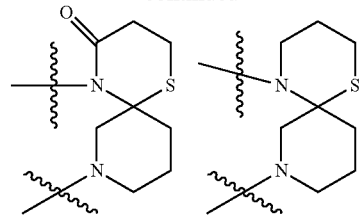

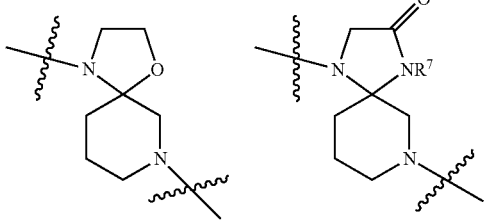

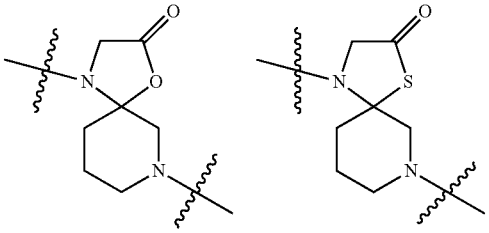

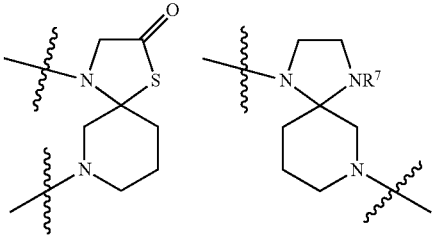

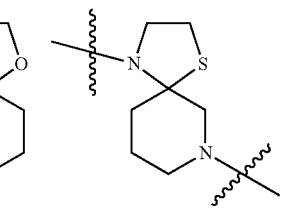

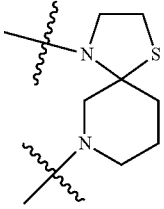

Illustrative compounds of Series C-2 Formula A in which d and e are each zero and $R^{11}$, $R^{12}$ and $R^{13}$ are each H have asymmetric spiro ring structures a few of which are shown below with wavy lines indicating the presence of covalent bonds to other entities, and $R^7$ is defined above and $R^8$ is again H for clarity.

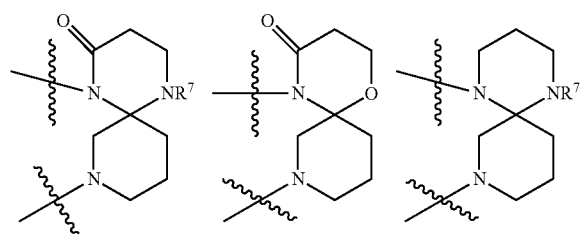

In preferred practice for the compounds of Series C-2 Formulas A, B and C, p is zero, e and g are both zero and $R^{11}$, $R^{12}$ and $R^{13}$ are all H, so the central ring is a spiro 5,6-ring system whose 6-membered ring is unsubstituted and in which the spiro bonds are in the 4-position relative to the nitrogen of the 6-membered ring. It is separately preferred that W be O, S or $NR^7$. It is also preferred that X be $SO_2$ (sulfonyl).

The aromatic substituent, the circle A, is linked to one nitrogen atom of the spiro rings by a X group that is $SO_2$, C(O), $CH_2$, $CD_2$, OC(=O), NHC(=NH), NHC(=S) or NHC(=O), preferably $SO_2$, C(O), $CH_2$, or $CD_2$, and most preferably $CH_2$ and $SO_2$. The resulting aromatic substituent is thereby linked to the spiro ring portion by a sulfonamide, an amide, a methylene, a urea, a thiourea or a guanidino linkage. Aryl sulfonamide bridges, aryl amide bridges and phenylmethylene bridges (benzyl compounds) are preferred, with aryl sulfonamide and phenylmethylene being particularly preferred.

Many of the compounds of Series A, Series B, Series C-1, and Series C-2, as well as compounds such as naloxone and naltrexone not only bind to the peptide of SEQ ID NO: 1, but also bind to MOR and activate or stimulate that receptor. Naloxone and naltrexone bind to MOR about 200 times more poorly than they bind to the pentapeptide of SEQ ID NO: 1. The tables of Example 2 illustrate relative binding abilities of exemplary compounds of Series A, Series B, Series C-1, and Series C-2 based on MOR stimulatory activity.

In some embodiments it is preferred that a compound useful in a contemplated method binds well to and activates MOR. In those cases, it is preferred that the compound bind to MOR to an extent of at least about ±20 percent as well as DAMGO at a concentration shown in the tables, indicating the compound is a complete agonist for the receptor. In other embodiments, it is preferred that a compound useful herein not bind well to MOR. In those embodiments, it is preferred that the compound exhibit less than about 80 percent the MOR stimulation provided by DAMGO at the same concentration, down to zero binding/stimulation. Illustrative binding percentages in the presence of stated concentrations of DAMGO are illustrated for exemplary compounds of Series A, Series B, Series C-1, and Series C-2 in the tables of Example 2, hereinafter.

Series D Compounds

A 1,4,8-triazaspiro[4,5]-decan-2-one compound of Series D corresponds in structure to the formula

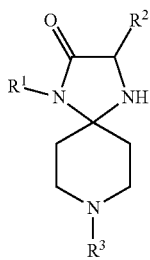

wherein $R^1$ represents hydrogen; a linear or branched unsubstituted or at least monosubstituted alkyl group that can comprise at least one heteroatom as a link; a linear or branched unsubstituted or at least monosubstituted alkenyl group that can comprise at least one heteroatom as a link; a linear or branched unsubstituted or at least monosubstituted alkynyl group that can comprise at least one heteroatom as a link; an unsubstituted or at least monosubstituted aryl group or an unsubstituted or at least monosubstituted heteroaryl group, which aryl and heteroaryl groups may be bonded via a linear or branched alkylene group that can comprise at least one heteroatom as a link; or a —C(═O)OR$^7$ group that can be bonded via a linear or branched alkylene group;

$R^2$ represents hydrogen; a linear or branched unsubstituted or at least monosubstituted alkyl group that can comprise at least one heteroatom as a link; a linear or branched unsubstituted or at least monosubstituted alkenyl group that can comprise at least one heteroatom as a link; a linear or branched unsubstituted or at least monosubstituted alkynyl group that can comprise at least one heteroatom as a link; an unsubstituted or at least monosubstituted aryl group or an unsubstituted or at least monosubstituted heteroaryl group, which aryl and heteroaryl group may be bonded via a linear or branched alkylene group that can comprise at least one heteroatom as a link;

$R^3$ represents a —S(═O)$_2$—R$^4$ group; a —C(═S)NH—R$^5$ group; or a —C(═O)NH—R$^6$ group;

$R^4$ represents a —NR$^{10}$R$^{11}$ group; a linear or branched unsubstituted or at least monosubstituted alkyl group that can comprise at least one heteroatom as a link; a linear or branched unsubstituted or at least monosubstituted alkenyl group that can comprise at least one heteroatom as a link; a linear or branched unsubstituted or at least monosubstituted alkynyl group that can comprise at least one heteroatom as a link; an unsubstituted or at least monosubstituted aryl group or an unsubstituted or at least monosubstituted heteroaryl group, which groups may be bonded via a linear or branched unsubstituted or at least monosubstituted alkylene group that can comprise at least one heteroatom as a link and may be condensed with an unsubstituted or at least monosubstituted monocyclic ring system; an unsubstituted or at least monosubstituted cycloaliphatic group, that can comprise at least one heteroatom as a ring member and that can be bonded via a linear or branched unsubstituted or at least monosubstituted alkylene group that can comprise at least one heteroatom as a link and that can be bridged by a linear or branched unsubstituted or at least monosubstituted alkylene group;

$R^5$ represents a linear or branched unsubstituted or at least monosubstituted alkyl group that can comprise at least one heteroatom as a link; a linear or branched unsubstituted or at least monosubstituted alkenyl group that can comprise at least one heteroatom as a link; a linear or branched unsubstituted or at least monosubstituted alkynyl group that can comprise at least one heteroatom as a link; an unsubstituted or at least monosubstituted aryl group or an unsubstituted or at least monosubstituted heteroaryl group, which group may be bonded via a linear or branched unsubstituted or at least monosubstituted alkylene group that can comprise at least one heteroatom as a link; an unsubstituted or at least monosubstituted cycloaliphatic group, that can comprise at least one heteroatom as a ring member or that can be bonded via a linear or branched unsubstituted or at least monosubstituted alkylene group that can comprise at least one heteroatom as a link; a —C(═O)OR$^8$ group or a —C(═O)OR$^9$ group, that can, in either case, be bonded via a linear or branched alkylene group;

$R^6$ represents an unsubstituted or at least monosubstituted aryl group or an unsubstituted or at least monosubstituted heteroaryl group, which aryl and heteroaryl groups may be bonded via a linear or branched unsubstituted or at least monosubstituted alkylene group that can comprise at least one heteroatom as a link; or for an unsubstituted or at least monosubstituted cycloaliphatic group, that can comprise at least one heteroatom as a ring member or that can be bonded via a linear or branched unsubstituted or at least monosubstituted alkylene group that can comprise at least one heteroatom as a link;

$R^7$, $R^8$, $R^9$, $R^{10}$, and $R^{11}$, each independently represent a linear or branched alkyl group, a linear or branched alkenyl group, or a linear or branched alkynyl group, or a physiologically acceptable salt thereof.

Preferably for a 1,4,8-triazaspiro[4,5]-decan-2-one compound corresponding to the formula above, $R^1$ represents hydrogen; a linear or branched unsubstituted or at least monosubstituted $C_{1-10}$ alkyl group that can comprise at least one heteroatom as a link; a linear or branched unsubstituted or at least monosubstituted $C_{2-10}$ alkenyl group that can comprise at least one heteroatom as a link; a linear or branched unsubstituted or at least monosubstituted $C_{2-10}$ alkynyl group that can comprise at least one heteroatom as a link; an unsubstituted or at least monosubstituted five-membered to fourteen-membered aryl group or heteroaryl group, that can be bonded via a linear or branched $C_{1-5}$ alkylene group that can comprise at least one heteroatom as a link; a —C(=O)OR$^7$ group that can be bonded via a linear or branched $C_{1-5}$ alkylene group;

$R^2$ represents hydrogen; a linear or branched unsubstituted or at least monosubstituted $C_{1-10}$ alkyl group that can comprise at least one heteroatom as a link; a linear or branched unsubstituted or at least monosubstituted $C_{2-10}$ alkenyl group that can comprise at least one heteroatom as a link; a linear or branched unsubstituted or at least monosubstituted $C_{2-10}$ alkynyl group that can comprise at least one heteroatom as a link; an unsubstituted or at least monosubstituted five-membered to fourteen-membered aryl or heteroaryl group, that can be bonded via a linear or branched $C_{1-5}$ alkylene group that can comprise at least one heteroatom as a link;

$R^4$ represents an NR$^{10}$R$^{11}$ group; a linear or branched unsubstituted or at least monosubstituted $C_{1-10}$ alkyl group that can comprise at least one heteroatom as a link; a linear or branched unsubstituted or at least monosubstituted $C_{2-10}$ alkenyl group that can comprise at least one heteroatom as a link; a linear or branched unsubstituted or at least monosubstituted $C_{2-10}$ alkynyl group that can comprise at least one heteroatom as a link; an unsubstituted or at least monosubstituted five-membered to fourteen-membered aryl group or heteroaryl group, that can be bonded via a linear or branched unsubstituted or at least monosubstituted $C_{1-5}$ alkylene group that can comprise at least one heteroatom as a link and may be condensed with a five-membered or six-membered monocyclic ring system; an unsubstituted or at least monosubstituted $C_{3-8}$-cycloaliphatic group that can comprise at least one heteroatom as a ring member or that can be bonded via a linear or branched unsubstituted or at least monosubstituted $C_{1-5}$ alkylene group that can comprise at least one heteroatom as a link and that can be bridged by a linear or branched unsubstituted or at least monosubstituted C.sub.1-5 alkylene group;

$R^5$ represents a linear or branched unsubstituted or at least monosubstituted $C_{1-10}$ alkyl group that can comprise at least one heteroatom as a link; a linear or branched unsubstituted or at least monosubstituted $C_{2-10}$ alkenyl group that can comprise at least one heteroatom as a link; a linear or branched unsubstituted or at least monosubstituted $C_{2-10}$ alkynyl group that can comprise at least one heteroatom as a link; an unsubstituted or at least monosubstituted five-membered to fourteen-membered aryl or heteroaryl group, that can be bonded via a linear or branched unsubstituted or at least monosubstituted $C_{1-5}$ alkylene group that can comprise at least one heteroatom as a link; an unsubstituted or at least monosubstituted $C_{3-8}$-cycloaliphatic group that can comprise at least one heteroatom as a ring member and that can be bonded via a linear or branched unsubstituted or at least monosubstituted $C_{1-5}$ alkylene group that can comprise at least one heteroatom as a link; a —C(=O)OR$^8$ group or a —C(=O)OR$^9$ group either of that can be bonded via a linear or branched $C_{1-10}$ alkylene group;

$R^6$ represents an unsubstituted or at least monosubstituted five-membered to fourteen-membered aryl or heteroaryl group, which aryl or heteroaryl group may be bonded via a linear or branched unsubstituted or at least monosubstituted $C_{1-5}$ alkylene group that can comprise at least one heteroatom as a link; an unsubstituted or at least monosubstituted $C_{3-8}$-cycloaliphatic group that can comprise at least one heteroatom as a ring member, or that can be bonded via a linear or branched unsubstituted or at least monosubstituted $C_{1-5}$ alkylene group that can comprise at least one heteroatom as a link; and $R^7$, $R^8$, $R^9$, $R^{10}$, and $R^{11}$, independently represent a linear or branched $C_{1-5}$ alkyl group, a linear or branched $C_{2-5}$ alkenyl group, or a linear or branched $C_{2-5}$ alkynyl group.

Compounds A, B and C whose structural formulas are shown below are illustrative preferred compounds of Series D.

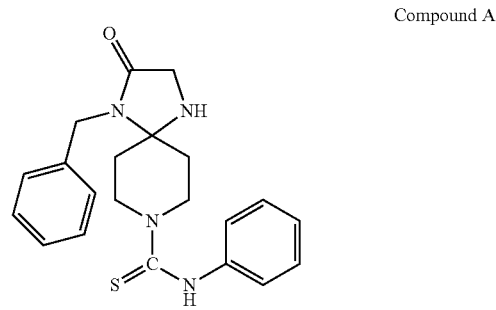

Compound A

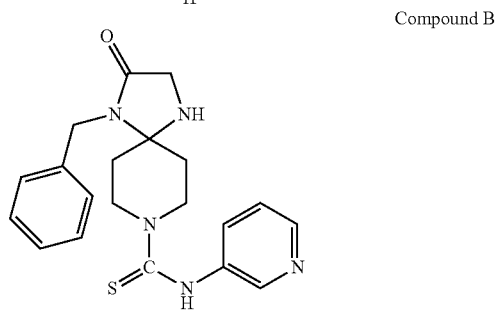

Compound B

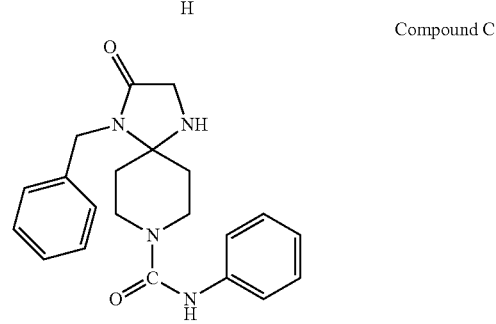

Compound C

Series E Compounds

A substituted 1-oxa-3,8-diazaspiro[4.5]-decan-2-one compound of Series E corresponds in structure to the formula

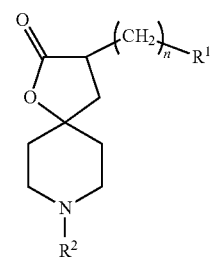

wherein n is 1, 2, 3, 4 or 5;

$R^1$ denotes:

an optionally substituted 6- or 10-membered aryl group or an optionally substituted 5- to 14-membered heteroaryl group, wherein the aryl or heteroaryl group optionally can be fused with a saturated or unsaturated, optionally substituted mono- or bicyclic ring system;

$R^2$ denotes:

—C(=S)—NH—$R^3$;   —C(=O)—NH—$R^4$;   —S(=O)$_2$—$R^5$;

—(CH$_2$)—C(=O)—NH—$R^6$;

—(CH$_2$)-D$_{aa}$-(CH$_2$)$_{bb}$-E$_{cc}$-(CH$_2$)$_{dd}$—$R^7$, wherein aa=0 or 1;

bb=0, 1 or 2;

cc=0 or 1; dd=0 or 1; and the sum of aa and cc does not equal 0; and

D and E each independently denote O, S, NH, N(CH$_3$), N(C$_2$H$_5$) or N[CH(CH$_3$)$_2$];

—C(=O)—$R^8$, or —S(=O)$_2$—NR$^9$R$^{10}$;

$R^3$ denotes:

—(CHR$^{11}$)—(CH$_2$)$_w$—C(=O)—O—$R^{12}$, wherein w=0 or 1;

—(CHR$^{13}$)—(CH$_2$)$_a$—K$_b$—(CH$_2$)$_c$-L$_d$-$R^{14}$, wherein a=0, 1 or 2; b=0 or 1; c=0, 1 or 2; d=0 or 1, and K and L each independently denote O, S, NH, N(CH$_3$), N(C$_2$H$_5$) or N[CH(CH$_3$)$_2$];

a linear or branched, saturated or unsaturated, optionally substituted C$_{1-10}$ aliphatic group;

an unsaturated or saturated, optionally substituted 3-, 4-, 5-, 6-, 7-, 8- or 9-membered cycloaliphatic group which optionally can be bridged with 1 or 2 linear or branched, optionally substituted C$_{1-5}$ alkylene groups or fused with a saturated, unsaturated or aromatic, optionally substituted mono- or bicyclic ring system, or both; or an optionally substituted 6- or 10-membered aryl group; or an optionally substituted 5- to 14-membered heteroaryl group, wherein the aryl or heteroaryl group optionally can be fused with a saturated or unsaturated, optionally substituted mono- or bicyclic ring system;

$R^4$ denotes:

—(CHR$^{15}$)—(CH$_2$)$_e$-M$_f$-(CH$_2$)$_g$—P$_h$—$R^{16}$, wherein e=0, 1 or 2; f=0 or 1; g=0, 1 or 2; h=0 or 1; and M and P each independently denote O, S, NH, N(CH$_3$), N(C$_2$H$_5$) or N[CH(CH$_3$)$_2$];

a linear or branched, saturated or unsaturated, optionally substituted C$_{1-10}$ aliphatic group;

an unsaturated or saturated, optionally substituted 3-, 4-, 5-, 6-, 7-, 8- or 9-membered cycloaliphatic group which optionally can be bridged with 1 or 2 linear or branched, optionally substituted C$_{1-5}$ alkylene groups or fused with a saturated, unsaturated or aromatic, optionally substituted mono- or bicyclic ring system, or both;

or an optionally substituted 6- or 10-membered aryl group or optionally substituted 5- to 14-membered heteroaryl group, wherein said aryl or heteroaryl group optionally can be fused with a saturated or unsaturated, optionally substituted mono- or bicyclic ring system;

$R^5$ denotes:

—(CHR$^{17}$)—(CH$_2$)$_k$-Q$_l$-(CH$_2$)$_m$-T$_o$-$R^{18}$, wherein k=0, 1 or 2; l=0 or 1; m=0, 1 or 2; o=0 or 1; and Q and T each independently denote O, S, NH, N(CH$_3$), N(C$_2$H$_5$) or N[CH(CH$_3$)$_2$];

a linear or branched, saturated or unsaturated, optionally substituted C$_{1-10}$ aliphatic group;

an unsaturated or saturated, optionally substituted 3-, 4-, 5-, 6-, 7-, 8- or 9-membered cycloaliphatic group which optionally can be bridged with 1 or 2 linear or branched, optionally substituted C$_{1-5}$ alkylene groups or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system;

$R^6$ denotes:

a linear or branched, saturated or unsaturated, optionally substituted C$_{1-10}$ aliphatic group;

an unsaturated or saturated, optionally substituted 3-, 4-, 5-, 6-, 7-, 8- or 9-membered cycloaliphatic group which optionally can be bridged with 1 or 2 linear or branched, optionally substituted C$_{1-5}$ alkylene groups or fused with a saturated, unsaturated or aromatic, optionally substituted mono- or bicyclic ring system, or both; an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system;

$R^7$ denotes:

a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein said group optionally can be substituted with 1, 2, 3, 4 or 5 substituents independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$,   —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_3$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$;

or a group selected from the group consisting of phenyl, naphthyl, and [1,2,3,4]-tetrahydronaphthyl, wherein said group optionally can be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_3$—CH$_2$—CH$_3$, —NH—C(=O)—CH$_3$, —NH—C(=O)—C$_2$H$_5$, —NH—C(=O)—C(CH$_3$)$_3$,   —C(=O)—OH,   —(CH$_2$)—C(=O)—OH, —C(=O)—O—CH$_3$,   —C(=O)—O—CH$_2$—CH$_3$, —C(=O)—O—CH(CH$_3$)$_2$,   —C(=O)—O—C(CH$_3$)$_3$, —NH—CH$_3$, —NH—C$_2$H$_5$, —NH—CH(CH$_3$)$_2$, —NH—C(CH$_3$)$_3$,   —N(CH$_3$)$_2$,   —N(C$_2$H$_5$)$_2$,   —N(CH$_3$)(C$_2$H$_5$), —C(=O)—H,   —C(=O)—CH$_3$,   —C(=O)—C$_2$H$_5$, —C(=O)—C(CH$_3$)$_3$, —C(=O)—CF$_3$, —C(=O)—C$_2$F$_5$, —C(=O)—NH$_3$,   —C(=O)—NH—CH$_3$,   —C(=O)—

NH—$C_2H_5$, —C(=O)—NH—C($CH_3$)$_3$, —C(=O)—N($CH_3$)$_2$, —C(=O)—N($C_2H_5$)$_2$, —S(=O)$_2$—$CH_3$, —S(=O)$_2$—$C_2H_5$, —NH—S(=O)$_2$—$CH_3$, —S(=O)$_3$—NH—$CH_3$, —S(=O)$_2$—$NH_2$, —S(=O)$_2$—NH-phenyl, phenyl and benzyl, wherein the cyclic moiety of the groups —S(=O)$_2$—NH-phenyl, phenyl and benzyl optionally can be substituted with 1, 2, 3, 4 or 5 substituents independently selected from the group consisting of F, Cl, Br, —OH, —$CF_3$, —$SF_5$, —$NO_2$, methyl, ethyl, n-propyl, isopropyl, n-butyl, sec-butyl, isobutyl, tert-butyl, n-pentyl, n-hexyl, n-heptyl, —O—$CH_3$, —O—$C_2H_5$, —O—CH($CH_3$)$_3$, —O—$CH_2$—$CH_3$—$CH_3$, —O—C($CH_3$)$_3$, —O—$CH_2$—$CH_2$—$CH_2$—$CH_3$, —O—$CF_3$, —S—$CF_3$, phenyl and —O— benzyl;

$R^8$ denotes —(CH$R^{19}$)—$V_p$—(CH$_2$)$_q$—(CH$_2$)$_r$—$W_s$—$R^{20}$, wherein
p=0 or 1;
q=0, 1 or 2;
r=0, 1 or 2;
s=0 or 1; and
V and W each independently denote O, S, NH, —NH—$CH_3$, —NH—$C_2H_5$, —NH—CH($CH_3$)$_2$;
—(CH=CH)—$R^{21}$;
—(C$R^{22}R^{23}$)—$Y_t$—(C$R^{24}R^{25}$)$_u$—(CH$_2$)$_v$—C(=O)—O$R^{26}$, wherein
t=0 or 1, u=0 or 1;
v=0 or 1, and Y denotes O, S, NH, —NH—$CH_3$, —NH—$C_2H_5$, —NH—CH($CH_3$)$_2$;
—(CH$R^{27}$)—O—C(=O)—$R^{28}$;
—CH[(CH$_2$)$R^{29}$][NH—S(=O)$_2$—$R^{30}$];
—CH[(CH$_2$)$R^{31}$][NH—C(=O)—O—$R^{32}$];

a linear or branched, saturated or unsaturated, optionally substituted $C_{1-10}$ aliphatic group selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl, n-octyl, —(CH$_2$)—(CH) ($C_2H_5$)—(CH$_2$)—(CH$_2$)—(CH$_2$)—(CH$_3$), vinyl, 1-propenyl, 2-propenyl, 1-butenyl, 2-butenyl and 3-butenyl;

an unsaturated or saturated, optionally substituted 3-, 4-, 5-, 6-, 7-, 8- or 9-membered cycloaliphatic group that optionally can be bridged with 1 or 2 linear or branched, optionally substituted $C_{1-5}$ alkylene groups, or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system;

$R^9$ and $R^{10}$ each independently denote a linear or branched, saturated or unsaturated, optionally substituted $C_{1-10}$ aliphatic group; $R^{11}$, $R^{13}$, $R^{15}$, $R^{17}$, $R^{19}$, $R^{22}$, $R^{23}$, $R^{24}$, $R^{25}$ and $R^{26}$ each independently denote a hydrogen or a linear or branched, saturated or unsaturated, optionally substituted $C_{1-10}$ aliphatic group;

$R^{12}$, $R^{28}$ and $R^{32}$ each independently denote a linear or branched, saturated or unsaturated, optionally substituted $C_{1-10}$ aliphatic group;

$R^{14}$, $R^{16}$, $R^{18}$ and $R^{20}$ each independently denote a linear or branched, saturated or unsaturated, optionally substituted $C_{1-10}$ aliphatic group;

an unsaturated or saturated, optionally substituted 3-, 4-, 5-, 6-, 7-, 8- or 9-membered cycloaliphatic group that optionally can be bridged with 1 or 2 linear or branched, optionally substituted $C_{1-5}$ alkylene groups, or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system; and $R^{21}$, $R^{27}$, $R^{29}$, $R^{30}$ and $R^{31}$ each independently denote an unsaturated or saturated, optionally substituted 3-, 4-, 5-, 6-, 7-, 8- or 9-membered cycloaliphatic group which optionally can be bridged with 1 or 2 linear or branched, optionally substituted $C_{1-5}$ alkylene groups, or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system; wherein the above-stated $C_{1-10}$ aliphatic groups each independently can optionally be substituted with 1, 2, 3, 4 or 5 substituents independently selected from the group consisting of F, Cl, Br, I, —CN, —$NO_2$, —OH, —SH and —$NH_2$;

the above-stated cycloaliphatic groups each independently can optionally be substituted with 1, 2, 3, 4 or 5 substituents independently selected from the group consisting of oxo (=O), thioxo (=S), F, Cl, Br, I, —CN, —$CF_3$, —$SF_5$, —OH, —O—$C_{1-5}$alkyl, —$NH_2$, —$NO_2$, —O—$CF_3$, —S—$CF_3$, —S—$CF_2$H, —S—$CFH_2$, —SH, —S—$C_{1-5}$-alkyl, —$C_{1-5}$alkyl, —C(=O)—OH, —(CH$_2$)—C(=O)—OH, —C(=O)—O—$C_{1-5}$alkyl, —(CH$_2$)—C(=O)—O—$C_{1-5}$alkyl, —O—C(=O)—$C_{1-5}$alkyl, —NH—$C_{1-5}$alkyl, —N($C_{1-5}$alkyl)$_2$, —NH-phenyl, —NH— pyridinyl, —N($C_{1-5}$alkyl)-phenyl, —N($C_{1-5}$alkyl)-pyridinyl, —NH—C(=O)—O—$C_{1-5}$alkyl, —C(=O)—H, —C(=O)—$C_{1-5}$alkyl, —C(=O)—$C_{1-5}$-perfluoroalkyl, —C(=O)—$NH_2$, —C(=O)—NH—$C_{1-5}$alkyl, C(=O)—N($C_{1-5}$alkyl)$_2$, —S(=O)$_2$—$C_{1-5}$ alkyl, —S(=O)$_2$-phenyl, —NH—S(=O)$_2$—$C_{1-5}$alkyl, —S(=O)$_2$—NH—$C_{1-5}$alkyl, —S(=O)$_2$—$NH_2$, —S(=O)$_2$—NH-phenyl, cyclohexyl, cyclopentyl, pyridinyl, [1,2,5]-thiadiazolyl, pyridazinyl, —(CH$_2$)-benzo[b]furanyl, —O-phenyl, —O-benzyl, phenyl and benzyl, wherein the cyclic moiety of the groups —S(=O)$_2$—NH-phenyl, —NH-phenyl, —NH-pyridinyl, —N($C_{1-5}$alkyl)phenyl, —N($C_{1-5}$ alkyl)pyridinyl, pyridinyl, cyclopentyl, [1,2,5]-thiadiazolyl, cyclohexyl, pyridazinyl, —S(=O)$_2$-phenyl, —O-phenyl, —O-benzyl, phenyl, —(CH$_2$)-benzo[b]furanyl and benzyl optionally can be substituted with 1, 2, 3, 4 or 5 substituents independently selected from the group consisting of F, Cl, Br, —OH, —$CF_3$, —$SF_5$, —CN, —$NO_2$, —$C_{1-5}$alkyl, —O—$C_{1-5}$alkyl, —O—$CF_3$, —S—$CF_3$, phenyl and —O-benzyl, and comprise 1, 2, 3, 4 or 5 heteroatom(s) mutually independently selected from the group consisting of oxygen, nitrogen and sulfur;

the above-stated $C_{1-5}$-alkylene groups each independently can optionally be substituted with 1, 2, 3, 4 or 5 substituents independently selected from the group consisting of F, Cl, Br, I, —CN, —$NO_2$, —OH, —SH and —$NH_2$;

the rings of the above-stated mono- or polycyclic ring systems each independently can optionally be substituted with 1, 2, 3, 4 or 5 substituents independently selected from the group consisting of oxo (=O), thioxo (=S), F, Cl, Br, I, —CN, —$CF_3$, —$SF_5$, —OH, —O—$C_{1-5}$alkyl —$NH_2$, —$NO_2$, —O—$CF_3$, —S—$CF_3$, —S—$CF_2$H, —S—$CFH_2$, —SH, —S—$C_{1-5}$-alkyl, —$C_{1-5}$alkyl, —C(=O)—OH, —(CH$_2$)—C(=O)—OH, —C(=O)—O—C$_{1-5}$alkyl, —(CH$_2$)—C(=O)—O—C$_{1-5}$alkyl, —O—C(=O)—C$_{1-5}$alkyl, —NH—C$_{1-5}$alkyl, —N(C$_{1-5}$alkyl)$_2$, —NH-phenyl, —NH-pyridinyl, —N(C$_{1-5}$alkyl)-phenyl, —N(C$_{1-5}$alkyl)-pyridinyl, —NH—C(=O)—O—C$_{1-5}$alkyl, —C(=O)—H, —C(=O)—C$_{1-5}$alkyl, —C(=O)—C$_{1-5}$-perfluoroalkyl, —C(=O)—NH$_2$, —C(=O)—NH—C$_{1-5}$alkyl, C(=O)—N—(C$_{1-5}$alkyl)$_2$, —S(=O)$_2$—C$_{1-5}$alkyl, —S(=O)$_2$-phenyl, —NH—S(=O)$_2$—C$_{1-5}$alkyl, —S(=O)$_2$—NH—C$_{1-5}$alkyl, —S(=O)$_2$—NH$_2$, —S(=O)$_2$—NH-phenyl, cyclohexyl, cyclopentyl, pyridinyl, [1,2,5]-thiadiazolyl, pyridazinyl, —(CH$_2$)-benzo[b]furanyl, —O-phenyl, —O-benzyl, phenyl and benzyl, wherein the cyclic moiety of the groups —S(=O)$_2$—NH-phenyl, —NH-phenyl, —NH-pyridinyl, —N(C$_{1-5}$alkyl)phenyl, —N(C$_{1-5}$alkyl)pyridinyl, pyridinyl, cyclopentyl, [1,2,5]-thiadiazolyl, cyclohexyl, pyridazinyl, —S(=O)$_2$-phenyl, —O-phenyl, —O-benzyl, phenyl, —(CH$_2$)-benzo[b]furanyl and benzyl optionally can be substituted with 1, 2, 3, 4 or 5 substituents independently selected from the group consisting of F, Cl, Br, —OH, —CF$_3$, —SF$_5$, —CN, —NO$_2$, C$_{1-5}$alkyl, —O—C$_{1-5}$ alkyl, —NH$_2$, —O—CF$_3$, —S—CF$_3$, phenyl and —O-benzyl;

the rings of the above-stated mono- or bicyclic ring systems are each independently 5-, 6- or 7-membered and each independently can optionally comprise as ring member(s), 1, 2, 3, 4 or 5 heteroatom(s) independently selected from the group consisting of oxygen, nitrogen and sulfur; the above-stated aryl or heteroaryl groups each independently can optionally be substituted with 1, 2, 3, 4 or 5 substituents independently selected from the group consisting of F, Cl, Br, I, —CN, —CF$_3$, —SF$_5$, —OH, —O—C$_{1-5}$alkyl —NH$_2$, —NO$_2$, —O—CF$_3$, —S—CF$_3$, —S—CF$_2$H, —S—CFH$_2$, —SH, —S—C$_{1-5}$-alkyl, —C$_{1-5}$alkyl, —C(=O)—OH, —(CH$_2$)—C(=O)—OH, —C(=O)—O—C$_{1-5}$alkyl, —(CH$_2$)—C(=O)—O—C$_{1-5}$alkyl, —O—C(=O)—C$_{1-5}$alkyl, —NH—C$_{1-5}$alkyl, —N(C$_{1-5}$alkyl)$_2$, —NH—C(=O)—O—C$_{1-5}$alkyl, —NH—C(=O)—C$_{1-5}$alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$alkyl, C(=O)—N—(C$_{1-5}$alkyl)$_2$, —S(=O)$_2$—C$_{1-5}$alkyl, —S(=O)$_2$-phenyl, —NH—S(=O)$_2$—C$_{1-5}$alkyl, —S(=O)$_2$—NH—C$_{1-5}$alkyl, —S(=O)$_2$—NH$_2$, —S(=O)$_2$—NH-phenyl, cyclohexyl, cyclopentyl, pyridinyl, —(CH$_2$)-benzo[b]furanyl, —O-phenyl, —O-benzyl, phenyl and benzyl, wherein the cyclic moiety of the groups pyridinyl, cyclopentyl, cyclohexyl, pyridazinyl, —S(=O)$_2$-phenyl, —S(=O)$_2$—NH-phenyl, —O-phenyl, —O-benzyl, phenyl, —(CH$_2$)-benzo[b]furanyl, optionally can be substituted with 1, 2, 3, 4 or 5 substituents independently selected from the group consisting of F, Cl, Br, —OH, —CF$_3$, —SF$_5$, —NO$_2$, C$_{1-5}$alkyl, —O—C$_{1-5}$alkyl, —O—CF$_3$, —S—CF$_3$, phenyl and -o-benzyl;

and the above-stated heteroaryl groups each independently can optionally comprise as ring member(s), 1, 2, 3, 4 or 5 heteroatom(s) independently selected from the group consisting of oxygen, nitrogen and sulfur; or a pharmaceutically acceptable salt or solvate thereof.

Preferably, in a contemplated compound, $R^1$ denotes a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, [3,4]-dihydro-2H-1,4-benzoxazinyl, oxazolyl, isoxazolyl, pyridazinyl, pyrazinyl, pyrimidinyl, indazolyl, quinazolinyl, quinolinyl and isoquinolinyl. That $R^1$ group can optionally be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, —SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, n-hexyl, n-heptyl, —NH—C(=O)—O—CH$_3$, —NH—C(=O)—O—C$_2$H$_5$, —NH—C(=O)—O—C(CH$_3$)$_3$, —NH—C(=O)—CH$_3$, —NH—C(=O)—C$_2$H$_5$, —NH—C(=O)—C(CH$_3$)$_3$, —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_3$—CH$_3$, —S(=O)$_3$—C$_2$H$_5$, —NH—S(=O)$_2$—CH$_3$, —S(=O)$_3$—NH—CH$_3$, —S(=O)$_2$—NH$_2$, —S(=O)$_2$—NH-phenyl and -benzyl, wherein the cyclic moiety of each phenyl or benzyl group independently can optionally be substituted with 1,2,3,4, or 5 substituents independently selected from the group consisting of F, Cl, Br, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O— benzyl.

It is also preferred that the $R^2$ group of a contemplated compound denote C(=S)—NH—$R^3$; —C(=O)—NH—$R^4$; —S(=O)$_2$$R^5$; —(CH$_2$)—C(=O)—NH—$R^6$; —(CH$_2$)—O—$R^7$, —(CH$_2$)—S—$R^7$, —(CH$_2$)—NH—$R^7$, —(CH$_2$)—N(CH$_3$)—$R^7$, —(CH$_2$)—(CH$_2$)—O—$R^7$, —(CH$_2$)—(CH$_2$)—S—$R^7$, —(CH$_2$)—NH—$R^7$, —(CH$_2$)—N(CH$_3$)—$R^7$, —(CH$_2$)—(CH$_2$)—(CH$_2$)—O—$R^7$, —(CH$_2$)—(CH$_2$)—(CH$_2$)—S—$R^7$, —(CH$_2$)—(CH$_2$)—(CH$_2$)—NH—$R^7$, —(CH$_2$)—(CH$_2$)—(CH$_2$)—N(CH$_3$)—$R^7$, —(CH$_2$)—O—(CH$_2$)—$R^7$, —(CH$_2$)—S—(CH$_2$)—$R^7$, —(CH$_2$)—NH—(CH$_2$)—$R^7$, —C(=O)—$R^8$, or —S(=O)$_2$—NR$^9$R$^{10}$.

Pharmaceutical Compositions

A contemplated FLNA-binding compound useful in the invention can be provided for use by itself, or as a pharmaceutically acceptable salt. Regardless of whether in the form of a salt or not, a contemplated composition is preferably present in a binding-effective amount dissolved or dispersed in a pharmaceutically acceptable diluent that forms a pharmaceutical composition, and that pharmaceutical composition is administered to the cancerous cells.

A contemplated FLNA-binding compound can be used in the manufacture of a medicament (pharmaceutical composition) that is useful for inhibiting growth of cancer cells as discussed herein in a mammal as well as in mammalian cells and mammalian cell preparations.

A mammal in need of treatment and to which a pharmaceutical composition containing a contemplated FLNA-binding compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like. Where in vitro mammalian cell contact is contemplated, a tissue culture of cancerous cells from an illustrative mammal is often utilized, as is illustrated hereinafter.

A contemplated pharmaceutical composition contains a binding-effective amount of a contemplated FLNA-binding compound or a pharmaceutically acceptable salt thereof dissolved or dispersed in a physiologically tolerable carrier. Such a composition can be administered to mammalian cells in vitro as in a cell culture, or in vivo as in a living, host mammal in need.

A contemplated composition is typically administered a plurality of times over a period of days. More usually, a contemplated composition is administered once or twice daily. It is contemplated that once administration of a contemplated FLNA-binding compound has begun, the compound is administered chronically for the duration of the study being carried out, until the cancerous cell growth is inhibited to a desired extent.

A contemplated compound can bind to FLNA at a 100 femtomolar concentration and effectively inhibits cytokine release from LPS-stimulated astrocytes in vitro at that concentration. A contemplated compound is more usually utilized at picomolar to micromolar amounts. Thus, another way to achieve an effective amount of a contemplated FLNA-binding compound present in a contemplated pharmaceutical composition is to provide an amount that provides a FLNA-binding compound concentration of about 100 femtomolar to about micromolar to a host animal's blood stream or to an in vitro cell medium in practicing a contemplated method of the invention. A more usual amount is about picomolar to about micromolar. A still more usual amount is about picomolar to about nanomolar. A skilled worker can readily determine an appropriate dosage level of a contemplated FLNA-binding compound to inhibit cancer cell proliferation (growth).

A contemplated pharmaceutical composition can be administered orally (perorally), parenterally, by inhalation spray in a formulation containing conventional nontoxic pharmaceutically acceptable carriers, adjuvants, and vehicles as desired. The term parenteral as used herein includes subcutaneous, intravenous, intramuscular, intrasternal injections, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., Pharmaceutical Dosage Forms, Marcel Decker, New York, N.Y., 1980.

As already noted, some contemplated FLNA-binding benzazocine-ring compounds are commercially available. Inasmuch as a contemplated pharmaceutical composition utilizes a far lesser amount of FLNA-binding benzazocine-ring compound than the commercially used amount of that active agent, a commercially available composition can be diluted appropriately for use herein. Thus, if the commercial product is a tablet, the commercial tablet can be crushed and then diluted with more of the same or similar diluent. Similarly, where the commercially available FLNA-binding benzazocine-ring compound is formulated to be a liquid for parenteral administration, that parenteral product can be diluted appropriately with normal saline, or other pharmaceutically acceptable liquid diluent. It is preferred that a contemplated pharmaceutical composition be prepared ab initio rather than by reformulating a commercially available product.

For injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline.

Liquid pharmaceutical compositions include, for example, solutions suitable for parenteral administration. Sterile water solutions of an active component or sterile solution of the active component in solvents comprising water, ethanol, or propylene glycol are examples of liquid compositions suitable for parenteral administration.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. In such solid dosage forms, a contemplated compound is ordinarily combined with one or more excipients appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets, capsules and pills can additionally be prepared with enteric coatings.

Preferably, the pharmaceutical composition is in unit dosage form. In such form, the composition is divided into unit doses containing appropriate quantities of the FLNA-binding benzazocine-ring compound as active agent. The unit dosage form can be a packaged preparation, the package containing discrete quantities of the preparation, for example, in vials or ampules.

Several useful contemplated FLNA-binding benzazocine-ring compounds are amines and can typically be used in the form of a pharmaceutically acceptable acid addition salt derived from an inorganic or organic acid. Exemplary salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

The reader is directed to Berge, *J. Pharm. Sci.* 68(1):1-19 (1977) for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the acid used and the salt prepared need not be pharmaceutically acceptable.

Materials and Methods

Antibodies

Antibodies Used for Immunoprecipitation

| Antigen | Antibody (Ab) Source Catalog No. | Ab Type |
| --- | --- | --- |
| Akt1 | Santa Cruz 5298 | Mouse mAb |
| ERK2 | Santa Cruz 154 | Rabbit pAb |
| mTOR | Santa Cruz 1550-R | Rabbit pAb |
| Filamin A | Santa Cruz 7565 | Goat pAb |

Antibodies Used for Western Blotting

| Antigen | Antibody (Ab) Source Catalog No. | Ab Type |
| --- | --- | --- |
| Akt1-3 | Santa Cruz 8312 | Rabbit pAb |
| Akt1-3 pS$^{473}$ | Santa Cruz 7985-R | Rabbit pAb |
| ERK2 | Santa Cruz 271458 | Mouse mAb |
| ERK2 pT$^{183}$/pY$^{185}$ | Santa Cruz 81492 | Mouse mAb |
| mTOR | Santa Cruz 136269 | Mouse mAb |
| mTOR pS$^{2448}$ | Cell Signaling 2971 | Rabbit pAb |
| Filamin A | Santa Cruz 28284 | Rabbit pAb |
| Filamin A pS$^{2152}$ | abcam 75978 | Rabbit pAb |
| Ki67 | Santa Cruz 15402 | Rabbit pAb |
| PCNA | Santa Cruz 56 | Mouse mAb |
| Actin | Santa Cruz 7210 | Rabbit pAb |
| PTEN | Santa Cruz 7974 | Mouse mAb |
| PP2A-Aα/β | Santa Cruz 81604 | Mouse mAb |
| Cleaved caspase-3 (Asp175) | Cell Signaling 9579 | Rabbit mAb |
| Cleaved PARP (Asp 214) | Cell Signaling 9541 | Rabbit mAb |

Cell Lines

Several cell lines were utilized in the following in vitro studies. Cell lines utilized in in vivo studies are noted hereinafter. The cell lines used in vitro were as follows: human brain epithelial cells, glioblastoma, astrocytoma U-87 MG/ATCC® HTB-14; human skin epithelial cells, melanoma A2058/ATCC® CRL-11147; human lung epithelial cells, small cell lung carcinoma DMS 114/ATCC® CRL-2066; human pancreas epithelial cells, carcinoma MIA PaCa-2/ATCC® CRL-1420; and human mammary gland/breast epithelial cells, adinocarcinoma MCF7/ATCC® HTB-22.

Glucose Utilization and Dependence of Cancer Cell Lines

To determine the effect of Compound C0105 on glucose utilization, the cancer and primary normal cells were plated extremely thinly (10%). Once cells attached, Compound C0105 was added at 0.1, 0.5, 1 or 5 nM in the medium twice daily (6 hours apart) for 4 days. The cells were serum-deprived (glucose deprived) for 2 hours. Cells were then rinsed with 1 ml PBS and glucose uptake was assessed by contacting the cells with [$^3$H]glucose (0.01 uCi/l ml) in Kreb's Ringer for 2 hours. Cells were then rinsed with 1 ml PBS 3 times, scraped off and their glucose content counted by liquid scintillation spectrophotometry.

To measure the effect of Compound C0105 on glucose dependence, the cancer and primary normal cells were grown to >90% confluency. The cells were washed with PBS, incubated in 0.1% fetal bovine serum (FBS) for 16 hours and incubated in glucose-free 0.1% FBS-containing medium for up to 4 days in the presence of vehicle or 1 nM Compound C0105. The cells in the entire well were collected by centrifugation. Following PBS washes, the cell pellets were sonicated in ice-cold immunoprecipitation buffer (25 mM HEPES, pH 7.5; 200 mM NaCl; 1 mM EDTA; 50 µg/ml leupeptin; 10 µg/ml aprotinin; 2 µg/ml soybean trypsin inhibitor; 0.04 mM PMSF; 5 mM NaF; 1 mM sodium vanadate; 0.5 mM β-glycerophosphate; and 0.02% 2-mercaptoethanol). The protein concentrations were measured by the Bradford method.

The cells were homogenized and the obtained homogenates were centrifuged to remove nucleus and mitochondria. The resultant post-mitochondrial lysates were solubilized by adding equal volume of 2×PAGE sample preparation buffer and boiled for 5 minutes. The level of apoptotic cell death was determined using Western blotting in 50 µg solubilized cell lysates with antibodies against cleaved PARP-1 (Asp$^{214}$) and caspase-3 (Asp$^{175}$), both at 1:1000 dilution. Immunoreactivity was visualized by reaction in ECL Plus chemiluminescent reagent for exactly 5 minutes, followed by immediate exposure of the blot to X-ray film (Z & Z Medical). Bands at the relevant molecular masses of Ki67 and PCNA were quantified by densitometric scan. Membranes were stripped, washed 5× in 0.1% PBST (2 minutes each wash) and the actin content analyzed by immunoblotting using monoclonal anti-actin to illustrate even loading.

In a separate series of studies, the effect of Compound C0105 on glucose dependence was assessed by changes in cell density. The cancer and primary normal cells were grown to >90% confluency. The cells were washed with PBS, incubated in 0.1% fetal bovine serum (FBS) for 16 hours and incubated in glucose-free 0.1% FBS-containing medium for up to 4 days in the presence of vehicle or 1 nM Compound C0105.

Proliferation of Cancer Cell Lines

To study the effect of Compound C0105 on PI3K activity, the cancer and primary normal cells were cultured to approximately 60-70% confluency, serum deprived for 4 hours, briefly washed with PBS and treated with vehicle or 0.1, 0.5, 1 or 5 nM Compound C0105 for 24 hours with in 0.1% FBS-containing culture medium. The cells were then washed with PBS, scraped off and collected by centrifugation. The cell pellets were sonicated in ice-cold immunoprecipitation buffer and protein concentrations measured by the Bradford method. The cell homogenates were solubilized by adding equal volume of 2×PAGE sample preparation buffer and boiling for 5 minutes. Fifty µl of solubilized cell lysates were separated using SDS-PAGE, and the separated proteins electrophoretically transferred to nitrocellulose membranes.

Samples from each set of vehicle- and Compound C0105-treated cells were run on the same blots. Membranes were washed with PBS, blocked overnight (about 18 hours) at 4° C. with 10% milk in PBS containing 0.1% Tween-20 (PBST), and washed 3× in 0.1% PBST baths (2 minutes each).

To assess the level of cell cycling, membranes loaded with the above-described cell lysates were incubated for 2 hours at room temperature with antibodies to the proliferation markers Ki67 and PCNA. Membranes were washed 3× in 0.1% PBST baths (2 minutes each), incubated for 1 hour with 1:7,500 dilution of species appropriate HRP-conjugated secondary antibodies, and washed 3× in 0.1% PBST baths (2 minutes each).

Immunoreactivity was visualized by reaction in ECL Plus chemiluminescent reagent for exactly 5 minutes, followed by immediate exposure of the blot to X-ray film (Z & Z Medical). Bands at the relevant molecular masses of Ki67 and PCNA were quantified by densitometric scan. Membranes were stripped, washed 5× in 0.1% PBST (2 minutes each) and the actin content analyzed by immunoblotting using monoclonal anti-actin to illustrate even loading.

In a separate experimental series, the effect of Compound C0105 on cell proliferation was determined by immunohistochemical method using monoclonal anti-Ki67. Cells were washed with PBS, fixed in 4% paraformaldehyde and incubated with monoclonal anti-Ki67 followed by FITC-conjugated anti-mouse IgG.

Levels of $pS^{2152}$FLNA, FLNA Associations and Akt, ERK and mTOR Activation

To study the effect of Compound C0105 on $pS^{2152}$FLNA levels, FLNA linkages to key regulators including protein phosphatases as well as activated Akt ($pS^{473}$-, $pT^{308}$-Akt), mTOR ($pS^{2442}$mTOR) and ERK (pY/pT-ERK) levels, the cancer and normal cells were cultured to approximately 90% confluency and treated with vehicle or varying concentrations of Compound C0105. The cells were washed with warm phosphate-buffered saline (PBS), pH 7.2, dissociated, homogenized by sonication and solubilized using 0.5% NP-40 (nonoxynol 40), 0.2% sodium cholate and 0.5% digitonin for 1 hour at 4° C.

The cell lysates were diluted 5-fold with immunoprecipitation buffer and immunoprecipitated with anti-FLNA, -Akt, -mTOR and -ERK2 as described previously [Talbot et al., J Clin Inv 122(4):1-23 (2012); Wang et al., J Neurosci 32(29):9773-9784 (2012)]. The levels of FLNA linkages, activated phosphorylated Akt ($pS^{473}$ and $pT^{308}$), phosphorylated mTOR ($pS^{2448}$) and phosphorylated ERK2 (pY/pT) were determined in anti-FLNA, -Akt, -mTOR and -ERK2 immunoprecipitates by Western blotting with appropriate antibodies directed against PTEN, PP2A, K-RAS, ras-GAP (FLNA linkages), $pS^{473}$Akt, $pT^{308}$Akt, $pS^{2448}$mTOR and pY/pT ERK2 (activation of Akt, mTOR and ERK2).

In a separate series of studies, the level of active K-RAS (GTP-bound K-RAS) was determined by precipitation using Raf RBD-conjugated agarose beads from 100 µg of lysates of cancer cells (prepared as described above) following 4-day treatment with varying concentrations of Compound C0105. To ascertain even loading, actin in the cell lysates was immunoprecipitated with goat anti-actin. The precipitates were collected by centrifugation, washed and the active K-RAS and actin eluted by boiling for 5 min in 1×SDS-PAGE. The levels of active K-RAS and actin in 50 µg of cell lysates were size-fractionated on 12% SDS-PAGE, electrophoretically transferred to nitrocellulose membranes and determined by Western blotting with specific monoclonal antibodies against K-RAS and actin.

Blocking PTI-910 Effects with FLNA Pentapeptide VAKGL and Assessment of FLNA Conformation To confirm that Compound C0105 effects are mediated by binding to FLNA pentapeptide VAKGL (SEQ ID NO: 1), cancer cells were incubated with vehicle or 1 nM Compound C0105 together with 10 µM of decoy pentapeptide (VAKGL) or control peptide, VAAGL (K-A decoy peptide; SEQ ID NO: 2) for 4 days as described previously.

Cells were harvested by centrifugation and solubilized, and lysates were immunoprecipitated with anti-FLNA. Levels of $pS^{2152}$FLNA, PTEN, PP2A-Aα, PP2A-Aβ and Ras-GAP in the anti-FLNA immunoprecipitates were determined by Western blotting. Blots were stripped and reprobed with anti-FLNA to demonstrate even immunoprecipitation and loading.

A separate series of studies was undertaken to determine whether Compound C0105's reduction in proliferation markers is also mediated by Compound C0105 binding to the pentapeptide region of FLNA. As above, cancer cells were incubated for 4 days with vehicle or 1 nM Compound C0105 together with 10 µM of decoy pentapeptide (VAKGL; SEQ ID NO: 1) or control peptide, VAAGL (SEQ ID NO: 2).

Cells were harvested by centrifugation and the resultant cell pellets were washed and sonicated in ice-cold immunoprecipitation buffer. Protein concentrations were measured by the Bradford method. Cell homogenates were solubilized by adding equal volumes of 2×PAGE sample preparation buffer and boiled for 5 minutes. Fifty µl of solubilized cell lysates were separated using SDS-PAGE, the protein bands electrophoretically transferred to nitrocellulose membranes and the level of cell proliferation was determined by Western blotting using the levels of Ki67 and PCNA as described previously.

To determine whether the conformation of FLNA is different in cancer and primary normal cells and whether Compound C0105 affects FLNA conformation, FLNA was purified from cancer and primary cells after incubation with vehicle or 1 nM Compound C0105 for 4 days. Cells were washed with PBS, scraped, sonicated for 10 seconds and solubilized using 0.5% digitonin/0.2% sodium cholate/0.5% NP-40 at 4° C. with end-over-end rotation for 1 hour. Following centrifugation to remove insoluble debris, the obtained lysate was treated with 1% SDS for 1 minute to dissociate the TrkB-associated proteins, diluted 10-fold with immunoprecipitation buffer, and immunopurified with immobilized anti-FLNA. The resultant FLNA was eluted using 200 µl antigen-elution buffer (Thermo), neutralized immediately with 100 mM Tris HCl (pH9.0), diluted to 500 µl with 50 mM Tris HCl, pH7.5, and passed through a 100 kD cut-off filter.

The purified FLNA was suspended in the 100 µl isoelectric focusing sample buffer. Samples (50 µl) were loaded onto pH 3-10 isoelectric focusing gels (Biorad) and the proteins were fractionated (100 V for 1 hour, 200 V for 1 hour, and 500 V for 30 minutes). The separated proteins were electrophoretically transferred to nitrocellulose membranes. TrkB was identified by Western blotting with anti-FLNA.

Results

C0105 and Other Illustrative Compounds Reduce Glucose Utilization and C0105 Also Reduce Glucose Dependency In Vitro in Cancer Cells To determine whether decreased $pS^{2152}$-FLNA and increased FLNA-linked PTEN correlate with growth arrest in these cells, glucose uptake was assessed as it has been known for decades that cancer cells have higher glucose utilization (glycolysis)—Warburg effect. Thus, as highly proliferative cells, cancer cells have increased glucose utilization and dependence, showing decreased resistance to glucose withdrawal [Sebastian et al. Cell 151:1185-1199 (2012)].

Figure 1C:
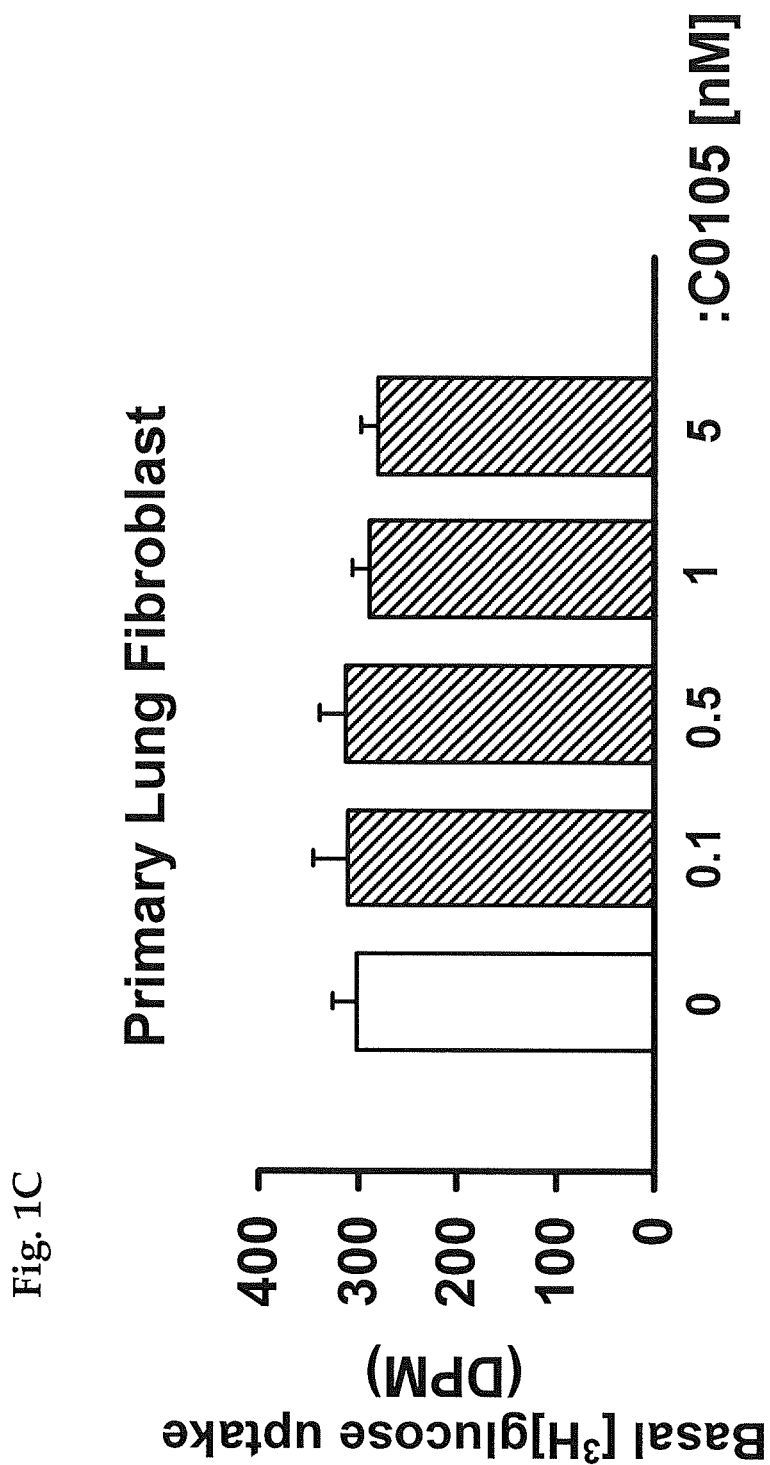
Figures 1D, 1E:
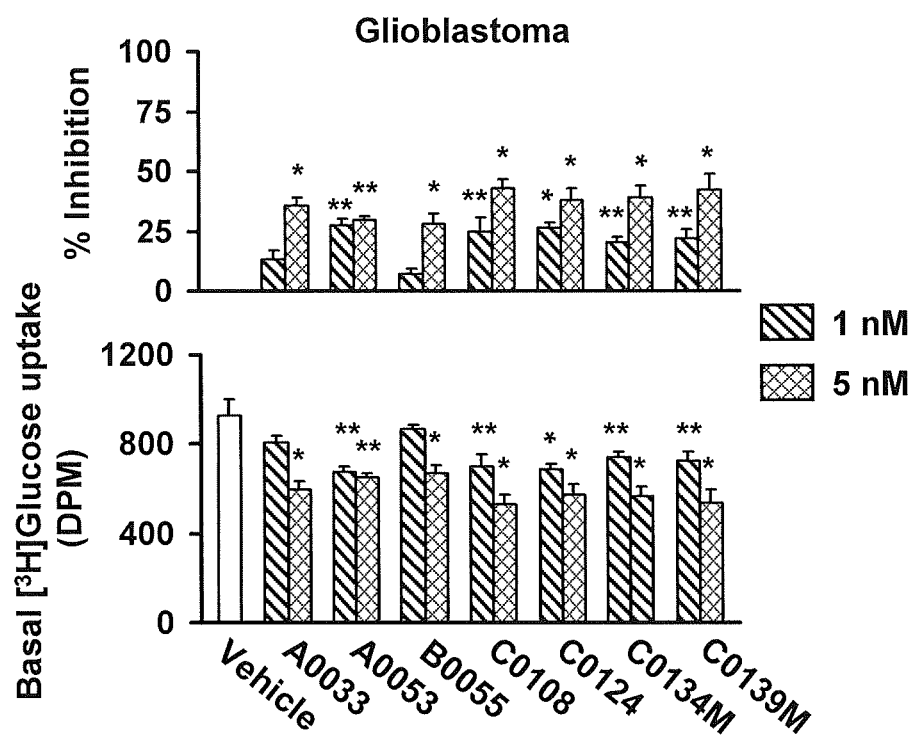
Figures 1F, 1G:
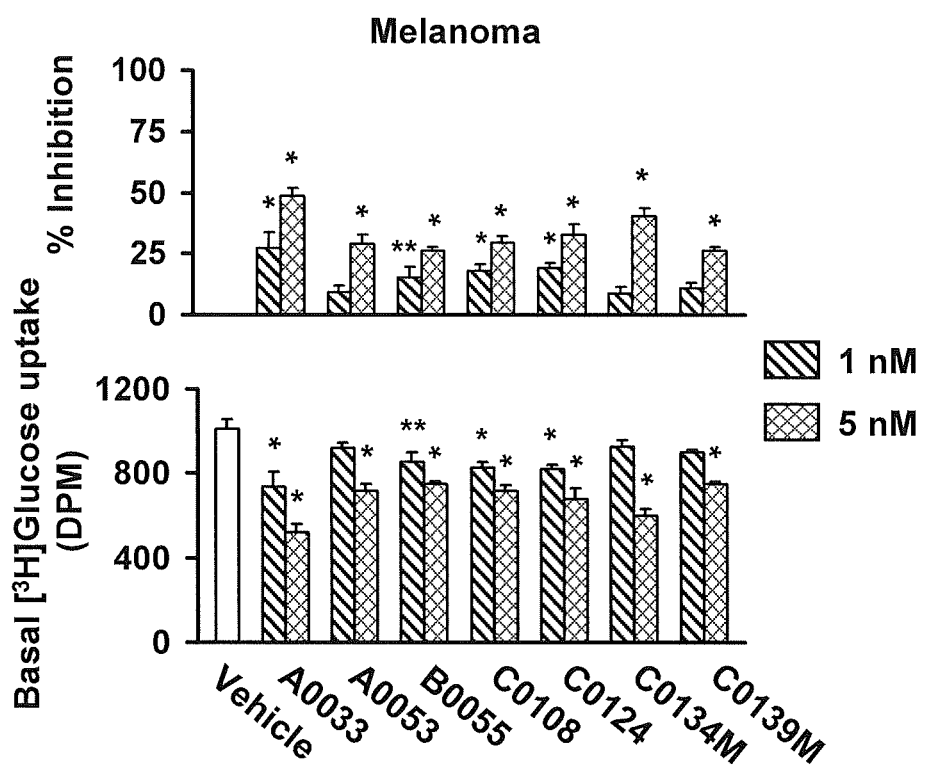
Figures 1H, 1I:
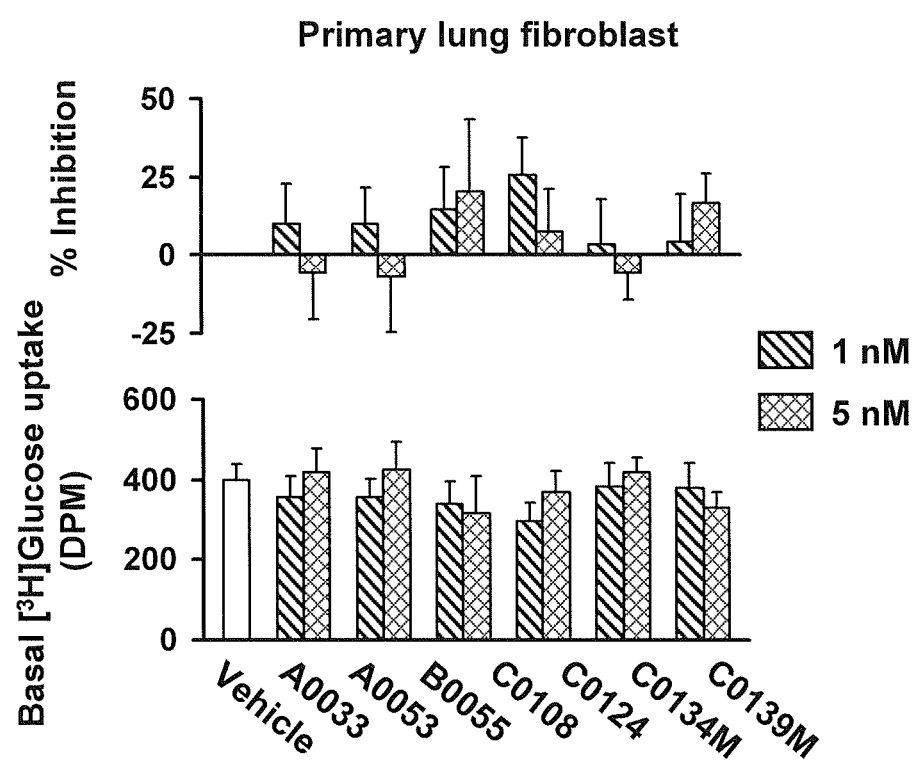
Figures 1J, 1K:
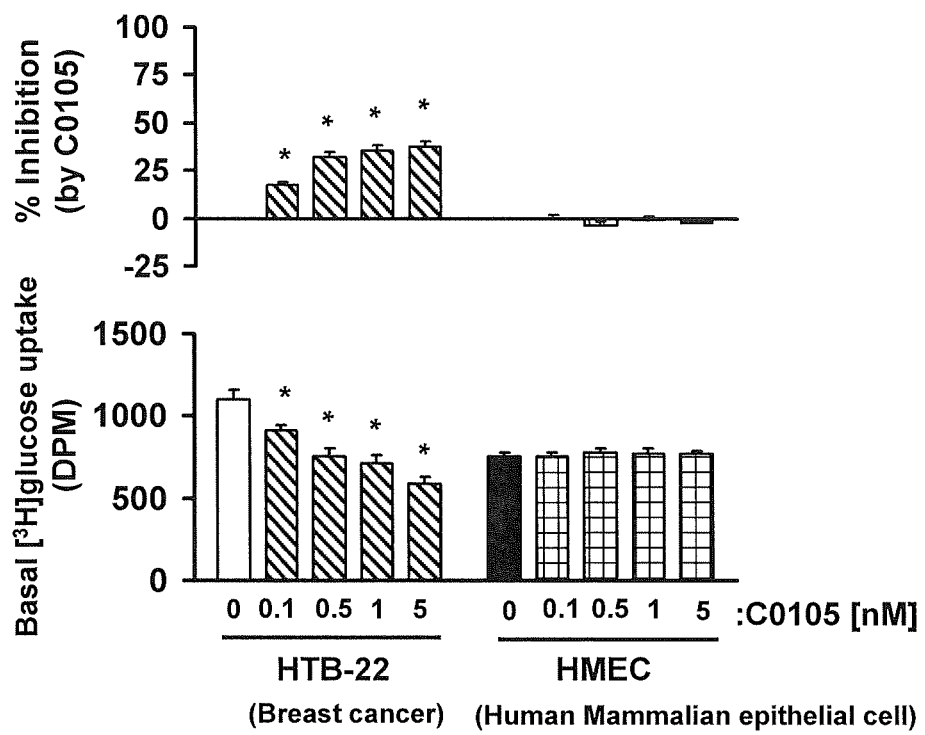
Figures 1L, 1M:
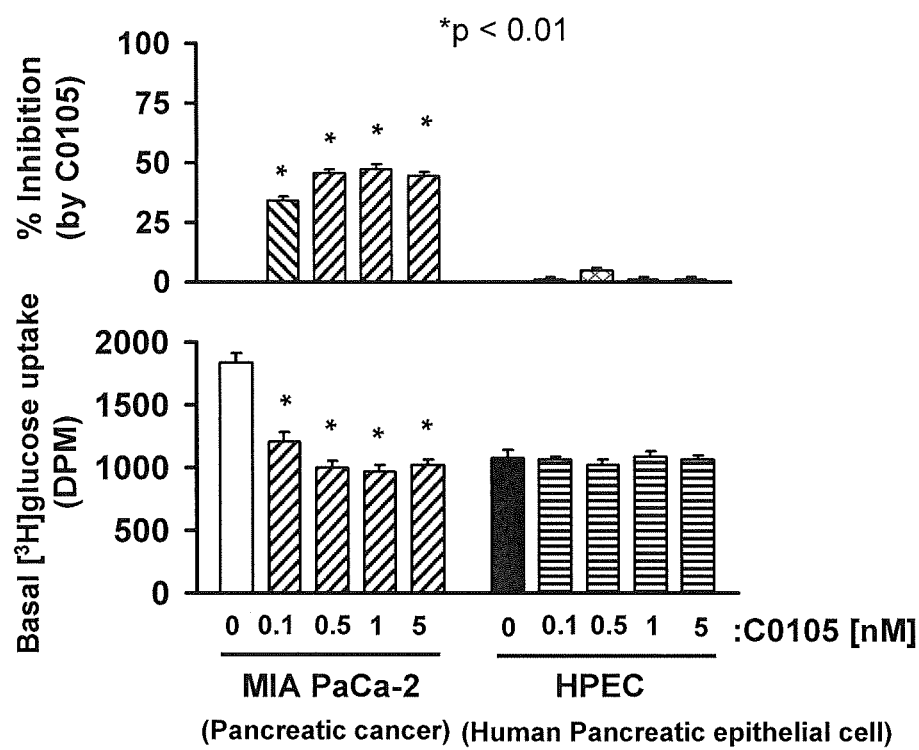
Figures 2A, 2B:
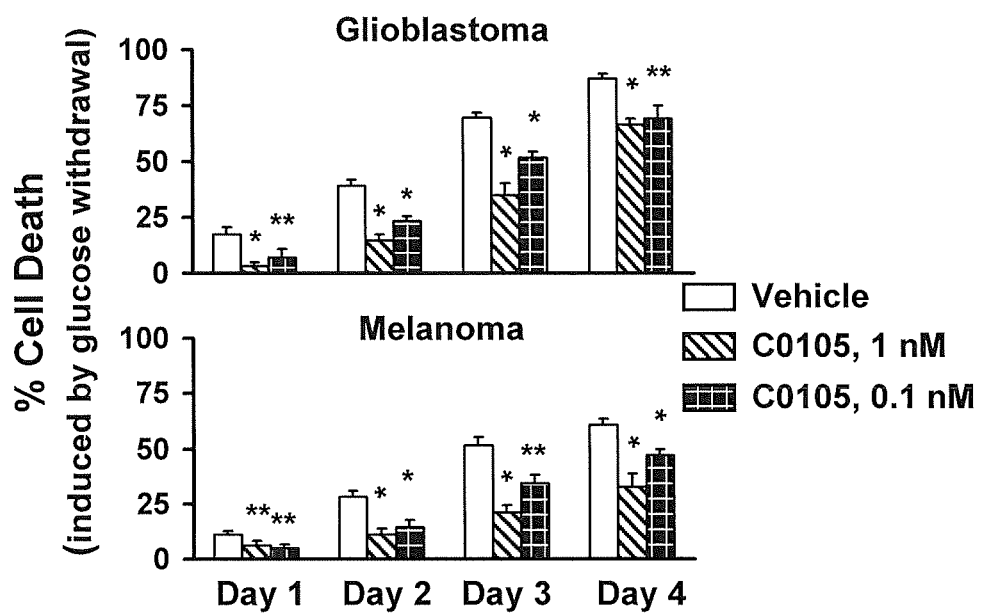
FIG. 2A and FIG. 2B show that Compound C0105 increases resilience to glucose deprivation-induced cell death. The effect of Compound C0105 on cell death induced by glucose withdrawal was assessed in glioblastoma and melanoma cells. Cells were grown to >90% confluence, washed and incubated in 0.1% fetal bovine serum (FBS) for 16 hours and incubated in glucose-free 0.1% FBS-containing medium without or with 0.1 or 1 nM C0105 for up to 4 days. Cell density was assessed at the indicated time point. Data are expressed as mean±S.E.M. of percentage change in cell density compared to cells grown in glucose- and 0.1% FBS-containing medium. Statistical significance was determined by ANOVA followed by Newman-Keuls test for multiple comparisons. **$p<0.05$, *$p<0.01$ compared to vehicle-treated group in each cell type (open bars). N=5-6.

Administration of illustrative Compound C0105 as well as Compounds A0033, A0053, B0055, C0108, C0124, C0134 and C0139 (structures shown hereinafter) decreased the elevated glucose utilization in melanoma, glioblastoma (FIG. 1A-1B, FIG. 1D-FIG. 1G) and non-small cell lung cancer cell lines (data not shown). Primary lung fibroblast cells were used as control, non-cancerous cells to illustrate the difference in effects observed (FIG. 1C, FIGS. 1H-1I).

Both glioblastoma and melanoma cells were plated extremely thinly. Once cells attached, Compound C0105 was added at 0.1, 0.5, 1 and 5 nM, whereas the other compounds were present at 1 and 5 nM in the medium twice daily (6 hours apart) for 4 days. The cells were serum-deprived (glucose deprived) for 2 hours. Cells were then rinsed with 1 ml PBS and glucose uptake was assessed by contacting the cells with [3H]glucose (0.01 uCi/1 ml) of Kreb's Ringer for 2 hours. Cells were then rinsed with 1 ml PBS 3 times, scraped off and their glucose contents counted by liquid scintillation spectrophotometry.

The results of glucose uptake studies show that Compound C0105 reduces glioblastoma uptake by 25% at 0.1 nM and reached its maximal effect at 1 nM with 50% inhibition of glucose uptake ($EC_{50}$ is about 0.1 nM). In contrast to glioblastoma, Compound C0105 is significantly less effective in melanoma cells. Thus, about 25% inhibition of glucose uptake was noted, and although Compound C0105 was quite efficacious at 1-5 nM, inhibition was not dose-dependent (FIGS. 1A-1B). Glucose uptake by the control, normal (cancer-free) primary lung fibroblast cells was not changed from that of the vehicle alone over a concentration range of 0.1-5 nM of Compound C0105. Importantly, Compound C0105-treated cancer cells were slenderer and elongated, suggesting that Compound C0105 is effective in slowing cell growth.

Figures 3B, 3C:
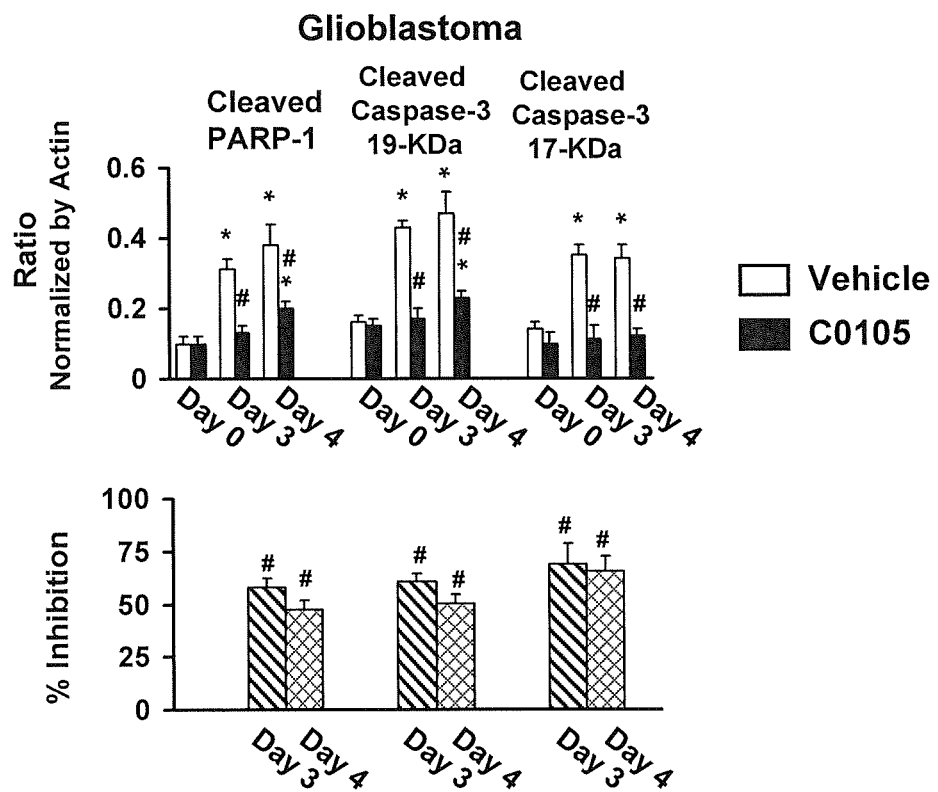
Figures 4B, 4C:
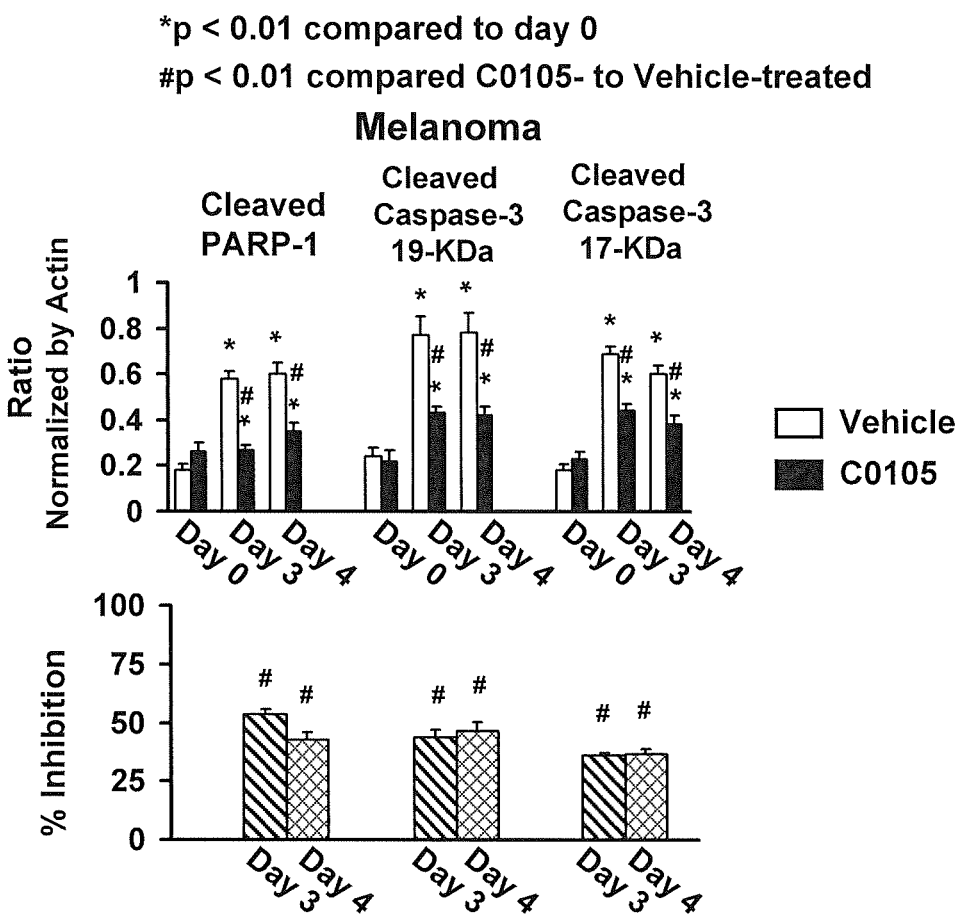
Figures 5B, 5C:
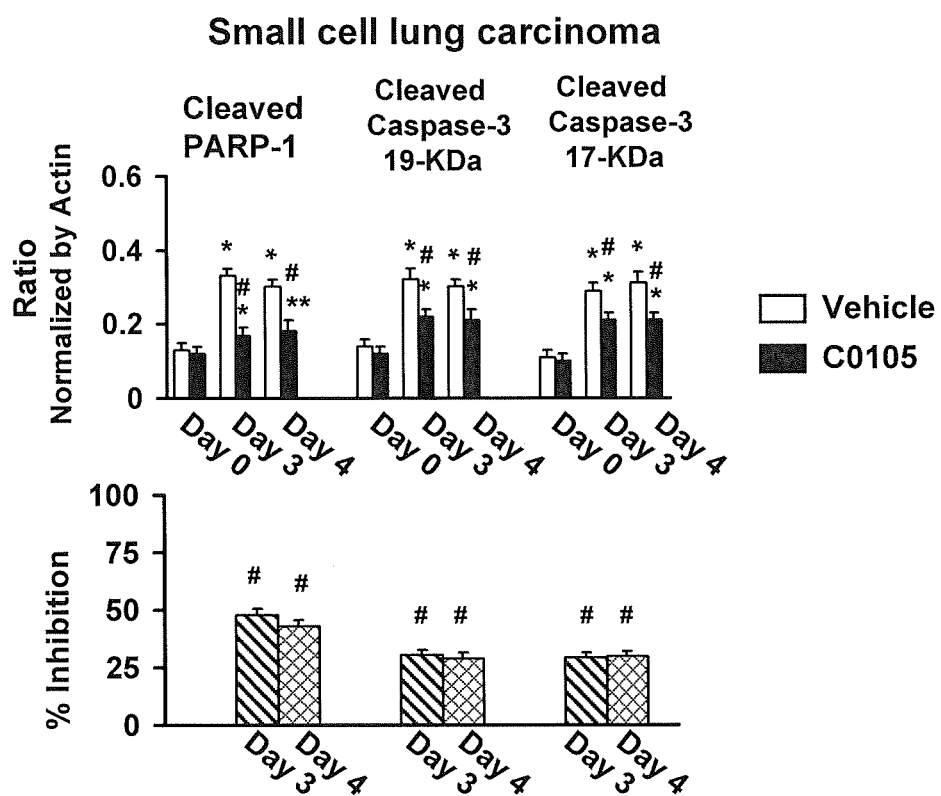

During glucose withdrawal over a 4-day time period, administration of Compound C0105 to the melanoma and glioblastoma cancer cells reduced the amount of cell death (FIG. 2A-2D). Apoptosis is indicated by cleaved PARP-1 and cleaved caspase-3 (FIGS. 3A-3C glioblastoma; FIGS. 4A-4C melanoma; FIGS. 5A-5C small cell lung carcinoma).

Together, the above results shown in FIGS. 1A-5C indicate that contacting (treating) the cancer cells with Compound C0105 or the other illustrative compounds normalizes cancer cells by reducing their dependency for glucose. N=4 (for C0105) and N=3-4 (for various other compounds), *p<0.01, **p<0.05.

Contact with Compound C0105 and Other Illustrative Compounds Reduce Cell Proliferation In melanoma, glioblastoma and small cell lung cancer cell lines, Compound C0105 administration inhibited cell proliferation at concentrations ranging from 0.1, 0.5, 1 and 5 nM as indicated by Ki67 and PCNA levels and by Ki67 immunostains in melanoma, small cell lung cancer, and glioblastoma cells (FIGS. 14A-14C, 15A-15C, and 16A-16C, respectively). N=4, *p<0.01.

Figure 6A:
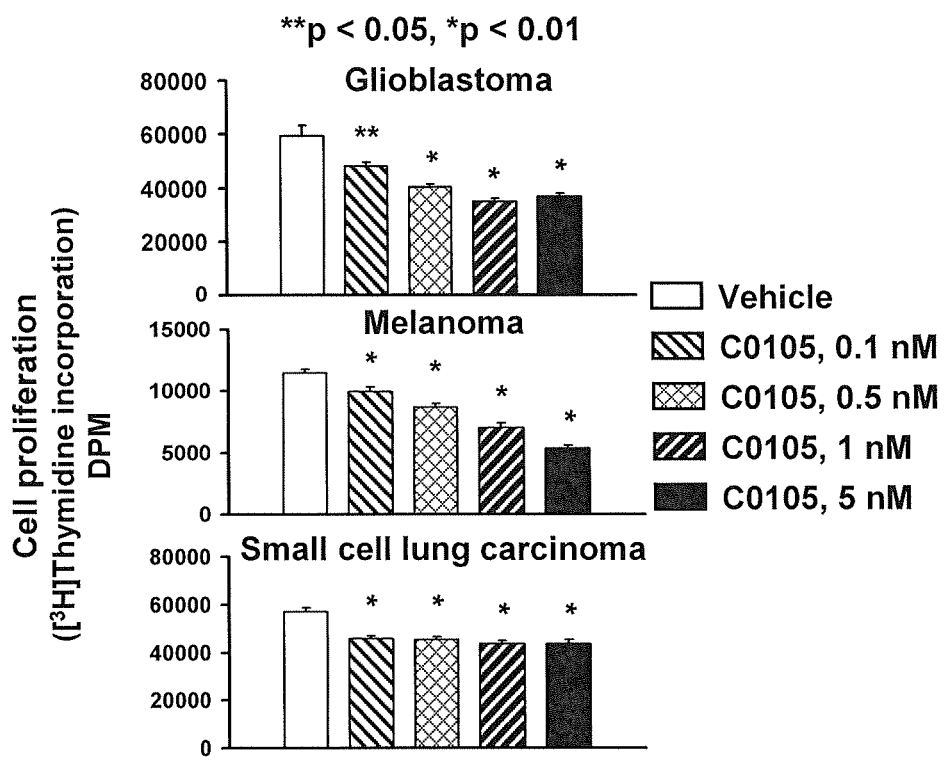
FIG. 6A and FIG. 6B illustrate that Compound C0105 reduces glioblastoma, melanoma and small-cell lung carcinoma cell proliferation. The effect of Compound C0105 on cell proliferation was determined by the level of [$^3$H] thymidine incorporation in glioblastoma, melanoma and small-cell lung carcinoma cells. Cells contacted with vehicle or 0.1-5 nM Compound C0105 were incubated with 5 µCi/ml of [$^3$H]thymidine for 96-hours. Cells were washed and the cell content of [$^3$H]thymidine was quantified using scintillation spectrometry.
Figure 6B:
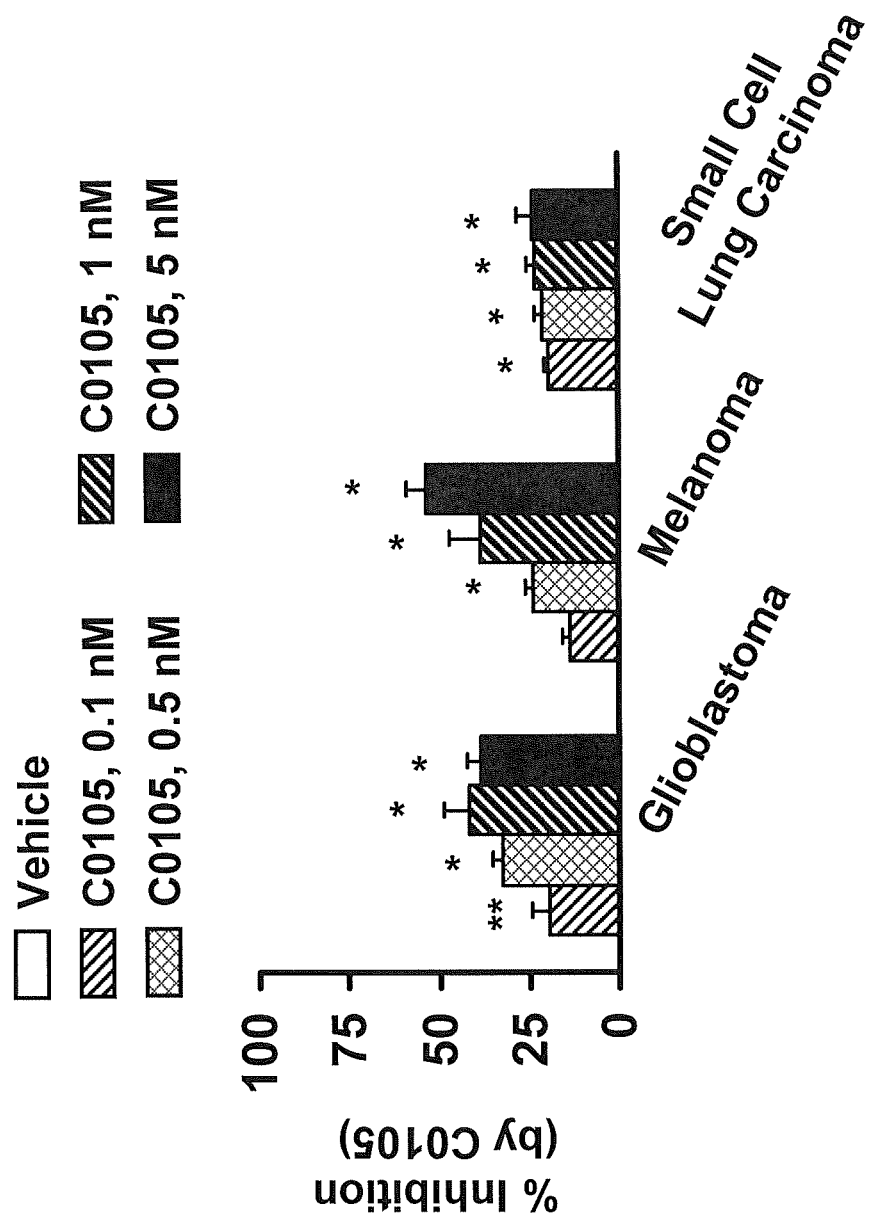
Figure 7A:
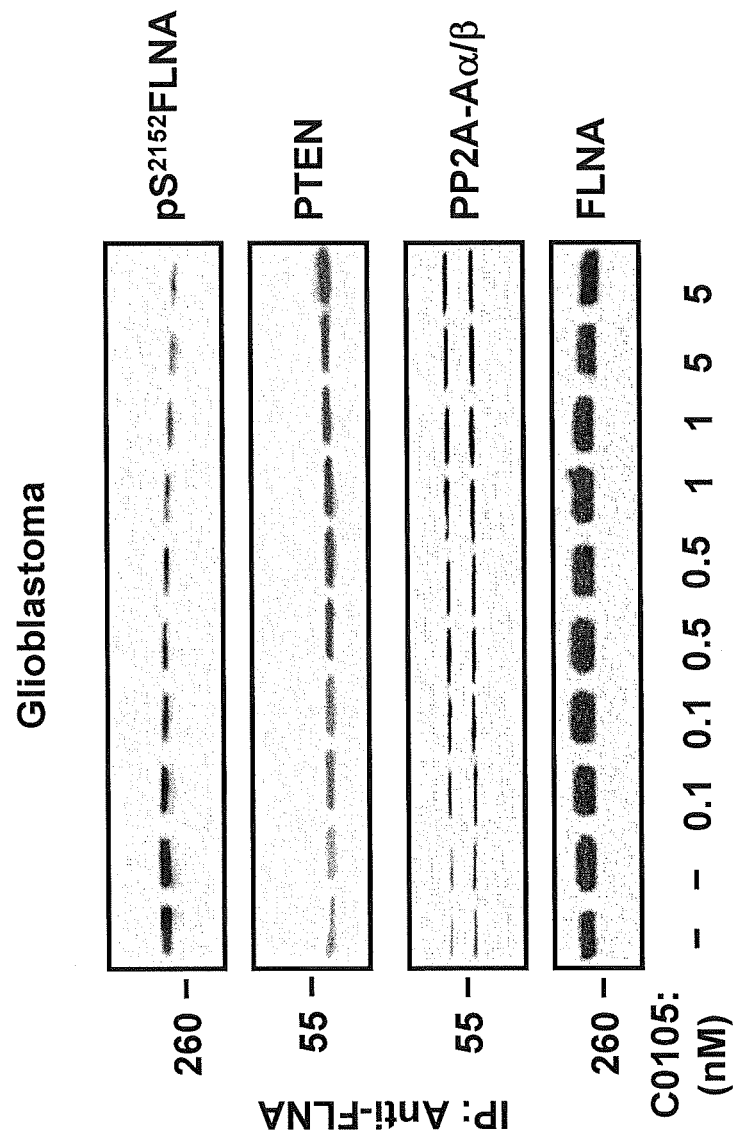
FIG. 7A through FIG. 7C illustrate that Compound C0105 contact reduces pS$^{2152}$FLNA but increases FLNA-associated PTEN and PP2A levels in glioblastoma cells. The effect of Compound C0105 on the levels of pS$^{2152}$FLNA and FLNA-associated phosphatases, PTEN and PP2A subclasses was determined in glioblastoma cells. Cells were treated with vehicle and 0.1-5 nM Compound C0105 for 4 days. Cells were washed and solubilized, and the resultant cell lysate was immunoprecipitated with anti-FLNA. The levels of pS$^{2152}$FLNA and FLNA-associated phosphatases, PTEN and PP2A subclasses in the anti-FLNA immunoprecipitate were determined by Western blotting. The density of protein bands was quantified by densitometric scan.
Figures 7B, 7C:
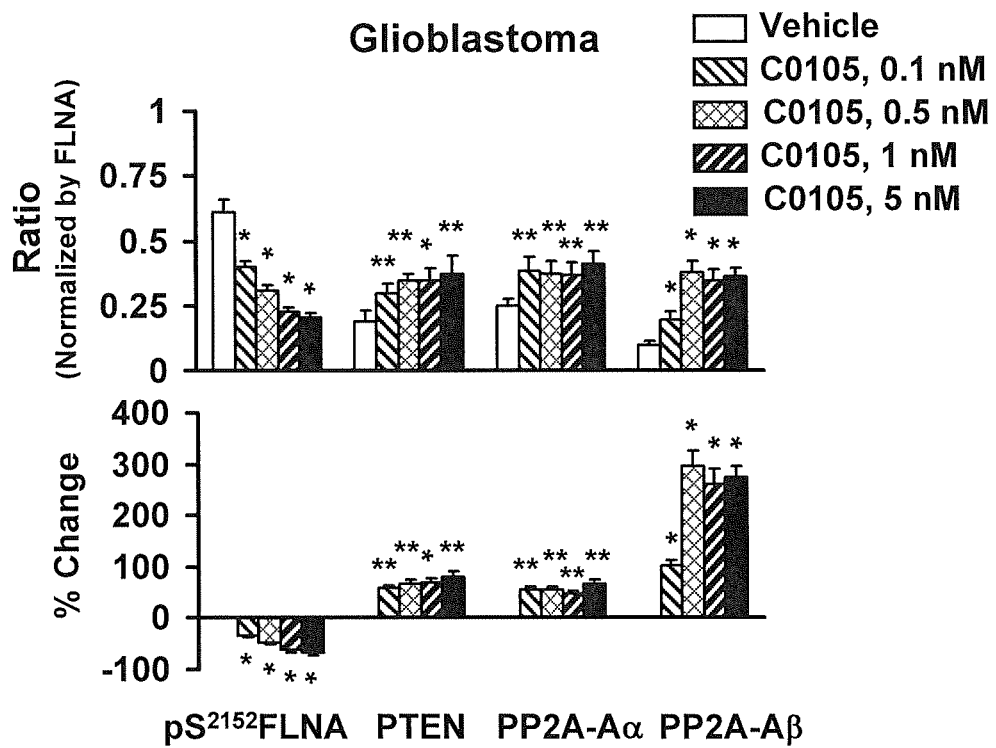

The proliferation attenuating effect of contacting with Compound C0105 on all three cancer cell types is further supported by tracking the amounts of [$^3$H]thymidine incorporated by the growing cells (FIG. 6A). Compound C0105 and the other illustrative compounds assayed had no effect on normal primary lung fibroblasts (FIGS. 1B and 1F) or normal astrocytes (data not shown), illustrating that the observed anti-proliferation effect is specific to cancer cells.

Figure 8A:
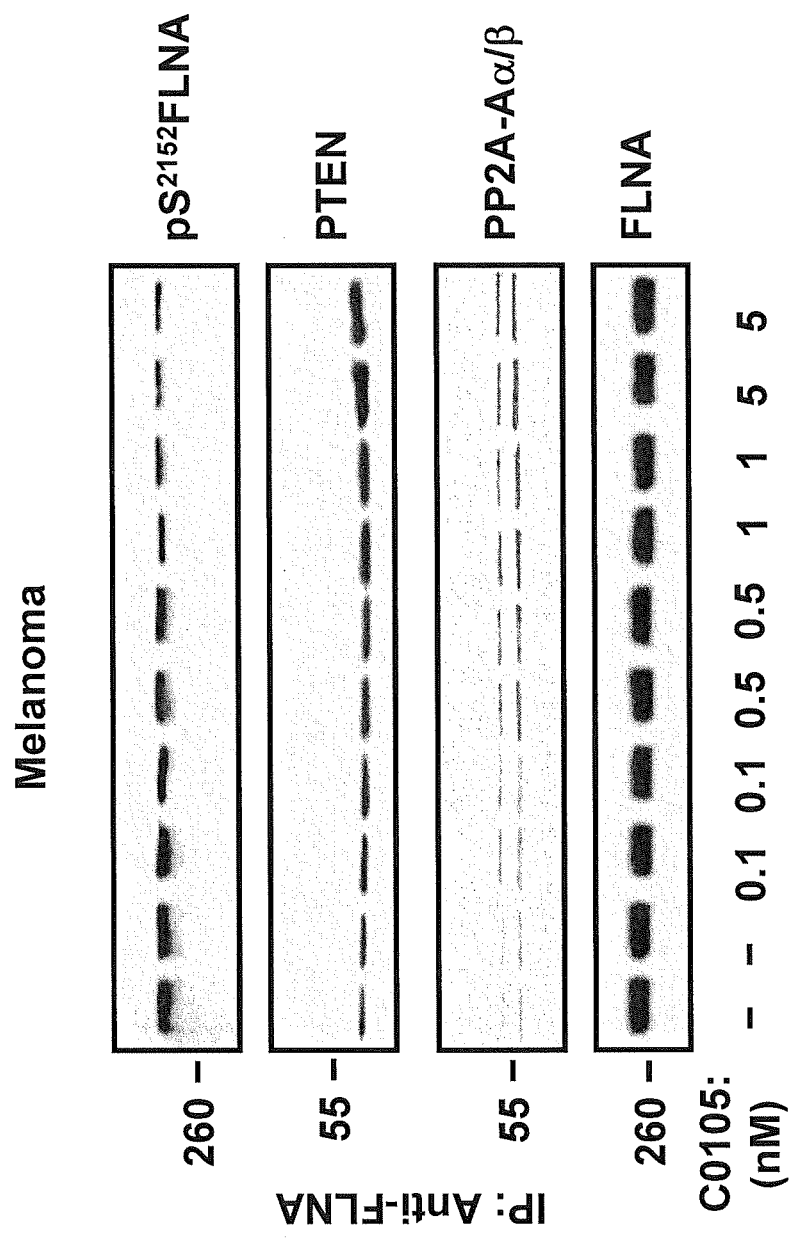
FIG. 8A through FIG. 8C show that contact with Compound C0105 reduces pS$^{2152}$FLNA but increases FLNA-associated PTEN and PP2A levels in melanoma cells. The effect of Compound C0105 on the levels of pS$^{2152}$FLNA and FLNA-associated phosphatases, PTEN and PP2A subclasses was determined in melanoma cells. Cells were treated with vehicle and 0.1-5 nM Compound C0105 for 4 days. Cells were washed, solubilized and the resultant cell lysate was immunoprecipitated with anti-FLNA. The levels of pS$^{2152}$FLNA and FLNA-associated phosphatases, PTEN and PP2A subclasses in the anti-FLNA immunoprecipitate were determined by Western blotting. The density of protein bands was quantified by densitometric scanning.
Figures 8B, 8C:
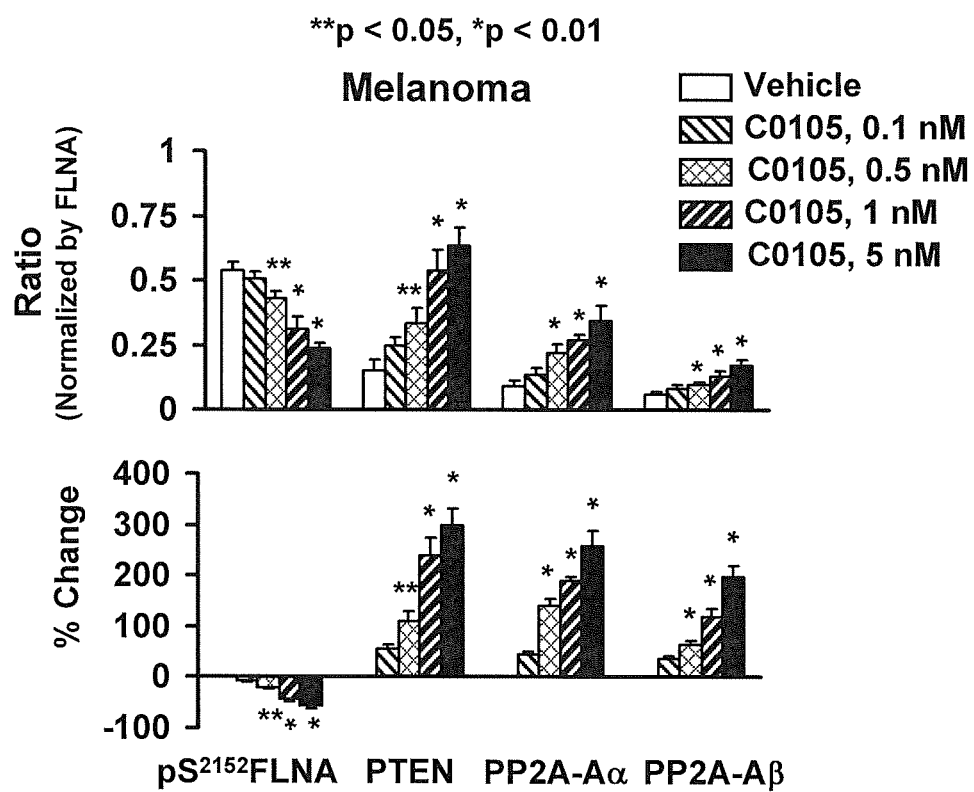
Figure 9A:
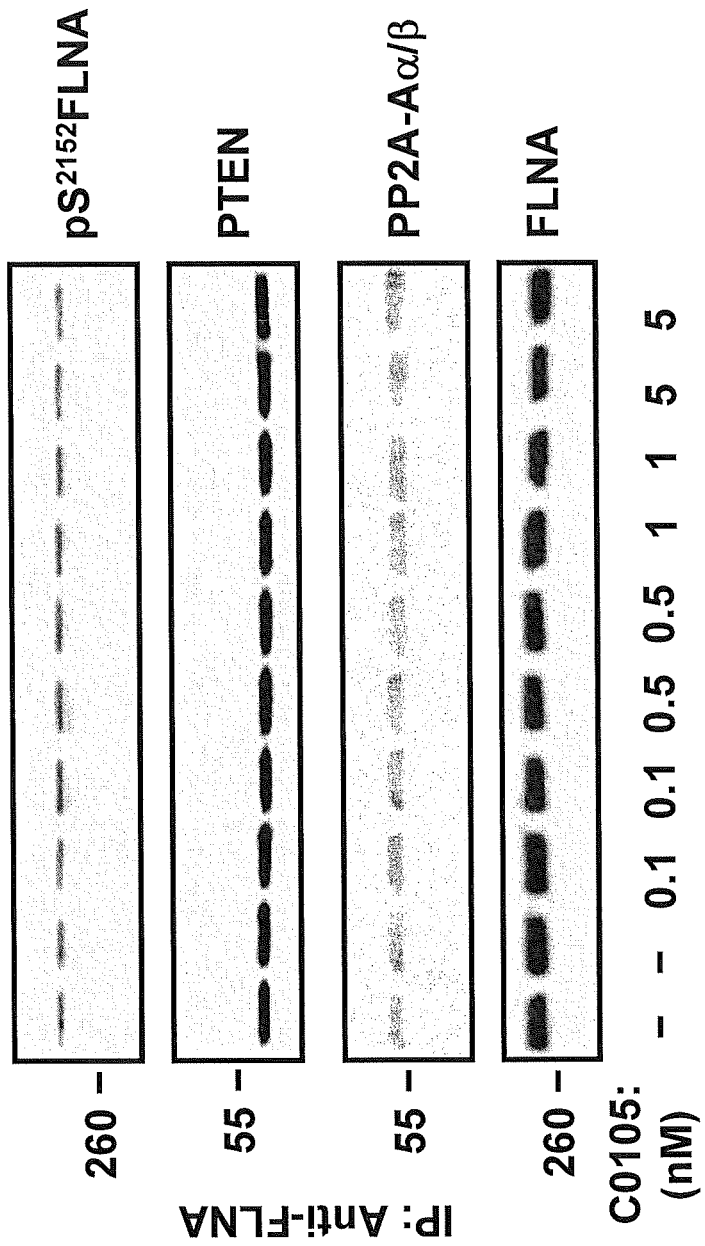
FIGS. 9A through 9C show that contact with Compound C0105 does not affect $pS^{2152}$FLNA, FLNA-associated PTEN and PP2A levels in primary lung fibroblast cells. The effect of contact with Compound C0105 on the levels of $pS^{2152}$FLNA and FLNA-associated phosphatases, PTEN and PP2A subclasses was determined in primary lung fibroblast cells. Cells were treated with vehicle and 0.1-5 nM Compound C0105 for 4 days. Cells were washed, solubilized and the resultant cell lysate was immunoprecipitated with anti-FLNA. The levels of $pS^{2152}$FLNA and FLNA-associated phosphatases, PTEN and PP2A subclasses in the anti-FLNA immunoprecipitate were determined by Western blotting. The density of protein bands was measured by densitometric scanning.
Figures 9B, 9C:
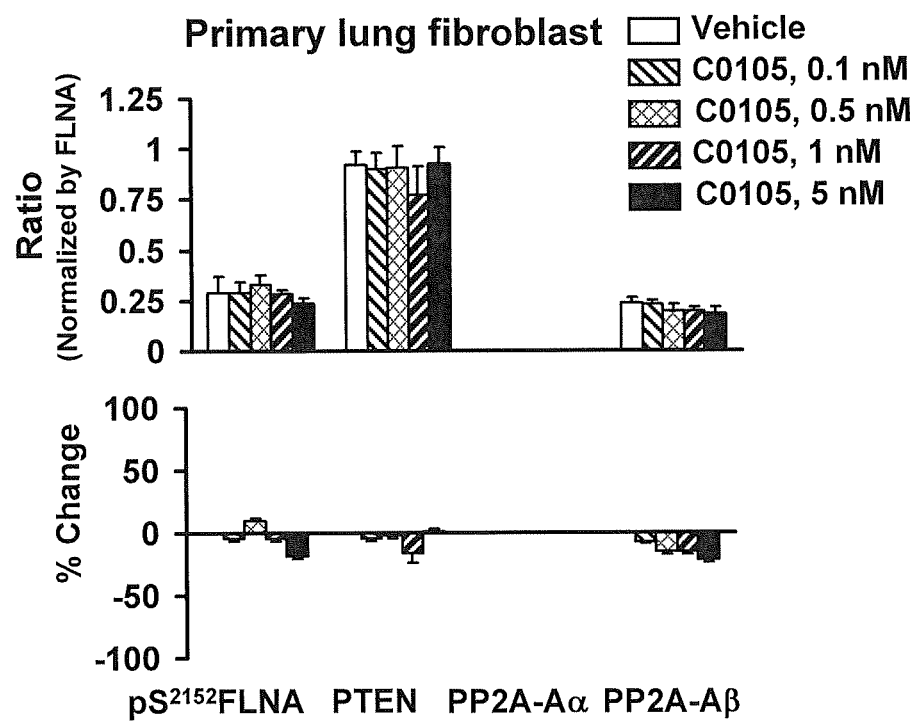
Figure 10A:
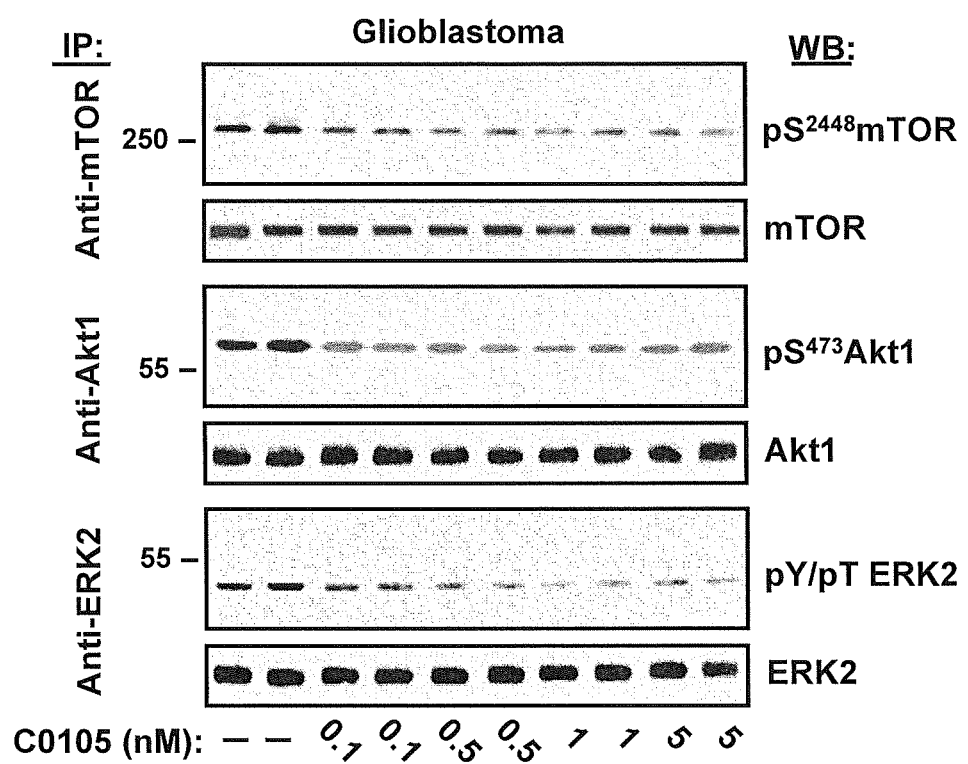
FIG. 10A through FIG. 10C illustrate the effect of contact with Compound C0105 on the levels of activated (phosphorylated) mTOR ($pS^{2448}$mTOR), Akt ($pS^{473}$Akt) and ERK2 (pY/pT-ERK2) in glioblastoma cells. Cells were treated with vehicle and 0.1-5 nM C0105 for 4 days. Cells were washed, solubilized and the resultant cell lysate was immunoprecipitated with anti-mTOR, -Akt or -ERK2. The levels of $pS^{2448}$mTOR, $pS^{473}$Akt, pY/pTERK2 in the respective anti-mTOR, -Akt, and -ERK2 immunoprecipitates were determined by Western blotting. The density of protein bands was measured by densitometric scanning. As is seen, contact with Compound C0105 robustly reduces mTOR, Akt and ERK activation (phosphorylated mTOR, Akt and ERK) in glioblastoma cells.
Figures 10B, 10C:
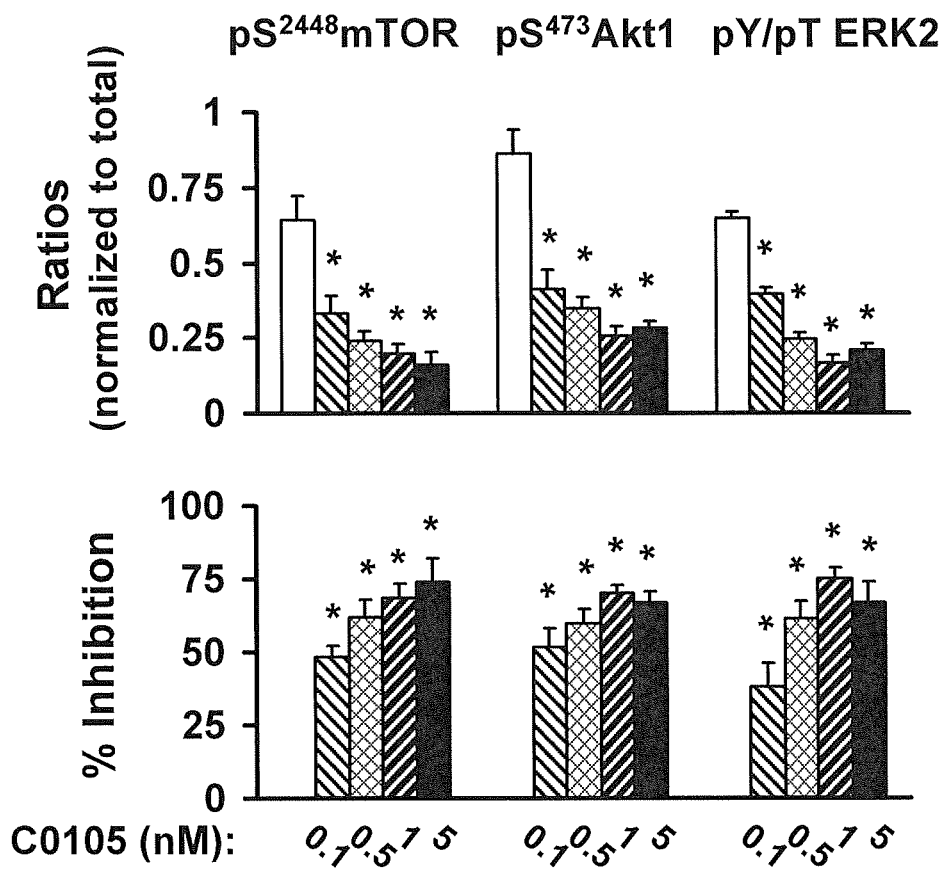
Figure 11A:
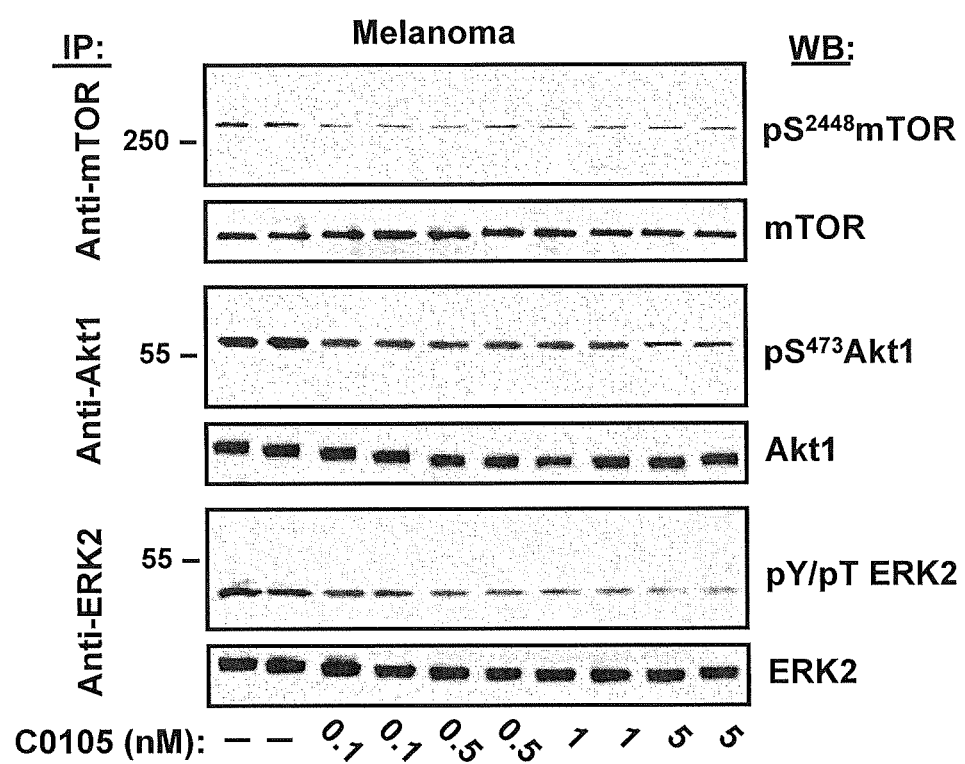
FIG. 11A through FIG. 11C illustrate the effect of contact with Compound C0105 on the levels of activated (phosphorylated) mTOR ($pS^{2448}$mTOR), Akt ($pS^{473}$Akt) and ERK2 (pY/pT-ERK2) in melanoma cells. Cells were treated with vehicle and 0.1-5 nM Compound C0105 for 4 days. Cells were washed, solubilized and the resultant cell lysate was immunoprecipitated with anti-mTOR, -Akt or -ERK2. The levels of $pS^{2448}$mTOR, $pS^{473}$Akt, pY/pTERK2 in the respective anti-mTOR, -Akt, and -ERK2 immunoprecipitates were determined by Western blotting. The density of protein bands was measured by densitometric scanning. As is seen, contact with Compound C0105 robustly reduces mTOR, Akt and ERK activation (phosphorylated mTOR, Akt and ERK) in melanoma cells.
Figures 11B, 11C:
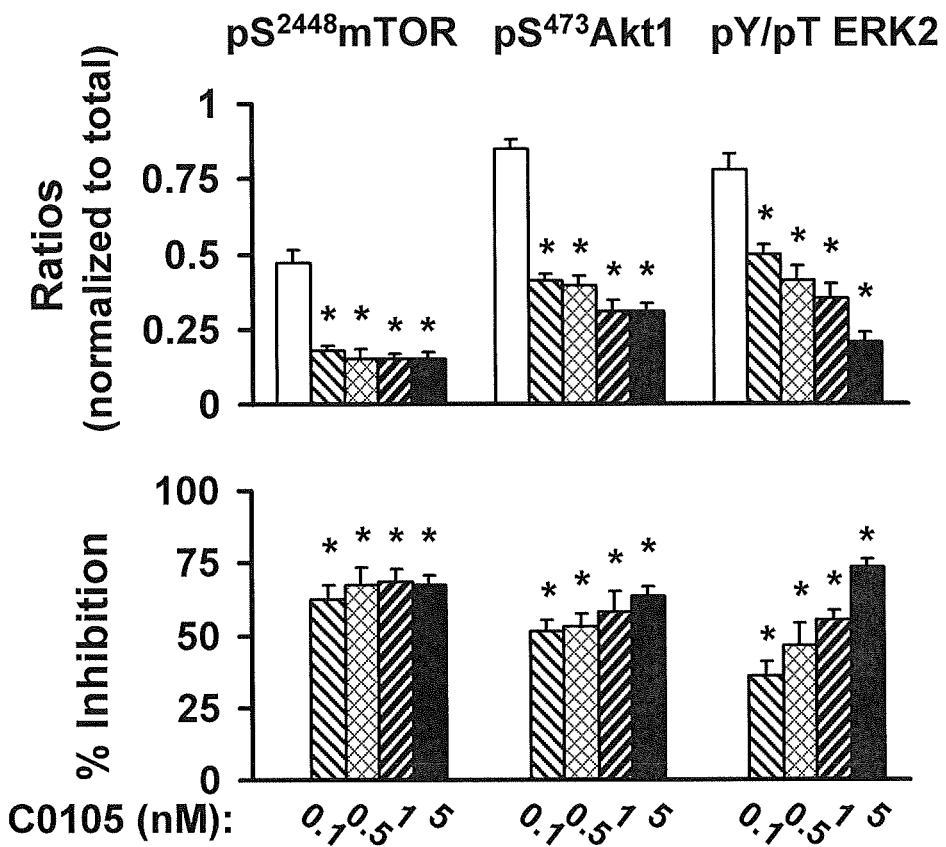
Figure 12A:
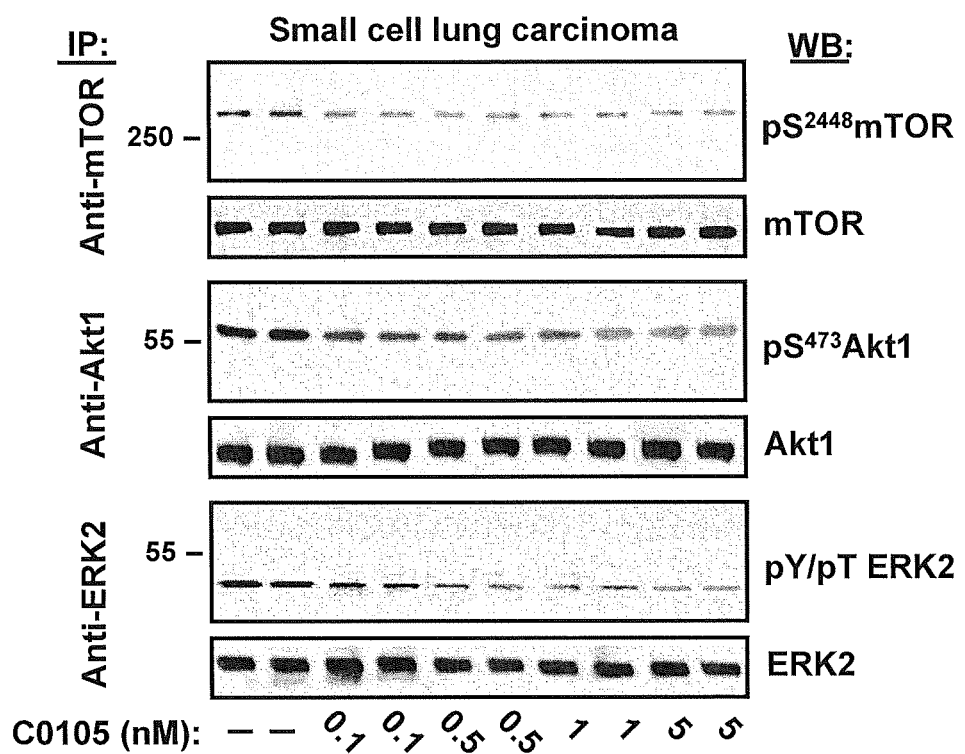
Figures 12B, 12C:
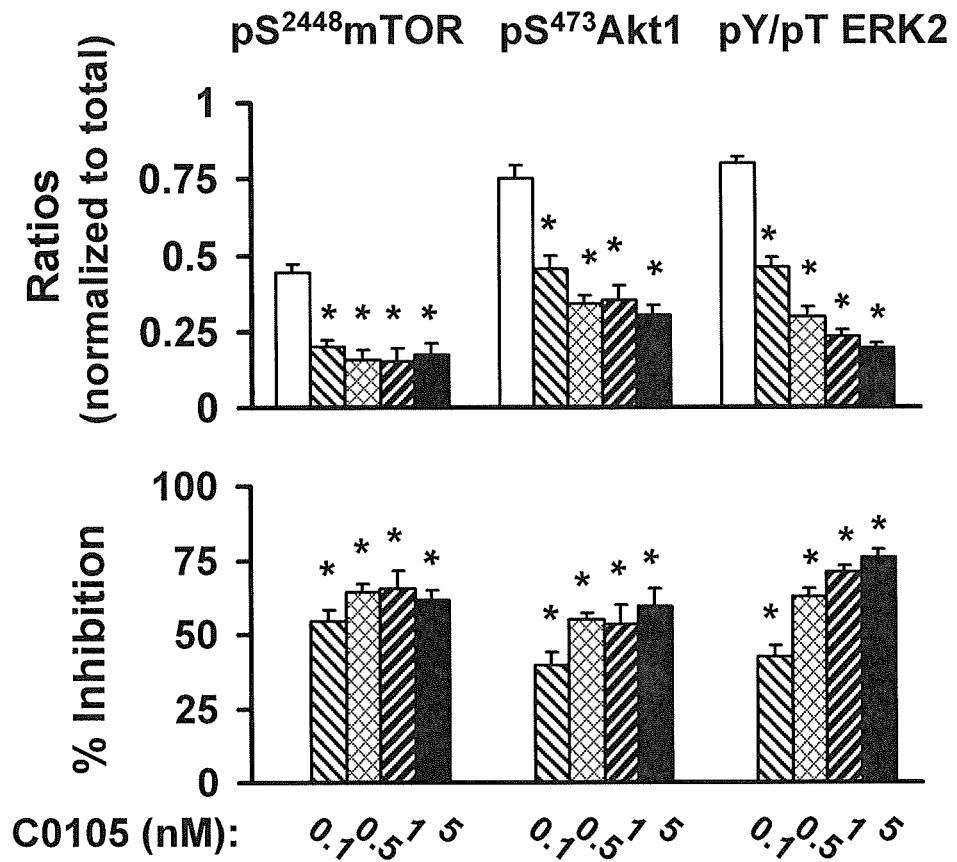
Figure 12D:
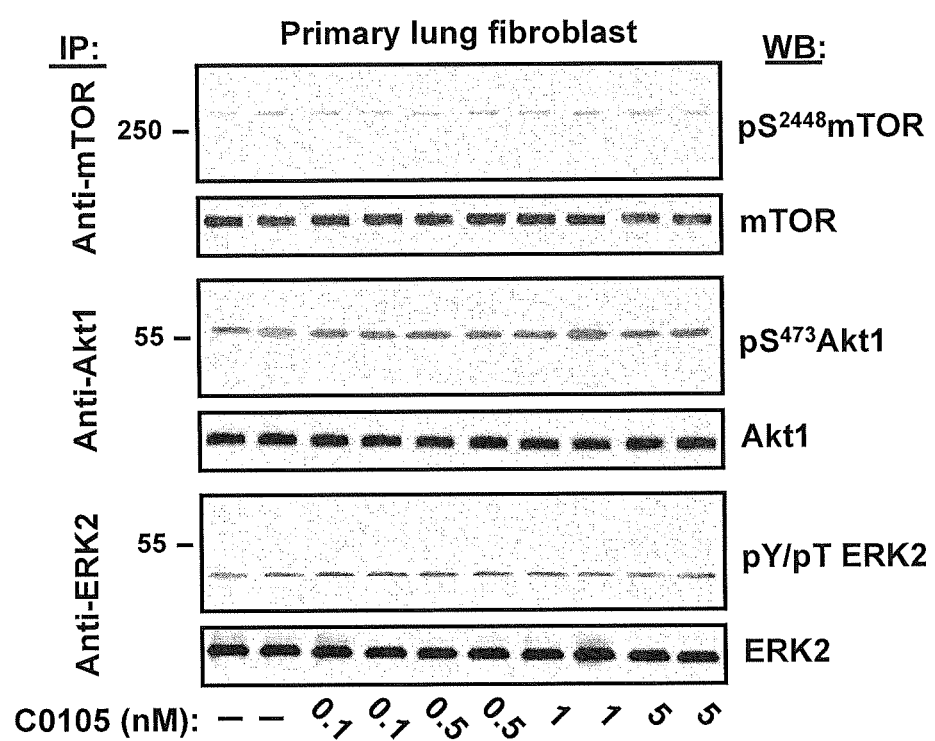

Compound C0105 and other illustrative compound administrations reduce $pS^{2152}$-FLNA and increases PTEN and PP2A association with FLNA In both glioblastoma and melanoma cell lines studied, FLNA is hyperphosphorylated at serine2152, coincident with decreased association of the phosphatase PTEN with FLNA as can be seen by comparing vehicle levels in glioblastoma and melanoma cancer cell lines (FIGS. 7A-7C, 8A-8C) with vehicle levels of primary fibroblasts (FIGS. 9A-9C).

With four-day twice daily Compound C0105 administration, $pS^{2152}$FLNA levels were normalized and the association of FLNA with PTEN is restored in both glioblastoma (FIGS. 7A and 7B) and melanoma cell lines (FIGS. 8A and 8B). FIGS. 9A and 9B show the results obtained using cancer-free (normal), primary lung fibroblast cells.

Because PTEN is a tyrosine phosphatase and cannot dephosphorylate FLNA at serine2152, a second phosphatase associated with FLNA was identified that is capable of this dephosphorylation: PP2A, a serine/threonine protein phosphatase. PP2A association with FLNA, noted with both subtypes of PP2A (PP2A-Aα and PP2A-Aβ), is similarly decreased in cancer cell lines and also restored by contact with Compound C0105 at 0.1-5 nM concentrations in glioblastoma cells (FIGS. 7A and 7B), in melanoma cells (FIGS. 8A and 8B) and in small cell lung carcinoma cells (data not shown). N=4, *p<0.01. In primary normal lung fibroblasts and human pancreatic epithelial cells (HPECs), there was no effect of Compound C0105 treatment on $pS^{2152}$FLNA levels or on these phosphatase associations with FLNA (FIGS. 9B and 9C, FIGS. 27C and 27D) N=4, *p<0.01.

Figures 13A, 13B:
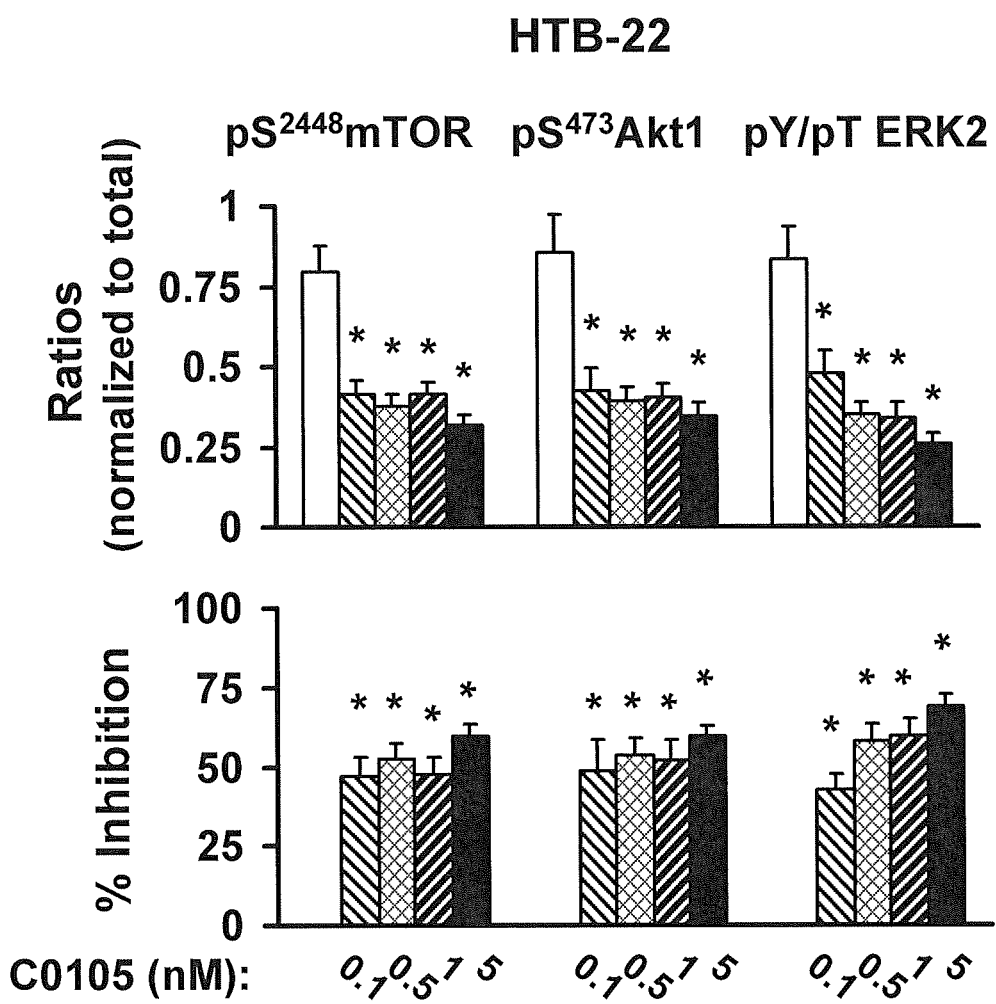
FIG. 13A through FIG. 13H show that contact with Compound C0105 has little effect on mTOR, Akt and ERK activation (phosphorylated mTOR, Akt and ERK) in two cancer cell lines (HTB-22 and MiaPaCa2.
Figures 13C, 13D:
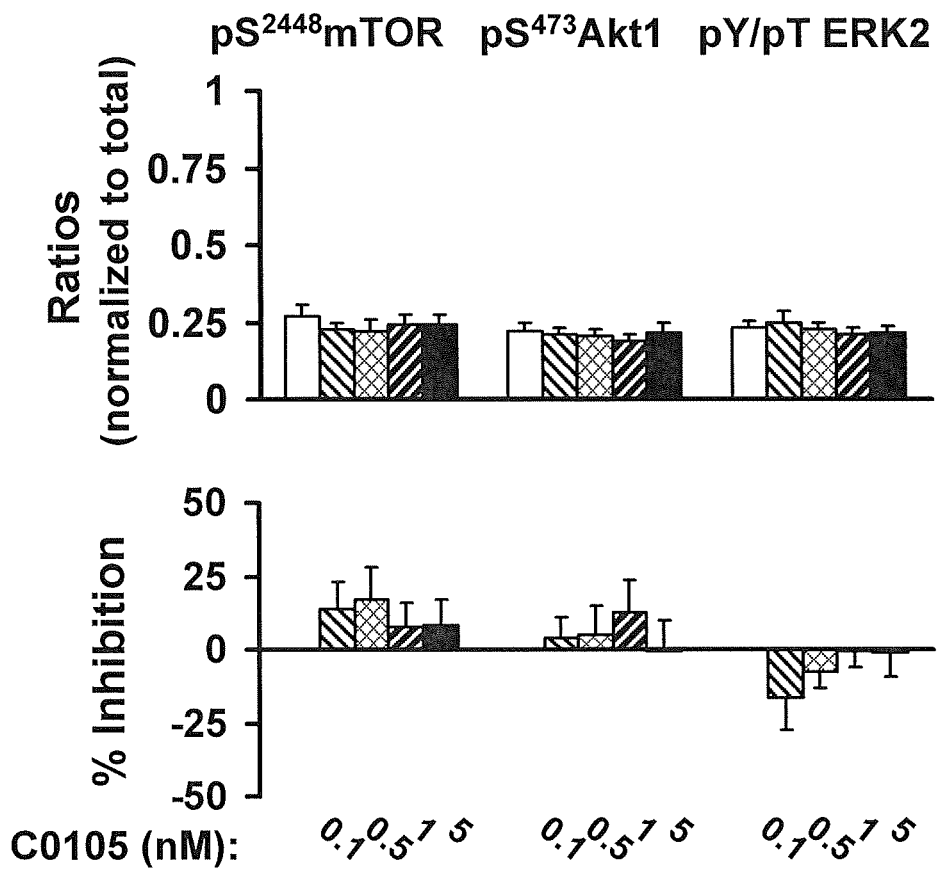
Figures 13E, 13F:
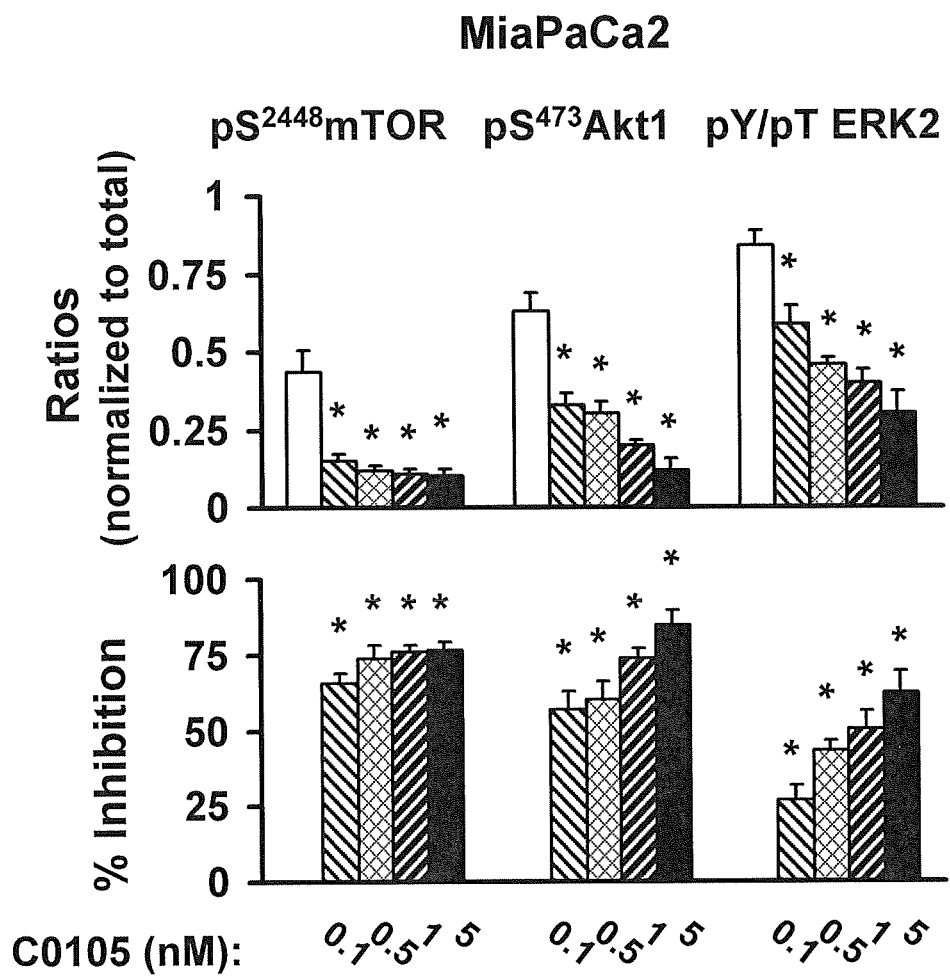
Figures 13G, 13H:
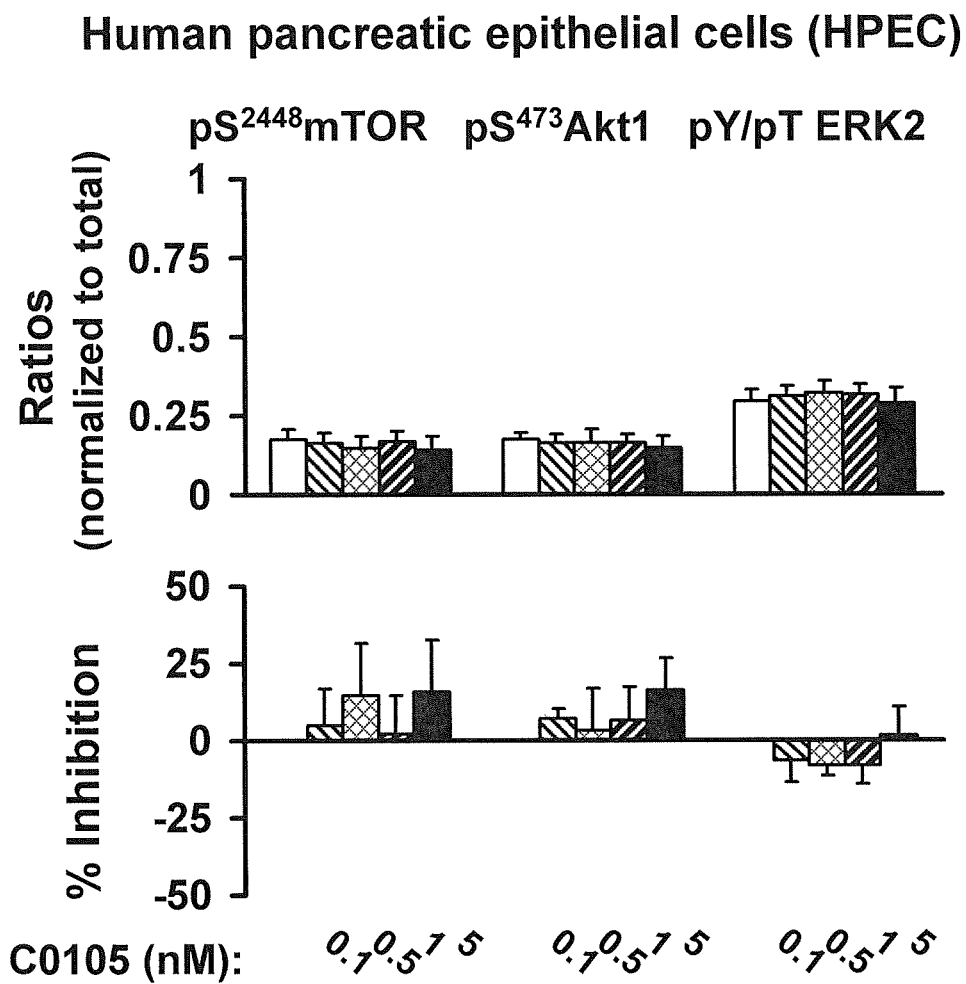
Figure 14A:
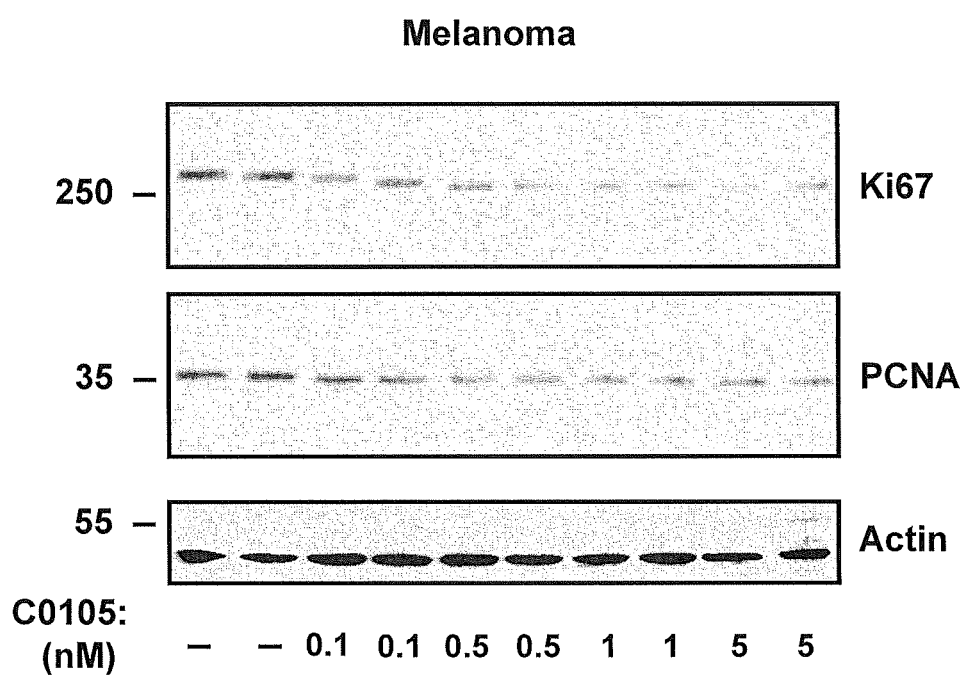
FIG. 14A through FIG. 14C illustrate that contact with Compound C0105 reduces cell proliferation in melanoma cells. The effect of contact with Compound C0105 on cell proliferation was determined by the levels of cell-cycling markers: Ki67 and PCNA (proliferating cell nuclear antigen)
Figures 14B, 14C:
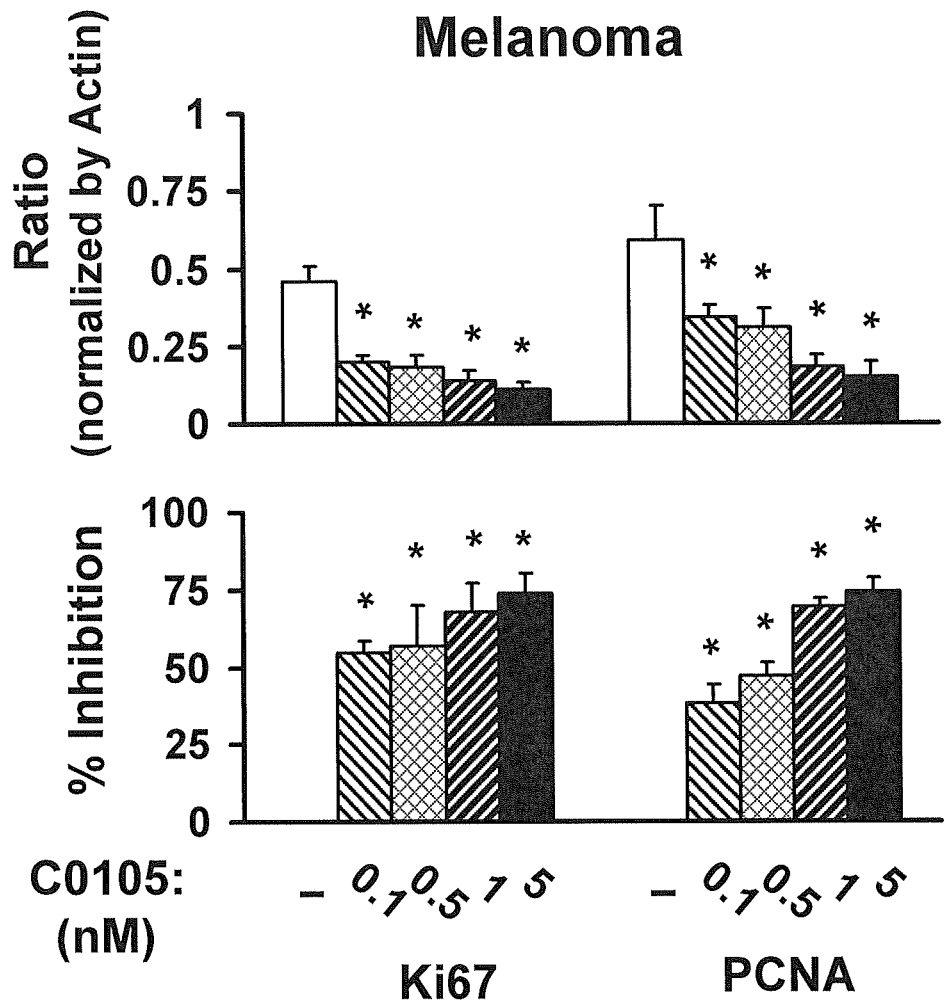
Figure 15A:
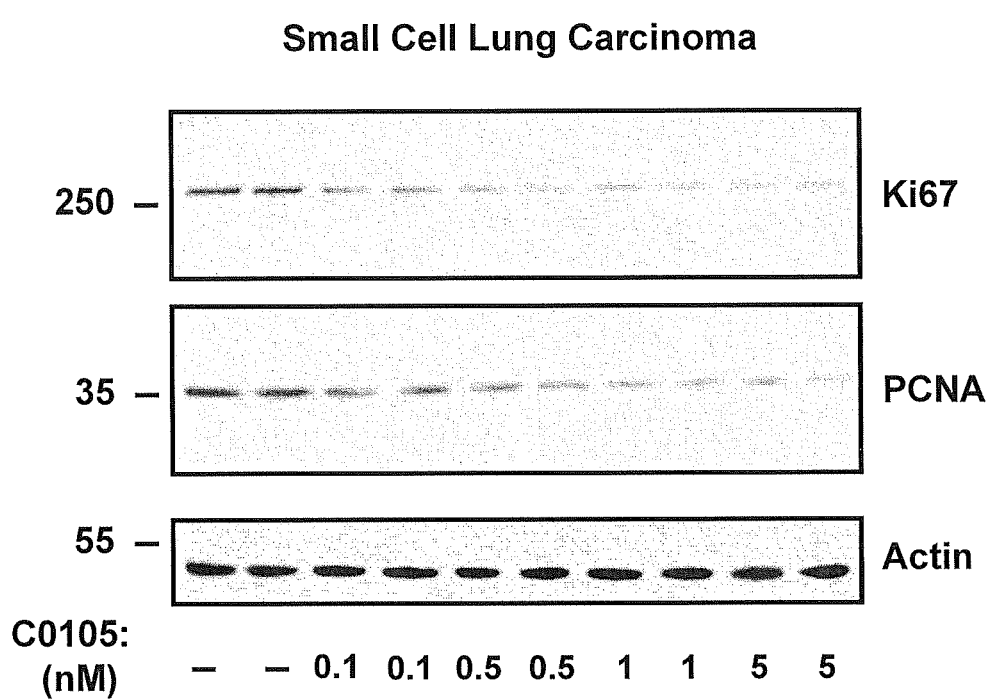
FIG. 15A through FIG. 15C illustrate that contact with Compound C0105 reduces cell proliferation in small-cell lung carcinoma cells. The effect of C0105 on cell proliferation was determined by the levels of cell-cycling markers: Ki67 and PCNA using Western blots in melanoma cells. Cells treated with vehicle and 0.1-5 nM C0105 for 4 days were collected, washed and solubilized. The resultant cell lysates were size-fractionated on SDS-PAGE and Western blotting to determine the levels of Ki67, PCNA and actin (loading control). The protein bands were quantified using densitometric scanning.
Figures 15B, 15C:
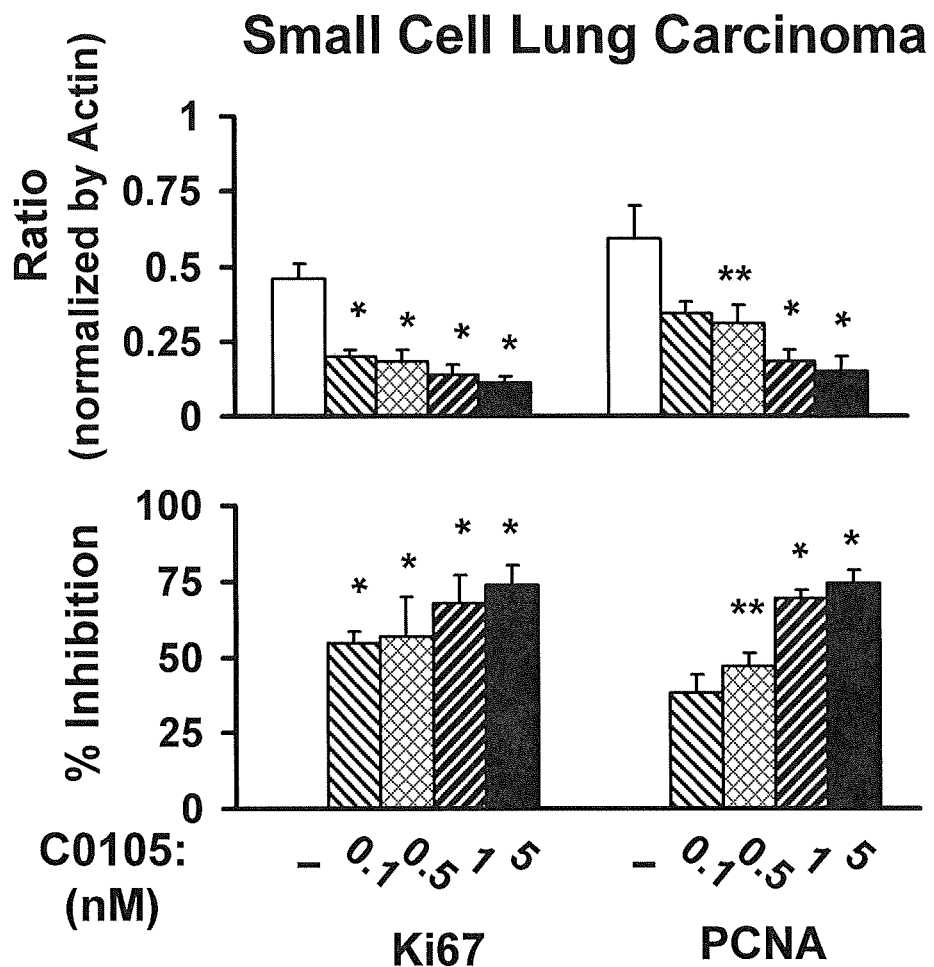
Figure 16A:
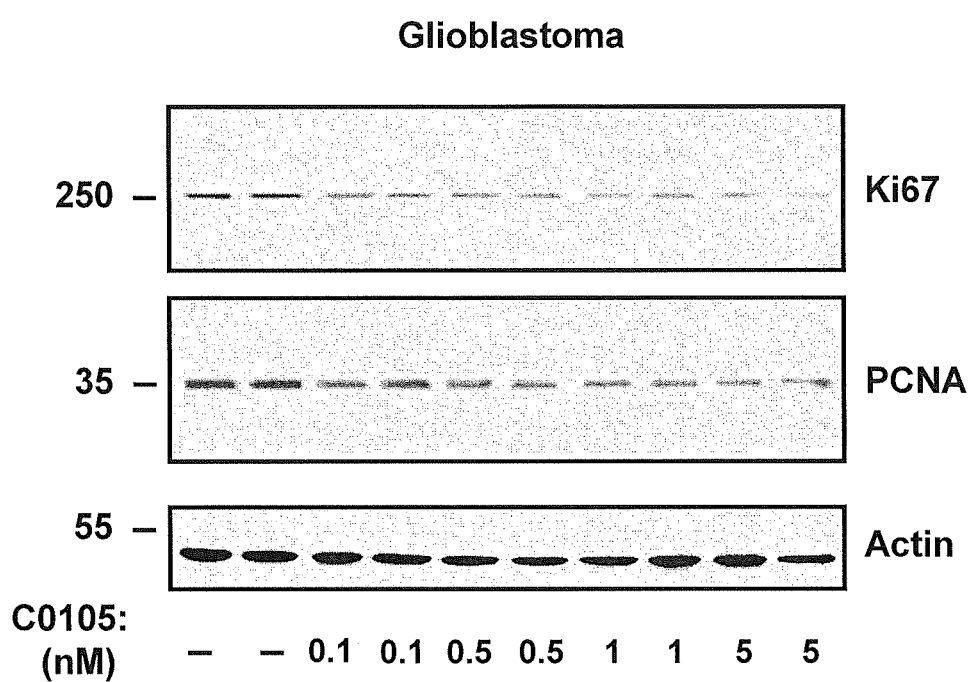
FIGS. 16A through 16C illustrate that contact with Compound C0105 reduces cell proliferation in glioblastoma cells. The effect of contact with Compound C0105 on cell proliferation was determined by the levels of cell-cycling markers: Ki67 and PCNA using Western blots in glioblastoma (U-87MG) cells. Cells contacted with vehicle and 0.1-5 nM Compound C0105 for 4 days were collected, washed and solubilized. The resultant cell lysates were size-fractionated on SDS-PAGE and Western blotting to determine the levels of Ki67, PCNA and actin (loading control). The protein bands were quantified using densitometric scanning.
Figures 16B, 16C:
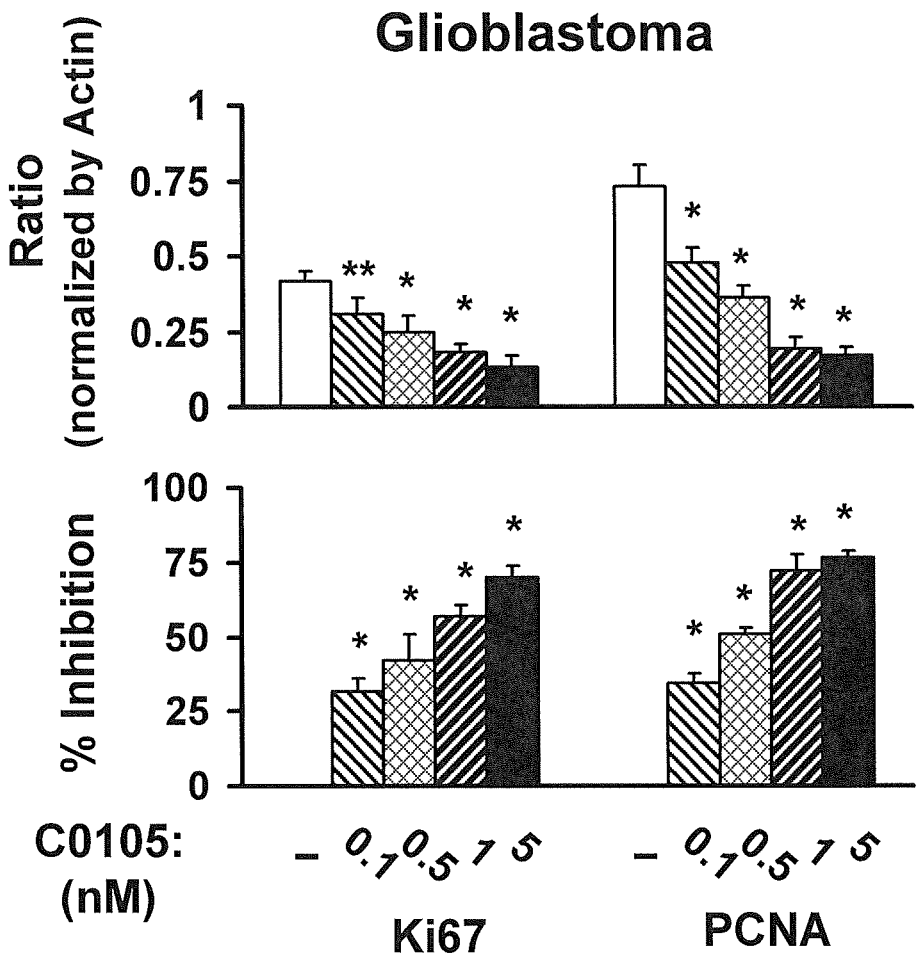
Figure 17A:
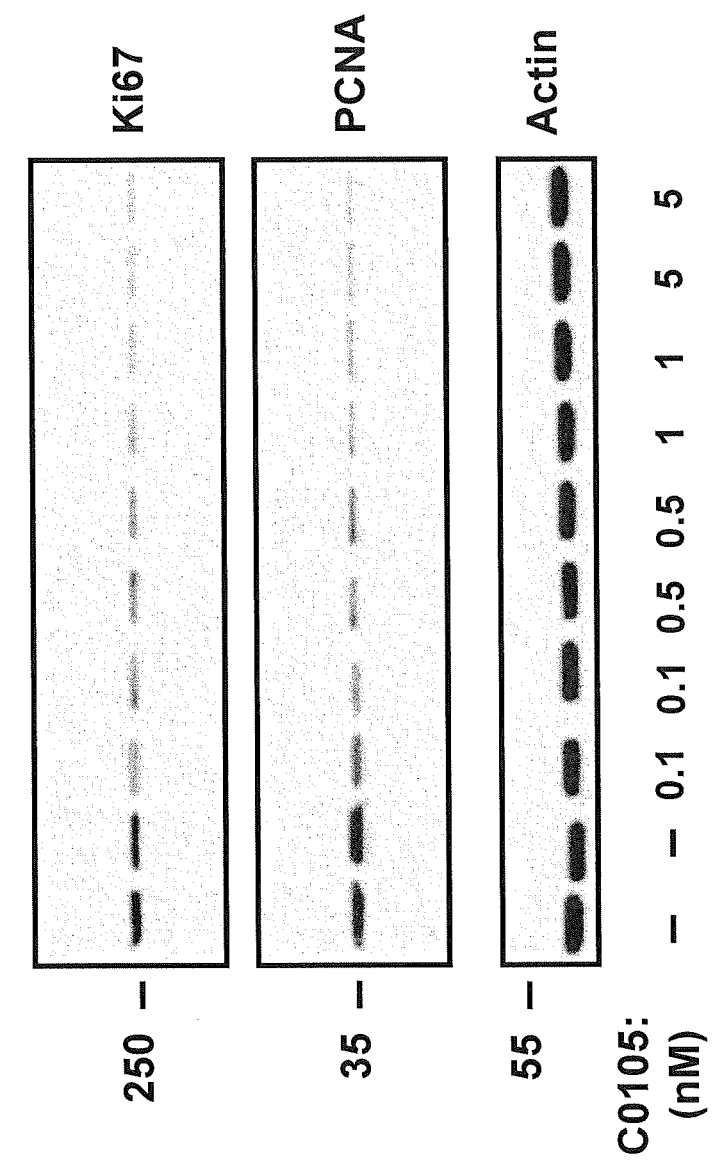
FIGS. 17A through 17F illustrate that contact with Compound C0105 reduces cell proliferation in breast cancer HTB-22 but not in primary human mammary epithelial cells (HMEC). The effect of contact with Compound C0105 on cell proliferation was determined by the levels of cell-cycling markers: Ki67 and PCNA using Western blots in HTB-22 and control human mammary epithelial cells (HMECs). Cells treated with vehicle and 0.1-5 nM Compound C0105 for 4 days were collected, washed and solubilized. The resultant cell lysates were size-fractionated on SDS-PAGE and Western blotting to determine the levels of Ki67, PCNA and actin (loading control). The protein bands were quantified using densitometric scanning.
Figure 17B:
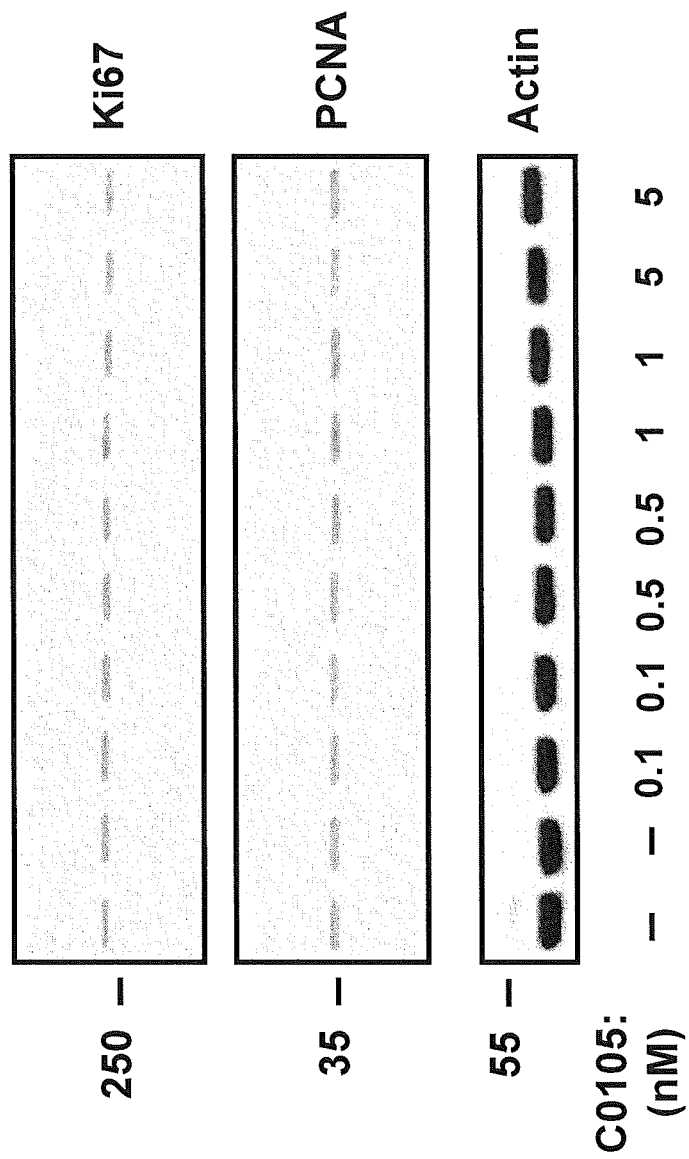
Figures 17C, 17D:
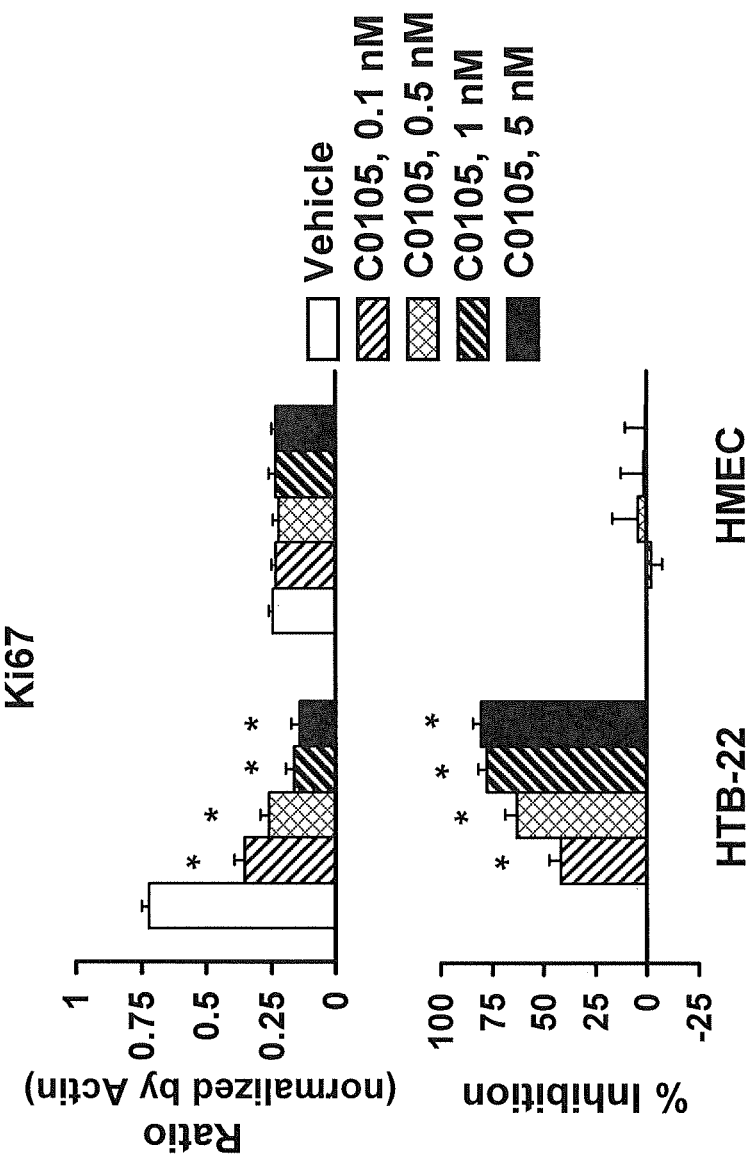
Figures 17E, 17F:
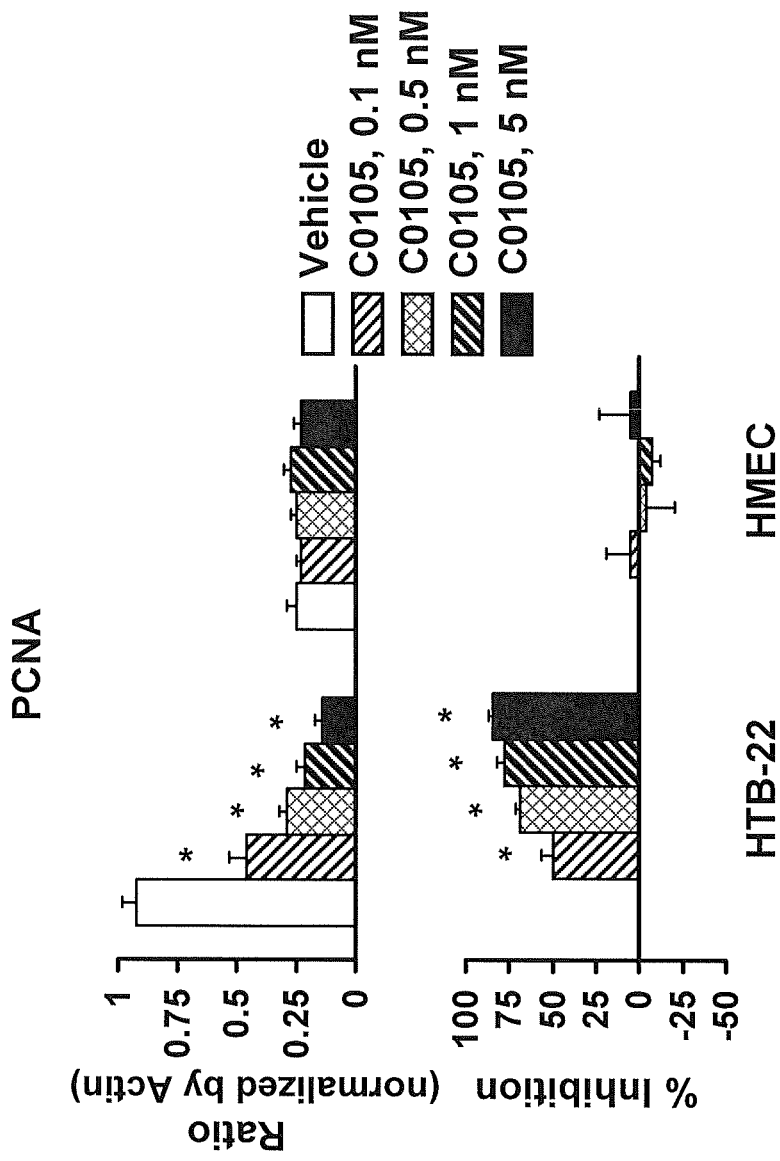

Compound C0105 Contact Reduces mTOR Activation as Well as PI3K and ERK Signaling The restoration of native FLNA associations by Compound C0105 results in reductions in cancer signaling. The heightened mTOR activity indicated by increased amounts of serine$^{2448}$-phosphorylated mTOR ($pS^{2448}$mTOR) in glioblastoma, melanoma and small cell lung carcinoma cells was reduced by contacting those cells with illustrative Compound C0105 (FIGS. 10A-10C, 11A-11C, and 12A-12C). No statistically significant differences were noted on similar treatment of normal, non-cancerous primary lung fibroblasts (FIGS. 13A-13C). These data together again indicate that the effects of C0105 administration are specific for cancer cells as compared to non-cancerous cells. N=4, *p<0.01.

Compound C0105 administration reduces PI3K and ERK signaling, the survival and mitogenic pathways, respectively. Reduction in PI3K signaling in cancer cell lines caused by Compound C0105 administration is reflected by reduction in $pS^{473}$-Akt (serine$^{473}$-phosphorylated Akt carried out by mTOR) (FIGS. 10A-12F). Likewise, reduction in ERK signaling caused by Compound C0105 administration is indicated by a reduction in tyrosine and/or threonine phosphorylated ERK2 (pY/pT-ERK2) (FIGS. 10A-12F).

Data for inhibition of $pS^{2448}$-mTOR, $pS^{473}$-Akt1 and pYpT-ERK2 in cancer cells versus a lack of such inhibition in non-cancerous cells is illustrated for melanoma cells, cancerous small cell lung carcinoma versus primary lung fibroblasts, breast cancer cells such as HTB-22 cells versus human mammary epithelial cells (HMEC), and pancreatic cancer cells such as MiaCa2 cells versus human pancreatic epithelial cells (HPEC) are shown in FIGS. 13A-13H.

These data together again indicate that contacting cells with Compound C0105 or a compound that binds similarly to the FLNA pentapeptide of SEQ ID NO: 1 is specific for cancer cells as compared to non-cancerous cells. N=4, *p<0.01.

Compound C0105 Reduces K-RAS but Increases RasGAP-FLNA Association, Thereby Reducing Active K-RAS In the cancer cell lines examined, glioblastoma, small cell lung, pancreatic and melanoma, K-ras association with FLNA was elevated compared to noncancerous primary cells (lung fibroblasts and HPECs) (FIGS. 30A-30L). In contrast, ras-GAP association with FLNA was lower in the cancer cell lines than in primary cells. Compound C0105 incubation reduced FLNA-associated K-ras and markedly increased FLNA-linked ras-GAP in the cancer lines as can be seen by examination of FIGS. 30A-30L. Compound C0105 had no effect on fibroblasts.

Figure 31A:
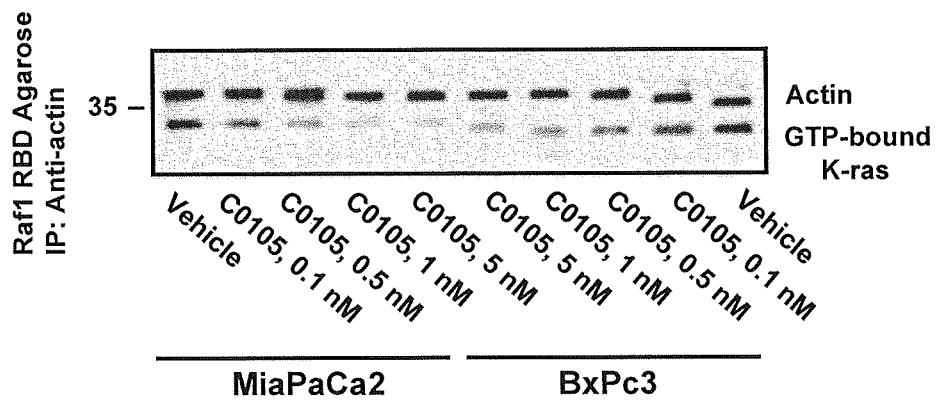
FIGS. 31A and 31B illustrate the effects of illustrative Compound C0105 on levels of active K-ras (GTP-bound K-ras), assessed using the agarose bead-bound Raf1 RBD pull-down assay in melanoma, two different pancreatic cancerous cell lines (MiaPaCa2 and BxPc3) and a glioblastoma cell line (U87). The cells were treated (contacted) with zero (vehicle), 0.1, 0.5, 1 and 5 nM Compound C0105 as previously discussed. The thus obtained GTP-bound K-ras was subjected to Western blotting using anti-ras antibodies for identification, the blot densities determined and statistically analyzed as discussed previously.
Figure 31B:
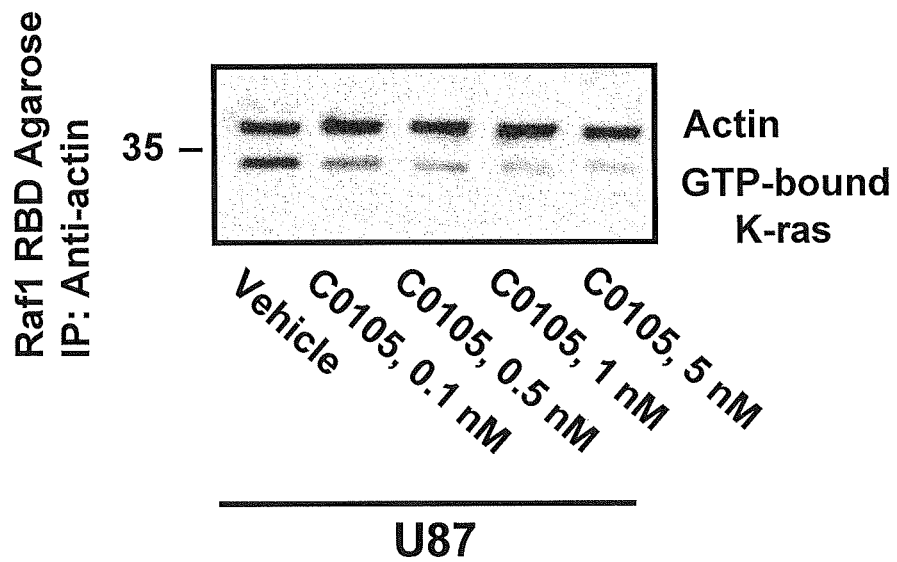

Elevated K-ras association with FLNA coupled with a lower level of ras-GAP—FLNA association observed in the cancer cell lines translates to heightened levels of active K-ras. The effects of Compound C0105 on levels of active K-ras was assessed using the Raf1 RBD pull-down assay in melanoma, two different pancreatic cancerous cell lines (MiaPaCa2 and BxPc3) and a glioblastoma cell line (U87). Compound C0105 reduced GTP-bound K-ras, the active form of K-ras, in a concentration-dependent manner in all four cell lines (FIGS. 31A and 31B).

Compound C0105 Inhibits Proliferation of Neuroendocrine Tumor Cells

Neuroendocrine tumor biopsies were minced into 1-3 mm prisms using a sterile #10 scalpel. The resultant tumor pieces were washed with three times with $Ca^{2+}$-, $Mg^{2+}$-containing PBS pH 7.2. Following brief centrifugation, the supernatant was aspirated and the tumor pieces were incubated with 500 µl PBS with 100 µg/ml DNAase I (Qiagen 79254) and 50-200 U/ml collagenase type I (Gibco 17100-017): Trypsin 0.25%/0.53 mM EDTA (ATCC 302101)=1:1 at 37° C. for 8 hours with constant shaking. The dissociated neuroendocrine cells were obtained by passing through a sterile 40 µm Falcon blue nylon mesh cell strainer (BD 352340). The remaining tissue fragments were digested again by incubating at 37° C. with additional 500 µl of fresh collagenase/trypsin mixture solution.

The resultant dissociated cells were washed three times with fresh 5 ml PBS, pH 7.2 and then the cell pellet was re-suspended in culture medium. Following determination of cell viability using trypan blue exclusion, cells were seeded and cultured in T25 flask (BD 354536) in DMEM/F12 medium containing 10% FBS, 5% horse serum, 2% glucose, 1% sodium pyruvate, 1% Hepes, 1% L-glutamine, 0.01 mg/ml insulin, 20 ng/ml EGF, 500 ng/ml hydrocortisone and 100 ng/ml cholera toxin. The cell culture continued until the neuroendocrine cell colonies was established.

Separate cell cultures were prepared from both primary tumor and liver metastatic tumors from a patient with intestinal neuroendocrine cancer. The cells were plated thinly (about 100,000 cells) and serum deprived for 16 hours to synchronize the cell cycle stage before the treatment starts. Treatment was (1 nM) of Compound C0105 or medium alone for 4 days. (These cells grow slower than other types of cells discussed herein.)

For the proliferation study, cells were washed, solubilized and the levels of Ki67 and PCNA were assessed to determine the effect of Compound C0105 on cell proliferation. The magnitude of Compound C0105-induced inhibition on neuroendocrine tumor cell proliferation is comparable to that in k-ras and $pS^{2152}$-FLNA inhibition discussed elsewhere herein. Compound C0105 is almost equally effective in both metastatic and primary neuroendocrine tumor cells. These results are shown in FIGS. 36A-36C and 37A-37B.

Figure 32A:
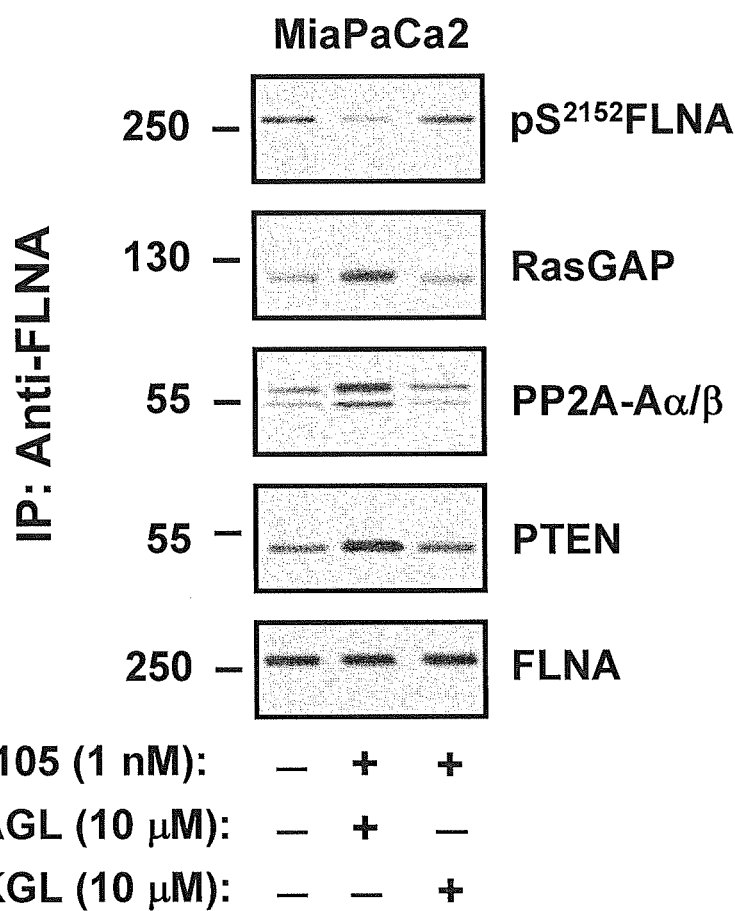
FIGS. 32A-32D illustrate Western blots of $pS^{2152}$FLNA, Ras-GAP, PP2A-Aα/β, PTEN and FLNA in FIG. 32A and Ki67, PCNA and actin in FIG. 32C after four days of incubation (contact) of MiaPaCa2 cells in the presence of medium alone, or medium containing 1 nM Compound C0105 with and without the presence of 10 µM peptide VAAGL (SEQ ID NO: 2) or peptide VAKGL (SEQ ID NO: 1). Densitometric quantification of the Western blot results are shown in the graphs of FIG. 32B for the amounts of $pS^{2152}$FLNA, Ras-GAP, PP2A-A$\alpha$/$\beta$ and PTEN in anti-FLNA immunoprecipitates and the amounts of Ki76 and PCNA (normalized by actin) in FIG. 32D. N=4, *p<0.01.
Figure 32B:
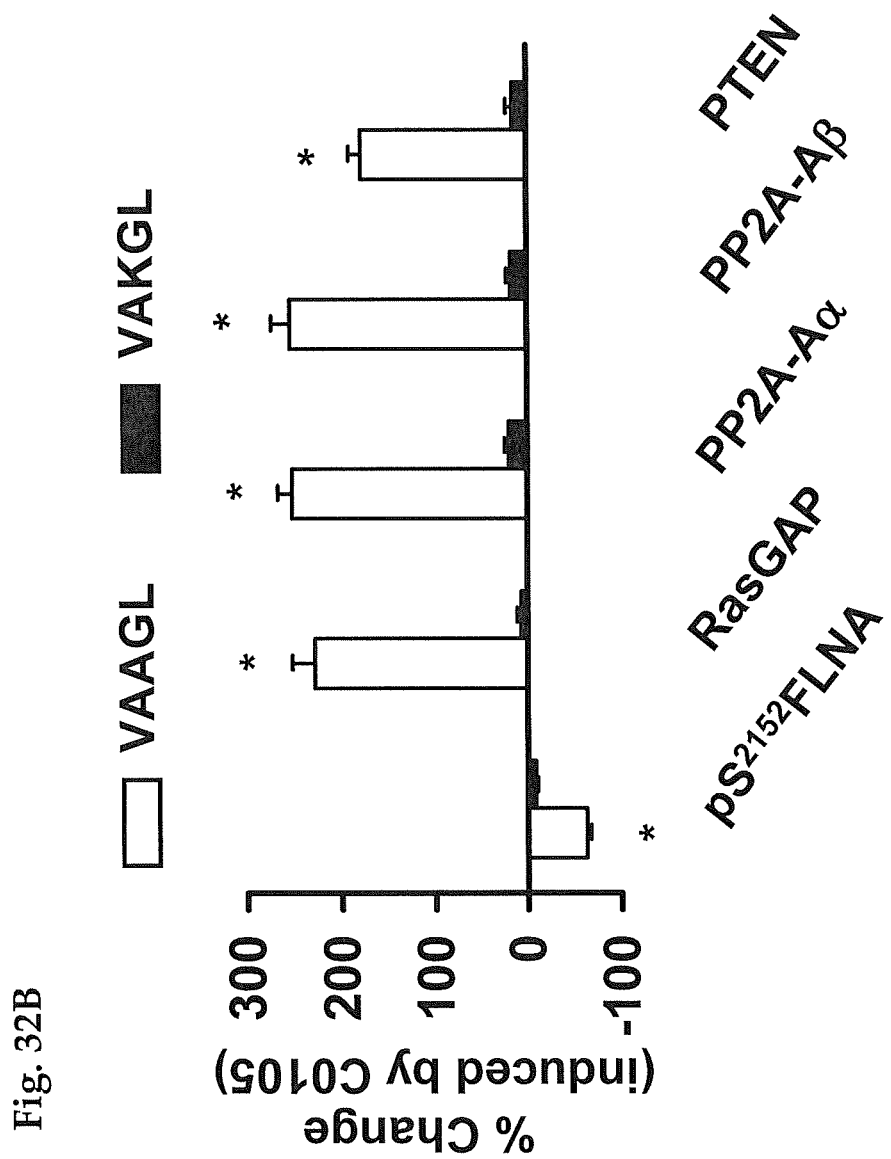
Figure 32C:
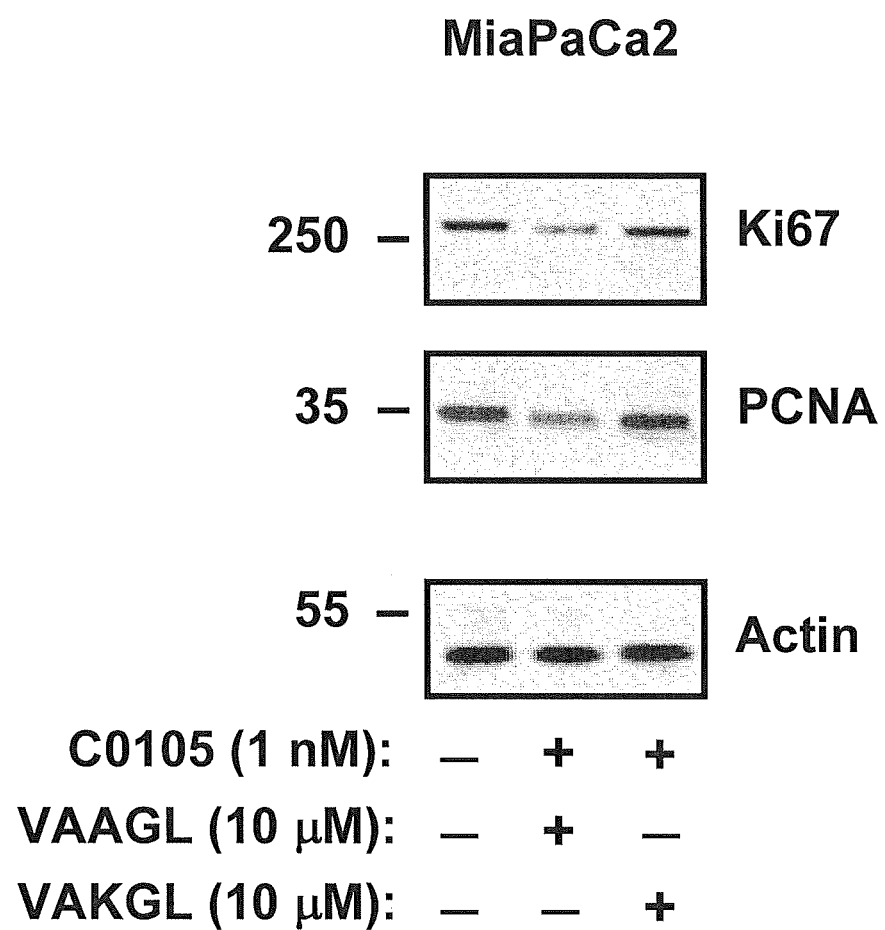
Figure 32D:
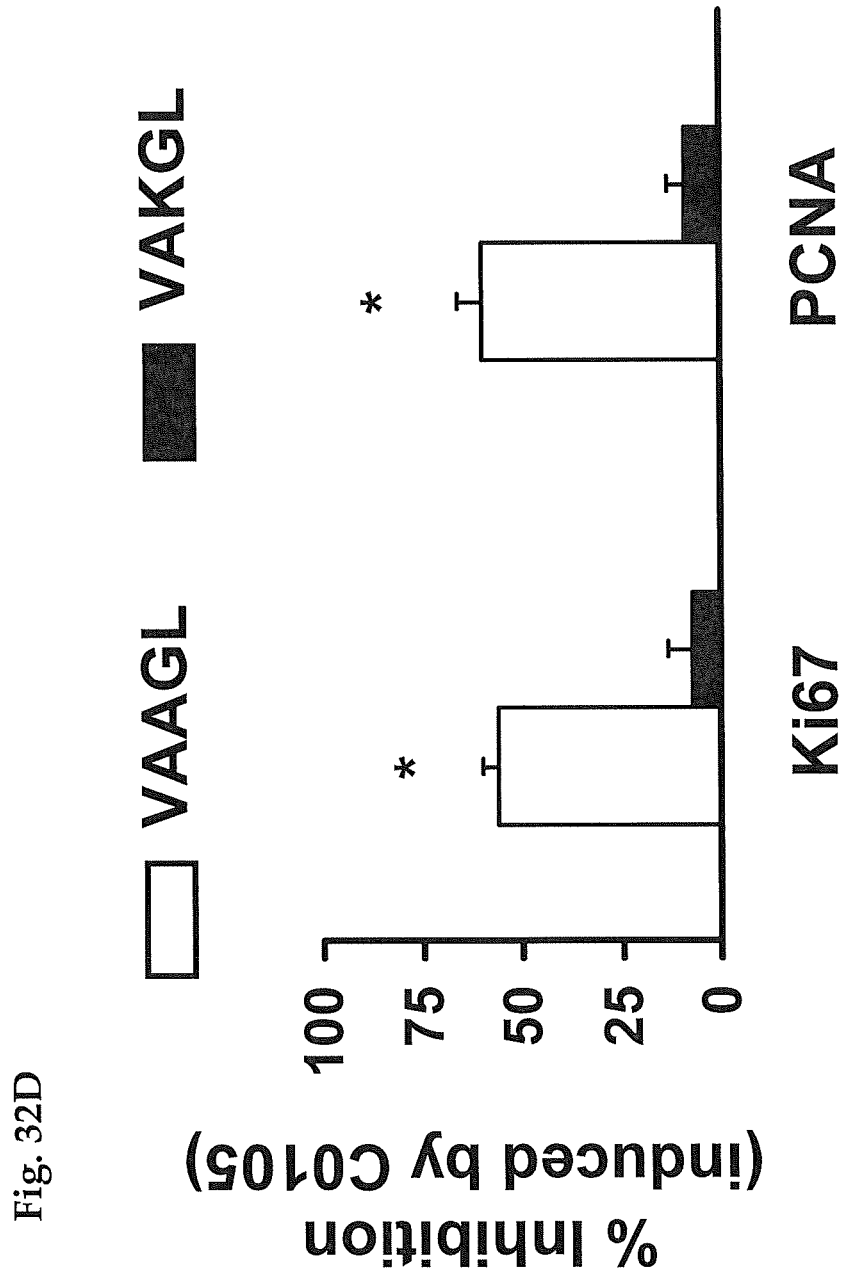

Compound C0105 Binds an Altered Conformation of FLNA and Restores its Native Conformation To demonstrate the mechanism of action of Compound C0105 is via binding its pentapeptide binding site on FLNA, illustrative MiaPaCa2 cells were treated with vehicle or 1 nM Compound C0105 in the presence of 10 µM of decoy (VAKGL; SEQ ID NO: 1) or control (VAAGL; SEQ ID NO: 2) pentapeptide for 4 days before measuring Compound C0105 mediated reduction in $pS^{2152}$FLNA, restoration of FLNA linkages and cell proliferation arrest. When incubated together with the VAKGL (SEQ ID NO: 1) decoy pentapeptide, Compound C0105 lost its effect on $pS^{2152}$FLNA hyperphosphorylation and on FLNA associations with ras-GAP, PTEN and PP2A (FIGS. 32A and 32B). In contrast, co-incubation with an alanine-substituted control peptide (SEQ ID NO: 2) that does not bind Compound C0105 did not disrupt Compound C0105 effects on FLNA associations or $pS^{2152}$FLNA hyperphosphorylation. Co-incubation with the decoy pentapeptide also disrupted Compound C0105's reduction in cell proliferation as indicated by the levels of cell-cycle markers, Ki67 and PCNA (FIGS. 32C and 32D).

Figure 33A:
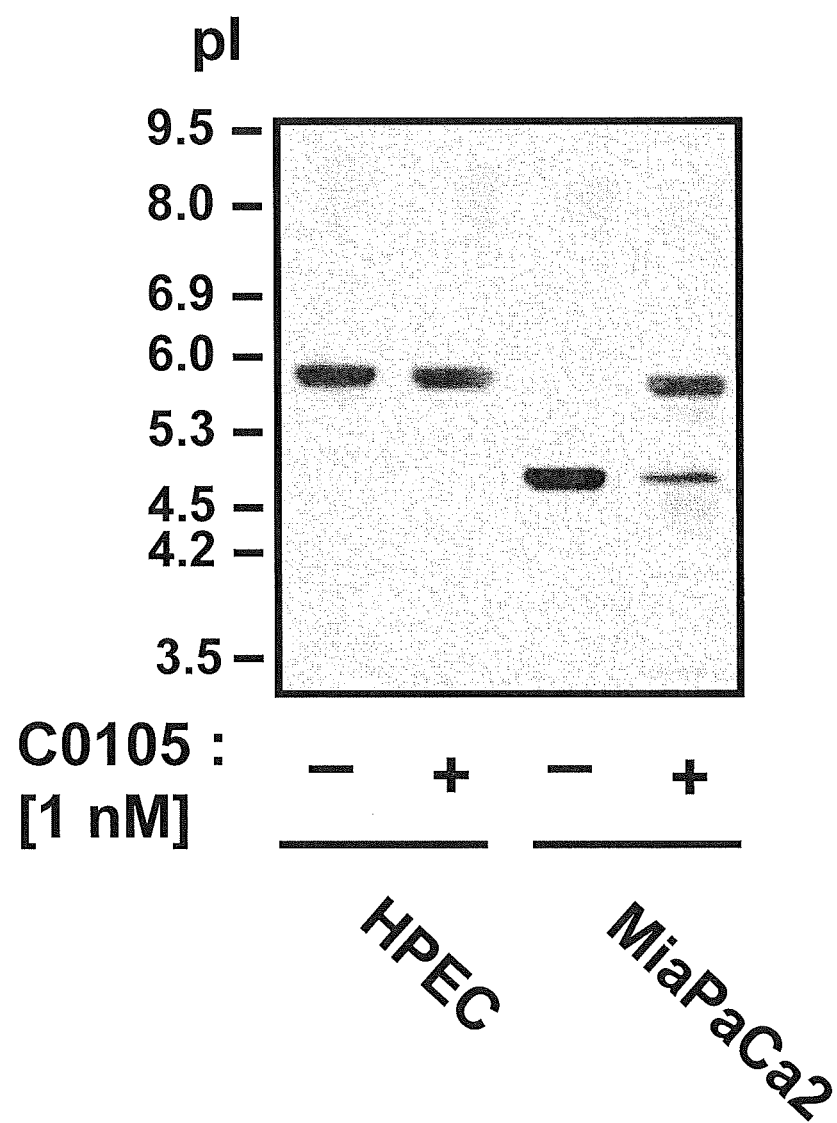
FIGS. 33A and 33B show isoelectric focusing result data (FIG. 33A) for FLNA separately isolated from HPEC and MiaPaCa2 cells after four days of incubation (contact) of those cells with medium alone or medium plus 1 nM Compound C0105.

An isoelectric focusing gel was used to determine whether FLNA in cancer cells has an altered conformation. FLNA was purified separately from MiaPaCa2 cells and from HPECs. FIG. 33A shows that the isoelectric focusing point (pI) of FLNA is more acidic (pI 4.8) when isolated from MiaPaCa2 than when isolated from HPECs (pI 5.9), indicating different conformations. Treatment of MiaPaCa-2 cells with Compound C0105 for 4 days followed by FLNA isolation and isoelectric focusing as above shifted the pI for the majority of the FLNA and hence restored conformation of about 75% of FLNA in the MiaPaCa2 cells to that present in HPECs. Similar treatment of HPECs with Compound C0105, isolation and isoelectric focusing of the FLNA showed that the treatment had no effect on the pI of the FLNA from those non-cancerous, normal cells.

Figure 33B:
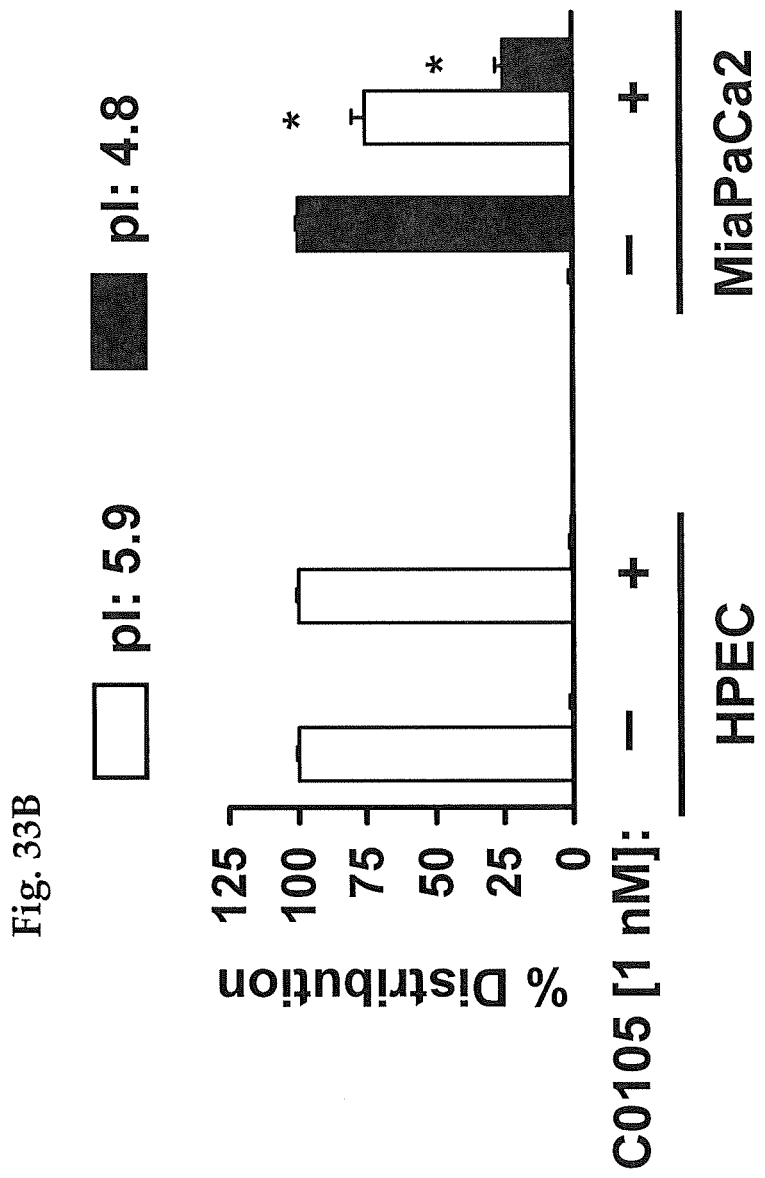

The above changes in isoelectric point might be due to a change in phosphorylation of the FLNA because a hyperphosphorylated protein is more acidic than its unphosphorylated form. As such, the results fit some of the data showing heightened phosphorylation on S2152 and likely other sites throughout the FLNA. However, only a fraction of FLNA molecules are hyperphosphorylated in all cancer cells assessed so that more than one protein band or a wide band for the cancer cell-derived protein would be expected if the change were due to a change in phosphorylation. The distribution of the isoelectric focused FLNA illustrated in FIG. 33A is illustrated in FIG. 33B.

One other clue that the conformational changes rather than hyperphosphorylation causes much of the pI change in cancer cells is that monoclonal antibodies produced using noncancerous platelet FLNA recognize tumor FLNA poorly. On the other hand, goat (immunopurification) antibodies against the N-terminus of FLNA and rabbit (Western blot) antibodies recognize FLNA in MiaPaCa2 and human pancreatic epithelial cells equally well. There is no doubt that hyperphosphorylation contributes in some degree to the acidification of FLNA and consequent change in pI in cancer cells.

Conclusions

A growing body of research is revealing a complex role of FLNA in cancer [Yue et al., *Cell & Bioscience* 3:7 (2013)]. As a key regulator of the cytoskeleton network, FLNA interacts with many proteins involved in cancer metastasis [Yue et al., *Cell & Bioscience* 3:7 (2013)], and its knockdown or inhibition has been shown to reduce cancer metastasis potential [Xi et al., *Int J Biol Sci* 9:67-77 (2013)].

FLNA also has been implicated in tumor progression. FLNA knockout mice show reduced oncogenic properties of K-ras, including the downstream activation of ERK and Akt [Nallapalli et al., *Mol Cancer* 11:50 (2012)]. Many different cancers show high levels of FLNA expression in contrast to low FLNA levels in corresponding normal tissue, including colorectal and pancreatic cancer [Uhlen et al., *Mol Cell Proteomics* 4:1920-1932 (2005)], and glioblastoma [Sun et al., *Cancer Cell* 9:287-300 (2006)]. Reduction or genetic modification of FLNA also sensitizes cancer cells to both cisplatin and radiation [Meng et al., *J Biol Chem* 279:6098-

6105 (2004)], and FLNA deficiency in cancer cells similarly sensitizes them to chemotherapeutic agents [Yue et al., *DNA Repair (Amst)* 11:192-200 (2012)] and radiation [Yue et al., *Cancer Res* 69:7978-7985 (2009); and Yuan et al., *J Biol Chem* 276:48318-48324 (2001)].

Amassed herein are extensive in vitro data (and in vivo data below) using five different cancer cell lines, one primary and metastasized cancer cells (neuroendocrine) and three different primary control cell types for comparison. The data indicate that Compound C0105 and those other illustrative compounds that bind similarly to FLNA reduce the number and aggressiveness of cancer cells by restoring the levels of natural signaling regulators and normalizing their glucose metabolism, thereby illustrating a novel cancer therapy.

Compound C0105 and those other illustrative compounds normalize the elevated FLNA phosphorylation at serine$^{2152}$ (pS$^{2152}$FLNA) in cancer cell lines. Compound C0105 and those other illustrative compounds increase associations of the phosphatases PTEN and PPA2 with FLNA, which are reduced in cancer cell lines.

Additionally, Compound C0105 and those other illustrative compounds reduce the elevated FLNA-associated K-ras in cancer cell lines compared to primary control cells, while increasing levels of FLNA-linked ras-GAP, the K-ras negative regulator. The restored FLNA associations with PTEN, PP2A and ras-GAP and the reduced FLNA—K-ras association lead to robust reduction in activated mTOR, Akt and ERK in the cancer cell lines tested but without an effect on mTOR, Akt and ERK in the primary normal cells. These signaling molecules represent the two major signaling pathways that drive the survival and proliferation of the cancer cells.

It is now shown that FLNA in cancer cells has an altered conformation, likely leading to its elevated association with K-ras and its reduced associations with ras-GAP and the phosphatases PP2A and PTEN. PP2A has the ability to dephosphorylate pS$^{2152}$FLNA, which could contribute to the altered FLNA conformation, and PTEN is known to regulate Akt and mTOR. Because K-ras activates Braf, which leads to ERK activation, reducing active K-ras reduces ERK signaling and eventual oncogenic drive. Importantly, administration of Compound C0105 and those other illustrative compounds restores the native conformation of FLNA and normal levels of its protein associations.

Functionally, administration of (contacting) Compound C0105 or those other illustrative compounds to pancreatic cancer, breast cancer, melanoma, glioblastoma and small cell lung cancer cell lines greatly reduces proliferation of those cancer cells, but has no effect on non-cancerous primary fibroblasts, astrocytes or epithelial cells. Administration of Compound C0105 and those other illustrative compounds also reduces the typical glucose dependence of these cell lines and restores resistance to glucose deprivation.

Overall, these in vitro data indicate Compound C0105 and those other illustrative compounds that bind similarly to FLNA are compounds with the ability to block the two predominant cancer signaling pathways by binding a single novel target.

In Vivo Mouse Studies
Pancreatic Cancer
Preparation of MiaPaCa2 or BxPC3 Cells for Implantation MiaPaca2/ATCC® CRL-cells (2rd-3rd passage) were maintained on BD cell culture flasks (75 cm$^2$) as monolayer cultures in 20 ml of DMEM supplemented with 10% FBS and 2.5% horse serum. BxPC3/ATCC® CRL-1687 cells (2rd-3rd passage) are maintained on BD cell culture flasks (75 cm$^2$) as monolayer cultures in 20 ml of RPMI supplemented with 10% FBS. When cells reached approximately 90% confluency, the medium from 75 cm$^2$ was removed by aspiration. The flask was first washed with 20 ml PBS and then trypsinized with 2.5 ml 0.25% trypsin solution (25-053-CL, Cellgro) for 5 minutes (until cell completely detached). The trypsinized cells were transferred into a 15 ml Falcon tube and 10 ml medium added. After centrifugation (5 minutes, 1100 rpm), cells were resuspended in 12 ml of sterilized PBS and centrifuged again. The cell pellets were then resuspended in DMEM or RPMI [serum-free], the volumes of medium used depend on the number of flasks (about 6 million MiaPaCa2 per flask). The cell pellets from 6 flasks were suspended with 7 ml of DMEM (MIaPaCa2) or RPMI (BxPC3). All of the cells for implantation were collected together in a 50 ml Falcon tube so that each mouse received an identical number of cells. One ml of cell suspension was removed for cell counting and viability test.

For viability tests, 900 μl cell suspensions were mixed 100 μl Trypan blue for 2 minutes at room temperature. Cell viability was calculated as the number of viable cells (that exclude Trypan blue) divided by the total number of cells within the grids on the hemocytometer. Cell concentration before injection was determined using a hemocytometer. The level of viable cells was at least 95%.

The cells were pelleted by centrifugation and then suspend in DMEM (or RPMI) to reach 4 million cells/50 μl for implants. The obtained cell suspensions were mixed with 50 μl of Matrigel (BD 354248) 50:50 immediately before implantation, kept in the ice and implanted by subcutaneous injection into right flank of a 8-month-old Nu/Nu mice. Approximately, 4 million ($4\times10^6$) cells were injected subcutaneously into either right flank of an 8-week-old athymic male (or female) nu/nu mouse. The injection volume was 100 μl per mouse. The data were collected for tumor volume (mm$^3$) and percentage change in volume, comparing to individual baseline tumors (day 0) on the indicated day of treatment.

Beginning 5-11 days after cancer cell implantation, tumors reached an average size of 200-250 mm$^3$ and mice were treated by administration of vehicle (0.9% NaCl in water), or 1 or 10 mg/kg C0105 or other drug twice daily (5 hours apart). Mice were checked twice daily, body weights were recorded twice weekly and tumor sizes were measured using digital caliper twice weekly to the conclusion of the studies. Mice were sacrificed on day 20 immediately after the volume of the tumors was determined.

Mice were monitored individually and the treatment effect was compared to each mouse's own original tumor on the treatment day 0. The endpoint of the study was a tumor volume of 1500 mm$^3$ or 45 days, whichever comes first. The animals were euthanized when the endpoint was reached. Responders were followed longer (survival study). The Table below illustrates the drug treatment administered to the mice.

TABLE*

| Group | Number/Group | Agent | Vehicle | mg/kg | Route of Admin | Schedule |
|---|---|---|---|---|---|---|
| 1# | 10 | vehicle | Sterilized 0.9% saline | — | gavage | bid to end, 10 am & 3 pm |
| 2 | 10 | gemcitabine | Sterilized 0.9% saline | 50 | ip | Bi-weekly |
| 3 | 10 | C0105 | Sterilized 0.9% saline | 1.28 | gavage | bid to end, 10 am & 3 pm |
| 4 | 10 | C0105 | Sterilized 0.9% saline | 12.82 | gavage | bid to end, 10 am & 3 pm |
| 5 | 10 | C0105 | Sterilized 0.9% saline | 128.21 | gavage | bid to end, 10 am & 3 pm |

*Number/Group = animal number in each treatment group; Route of Admin = Route of Administration.

Compound C0105 Shrinks Tumors in Xenograft of MiaPaCa-2 Cells

Nu/Nu mice were inoculated with 4 million MiaPaCa2 pancreatic cancer cells and treated 11 days later (when tumors were established) with vehicle (0.9% NaCl), 1 or 10 mg/kg Compound C0105 twice daily orally for 20 days (n=4). Compound C0105 shrank tumors at 10 mg/kg and arrested growth at 1 mg/kg (FIG. 26A). **$p<0.05$, *$p<0.01$ compared to individual baseline. ++$p<0.05$, +$p<0.01$ compared to vehicle control group.

Figure 26A:
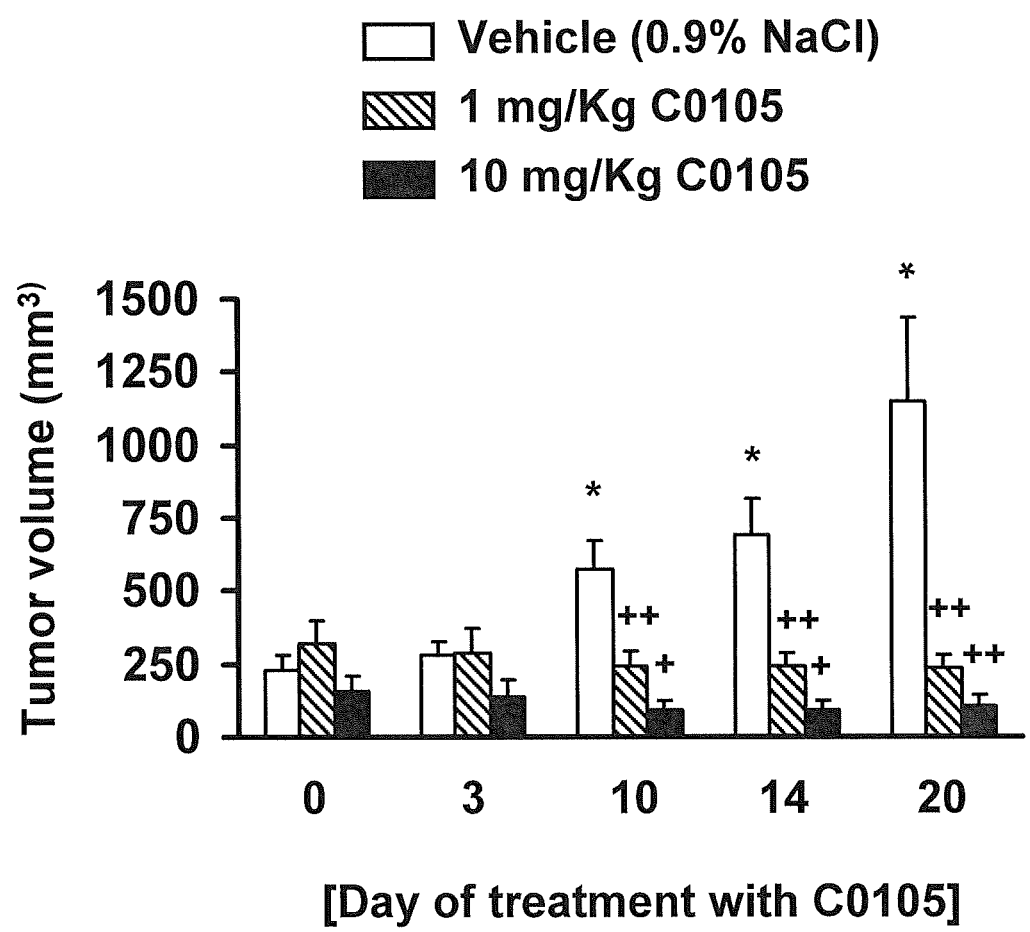
FIGS. 26A-26B illustrate that contact with Compound C0105 robustly reduces tumor sizes in Nu/Nu mice with MiaPaCa2 or BxPC3 pancreatic cancer cell implants. MiaPaCa2 cells mixed with Matrigel® [BD Biosciences] (50:50) on ice were injected into the flanks of Nu/Nu mice. One-week following injection, the baseline tumor volumes were measured by a digital external caliper (day 0). Mice were divided into three groups that received orally administered vehicle (0.9% NaCl), 1 mg/kg Compound C0105 (dissolved in 0.9% NaCl) or 10 mg/kg Compound C0105 (dissolved in 0.9% NaCl) twice daily. The tumor volumes were also measured at 3, 10, 14 and 20 days after the baseline tumor volume assessment. Mice were sacrificed at Day 21 and tumors were harvested and photographed. There were no gender differences in the effect of Compound C0105 contact on tumor volume.
Figure 26B:
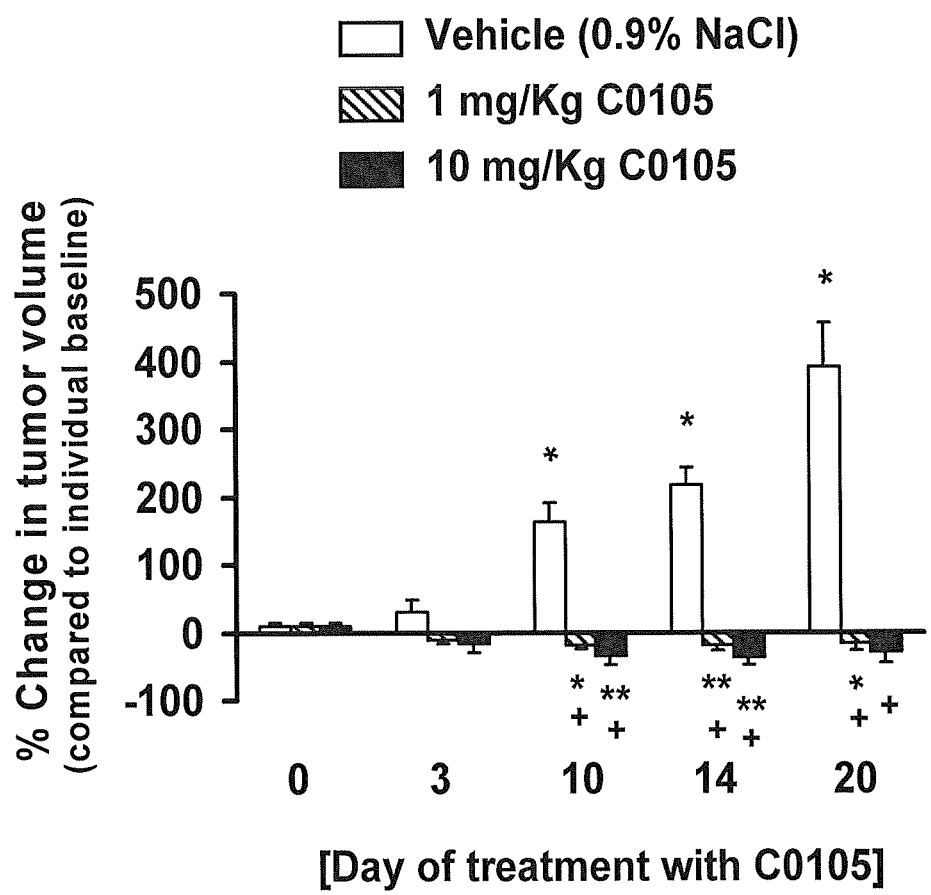
Figures 27A, 27B:
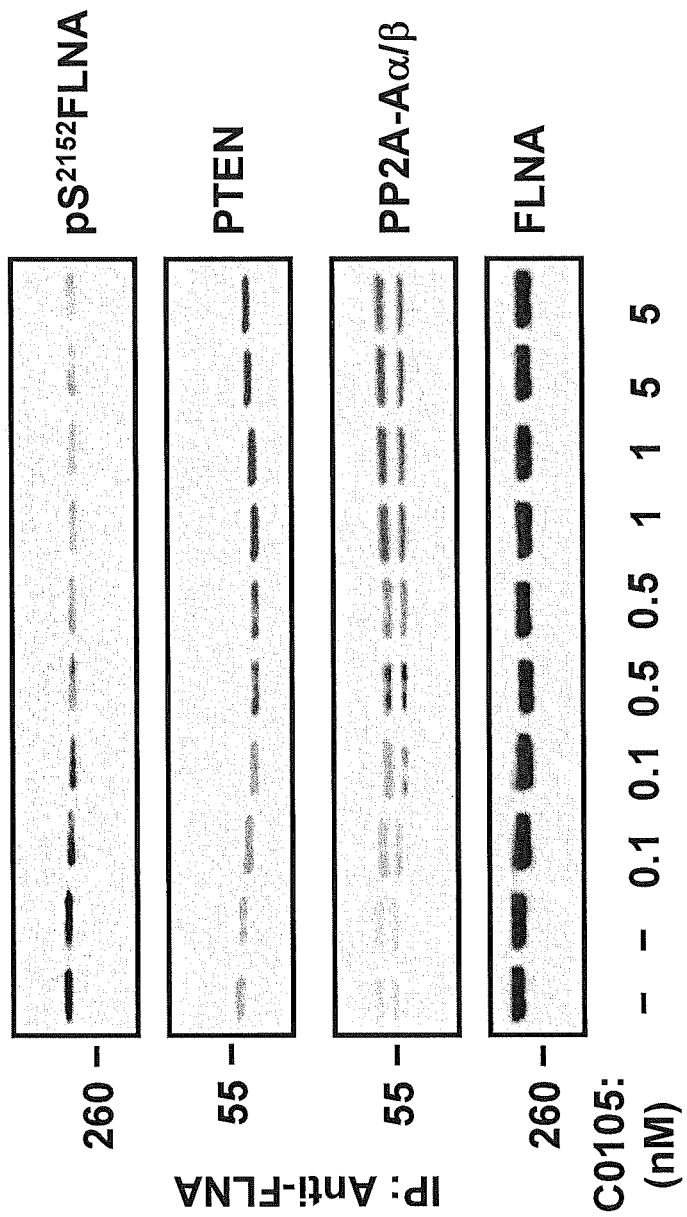
Figure 27C:
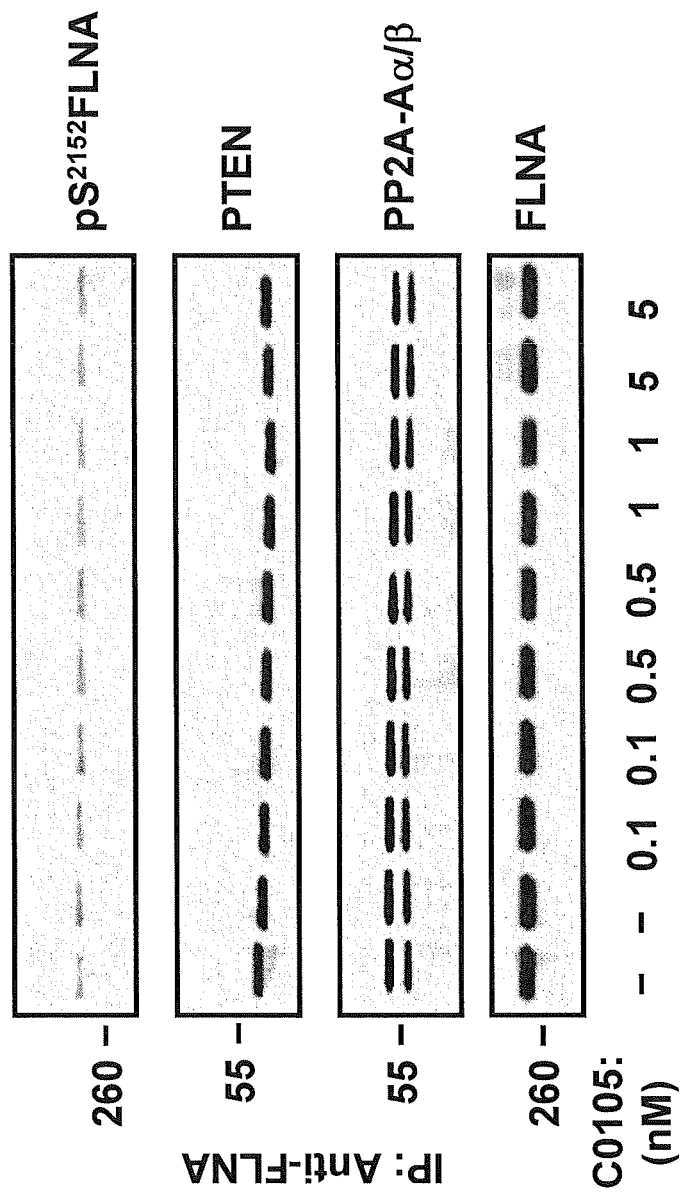
Figure 27D:
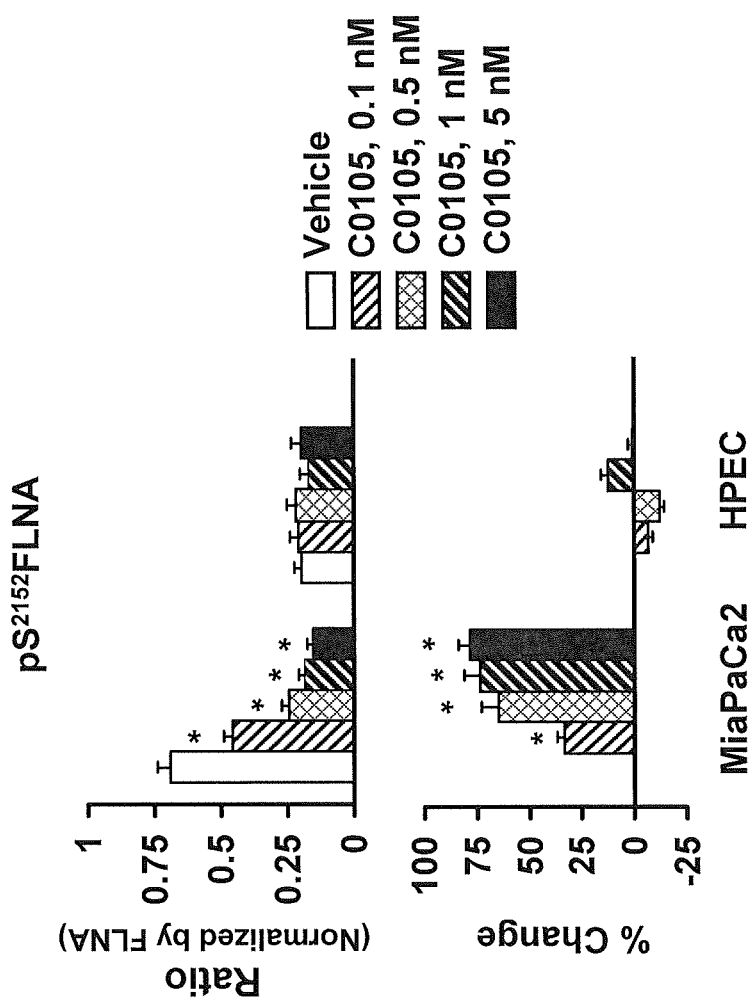
Figures 27E, 27F:
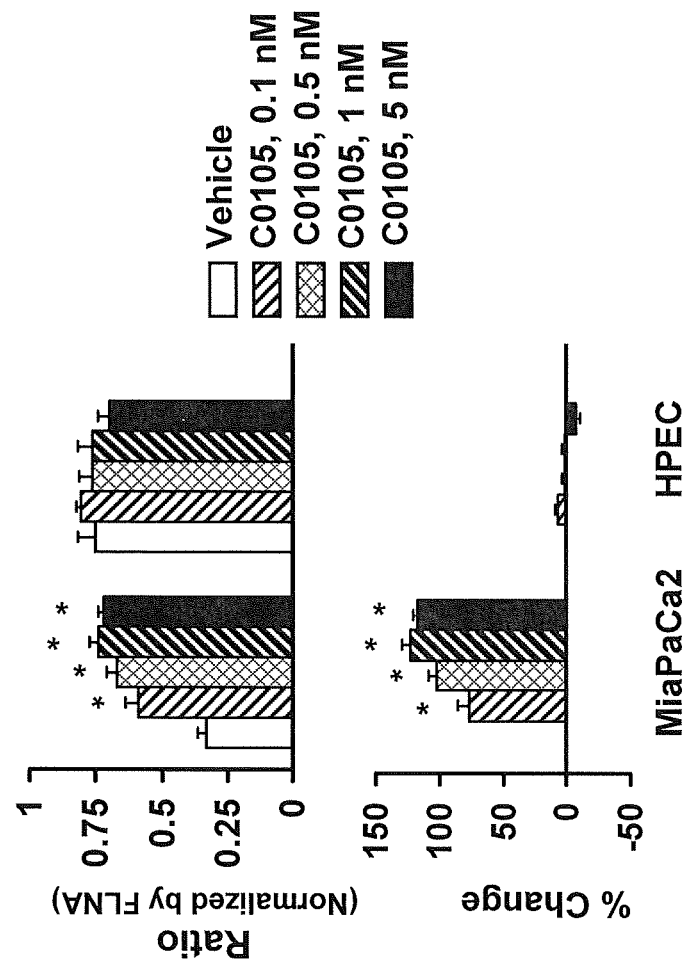
Figures 27I, 27J:
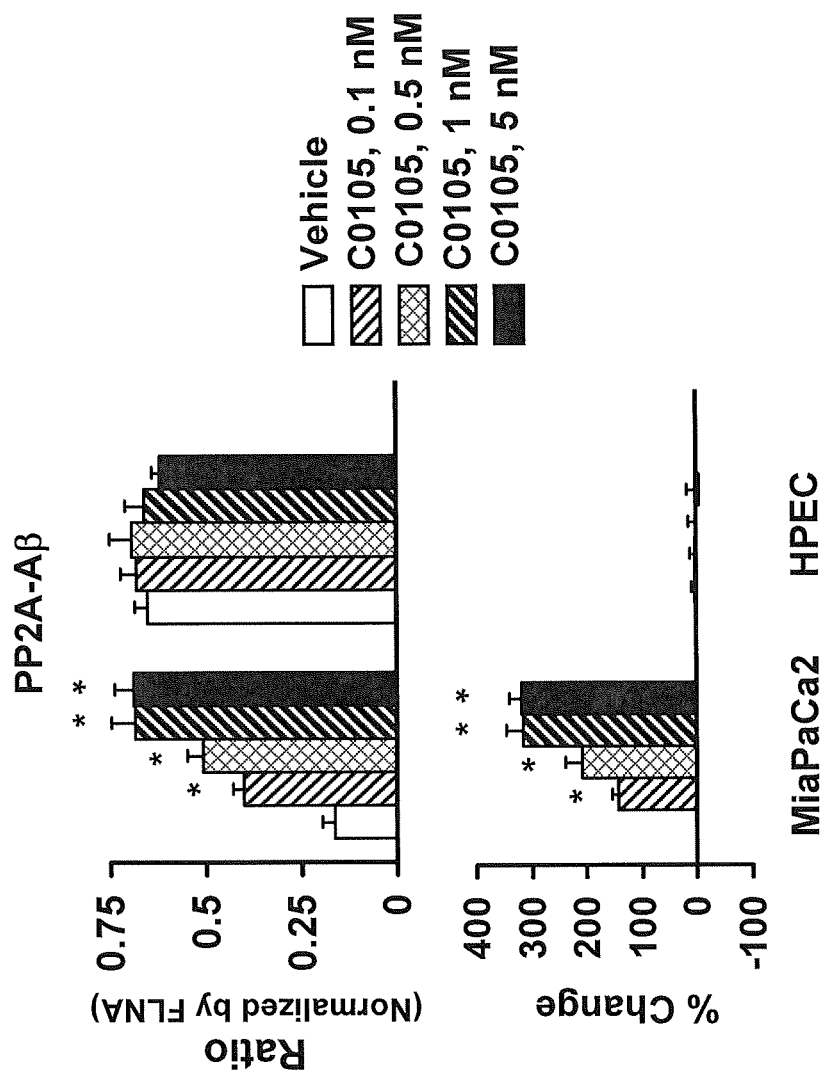

The representative data of FIG. 26A indicate the sharp differences in tumor sizes without and with Compound C0105 treatment. The data of FIG. 26B clearly indicate that contact with Compound C0105 stops MiaPaCa-2 cells from growing—actually shrinks the tumor—whereas the tumors in the vehicle-treated group keep getting larger. There is a small dose-dependent effect that indicates that 10 mg/kg treatment has a more stable effect. **$p<0.05$, *$p<0.01$ when compared to individual baseline, n=3 and 2 for baseline; ++$p<0.05$, +$p<0.01$ when compared to vehicle control group, n=3 and 3.

In addition to reducing tumor volume, contacting the tumor cells with Compound C0105 visibly reduced the vasculature of tumor masses, suggesting an additional effect on angiogenesis by decreasing inflammatory cytokine levels by preventing FLNA recruitment to TLR4.

Compound C0105 Shrinks Tumors in Xenograft of BxPC3 Cells

In a second xenograft study, Nu/Nu mice were implanted with a second pancreatic cancer cell line, BxPC3, and using the pancreatic cancer standard of care Gemcitabine (50 mg/kg i.p. bi-weekly) as an additional control. Compound C0105 was given by oral gavage twice daily at 1 and 10 mg/kg as before. Additionally, a combination group was given the gemcitabine plus the high dose of Compound C0105. Compound C0105 alone at each of the three concentrations used outperformed gemcitabine as well as gemcitabine plus 10 mg/kg Compound C0105 and once again shrank tumors from their original baselines (FIG. 35). *$p<0.01$ compared to individual baseline. +$p<0.01$ compared to vehicle control group.

Figure 34A:
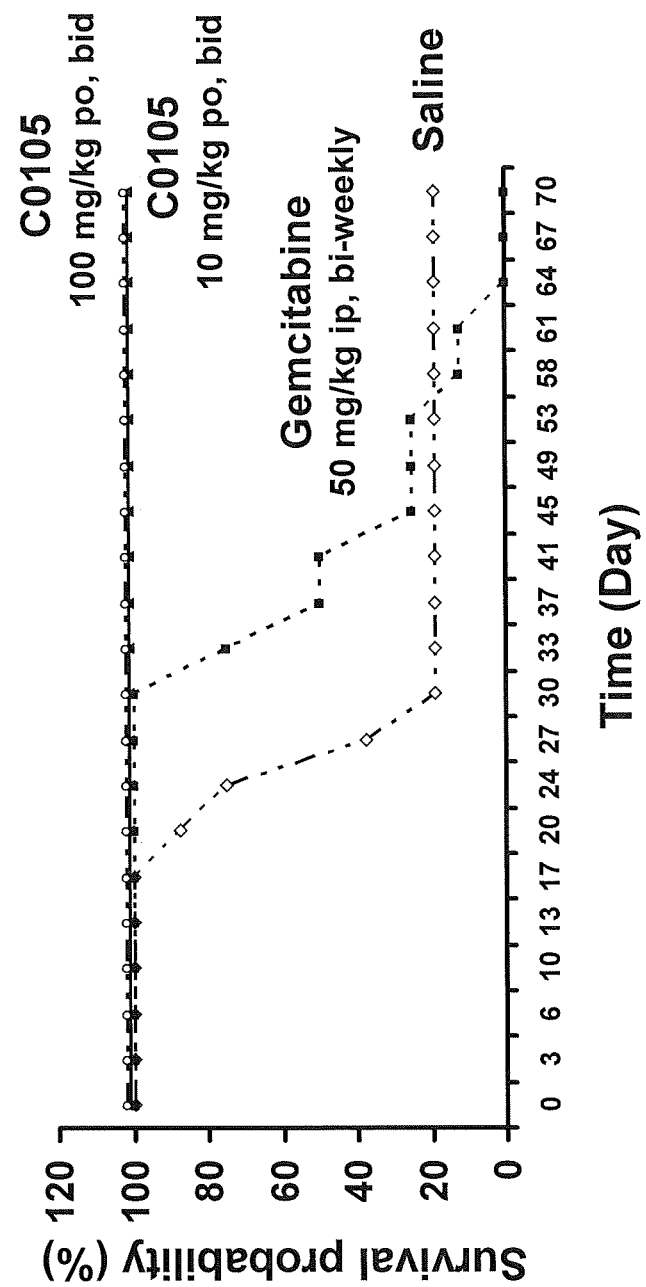
FIGS. 34A and 34B illustrate Kaplan-Meier survival curves (FIG. 34A) and averaged tumor volumes (FIG. 34B) in a xenograft study in which MiaPaCa2 cells were implanted in Nu/Nu mice. After tumors were established at 5 days, the mice received vehicle (open diamonds), gemcitabine (50 mg/kg i.p. bi-weekly; black squares) or Compound C0105 PO at 10 mg/kg (black triangles) or 100 mg/kg (open circles) b.i.d (n=8) (FIG. 34A) through 45 days for those animals that survived.
Figure 34B:
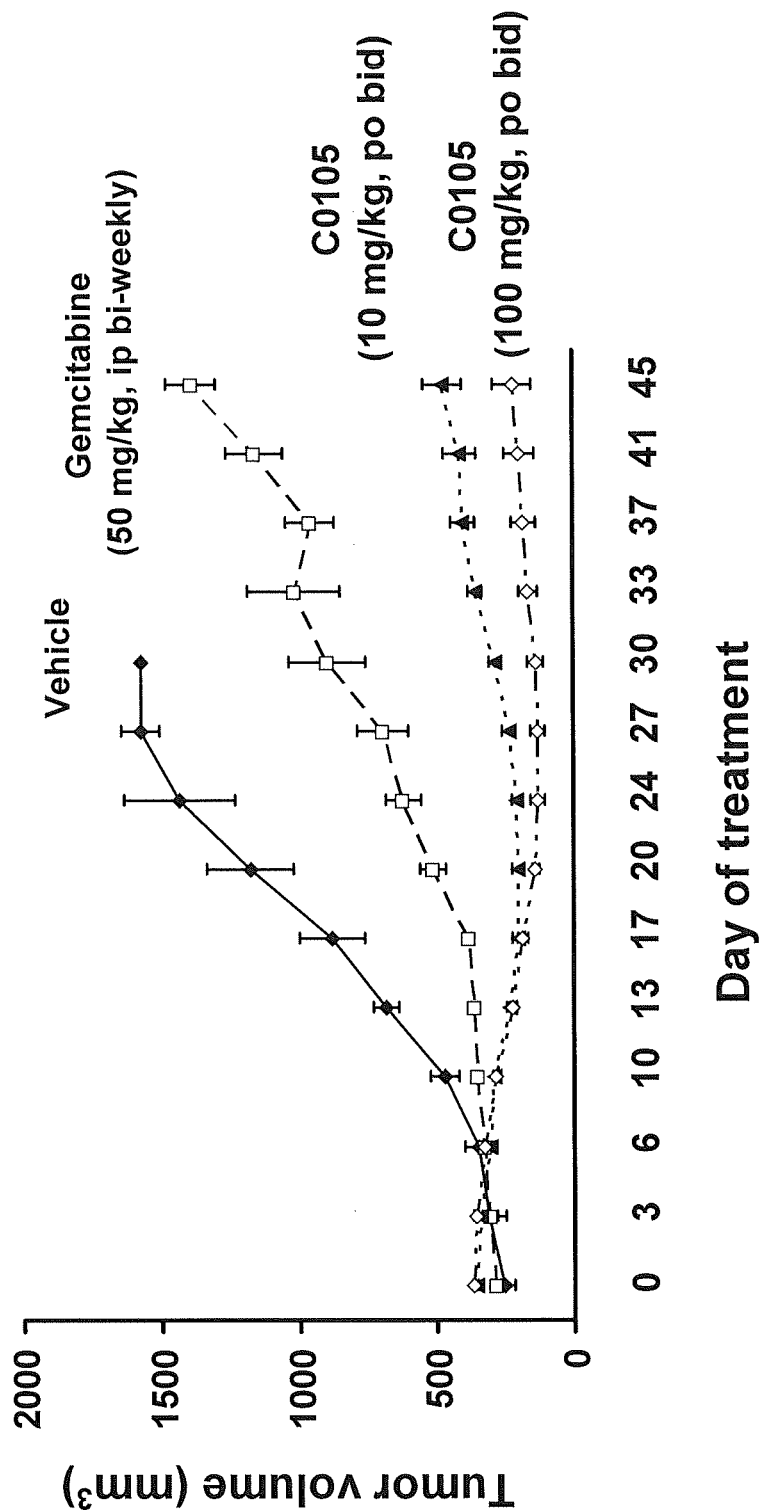
Figure 36A:
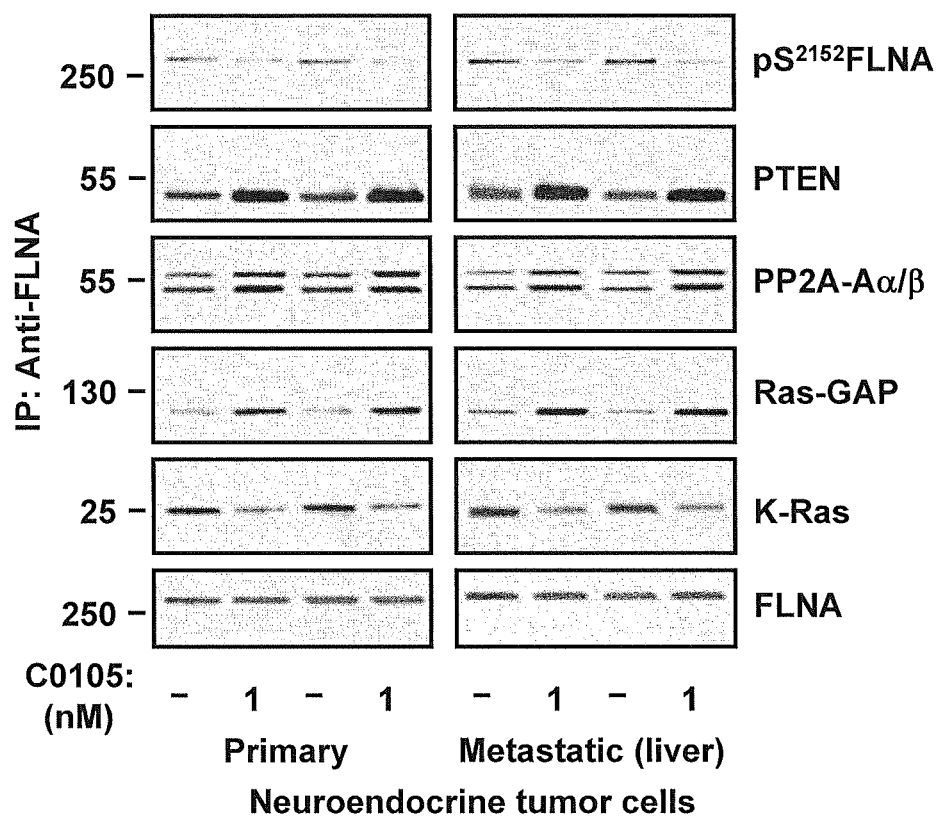
FIGS. 36A through 36C illustrate the effects of administration and contacting of primary and metastatic (liver) neuroendocrine tumor cells in culture with Compound C0105.
Figure 36B:
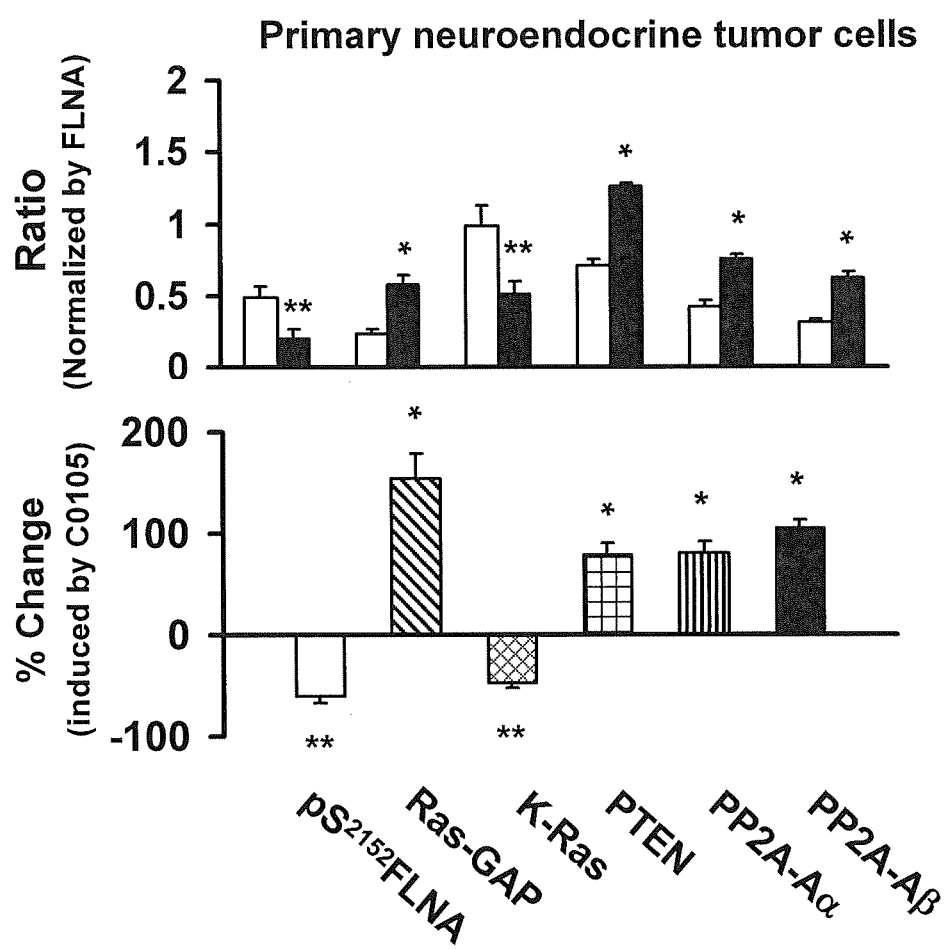
Figure 36C:
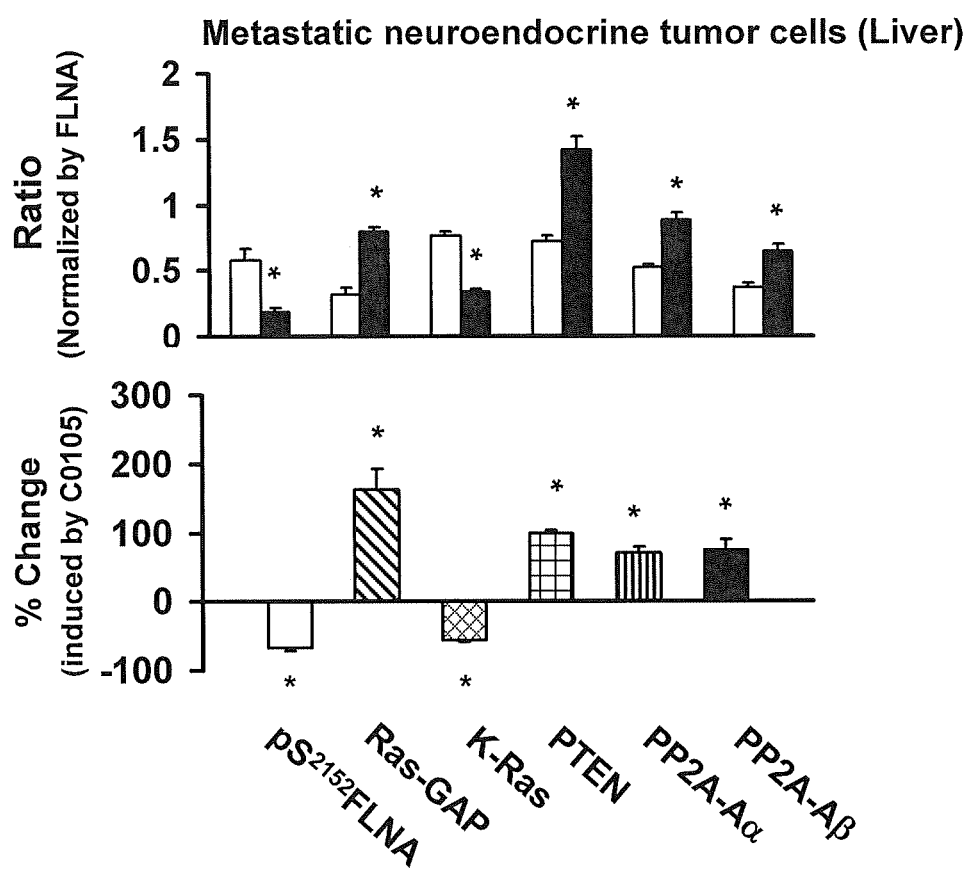
Figure 37A:
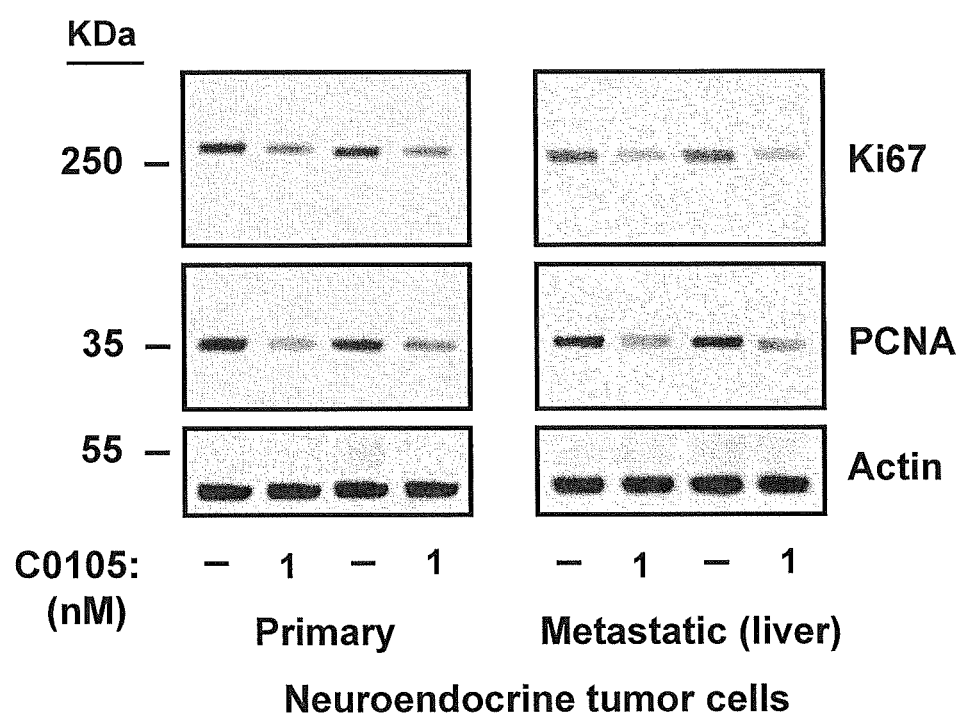
FIG. 37A and FIG. 37B show Western blotting results for the above primary and metastatic (liver) neuroendocrine tumor cells in which the cells were plated and serum-deprived for 16 hours to synchronize the cell cycle prior to Compound C0105 administration. The cells were treated with 1 nM Compound C0105 or 0.1% FBS-containing medium alone for 4 days. Cells were washed, solubilized and the levels of Ki67 and PCNA were assessed by Western blotting (FIG. 37A). The density of protein bands was quantified by densitometric scan. The ratio of protein normalized by actin in the presence and absence of Compound C0105 and percentage inhibition results for Ki67 and PCNA from those cells were determined (FIG. 37B). Statistical data were obtained using a two-tailed Student's t-test, with p<0.02 for all comparisons between treatment and control showing a *.
Figure 37B:
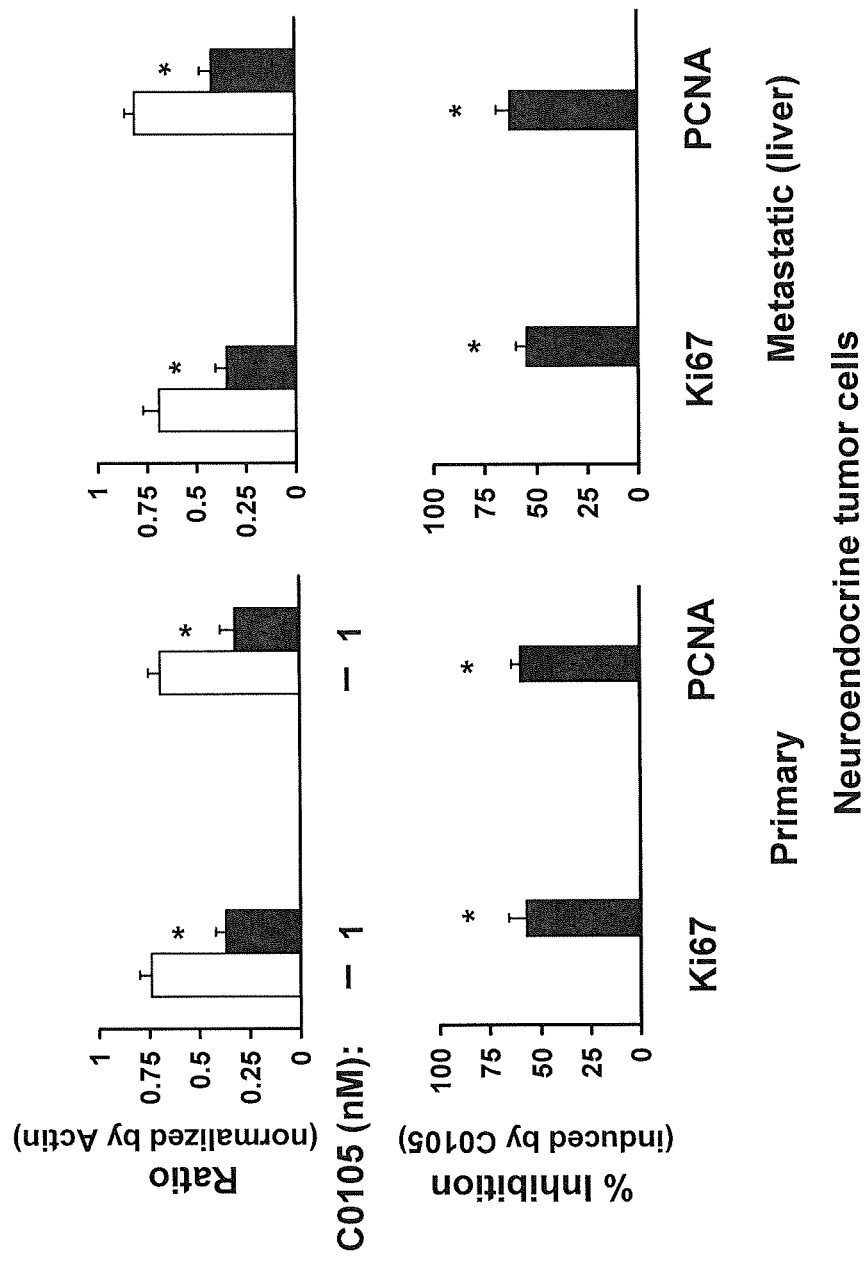

Survival Study: All Compound C0105-Treated Mice Reached 45-Day Survival Endpoint A third xenograft study was designed to measure survival rather than tumor volume at a designated time point. The MiaPaCa2 cells implanted and after tumors were established at 5 days, mice received vehicle, gemcitabine (50 mg/kg i.p. bi-weekly) or Compound C0105 PO at 10 or 100 mg/kg b.i.d (n=8). All mice in both Compound C0105 groups reached 45 days, whereas only one vehicle treated mouse and two mice treated with gemcitabine reached 45 days without tumors reaching 1500 mm$^3$ (FIG. 34A). Tumor volumes averaged for each treatment group are shown in FIG. 34B. As is seen from FIGS. 34A and 34B, administration of Compound C0105 at either concentration provided dose-dependent, superior anti-tumor results compared to gemcitabine or vehicle.

At 45 days, one-half the Compound C0105 groups were sacrificed and all remaining Compound C0105 mice reached 70 days. Three mice died during the study, one in each of control, low and high-dose Compound C0105 groups. The 100 mg/kg Compound C0105 mouse found dead at 30 days had a tumor shrunken by more than 90% compared to mice receiving vehicle. At 50 days, a mouse with no detectable tumor (as of 24 days) was maintained with no further treatment. At 70 days, treatments were terminated and mice were sacrificed at 80 days.

After 10 days of no treatment (80 days total), the tumors with more than 90% shrinkage were unchanged. In contrast, tumors over 400 mm$^3$ grew quickly once treatment stopped.

These in vivo studies demonstrate a potent and efficacious anti-tumor activity of illustrative Compound C0105 against two very aggressive pancreatic cancer cell lines MiaPaCa-2 and BxPC3. The first two studies showed tumor shrinkage by the 10 mg/kg dose and tumor growth arrest by the 1 mg/kg dose. In contrast, gemcitabine at 50 mg/kg i.p. b.i.d. slowed growth but did not shrink BxPC3 xenograft tumors.

Based on the results of the first two studies, the third study used higher doses (10 and 100 mg/kg) and a survival format with MiaPaCa2 xenografts. All Compound C0105-treated mice reached the 45-day survival endpoint, whereas none of the vehicle-treated mice and only two gemcitabine-treated mice reached 45 days without a tumor size of 1500 mm$^3$. Having completely shrunk tumors to being undetectable in three high-dose (100 mg/kg) mice, Compound C0105 shows powerful new cancer therapeutic activity.

These data corroborate the previously-discussed in vitro data in five cancer cell lines, demonstrating marked reduction in proliferation and in activation of K-RAS, ERK, Akt and mTOR, representing the two major cancer signaling pathways mTOR and ERK. Each of those cell lines exhibits an enhanced amount of one or more of phosphorylated-mTOR, phosphorylated-Akt1, phosphorylated-ERK2 and serine2152-phosphorylated filamin A. Thus, these two major cancer signaling pathways are blocked by an illustrative compound that binds to only a single target.

Glioma

Adult (10-week-old) NuNu SCID mice were used in dose groups of 12. The cancerous cell lines used include 1) HS 683 glioma (oligodendroglioma; ATCC® HTB-138), 2) HMCB (human melanoma cell Bowes; ATCC® CRL-9607), 3) DMS 114 (small cell lung carcinoma; ATCC® CRL-2066) and 4) MDA 231 [human ER(−) breast cancer cells; ATCC® HTB-26).

For the in vivo brain xenograft model, mice received unilateral stereotaxic implantation of 500,000 human glioma cells in a volume of 3 microliters into the frontal cortex. Peripheral xenografts were implanted subcutaneously with 5 million cells in a volume of 100 microliters. One week after surgery, animals were administered Compound C0105 PO via the drinking water for two weeks. Animals were sacrificed at the end of drug administration. Assessments include 1) tumor volume and mass, 2) cell morphology and function, 3) proliferation by measuring proliferating-cell nuclear antigen (PCNA), 4) apoptosis by Annexin V and TUNEL staining, and 5) signaling properties by measuring Akt, mTOR, PTEN and P53 activity.

Example 1: FITC-NLX-Based FLNA Screening Assay

A. Streptavidin-coated 96-well plates Streptavidin-coated 96-well plates (Reacti-Bind™ NeutrAvidin™ High binding capacity coated 96-well plate, Pierce-ENDOGEN) are washed three times with 200 μl of 50 mM Tris HCl, pH 7.4 according to the manufacturer's recommendation.

B. N-Biotinylated VAKGL Pentapeptide (Bn-VAKGL) (SEQ ID NO: 1)

Bn-VAKGL (SEQ ID NO: 1) peptide (0.5 mg/plate) is dissolved in 50 μl DMSO and then added to 4450 μl of 50 mM Tris HCl, pH 7.4, containing 100 mM NaCl and protease inhibitors (binding medium) as well as 500 μl superblock in PBS (Pierce-ENDOGEN) [final concentration for DMSO: 1%].

C. Coupling of Bn-VAKGL Peptides to Streptavidin-Coated Plate

The washed streptavidin-coated plates are contacted with 5 μg/well of Bn-VAKGL (100 μl) for 1 hour (incubated) with constant shaking at 25° C. [50 μl of Bn-VAKGL peptide solution from B+50 μl binding medium, final concentration for DMSO: 0.5%]. At the end of the incubation, the plate is washed three times with 200 μl of ice-cold 50 mM Tris HCl, pH 7.4.

D. Binding of FITC-Tagged Naloxone [FITC-NLX] to VAKGL

Bn-VAKGL coated streptavidin plates are incubated with 10 nM fluorescein isothiocyanate-labeled naloxone (FITC-NLX; Invitrogen) in binding medium (50 mM Tris HCl, pH 7.4 containing 100 mM NaCl and protease inhibitors) for 30 minutes at 30° C. with constant shaking. The final assay volume is 100 μl. At the end of incubation, the plate is washed twice with 100 μl of ice-cold 50 mM Tris, pH 7.4. The signal, bound-FITC-NLX is detected using a DTX-880 multi-mode plate reader (Beckman).

E. Screening of Medicinal Chemistry Analogs

The compounds are first individually dissolved in 25% DMSO containing 50 mM Tris HCl, pH 7.4, to a final concentration of 1 mM (assisted by sonication when necessary) and then plated into 96-well compound plates. To screen the medicinal chemistry analogs (new compounds), each compound solution (1 μl) is added to the Bn-VAKGL coated streptavidin plate with 50 μl/well of binding medium followed immediately with addition of 50 μl of FITC-NLX (total assay volume/well is 100 μl). The final screening concentration for each new compound is initially 10 μM.

Each screening plate includes vehicle control (total binding) as well as naloxone (NLX) and/or naltrexone (NTX) as positive controls. Compounds are tested in triplicate or quadruplicate. Percent inhibition of FITC-NLX binding for each compound is calculated [(Total FITC-NLX bound in vehicle—FITC-NLX bound with compound)/Total FITC-NLX bound in vehicle]×100%]. To assess the efficacies and potencies of the selected compounds, compounds that achieve approximately 60-70% inhibition at 10 μM are screened further at 1 and 0.1 μM concentrations.

The results of this screening assay are shown in the tables below.

FLNA Peptide Binding Assays
A-Series Compounds

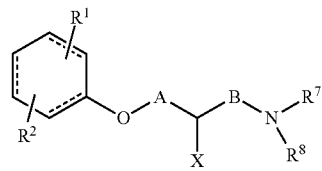

The $R^1$, $R^2$, $R^7$ and $R^8$, A, B and X groups are defined elsewhere herein.

| FLNA-binding Compound | Concentration of FLNA-binding Compound | | |
|---|---|---|---|
| | 0.01 μM | 0.1 μM | 1 μM |
| | Percent Binding Inhibition | | |
| Naloxone Control Average | 39.87% | 46.29% | 50.91% |
| 3333 | 40.4% | 48.5% | 54.2% |
| A0001 | 39.7% | 45.6% | 52.4% |
| A0002 | 38.7% | 43.7% | 49.9% |
| A0003 | 21.3% | 31.6% | 37.4% |
| A0004 | 40.0% | 43.7% | 47.6% |
| A0005 | 34.2% | 38.2% | 43.8% |
| A0006 | 37.9% | 43.5% | 47.5% |
| A0007 | 39.2% | 46.2% | 52.9% |
| A0008 | 34.5% | 33.5% | 39.8% |
| A0009 | 26.4% | 37.8% | 38.9% |
| A0010 | 36.0% | 36.5% | 39.0% |
| A0011 | 45.7% | 51.1% | 52.8% |
| A0012 | 39.7% | 49.6% | 54.4% |
| A0013 | 30.2% | 40.2% | 47.7% |
| A0014 | 33.8% | 39.7% | 44.7% |
| A0015 | 36.3% | 46.8% | 55.0% |
| A0017 | 29.8% | 38.6% | 44.0% |
| A0020 | 37.8% | 38.8% | 45.8% |
| A0021 | 36.8% | 43.4% | 49.5% |
| A0022 | 41.9% | 49.7% | 56.8% |
| A0025 | 39.0% | 49.8% | 53.2% |
| A0026 | 36.4% | 42.4% | 49.2% |
| A0028 | 39.5% | 43.8% | 50.5% |
| A0029 | 44.4% | 44.4% | 50.8% |
| A0030 | 35.6% | 44.4% | 48.9% |
| A0031 | 40.8% | 47.6% | 52.9% |
| A0032-1 | 35.6% | 43.9% | 50.0% |
| A0032 | 43.0% | 50.3% | 54.5% |
| A0033 | 46.4% | 51.8% | 56.5% |
| A0035 | 40.3% | 45.5% | 54.9% |
| A0036 | 45.6% | 50.1% | 54.4% |
| A0037 | 49.3% | 51.3% | 56.8% |
| A0038 | 46.4% | 52.3% | 56.6% |
| A0039 | 49.0% | 53.5% | 60.3% |
| A0040 | 45.0% | 50.4% | 56.3% |
| A0041 | 45.8% | 51.7% | 56.9% |
| A0042 | 47.2% | 48.3% | 55.8% |
| A0043 | 46.4% | 48.9% | 51.8% |
| A0044 | 32.4% | 36.9% | 39.6% |
| A0045 | 28.1% | 35.0% | 37.8% |
| A0046 | 34.3% | 38.4% | 40.9% |
| A0047 | 40.9% | 42.9% | 44.5% |
| A0048 | 38.5% | 44.0% | 46.9% |

| FLNA-binding Compound | Concentration of FLNA-binding Compound | | |
|---|---|---|---|
| | 0.01 µM | 0.1 µM | 1 µM |
| | Percent Binding Inhibition | | |
| A0049 | 46.2% | 49.4% | 49.3% |
| A0050 | 42.9% | 49.8% | 52.1% |
| A0051 | 45.9% | 45.4% | 52.1% |
| A0053 | 34.8% | 40.0% | 46.9% |
| A0054 | 28.7% | 35.8% | 41.4% |
| A0055 | 28.1% | 32.4% | 41.8% |
| A0056 | 34.4% | 40.9% | 41.3% |
| A0057 | 29.1% | 37.0% | 43.4% |
| A0058 | 28.9% | 36.6% | 42.1% |
| A0059 | 27.4% | 36.6% | 38.7% |
| A0060 | 32.4% | 39.0% | 42.0% |
| A0061 | 27.5% | 38.9% | 42.8% |
| A0062 | — | — | — |
| A0063 | 21.2% | 31.0% | 38.8% |
| A0064 | 41.8% | 46.2% | 53.6% |
| A0065 | 38.7% | 50.0% | 50.8% |
| A0066 | 36.7% | 45.4% | 53.7% |
| A0067 | 32.7% | 39.1% | 44.3% |
| A0068 | 51.9% | 54.2% | 58.3% |
| A0069 | 32.0% | 40.4% | 46.1% |
| A0070 | 32.9% | 39.1% | 41.7% |
| A0071 | 44.7% | 46.8% | 53.9% |
| A0072 | 45.5% | 52.2% | 59.4% |
| A0073 | 47.3% | 54.8% | 59.7% |
| A0074 | — | — | — |
| A0075 | — | — | — |
| A0076 | 36.1% | 40.0% | 44.9% |
| A0077 | 41.1% | 48.7% | 49.4% |
| A0078 | 50.1% | 55.8% | 57.6% |
| Naloxone Control Average | 39.87% | 46.29% | 50.91% |

B-Series Compounds

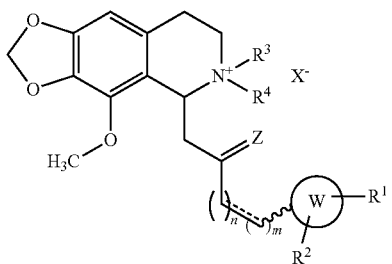

The $R^1$, $R^2$, $R^3$ and $R^4$, W, $X^-$ and Z groups, the dashed line, n and m are defined elsewhere herein.

| FLNA-binding Compound | Concentration of FLNA-binding Compound | | |
|---|---|---|---|
| | 0.01 µM | 0.1 µM | 1 µM |
| | Percent Binding Inhibition | | |
| Naloxone Control Average | 39.87% | 46.29% | 50.91% |
| 5009 | 42.5% | 47.3% | 54.3% |
| B0001 | 37.1% | 48.8% | 54.3% |
| B0002 | 40.2% | 46.4% | 55.0% |
| B0003 | 45.4% | 52.9% | 63.5% |
| B0004 | 38.9% | 50.0% | 54.8% |
| B0005 | 31.8% | 34.8% | 41.7% |
| B0006 | 45.1% | 53.5% | 61.3% |
| B0007 | 43.6% | 53.1% | 57.3% |
| B0008 | 35.5% | 40.3% | 52.8% |
| B0009 | 39.6% | 47.6% | 53.6% |
| B0010 | 39.4% | 43.4% | 50.3% |
| B0011 | 40.9% | 50.3% | 55.8% |
| B0012 | 39.4% | 46.9% | 51.7% |
| B0013 | 25.2% | 35.1% | 43.4% |
| B0014 | 25.7% | 30.9% | 37.8% |
| B0015 | 30.4% | 35.3% | 42.3% |
| B0016 | 27.1% | 33.7% | 41.9% |
| B0017 | 28.3% | 36.6% | 44.6% |
| B0018 | 37.2% | 43.7% | 47.6% |
| B0019 | 34.3% | 41.0% | 49.0% |
| B0020 | 38.1% | 45.5% | 50.6% |
| B0021 | 32.5% | 43.1% | 47.6% |
| B0022 | 34.3% | 40.4% | 45.6% |
| B0023 | 28.5% | 37.8% | 46.4% |
| B0024 | 34.8% | 43.4% | 47.7% |
| B0025 | 41.7% | 49.4% | 56.6% |
| B0026 | 41.1% | 43.3% | 48.2% |
| B0027 | 40.2% | 46.7% | 49.8% |
| B0028 | 38.2% | 42.8% | 49.1% |
| B0029 | 33.4% | 42.9% | 50.2% |
| B0030 | 47.0% | 50.5% | 57.6% |
| B0031 | 36.2% | 44.2% | 50.5% |
| B0032 | 45.1% | 51.3% | 48.9% |
| B0033 | 42.1% | 46.8% | 49.4% |
| B0034 | 49.1% | 54.2% | 59.1% |
| B0035 | 45.4% | 44.7% | 51.0% |
| B0036 | 46.6% | 52.8% | 62.1% |
| B0037 | 47.4% | 53.0% | 52.4% |
| B0038 | 41.2% | 50.1% | 57.0% |
| B0039 | 43.3% | 45.7% | 50.9% |
| B0040 | 40.0% | 53.1% | 57.1% |
| B0041 | 44.0% | 46.8% | 52.8% |
| B0042 | 40.8% | 46.4% | 51.6% |
| B0043 | 30.8% | 39.2% | 46.8% |
| B0044 | 35.2% | 39.5% | 44.4% |
| B0045 | 63.2% | 68.2% | 73.9% |
| B0046 | 42.2% | 50.2% | 55.4% |
| B0047 | 30.7% | 37.6% | 47.1% |
| B0048 | 34.7% | 41.9% | 43.9% |
| B0049 | 32.2% | 40.1% | 47.1% |
| B0050 | 29.2% | 34.5% | 39.8% |
| B0051 | 29.9% | 35.7% | 43.7% |
| B0052 | 30.2% | 39.1% | 44.3% |
| B0053 | 33.1% | 37.3% | 47.6% |
| B0054 | 25.6% | 32.6% | 43.3% |
| B0055 | 63.2% | 68.2% | 73.9% |
| Naloxone Control Average | 39.87% | 46.29% | 50.91% |

C-Series-1 Compounds

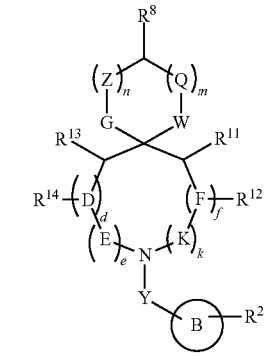

Each designation in the above formula is defined elsewhere herein.

| FLNA-binding Compound | Concentration of FLNA-binding Compound | | |
|---|---|---|---|
| | 0.01 μM | 0.1 μM | 1 μM |
| | Percent Binding Inhibition | | |
| Naloxone Control Average | 39.87% | 46.29% | 50.91% |
| 7866 | 38.5% | 47.9% | 53.4% |
| C0001 | 34.8% | 42.9% | 51.3% |
| C0002 | 38.4% | 45.6% | 42.8% |
| C0003 | 38.3% | 45.3% | 48.8% |
| C0004 | 37.6% | 42.3% | 44.7% |
| C0005 | 35.2% | 44.5% | 51.5% |
| C0006 | 41.6% | 46.8% | 51.8% |
| C0007 | 40.5% | 46.3% | 48.9% |
| C0008 | 42.2% | 52.3% | 54.4% |
| C0009 | 41.7% | 49.0% | 53.9% |
| C0010 | 39.8% | 42.7% | 47.1% |
| C0011 | 37.6% | 41.4% | 46.0% |
| C0012 | 26.3% | 39.5% | 46.4% |
| C0013 | 39.6% | 42.4% | 49.1% |
| C0014 | 29.5% | 38.8% | 40.0% |
| C0015 | 31.2% | 40.6% | 45.5% |
| C0016 | 38.3% | 43.8% | 49.1% |
| C0017 | 28.9% | 35.4% | 40.7% |
| C0018 | 42.3% | 45.9% | 53.4% |
| C0019 | 30.1% | 38.2% | 43.6% |
| C0021 | 34.0% | 38.4% | 40.6% |
| C0022 | 34.5% | 37.6% | 43.9% |
| C0023 | 35.9% | 41.7% | 47.2% |
| C0024 | 37.9% | 46.4% | 50.4% |
| C0025 | 37.2% | 41.4% | 45.1% |
| C0028 | 32.2% | 36.6% | 43.3% |
| C0029 | 38.6% | 43.2% | 50.5% |
| C0030 | 37.4% | 45.4% | 56.0% |
| C0032 | 41.5% | 50.5% | 55.3% |
| C0033 | 43.9% | 48.4% | 51.3% |
| C0034 | 29.6% | 38.3% | 44.8% |
| C0038 | 31.7% | 36.0% | 43.5% |
| C0041 | 38.3% | 47.0% | 51.2% |
| C0042 | 42.4% | 49.7% | 56.1% |
| C0047 | 30.8% | 35.2% | 41.4% |
| C0048 | 28.5% | 38.9% | 45.9% |
| C0049 | 25.3% | 27.9% | 30.3% |
| C0051 | 27.0% | 30.4% | 36.4% |
| C0052 | 28.0% | 35.6% | 40.8% |
| C0053 | 28.9% | 33.8% | 39.3% |
| C0054 | 32.9% | 39.4% | 43.3% |
| C0057 | ND* | ND | ND |
| C0060 | 60.3% | 64.0% | 68.0% |
| C0061 | ND | ND | ND |
| C0062 | 39.5% | 49.5% | 48.0% |
| C0064 | 37.3% | 44.4% | 49.2% |
| C0065 | 37.1% | 44.0% | 47.0% |
| C0067 | 31.3% | 39.7% | 45.0% |
| C0068 | 53.7% | 58.6% | 62.2% |
| C0069 | ND | ND | ND |
| C0070 | 42.6% | 50.6% | 53.6% |
| C0071 | 39.1% | 49.6% | 55.2% |
| C0072 | 28.4% | 37.4% | 44.0% |
| C0073 | ND | ND | ND |
| C0077 | 45.7% | 47.7% | 51.0% |
| C0078 | 46.6% | 48.0% | 50.5% |
| C0080M | 46.8% | 53.3% | 54.6% |
| C0084M | 47.2% | 53.7% | 55.9% |
| C0085M | 45.7% | 53.7% | 60.7% |
| C0138M | 53.0% | 52.0% | 59.5% |
| C0139M | 48.9% | 53.1% | 61.6% |
| C0140M | 42.3% | 49.2% | 54.4% |
| C0141M | 33.1% | 39.0% | 46.9% |
| C0143M | 45.3% | 48.4% | 57.8% |
| C0144M | 46.4% | 50.7% | 55.7% |
| C0145M | 45.1% | 53.7% | 58.3% |
| C0148M | 46.2% | 52.0% | 57.0% |
| C0149M | 48.5% | 52.3% | 62.0% |
| C0150M | 47.3% | 51.8% | 61.4% |
| C0151M | 48.3% | 51.7% | 58.7% |
| C0152M | ND | ND | ND |

| FLNA-binding Compound | Concentration of FLNA-binding Compound | | |
|---|---|---|---|
| | 0.01 μM | 0.1 μM | 1 μM |
| | Percent Binding Inhibition | | |
| C0154M | ND | ND | ND |
| Naloxone Control Average | 39.87% | 46.29% | 50.91% |

*ND = Not Done.

C-Series-2 Compounds

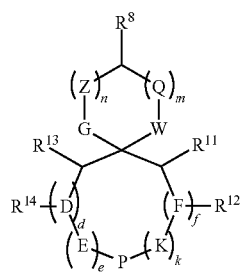

Each designation in the above formula is defined elsewhere herein.

| FLNA-binding Compound | Concentration of FLNA-binding Compound | | |
|---|---|---|---|
| | 0.01 μM | 0.1 μM | 1 μM |
| | Percent Binding Inhibition | | |
| Naloxone Control Average | 39.87 | 46.29% | 50.91 |
| C0011 | 37.6% | 41.4% | 46.0% |
| C0026 | 42.3% | 44.8% | 49.0% |
| C0027 | 50.8% | 61.2% | 63.8% |
| S-C0027 | 39.1% | 46.5% | 53.6% |
| C0034-3 | 29.6% | 38.3% | 44.8% |
| C0037-2 | ND* | ND | ND |
| C0040 | 38.4% | 46.3% | 55.9% |
| C0043 | 43.9% | 51.3% | 58.0% |
| C0044 | 37.3% | 43.9% | 50.6% |
| C0045 | 39.1% | 48.9% | 53.7% |
| C0046 | 30.8% | 35.7% | 42.2% |
| C0050 | 26.7% | 34.5% | 36.4% |
| C0055 | 29.0% | 34.9% | 39.5% |
| C0056 | 33.7% | 38.9% | 41.4% |
| C0060 | 60.3% | 64.0% | 68.0% |
| C0086M | 37.9% | 48.1% | 53.4% |
| C0087M | 51.6% | 57.9% | 61.5% |
| C0088M | 40.1% | 52.4% | 56.1% |
| C0089M | 40.7% | 46.1% | 51.2% |
| C0090M | 42.5% | 52.5% | 55.8% |
| C0091M | 38.1% | 39.8% | 46.3% |
| C0093M | 44.8% | 49.9% | 53.5% |
| C0094M | 43.0% | 52.8% | 57.5% |
| C0095M | 40.1% | 46.6% | 50.5% |
| C0096M | 43.0% | 48.3% | 55.0% |
| C0099M | 46.9% | 53.3% | 56.0% |
| C0100M | 52.2% | 58.2% | 64.5% |
| C0101M | 50.5% | 56.4% | 59.0% |
| C0102M | 52.3% | 53.1% | 56.6% |
| C0104M | 51.4% | 54.1% | 55.2% |
| C0105M | 55.7% | 62.0% | 68.8% |
| C0106M | 45.8% | 55.6% | 58.9% |
| C0108M | 54.6% | 61.4% | 68.7% |
| C0114M | 57.1% | 63.2% | 66.7% |
| C0115M | 47.8% | 57.8% | 59.9% |
| C0116M | 53.9% | 60.0% | 62.9% |
| C0118M | 56.6% | 61.4% | 62.4% |

-continued

| FLNA-binding Compound | Concentration of FLNA-binding Compound | | |
|---|---|---|---|
| | 0.01 µM | 0.1 µM | 1 µM |
| | Percent Binding Inhibition | | |
| C0119M | 41.6% | 55.5% | 60.0% |
| C0123M | 51.9% | 60.5% | 62.9% |
| C0124M | 47.7% | 52.2% | 58.7% |
| C0125M | 54.2% | 59.7% | 63.3% |
| C0126M | 50.7% | 55.4% | 67.3% |
| C0128M | 46.5% | 54.4% | 58.2% |
| C0133M | 47.8% | 54.9% | 58.5% |
| C0134M | 55.7% | 60.5% | 61.9% |
| F-C0134 | 37.4% | 45.7% | 53.1% |
| C0135M | 53.9% | 55.1% | 62.3% |
| C0136M(P5) | 46.7% | 55.2% | 58.2% |
| C0137M(P7) | 42.4% | 49.9% | 61.2% |
| C0142M | 35.1% | 39.4% | 56.0% |
| C0143M | 45.3% | 48.4% | 57.8% |
| C0148M | 46.2% | 52.0% | 57.0% |
| C0149M | 48.5% | 52.3% | 62.0% |
| C0150M | 47.3% | 51.8% | 61.4% |
| C0151M | 48.3% | 51.7% | 58.7% |
| C0152M-4 | ND | ND | ND |
| C0153M-3 | ND | ND | ND |
| Naloxone Control Average | 39.87% | 46.29% | 50.91% |

*ND = Not Done.

A preliminary study similar to that immediately above was carried out using Compounds 4, 9 and 10 and 100 nM of frozen-stored FITC-NLX rather than 10 nM FITC-NLX. The results of an average of two runs for this study are shown below.

| Compound | 0.1 nM | 1 nM | 10 nM | 100 nM | 1 µM |
|---|---|---|---|---|---|
| 4 | 18.8% | 21.3% | 17.9% | 28.8% | 42.9% |
| 9 | 22.5% | 24.8% | 27.7% | 35.3 | 49.6% |
| 10 | 27.5% | 27.3% | 26.6% | 27.3% | 34.5% |
| (+) NLX | 22.7% | 22.8% | 23.1% | 22.8% | 39.8% |

Example 2: MOR Agonist Activity Using GTPγS Binding Assay

To assess the mu opiate receptor (MOR) agonist activity of positive compounds from the FLNA screening, compounds were tested in a [$^{35}$S]GTPγS binding assay using striatal membranes. A previous study has shown that in striatal membranes, activation of MOR leads to an increase in [$^{35}$S]GTPγS binding to Gαo (Wang et al., 2005 *Neuroscience* 135:247-261). This assay measures a functional consequence of receptor occupancy at one of the earliest receptor-mediated events. The assay permits traditional pharmacological parameters of potency, efficacy and antagonist affinity, with the advantage that agonist measures are not subjected to amplification or other modulation that may occur when analyzing parameters further downstream of the receptor.

Thus, striatal tissue was homogenized in 10 volumes of ice cold 25 mM HEPES buffer, pH 7.4, which contained 1 mM EGTA, 100 mM sucrose, 50 µg/ml leupeptin, 0.04 mM PMSF, 2 µg/ml soybean trypsin inhibitor and 0.2% 2-mercaptoethanol. The homogenates were centrifuged at 800×g for 5 minutes and the supernatants were centrifuged at 49,000×g for 20 minutes. The resulting pellets were suspended in 10 volume of reaction buffer, which contained 25 mM HEPES, pH 7.5, 100 mM NaCl, 50 µg/ml leupeptin, 2 µg/ml soybean trypsin inhibitor, 0.04 mM PMSF and 0.02% 2-mercaptomethanol.

The resultant striatal membrane preparation (200 µg) was admixed and maintained (incubated) at 30° C. for 5 minutes in reaction buffer as above that additionally contained 1 mM MgCl$_2$ and 0.5 nM [$^{35}$S]GTPγS (0.1 µCi/assay, PerkinElmer Life and Analytical Sciences) in a total volume of 250 µl and continued for 5 minutes in the absence or presence of 0.1-10 µM of an assayed compound of interest. The reaction was terminated by dilution with 750 µl of ice-cold reaction buffer that contained 20 mM MgCl$_2$ and 1 mM EGTA and immediate centrifugation at 16,000×g for 5 minutes.

The resulting pellet was solubilized by sonicating for 10 seconds in 0.5 ml of immunoprecipitation buffer containing 0.5% digitonin, 0.2% sodium cholate and 0.5% NP-40. Normal rabbit serum (1 µl) was added to 1 ml of lysate and incubated at 25° C. for 30 minutes. Nonspecific immune complexes were removed by incubation with 25 µl of protein A/G-conjugated agarose beads at 25° C. for 30 minutes followed by centrifugation at 5,000×g at 4° C. for 5 minutes. The supernatant was divided and separately incubated at 25° C. for 30 minutes with antibodies raised against Gαo proteins (1:1,000 dilutions).

The immunocomplexes so formed were collected by incubation at 25° C. for 30 minutes with 40 µl of agarose-conjugated protein A/G beads and centrifugation at 5,000×g at 4° C. for 5 minutes. The pellet was washed and suspended in buffer containing 50 mM Tris-HCl, pH 8.0, and 1% NP-40. The radioactivity in the suspension was determined by liquid scintillation spectrometry. The specificity of MOR activation of [$^{35}$S]GTPγS binding to Gαo induced by a selective compound was defined by inclusion of 1 µM β-funaltrexamine (β-FNA; an alkylating derivative of naltrexone that is a selective MOR antagonist). DAMGO (1 or 10 µM) was used as a positive control.

The results of this study are shown in the Tables below. Series a FLNA-Binding Compound MOR Agonist Activity

| FLNA-Binding Compound | Concentration of FLNA-Binding Compound as Agonist | | | | | |
|---|---|---|---|---|---|---|
| | 0.1 µM | 1 µM | 1 µM + BFNA | % DAMGO (0.1 µM) | % DAMGO (1 µM) | % DAMGO + BFNA |
| A3333 | 170.7% | 328.3% | 65.9% | 88.9% | 101.0% | 136.7% |
| A0001 | 94.3% | 181.7% | 22.2% | 63.1% | 78.9% | 83.8% |
| A0002 | 155.6% | 199.4% | 6.5% | 104.1% | 86.6% | 24.5% |
| A0003 | 176.8% | 276.0% | 17.1% | 118.3% | 119.9% | 64.5% |
| A0004 | 97.4% | 144.2% | 86.0% | 55.2% | 55.6% | 130.9% |
| A0005 | 179.7% | 239.2% | 23.5% | 105.0% | 89.6% | 45.1% |
| A0006 | 170.0% | 190.9% | 18.2% | 113.8% | 82.9% | 68.7% |
| A0007 | 102.0% | 221.9% | 40.4% | 68.3% | 96.4% | 152.5% |
| A0008 | 163.8% | 235.0% | 133.9% | 109.6% | 102.1% | 505.3% |
| A0009 | 70.2% | 126.4% | 93.9% | 39.8% | 48.7% | 142.9% |

-continued

| FLNA-Binding Compound | Concentration of FLNA-Binding Compound as Agonist | | | | | |
|---|---|---|---|---|---|---|
| | 0.1 μM | 1 μM | 1 μM + BFNA | % DAMGO (0.1 μM) | % DAMGO (1 μM) | % DAMGO + BFNA |
| A0010 | 277.2% | 319.0% | 190.3% | 161.9% | 119.5% | 365.3% |
| A0011 | 236.3% | 287.5% | 47.0% | 158.2% | 124.9% | 177.4% |
| A0012 | 149.3% | 185.7% | 122.4% | 99.9% | 80.7% | 461.9% |
| A0013 | 102.1% | 164.8% | 86.1% | 57.8% | 63.6% | 131.1% |
| A0014 | 147.0% | 174.9% | 140.8% | 83.2% | 67.5% | 214.3% |
| A0015 | 110.9% | 150.1% | 62.5% | 64.8% | 56.2% | 120.0% |
| A0017 | 161.9% | 246.0% | 65.2% | 96.9% | 100.4% | 187.9% |
| A0020 | 168.6% | 217.4% | 67.4% | 100.9% | 88.7% | 194.2% |
| A0021 | 133.3% | 275.3% | 12.1% | 79.8% | 112.4% | 34.9% |
| A0022 | 154.1% | 216.0% | 28.0% | 90.0% | 80.9% | 53.7% |
| A0025 | 58.6% | 138.7% | 52.2% | 33.2% | 54.5% | 198.5% |
| A0026 | 140.7% | 179.8% | 120.8% | 79.7% | 70.7% | 459.3% |
| A0028 | 143.6% | 187.7% | 116.7% | 81.3% | 73.8% | 443.7% |
| A0029 | 173.8% | 206.5% | 22.3% | 98.4% | 81.2% | 84.8% |
| A0030 | 133.4% | 287.8% | 165.2% | 75.5% | 113.2% | 628.1% |
| A0031 | 178.2% | 297.0% | 150.9% | 100.9% | 116.8% | 573.8% |
| A0032-1 | 187.4% | 324.5% | 224.5% | 95.5% | 117.6% | 303.8% |
| A0032 | 226.9% | 257.8% | 133.0% | 115.6% | 93.4% | 180.0% |
| A0033 | 155.8% | 254.6% | 118.2% | 79.4% | 92.2% | 159.9% |
| A0035 | 120.6% | 158.8% | 88.6% | 61.5% | 57.5% | 119.9% |
| A0036 | 144.1% | 167.5% | 63.2% | 73.4% | 60.7% | 85.5% |
| A0037 | 177.9% | 236.2% | 104.6% | 90.7% | 85.6% | 141.5% |
| A0038 | 176.7% | 234.5% | 107.0% | 90.1% | 85.0% | 144.8% |
| A0039 | 267.8% | 339.6% | 173.5% | 136.5% | 123.0% | 234.8% |
| A0040 | 46.1% | 149.0% | 16.7% | 23.5% | 54.0% | 22.6% |
| A0041 | 212.7% | 283.6% | 50.6% | 108.4% | 102.8% | 68.5% |
| A0042 | 147.5% | 233.1% | 89.5% | 75.2% | 84.5% | 121.1% |
| AO043 | 183.3% | 223.8% | 89.1% | 93.4% | 81.1% | 120.6% |
| A0044 | 176.2% | 209.1% | 134.7% | 89.8% | 75.8% | 182.3% |
| A0045 | 143.9% | 274.2% | 99.2% | 73.3% | 99.3% | 134.2% |
| A0046 | 257.5% | 354.1% | 140.0% | 131.2% | 128.3% | 189.4% |
| A0047 | 233.0% | 255.0% | 116.5% | 118.8% | 92.4% | 157.6% |
| A0048 | 233.7% | 302.9% | 167.2% | 119.1% | 109.7% | 226.3% |
| A0049 | 232.3% | 370.3% | 107.1% | 118.4% | 134.2% | 144.9% |
| A0050 | 151.0% | 189.3% | 81.0% | 77.0% | 68.6% | 109.6% |
| A0051 | 290.4% | 386.6% | 211.6% | 148.0% | 140.1% | 286.3% |
| A0053 | 78.5% | 118.2% | 15.1% | 46.5% | 47.5% | 46.2% |
| A0054 | 74.9% | 159.2% | 114.1% | 44.4% | 63.9% | 348.9% |
| A0055 | 89.8% | 195.2% | 33.5% | 53.2% | 78.4% | 102.4% |
| A0056 | 115.6% | 129.6% | 17.4% | 74.1% | 56.2% | 43.6% |
| A0057 | 124.2% | 192.1% | 44.8% | 79.6% | 83.3% | 112.3% |
| A0058 | 70.7% | 244.3% | 59.9% | 45.3% | 106.0% | 150.1% |
| A0059 | 99.2% | 129.9% | 85.7% | 63.5% | 56.4% | 214.8% |
| A0060 | 99.7% | 158.2% | 14.3% | 63.9% | 68.6% | 35.8% |
| A0061 | 110.3% | 197.1% | 10.7% | 70.7% | 85.5% | 26.8% |
| A0062 | ND | ND | ND | ND | ND | ND |
| A0063 | 122.8% | 245.8% | 310% | 78.7% | 106.6% | 77.7% |
| A0064 | 219.2% | 262.9% | 43.7% | 127.4% | 119.7% | 126.7% |
| A0065 | 197.6% | 266.8% | 44.9% | 126.6% | 115.7% | 112.5% |
| A0066 | 151.9% | 195.6% | 59.2% | 88.3% | 89.0% | 171.6% |
| A0067 | 170.8% | 254.4% | 33.9% | 99.2% | 115.8% | 98.3% |
| A0068 | 73.9% | 110.4% | 98.1% | 36.8% | 35.2% | 182.0% |
| A0069 | 122.7% | 244.2% | 29.5% | 71.3% | 111.2% | 85.5% |
| A0070 | 128.6% | 195.3% | 80.3% | 74.7% | 88.9% | 232.8% |
| A0071 | 225.7% | 310.9% | 239.4% | 128.2% | 122.9% | 1088.2% |
| A0072 | 254.3% | 305.1% | 171.8% | 126.8% | 97.2% | 318.7% |
| A0073 | 201.7% | 325.7% | 185.8% | 100.5% | 103.7% | 344.7% |
| A0074 | ND | ND | ND | ND | ND | ND |
| A0075 | ND | ND | ND | ND | ND | ND |
| A0076 | 79.8% | 172.6% | 41.2% | 46.4% | 78.6% | 119.4% |
| A0077 | 300.1% | 334.7% | 103.5% | 170.5% | 132.3% | 470.5% |
| A0078 | 250.5% | 289.9% | 147.8% | 124.9% | 92.3% | 274.2% |

Series B FLNA-Binding Compound MOR Agonist Activity

| FLNA-Binding Compound | Concentration of FLNA-Binding Compound as Agonist | | | % DAMGO (0.1 μM) | % DAMGO (1 μM) | % DAMGO + BFNA |
|---|---|---|---|---|---|---|
| | 0.1 μM | 1 μM | 1 μM + BFNA | | | |
| 5009 | 128.5% | 270.4% | 87.5% | 66.9% | 83.2% | 181.5% |
| B0001 | 128.2% | 202.3% | 28.0% | 77.4% | 74.9% | 43.1% |
| B0002 | 165.7% | 219.0% | 101.4% | 100.0% | 81.1% | 156.0% |
| B0003 | 103.0% | 131.1% | 18.6% | 59.9% | 47.4% | 29.0% |
| B0004 | 170.3% | 231.7% | 72.0% | 102.8% | 85.8% | 110.8% |
| B0005 | 89.2% | 110.4% | 45.1% | 50.5% | 42.6% | 68.6% |
| B0006 | 77.0% | 131.3% | 18.6% | 44.8% | 47.5% | 29.0% |
| B0007 | 168.3% | 223.3% | 64.5% | 95.3% | 86.1% | 98.2% |
| B0008 | 148.3% | 264.1% | 46.0% | 84.0% | 101.9% | 70.0% |
| B0009 | 144.4% | 219.9% | 119.4% | 81.8% | 84.8% | 181.7% |
| B0010 | 132.9% | 184.4% | 152.0% | 75.3% | 71.1% | 231.4% |
| B0011 | 158.6% | 212.6% | 78.0% | 95.7% | 78.7% | 120.0% |
| B0012 | 167.4% | 212.0% | 145.1% | 97.8% | 79.4% | 278.5% |
| B0013 | 51.4% | 154.1% | 34.4% | 29.1% | 59.4% | 52.4% |
| B0014 | 166.6% | 250.5% | 44.3% | 98.5% | 93.7% | 67.1% |
| B0016 | 167.7% | 213.6% | 72.2% | 99.2% | 79.9% | 109.4% |
| B0017 | 99.6% | 122.0% | 49.6% | 58.9% | 45.6% | 75.2% |
| B0018 | 118.8% | 143.0% | 45.6% | 70.3% | 53.5% | 69.1% |
| B0019 | 101.0% | 256.5% | 81.4% | 59.7% | 96.0% | 123.3% |
| B0020 | 51.6% | 181.6% | 24.9% | 30.1% | 68.0% | 47.8% |
| B0021 | 126.9% | 256.4% | 42.9% | 75.9% | 104.7% | 123.6% |
| B0022 | 131.9% | 182.7% | 45.8% | 78.9% | 74.6% | 132.0% |
| B0023 | 166.1% | 245.3% | 28.4% | 99.4% | 100.1% | 81.8% |
| B0024 | 155.8% | 285.9% | 20.2% | 93.2% | 116.7% | 58.2% |
| B0025 | 159.6% | 234.6% | 137.7% | 96.3% | 86.8% | 211.8% |
| B0026 | 152.0% | 233.3% | 28.8% | 88.8% | 87.4% | 55.3% |
| B0027 | 140.9% | 266.9% | 21.6% | 82.3% | 100.0% | 41.5% |
| B0028 | 199.1% | 357.7% | 55.0% | 103.5% | 131.0% | 125.3% |
| B0029 | 171.9% | 210.3% | 17.6% | 89.4% | 77.0% | 40.1% |
| B0030 | 107.2% | 276.1% | 90.1% | 62.6% | 103.4% | 172.9% |
| B0031 | 210.8% | 272.0% | 28.8% | 109.6% | 99.6% | 65.6% |
| B0032 | 221.1% | 297.7% | 15.6% | 115.0% | 109.0% | 35.5% |
| B0033 | 149.3% | 188.9% | 41.9% | 77.6% | 69.2% | 95.4% |
| B0034 | 122.5% | 235.2% | 41.8% | 71.6% | 88.1% | 80.2% |
| B0035 | 188.0% | 248.7% | 74.2% | 109.8% | 93.2% | 142.4% |
| B0036 | 61.4% | 120.6% | 65.1% | 39.2% | 52.1% | 199.7% |
| B0037 | 119.8% | 186.0% | 106.2% | 76.5% | 80.4% | 325.8% |
| B0038 | 147.5% | 205.3% | 117.1% | 94.2% | 88.7% | 359.2% |
| B0039 | 171.8% | 290.5% | 78.3% | 100.4% | 108.8% | 150.3% |
| B0040 | 146.0% | 243.3% | 55.3% | 93.2% | 105.1% | 169.6% |
| B0041 | 61.6% | 109.3% | 41.9% | 39.3% | 47.2% | 128.5% |
| B0042 | 69.9% | 107.5% | 43.1% | 39.6% | 42.3% | 163.9% |
| B0043 | 74.8% | 248.1% | 166.4% | 42.4% | 97.6% | 632.7% |
| B0044 | 87.3% | 170.0% | 134.6% | 49.4% | 66.9% | 511.8% |
| B0045 | 129.3% | 193.1% | 83.8% | 82.6% | 83.4% | 257.1% |
| B0046 | 99.9% | 141.9% | 90.5% | 63.8% | 61.3% | 277.6% |
| B0047 | 187.8% | 235.6% | 68.4% | 106.3% | 92.6% | 260.1% |
| B0048 | 185.1% | 223.4% | 78.5% | 104.8% | 87.8% | 298.5% |
| B0049 | 181.6% | 364.0% | 133.2% | 102.8% | 143.1% | 506.5% |
| B0050 | 98.2% | 211.0% | 48.8% | 58.1% | 96.4% | 294.0% |
| B0051 | 115.6% | 167.9% | 43.8% | 68.4% | 76.7% | 263.9% |
| B0052 | 98.2% | 151.7% | 40.9% | 58.1% | 69.3% | 246.4% |
| B0053 | 160.2% | 299.8% | 134.3% | 94.8% | 137.0% | 809.0% |
| B0054 | 157.8% | 186.7% | 111.0% | 93.4% | 85.3% | 668.7% |
| B0055 | 162.1% | 338.5% | 117.5% | 91.8% | 133.1% | 446.8% |
| B0056 | 174.7% | 288.8% | 41.8% | 98.9% | 113.6% | 158.9% |

Series C-1 FLNA-Binding Compound MOR Agonist Activity

| FLNA-Binding Compound | Concentration of FLNA-Binding Compound as Agonist | | | % DAMGO (0.1 μM) | % DAMGO (1 μM) | % DAMGO + BFNA |
|---|---|---|---|---|---|---|
| | 0.1 μM | 1 μM | 1 μM + BFNA | | | |
| 7866 | 152.3% | 308.2% | 62.4% | 79.3% | 94.8% | 129.5% |
| C0001 | 129.3% | 184.3% | 33.9% | 75.2% | 66.6% | 52.9% |
| C0002 | 88.4% | 93.8% | 3.9% | 51.4% | 33.9% | 6.1% |
| C0003 | 162.3% | 215.9% | 107.7% | 91.9% | 83.3% | 163.9% |
| C0004 | 122.0% | 228.4% | 65.8% | 72.1% | 85.4% | 99.7% |

-continued

| FLNA-Binding Compound | Concentration of FLNA-Binding Compound as Agonist | | | | | |
|---|---|---|---|---|---|---|
| | 0.1 μM | 1 μM | 1 μM + BFNA | % DAMGO (0.1 μM) | % DAMGO (1 μM) | % DAMGO + BFNA |
| C0005 | 180.4% | 227.2% | 166.4% | 105.4% | 85.1% | 319.4% |
| C0006 | 121.5% | 204.0% | 4.6% | 70.6% | 73.8% | 7.2% |
| C0007 | 79.1% | 195.0% | 10.9% | 46.0% | 70.5% | 17.0% |
| C0008 | 71.2% | 201.6% | 2.8% | 41.4% | 72.9% | 4.4% |
| C0009 | 146.3% | 256.2% | 26.4% | 85.1% | 92.6% | 41.2% |
| C0010 | 136.5% | 307.0% | 89.1% | 80.7% | 114.9% | 135.0% |
| C0011 | 217.0% | 305.0% | 19.0% | 126.8% | 114.3% | 36.5% |
| C0012 | 96.8% | 224.8% | 184.4% | 54.8% | 86.7% | 280.7% |
| C0013 | 156.6% | 301.2% | 39.6% | 91.0% | 108.9% | 61.8% |
| C0014 | 144.9% | 153.5% | 76.3% | 82.0% | 59.2% | 116.1% |
| C0015 | 138.7% | 204.7% | 126.8% | 78.5% | 78.9% | 193.0% |
| C0016 | 172.7% | 230.5% | 96.7% | 100.4% | 83.3% | 150.9% |
| C0017 | 153.8% | 284.5% | 94.1% | 87.1% | 109.7% | 143.2% |
| C0018 | 195.5% | 247.7% | 106.5% | 110.7% | 95.5% | 162.1% |
| C0019 | 104.4% | 176.6% | 52.8% | 59.1% | 68.1% | 80.4% |
| C0021 | 159.7% | 192.0% | 90.7% | 94.5% | 87.8% | 546.4% |
| C0022 | 194.3% | 328.7% | 13.4% | 113.5% | 123.2% | 25.7% |
| C0023 | 153.2% | 233.7% | 23.2% | 89.5% | 87.6% | 44.5% |
| C0024 | 178.4% | 229.6% | 59.3% | 92.8% | 84.1% | 135.1% |
| C0025 | 235.7% | 320.7% | 80.2% | 122.6% | 117.5% | 182.7% |
| C0028 | 93.9% | 132.4% | 78.4% | 55.6% | 60.5% | 472.3% |
| C0029 | 175.4% | 308.8% | 16.6% | 91.2% | 113.1% | 37.8% |
| C0030 | 150.3% | 226.8% | 95.0% | 96.0% | 98.0% | 291.4% |
| C0032 | 145.4% | 202.0% | 80.9% | 92.8% | 87.3% | 248.2% |
| C0033 | 134.5% | 186.4% | 76.6% | 85.9% | 80.6% | 235.0% |
| C0034 | 103.6% | 167.9% | 80.1% | 61.3% | 76.7% | 482.5% |
| C0041 | 186.1% | 244.4% | 95.5% | 110.1% | 111.7% | 575.3% |
| C0042 | 167.1% | 260.9% | 110.6% | 98.9% | 119.2% | 666.3% |
| C0047 | 142.2% | 206.1% | 80.1% | 98.1% | 88.5% | 182.0% |
| C0048 | 209.1% | 245.3% | 89.9% | 144.2% | 105.3% | 204.3% |
| C0049 | 106.6% | 210.0% | 81.0% | 73.5% | 90.1% | 184.1% |
| C0051 | 94.4% | 170.4% | 55.9% | 65.1% | 73.1% | 127.0% |
| C0052 | 108.4% | 162.8% | 42.7% | 74.8% | 69.9% | 97.0% |
| C0053 | 104.0% | 157.2% | 93.1% | 71.7% | 67.5% | 211.6% |
| C0054 | 68.2% | 127.0% | 43.5% | 47.0% | 54.5% | 98.9% |
| C0057 | ND* | ND | ND | ND | ND | ND |
| C0061 | ND | ND | ND | ND | ND | ND |
| C0062 | 127.8% | 310.5% | 59.8% | 81.9% | 134.7% | 149.9% |
| C0064 | 213.8% | 349.6% | 38.1% | 124.2% | 159.1% | 110.4% |
| C0065 | 198.3% | 279.5% | 47.7% | 127.0% | 121.3% | 119.5% |
| C0067 | 142.7% | 179.0% | 33.5% | 82.9% | 81.5% | 97.1% |
| C0068 | 107.2% | 263.1% | 165.9% | 53.4% | 83.8% | 307.8% |
| C0069 | ND | ND | ND | ND | ND | ND |
| C0070 | 165.6% | 210.8% | 114.2% | 96.2% | 95.9% | 331.0% |
| C0071 | 276.3% | 355.3% | 177.1% | 160.5% | 161.7% | 513.3% |
| C0072 | 172.7% | 259.1% | 67.1% | 100.3% | 117.9% | 194.5% |
| C0073 | ND | ND | ND | ND | ND | ND |
| C0077 | 192.7% | 265.4% | 136.7% | 109.5% | 104.9% | 621.4% |
| C0078 | 138.1% | 236.6% | 170.7% | 82.4% | 106.4% | 359.4% |
| C0080M | 187.9% | 205.4% | 167.1% | 112.1% | 92.4% | 351.8% |
| C0082M | 228.1% | 338.4% | 97.6% | 113.7% | 107.8% | 181.1% |
| C0084M | 163.1% | 255.5% | 133.2% | 97.3% | 114.9% | 280.4% |
| C0085M | 211.6% | 246.2% | 43.7% | 105.5% | 78.4% | 112.6% |
| C0138M | 126.9% | 183.9% | 51.5% | 86.3% | 90.9% | 131.0% |
| C0139M | 156.1% | 206.6% | 51.0% | 106.2% | 102.2% | 129.8% |
| C0140M | 126.1% | 215.4% | 83.0% | 85.8% | 106.5% | 211.2% |
| C0141M | 161.5% | 213.9% | 47.9% | 109.9% | 105.8% | 121.9% |
| C0143M | 81.0 | 193.3 | 86.5 | 47.1% | 59.3% | 94.7% |
| C0144M | 186.3 | 295.9 | 125.9 | 108.3% | 90.8% | 137.9% |
| C0145M | 193.0 | 289.2 | 87.0 | 112.2% | 88.7% | 95.3% |
| C0146M | ND | ND | ND | ND | ND | ND |
| C0147M A2 | ND | ND | ND | ND | ND | ND |
| C0148M A2 | 181.3 | 360.6 | 87.6 | 105.4% | 110.6% | 95.9% |
| C0149M | 209.8 | 406.7 | 93.4 | 122.0% | 124.8% | 102.3% |
| C0150M | 167.1 | 423.1 | 93.4 | 97.2% | 129.8% | 173.2% |
| C0151M | 346.8 | 397.6 | 212.8 | 201.6% | 122.0% | 233.1% |
| C0152M | ND | ND | ND | ND | ND | ND |
| DAMGO Average | 168.5% | 266.1% | 53.2% | 100% | 100% | 100% |

*DN = Not Done.

Series C-2 FLNA-Binding Compound MOR Agonist Activity

| FLNA-Binding Compound | Concentration of FLNA-Binding Compound as Agonist | | | | | |
|---|---|---|---|---|---|---|
| | 0.1 µM | 1 µM | 1 µM + BFNA | % DAMGO (0.1 µM) | % DAMGO (1 µM) | % DAMGO + BFNA |
| C0011 | 217.0% | 305.0% | 19.0% | 126.8% | 114.3% | 36.5% |
| C0026 | 207.2% | 288.4% | 21.2% | 107.7% | 105.6% | 48.3% |
| C0027 | 233.2% | 313.9% | 72.2% | 121.3% | 115.0% | 164.5% |
| S-C0027 | 156.2% | 286.8% | 56.2% | 74.2% | 84.4% | 98.1% |
| C0034-3 | ND* | ND | ND | ND | ND | ND |
| C0037-2 | ND | ND | ND | ND | ND | ND |
| C0040 | 145.8% | 308.3% | 90.4% | 93.1% | 133.2% | 277.3% |
| C0043 | 175.4% | 242.6% | 83.3% | 103.8% | 110.9% | 501.8% |
| C0044 | 173.7% | 280.1% | 59.1% | 102.8% | 128.0% | 356.0% |
| C0045 | 149.2% | 238.8% | 105.3% | 88.3% | 109.1% | 634.3% |
| C0046 | 286.2% | 492.9% | 156.8% | 197.4% | 211.5% | 356.4% |
| C0050 | 110.3% | 127.6% | 59.0% | 76.1% | 54.8% | 134.1% |
| C0055 | ND | ND | ND | ND | ND | ND |
| C0056 | 98.6% | 193.4% | 86.3% | 68.0% | 83.0% | 196.1% |
| C0060 | 166.5% | 218.9% | 143.9% | 114.8% | 93.9% | 327.0% |
| C0086M | 206.8% | 265.3% | 152.3% | 117.5% | 104.9% | 692.3% |
| C0087M | 262.8% | 329.6% | 142.5% | 138.9% | 132.8% | 293.8% |
| C0088M | 276.3% | 355.3% | 177.1% | 160.5% | 161.7% | 513.3% |
| C0089M | 234.5% | 295.3% | 81.9% | 136.3% | 134.4% | 237.4% |
| C0090M | 237.0% | 341.0% | 41.0% | 137.7% | 155.2% | 118.8% |
| C0091M | 207.9% | 274.4% | 80.8% | 118.1% | 108.5% | 367.3% |
| C0093M | 140.0% | 211.8% | 44.0% | 81.3% | 96.4% | 127.5% |
| C0094M | 172.5% | 263.5% | 115.3% | 100.2% | 119.9% | 334.2% |
| C0095M | 189.1% | 224.6% | 107.7% | 107.4% | 88.8% | 489.5% |
| C0096M | 186.4% | 328.9% | 127.1% | 105.9% | 130.0% | 577.7% |
| C0099M | 157.2% | 195.7% | 114.7% | 93.8% | 88.0% | 241.5% |
| C0100M | 173.6% | 245.9% | 195.6% | 103.6% | 110.6% | 411.8% |
| C0101M | 138.2% | 274.3% | 174.8% | 82.5% | 123.4% | 368.0% |
| C0102M | 131.8% | 272.0% | 150.4% | 78.6% | 122.4% | 316.6% |
| C0104M | 188.2% | 238.9% | 143.8% | 99.5% | 96.3% | 296.5% |
| C0105M | 198.1% | 220.3% | 73.1% | 104.7% | 88.8% | 150.7% |
| C0106M | 171.8% | 240.7% | 117.2% | 102.5% | 108.3% | 246.7% |
| C0108M | 205.6% | 258.5% | 76.9% | 108.7% | 104.1% | 158.6% |
| C0114M | 114.0% | 144.3% | 35.9% | 77.6% | 71.4% | 91.3% |
| C0115M | 177.2% | 226.8% | 118.4% | 105.7% | 102.0% | 249.3% |
| C0116M | 258.4% | 302.8% | 152.0% | 136.6% | 122.0% | 313.4% |
| C0118M | 166.2% | 261.5% | 79.2% | 87.8% | 105.4% | 163.3% |
| C0119M | 105.7% | 167.8% | 35.1% | 71.9% | 83.0% | 89.3% |
| C0124M | 252.0% | 305.1% | 61.4% | 133.2% | 122.9% | 126.6% |
| C0125M | 168.6% | 195.2% | 159.7% | 89.1% | 78.6% | 329.3% |
| C0126M | 181.8% | 265.3% | 108.5% | 108.5% | 119.3% | 228.4% |
| C0128M | 197.8% | 286.0% | 63.9% | 104.5% | 115.2% | 131.8% |
| C0133M | 139.4% | 214.8% | 72.4% | 83.2% | 96.6% | 152.4% |
| C0134M | 158.5% | 207.3% | 46.6% | 94.6% | 93.3% | 98.1% |
| F-C0134 | 290.6% | 378.9% | 66.6% | 138.1% | 111.4% | 116.2% |
| C0135M | 161.3% | 310.1% | 113.3% | 85.3% | 124.9% | 233.6% |
| C0136M (P5) | 176.8% | 237.3% | 74.5% | 93.4% | 95.6% | 153.6% |
| C0137M (P7) | 180.8% | 193.8% | 55.8% | 95.6% | 78.1% | 115.1% |
| C0142M | 143.7% | 192.5% | 98.7% | 97.8% | 95.2% | 251.1% |
| C0143M | 81.0% | 193.3% | 86.5% | 47.1% | 59.3% | 94.7 |
| C0144M-2 | 186.3% | 295.9% | 125.9% | 108.3% | 90.8% | 137.9% |
| C0145M-3 | 193.0% | 289.2% | 87.0% | 112.2% | 88.7% | 95.3% |
| C0149M-2 | 209.8% | 406.7% | 93.4% | 122.0% | 124.8% | 102.3% |
| C0150M-2 | 167.1% | 423.1% | 158.1% | 97.2% | 129.8% | 173.2% |
| C0151M-2 | 346.8% | 397.6% | 212.8% | 201.6% | 122.0% | 233.1% |
| C0152M-2 | ND | ND | ND | ND | ND | ND |
| C0153M-3 | ND | ND | ND | ND | ND | ND |
| DAMGO Average | 168.5% | 266.1% | 53.2% | 100% | 100% | 100% |

*ND = Not Done.

A preliminary study similar to that immediately above was carried out using Compounds 4, 9 and 10 and resynthesized Compound C0134M and DAMGO. The results of an average of two runs for this study are shown below.

|  | Concentration of FLNA-Binding Compound as Agonist | | |
| --- | --- | --- | --- |
| Compound | 0.1 µM | 1 µM | 1 µM + βNFA |
| 4 | 133.9% | 165.2% | 49.5% |
| 9 | 156.6% | 197.2% | 56.6% |
| 10 | 163.1% | 191.8% | 60.4% |
| C0134M | 150.7% | 224.0% | 53.2% |
| DAMGO | 144.7% | 233.4% | 56.8% |

The above results indicate that Compounds 9 and 10 not only bind well to FLNA, but are also MOR agonists, whereas Compound 4 bound well to FLNA, but was not as potent a MOR agonist as were the other two compounds. The newly synthesized Compound C0134M exhibited similar MOR agonist activity to that shown previously.

Compound Syntheses

Compounds were synthesized and provided by Medicilon, Shanghai. Aside from the three syntheses described herein, more detailed syntheses are set out in one or more of U.S. patent application Ser. No. 12/435,284, Ser. No. 12/607,883, and Ser. No. 12/435,355, and U.S. Pat. Nos. 8,722,851, 8,580,809, and 8,614,324.

A compound having an asymmetrical (chiral) carbon or a salt thereof can exist in the form of two enantiomers. The invention relates both to each enantiomer and to their mixture; i.e., to both enantiomeric forms and to their mixture. Additionally, where two or more chiral centers are present, diastereomers can form.

Where a contemplated compound or a pharmaceutically acceptable salt of a compound of Series A, B, C-1 or C-2 or any of the other formulas herein is obtained in the form of a mixture of the stereoisomers, preferably in the form of the racemates or other mixtures of the various enantiomers and/or diastereoisomers, they can be separated and optionally isolated by conventional methods known to the person skilled in the art. Illustratively, for example, chromatographic separation processes are useful, particularly liquid chromatography processes under standard pressure or under elevated pressure, preferably MPLC and HPLC methods, and also methods involving fractional crystallization. This can particularly involve the separation of individual enantiomers, e.g., diastereoisomeric salts separated by means of HPLC in the chiral phase or by means of crystallization with chiral acids, for example (+)-tartaric acid, (−)-tartaric acid, or (+)-10-camphorsulfonic acid. An enantiomer separated by chiral salt formation can readily be converted into an achiral or racemic pharmaceutically acceptable salt for use.

A compound of Series A, B, C—I or C-2 or a pharmaceutically acceptable salt thereof is contemplated to be optionally used in a process of the invention in enantiomerically pure form; i.e., in (S) or (R) configuration or d and l forms, or in the form of a racemic mixture showing an (S,R) or (d,l) configuration, or as one or more diastereomers, and mixtures thereof.

Thus, a contemplated compound or its pharmaceutically acceptable salt can optionally be present in one or more forms. Illustratively, the compound or its salt can be in the form of an individual enantiomer or diastereoisomer. A contemplated compound or its salt can also be present in the form of a mixture of stereoisomers. A contemplated compound or salt can also be present in the form of a racemic mixture.

A compound useful as an active ingredient in a contemplated method can be readily synthesized. An illustrative synthetic scheme (Scheme 1) is shown below for the compounds of Series A. Similar schemes are set out thereafter for the preferred compound types.

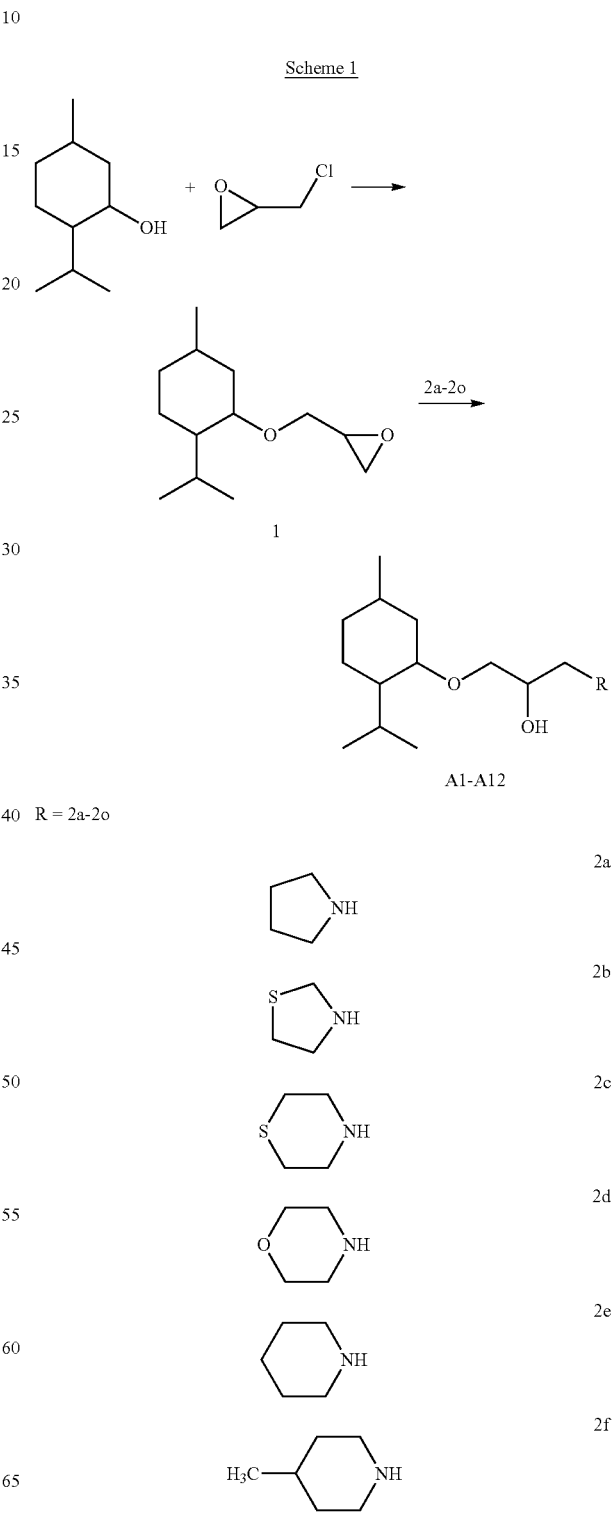

-continued

2g 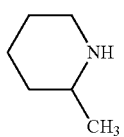

2h 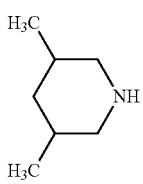

2i 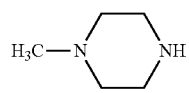

2j 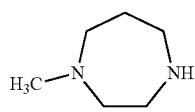

2k 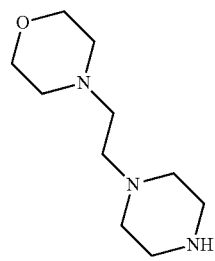

2l 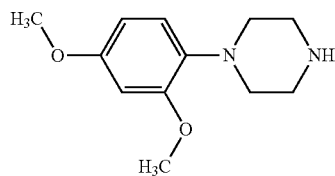

2m 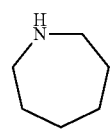

2n 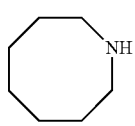

2o 

Similar syntheses can be carried out for phenolic compounds, starting with phenol or a substituted phenol in place of D-menthol that is shown in Scheme 1. Another cyclohexanol or cyclohexenol can also be used in place of D-menthol. The alcohol formed by reaction of Compound 1 with an amine can be readily oxidized by known methods.

Table of Series-A Compounds

A3333

A0001

A0002

A0003

A0004

A0005

A0006

| Table of Series-A Compounds | | Table of Series-A Compounds | |
|---|---|---|---|
| 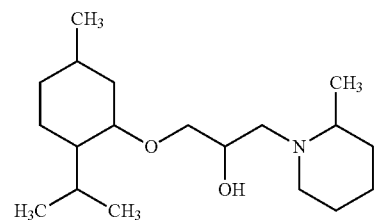 | A0007 | 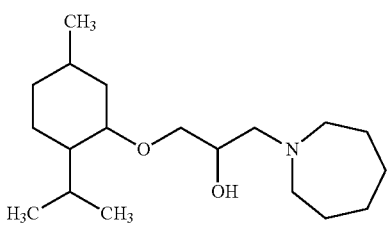 [SMILES: CC1CCC(C(C)C)C(OCC(O)CN2CCCCCC2)C1] | A0013 |
| 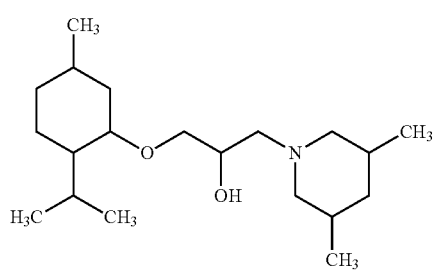 | A0008 | 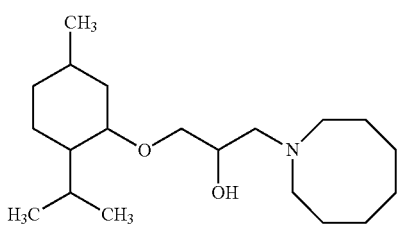 [SMILES: CC1CCC(C(C)C)C(OCC(O)CN2CCCCCCC2)C1] | A0014 |
| 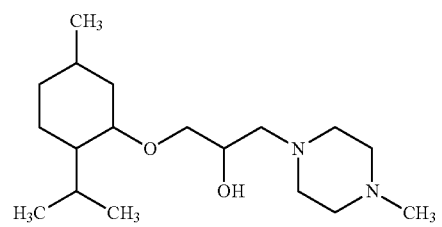 | A0009 | 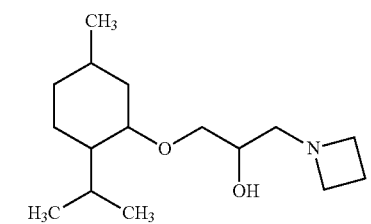 [SMILES: CC1CCC(C(C)C)C(OCC(O)CN2CCC2)C1] | A0015 |
| 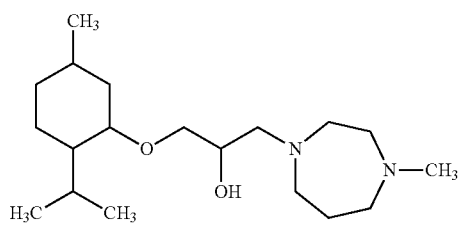 | A0010 | 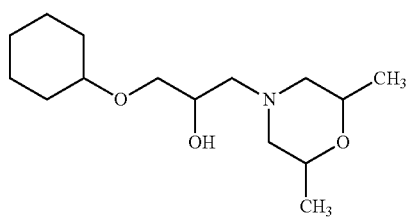 [SMILES: CC1CN(CC(O)COC2CCCCC2)CC(C)O1] | A0017 |
| 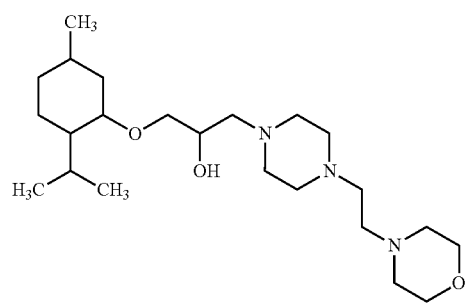 | A0011 | 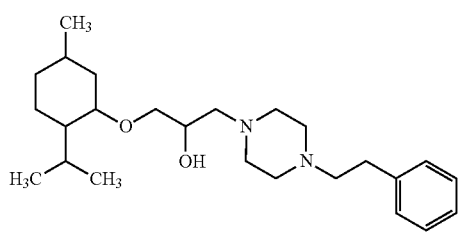 [SMILES: CC1CCC(C(C)C)C(OCC(O)CN2CCN(CCc3ccccc3)CC2)C1] | A0020 |
| 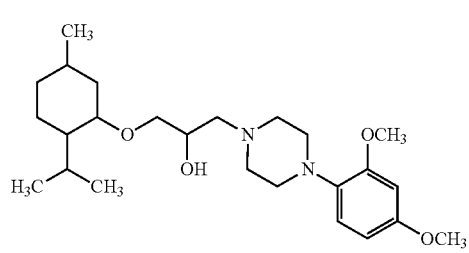 | A0012 | 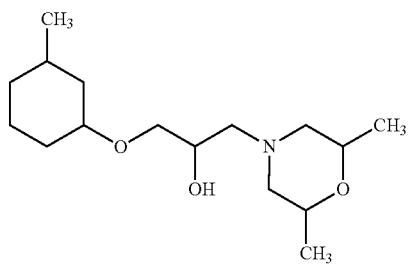 [SMILES: CC1CCCC(OCC(O)CN2CC(C)OC(C)C2)C1] | A0021 |

Table of Series-A Compounds
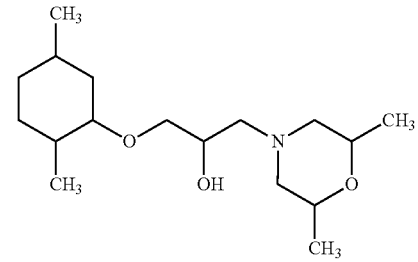 [SMILES: CC1CCC(C)C(OCC(O)CN2CC(C)OC(C)C2)C1] A0022
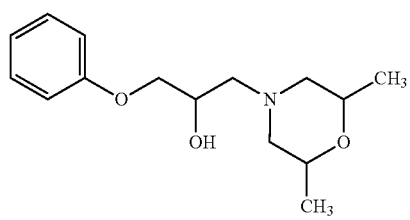 [SMILES: CC1CN(CC(O)COc2ccccc2)CC(C)O1] A0025
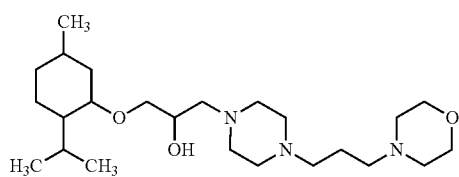 [SMILES: CC1CCC(C(C)C)C(OCC(O)CN2CCN(CCCN3CCOCC3)CC2)C1] A0026
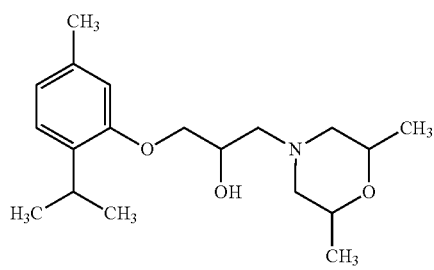 [SMILES: Cc1ccc(C(C)C)c(OCC(O)CN2CC(C)OC(C)C2)c1] A0028
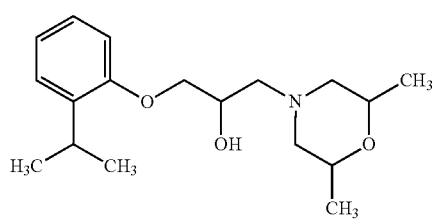 [SMILES: CC1CN(CC(O)COc2ccccc2C(C)C)CC(C)O1] A0029
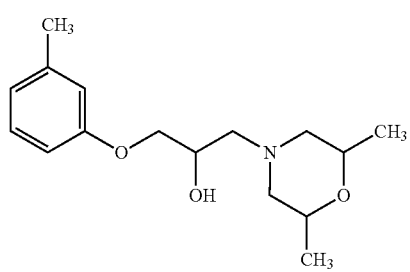 [SMILES: Cc1cccc(OCC(O)CN2CC(C)OC(C)C2)c1] A0030
Table of Series-A Compounds
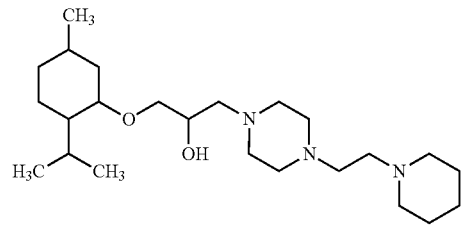 [SMILES: CC1CCC(C(C)C)C(OCC(O)CN2CCN(CCN3CCCCC3)CC2)C1] A0031
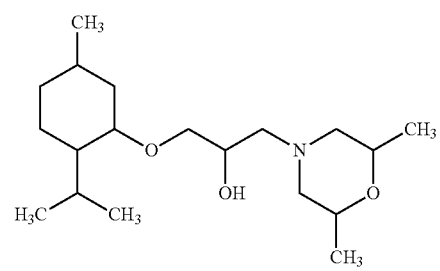 A0032-1
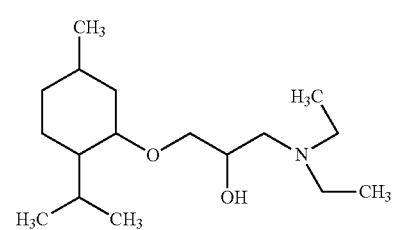 [SMILES: CCN(CC)CC(O)COC1CC(C)CCC1C(C)C] A0032
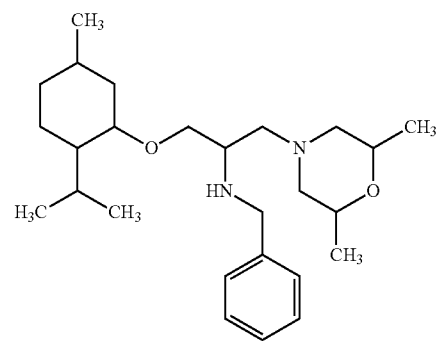 [SMILES: CC1CCC(C(C)C)C(OCC(CN2CC(C)OC(C)C2)NCc2ccccc2)C1] A0033
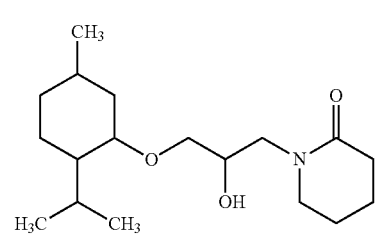 [SMILES: CC1CCC(C(C)C)C(OCC(O)CN2CCCCC2=O)C1] A0035
 A0036

Table of Series-A Compounds (chemical structures A0037–A0050)

Table of Series-A Compounds
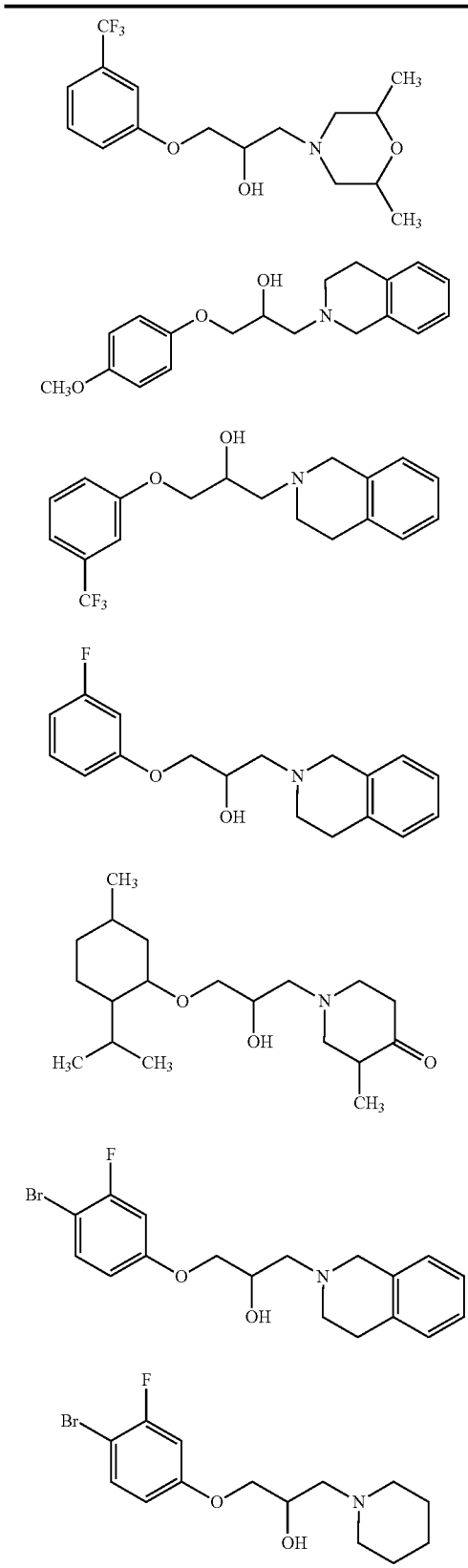
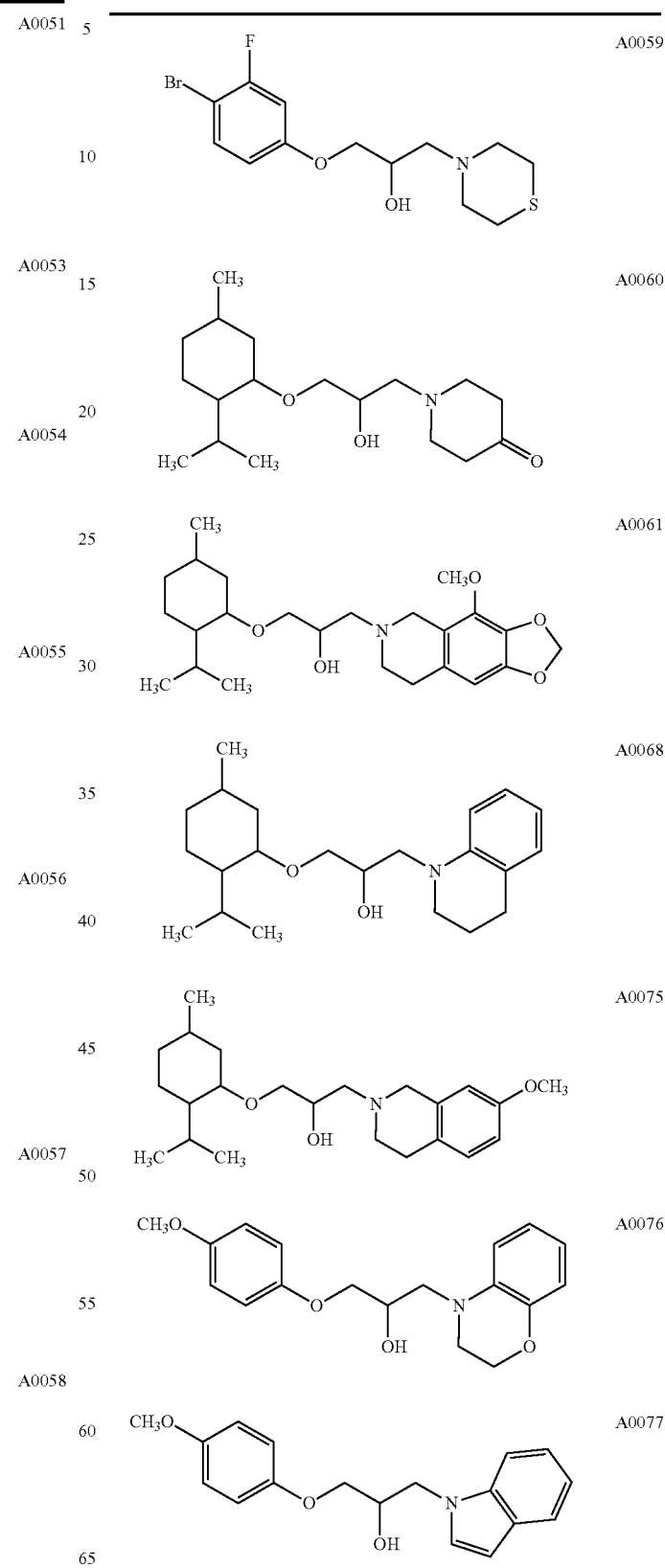

115
-continued

Table of Series-A Compounds

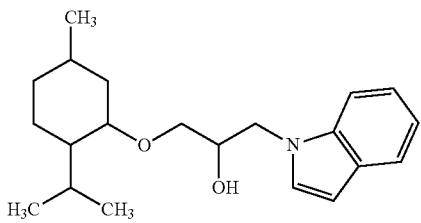 [SMILES: CC1CCC(C(C)C)C(OCC(O)Cn2ccc3ccccc32)C1]

A0078

116

A compound of Series B can be prepared by following the synthetic route illustrated in Scheme 2, below. An illustrative synthetic scheme is shown below for the preparation of a first portion of a contemplated compound, with the second portion being added by a reaction with an appropriately substituted methylketone compound in the presence of a strong base such as sodium ethoxide. The resulting ketone can be converted into the corresponding alcohol by mild reduction as with sodium borohydride. A ketone or alcohol can be converted to the quaternary nitrogen atom-containing compound using an alkylating agent such as methyl iodide.

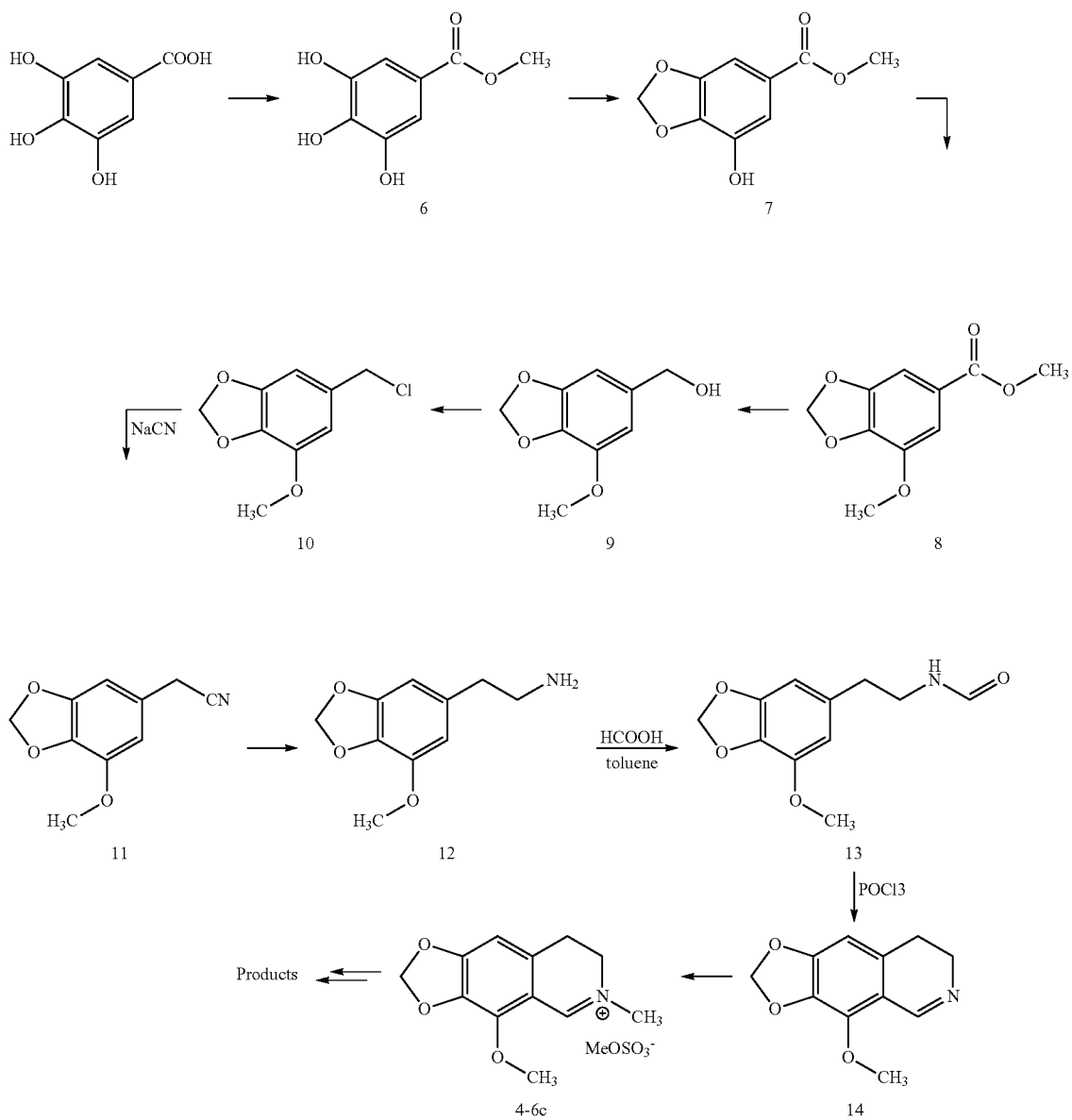

Table of Series-B Compounds
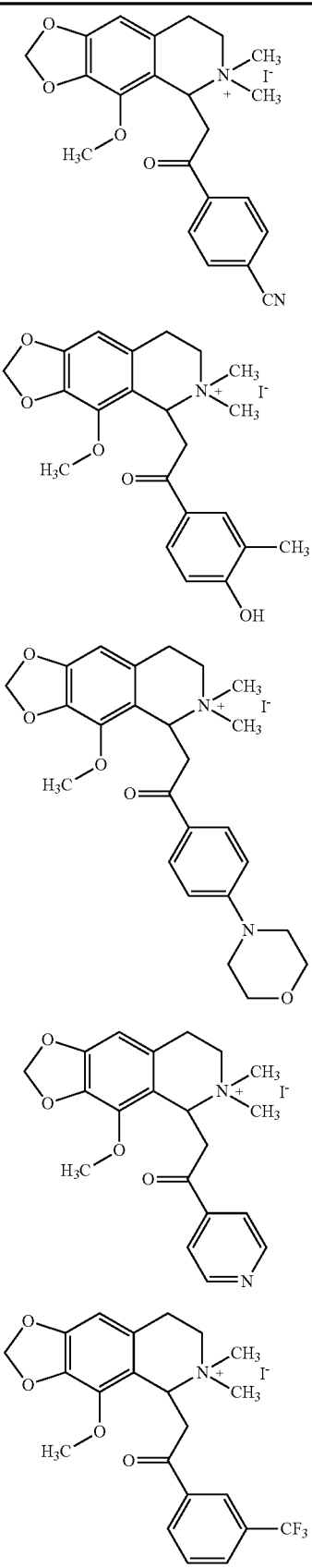
B0001
B0002
B0004
B0005
B0006
-continued
Table of Series-B Compounds
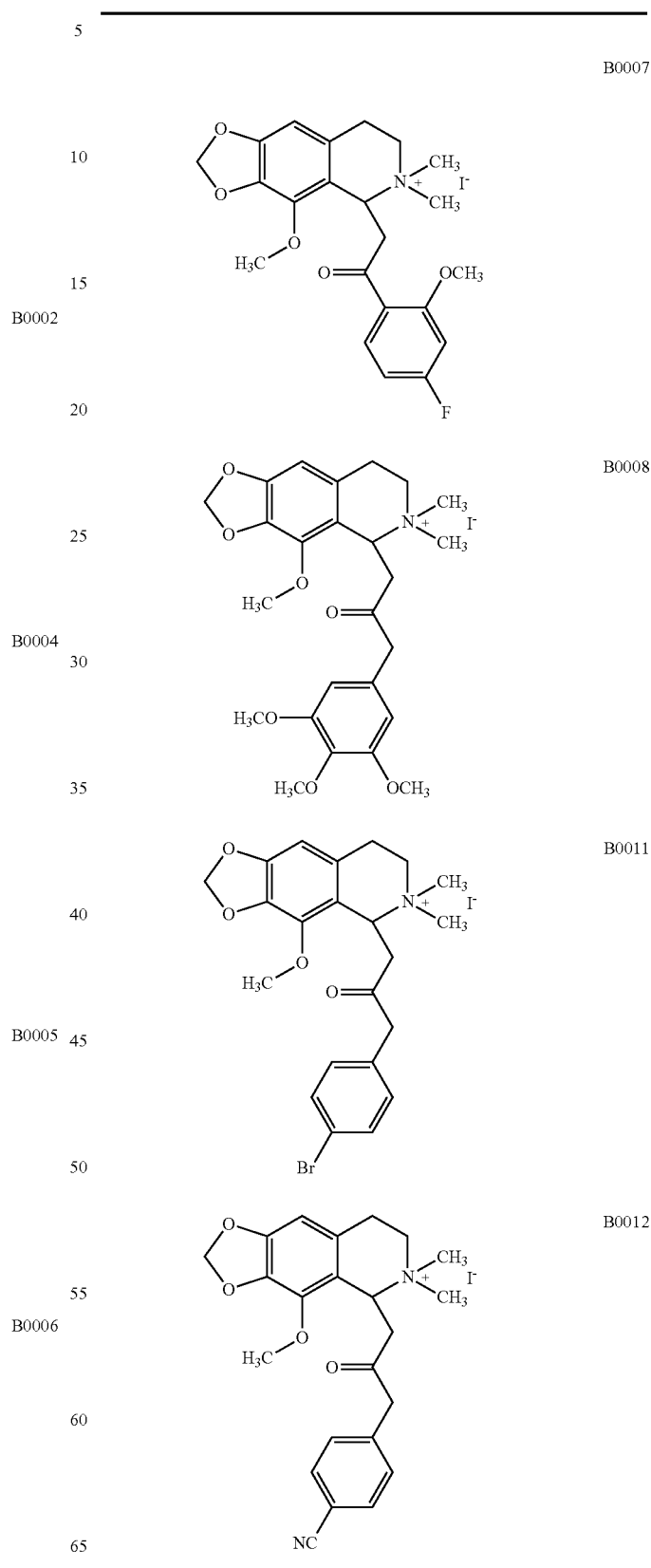
B0007
B0008
B0011
B0012

| Table of Series-B Compounds | |
|---|---|
| 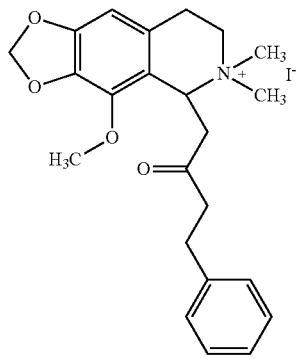 | B0015 |
| 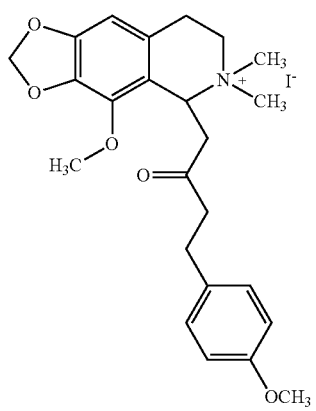 | B0016 |
| 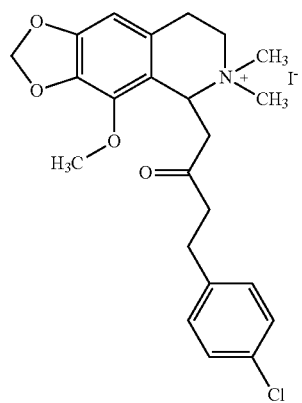 | B0017 |
| 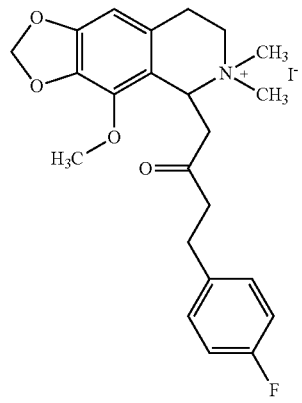 | B0018 |
| Table of Series-B Compounds | |
|---|---|
| 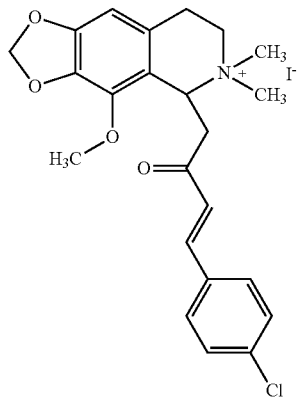 | B0019 |
| 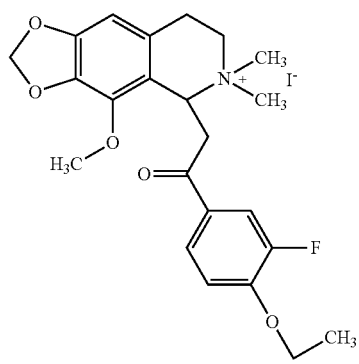 | B0020 |
| 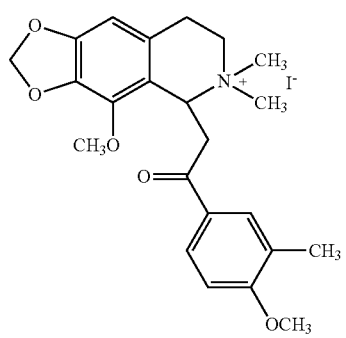 | B0021 |
| 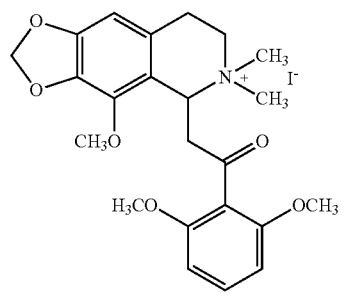 | B0023 |

TABLE of Series-B Compounds
B0024
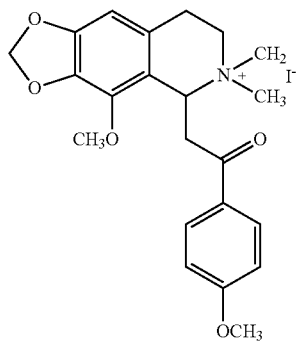
B0025
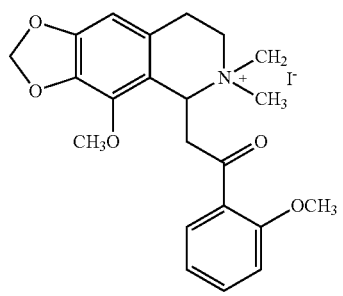
B0026
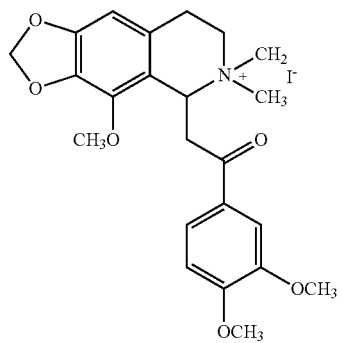
B0027
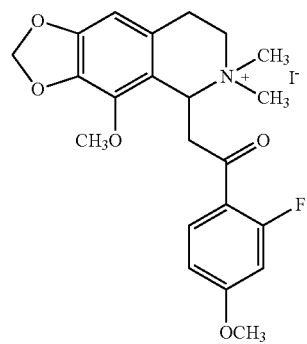
B0028
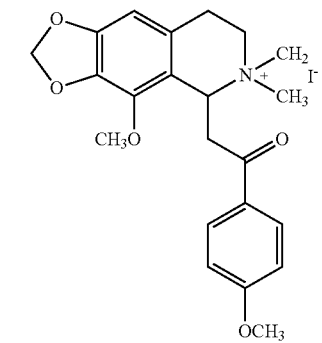
B0029
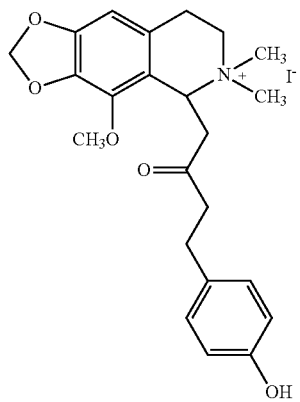
B0030
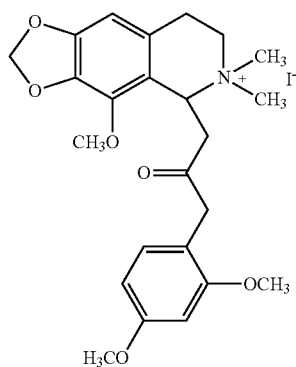
B0031
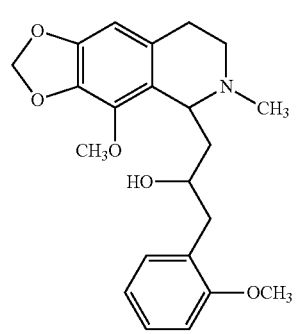

Table of Series-B Compounds
B0032
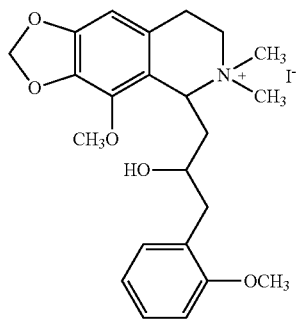
B0033
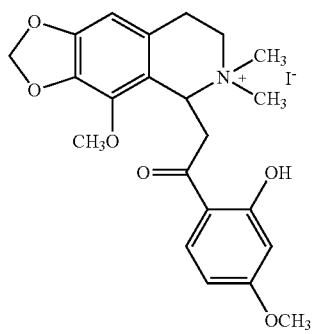
B0034
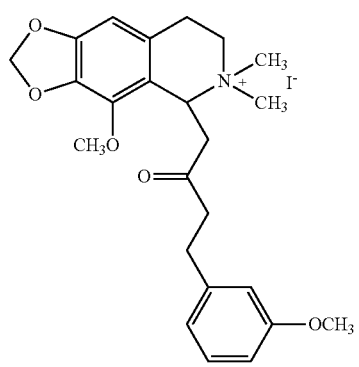
B0035
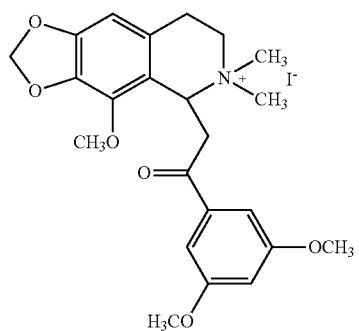
Table of Series-B Compounds
B0036
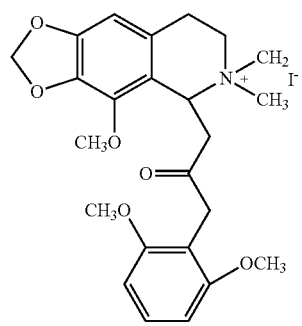
B0037
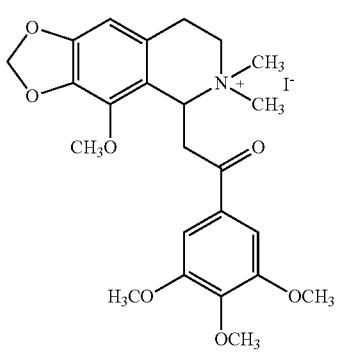
B0038
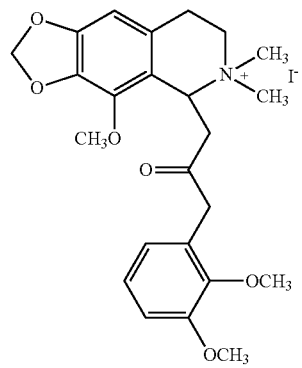
B0039
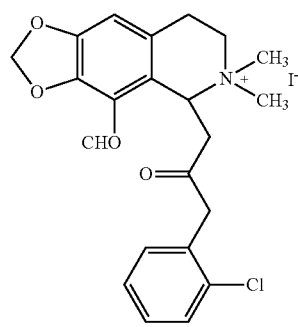

Table of Series-B Compounds
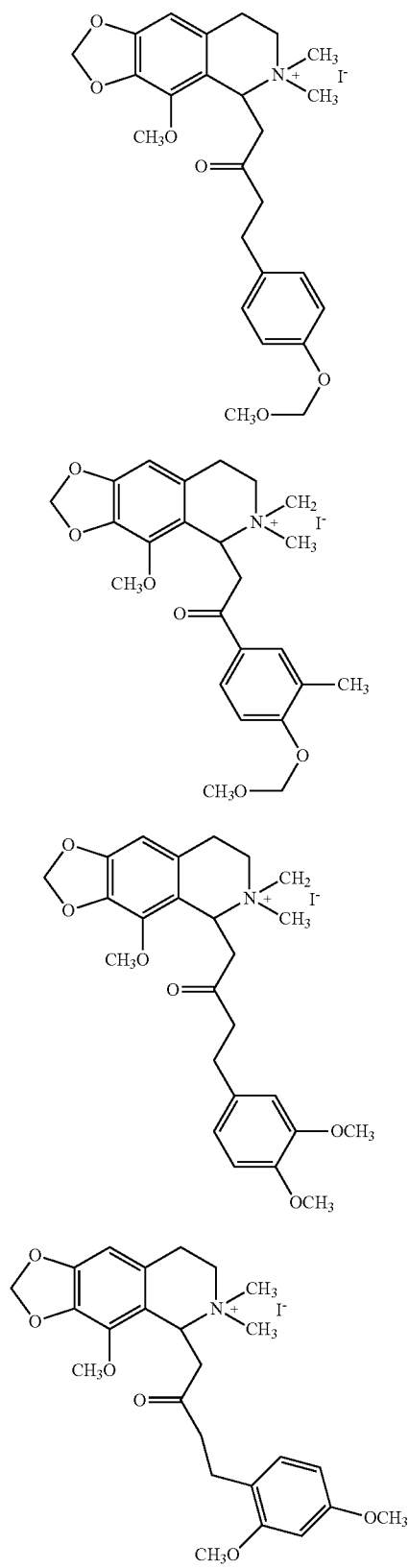
B0040
B0041
B0042
B0043
Table of Series-B Compounds
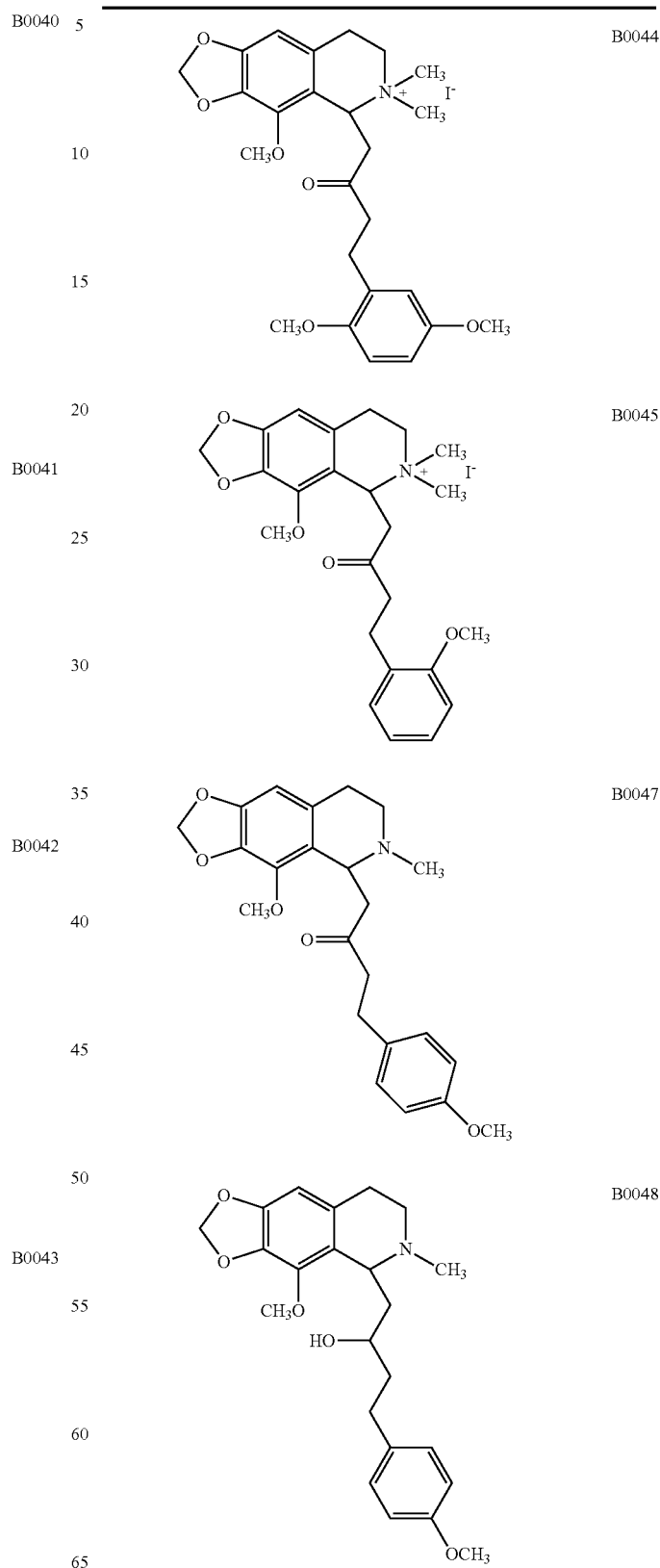
B0044
B0045
B0047
B0048

Table of Series-B Compounds
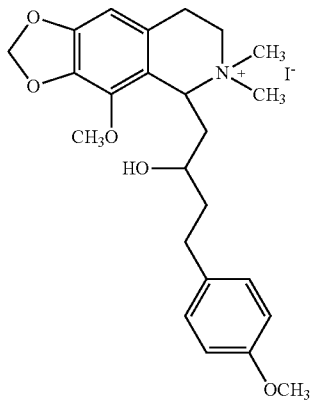
B0049
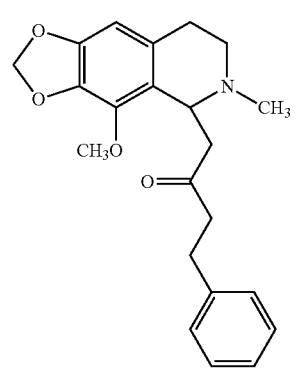
B0050
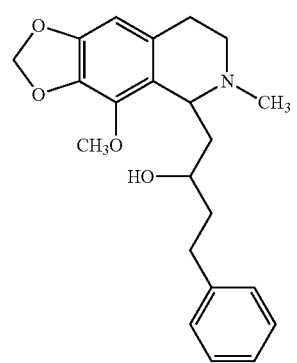
B0051
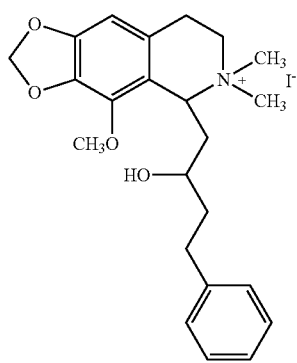
B0052
Table of Series-B Compounds
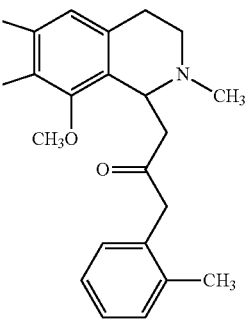
B0053
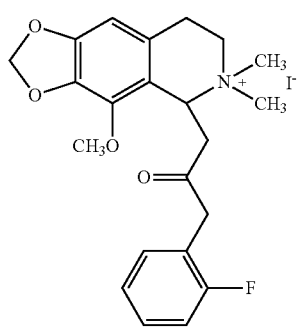
B0055
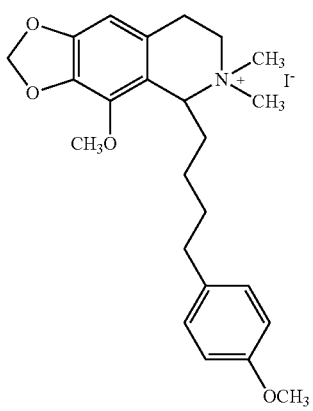
B0056
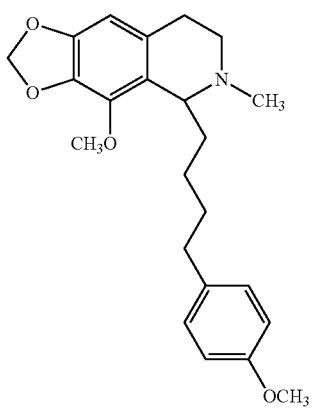
B0057

Table of Series-B Compounds
B0058
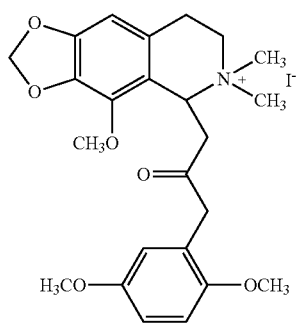
B0059
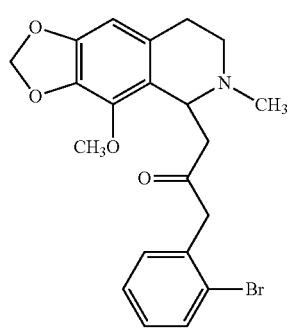
B0060
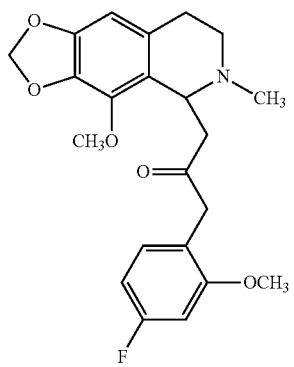
B0061
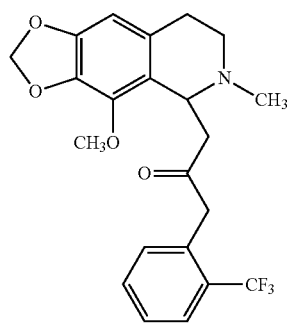
Table of Series-B Compounds
B0062
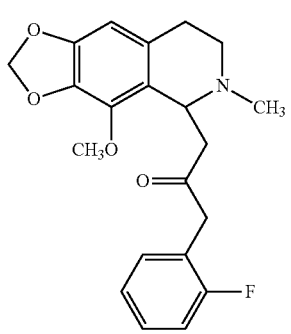
B0063
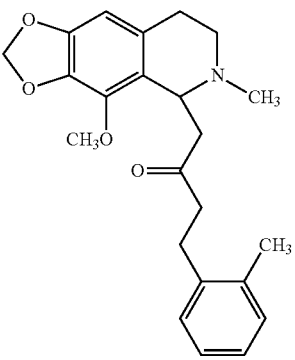
B0064
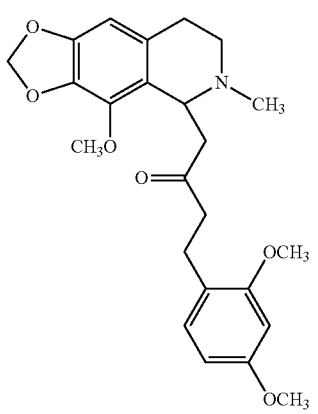

Table of Series-B Compounds

B0065

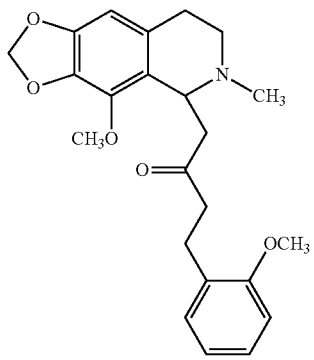

B0067

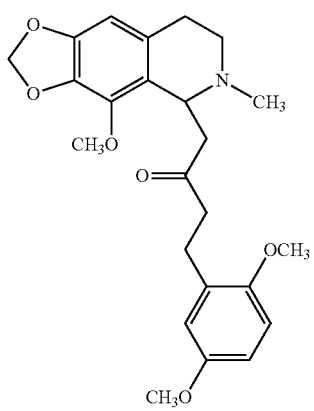

B0068

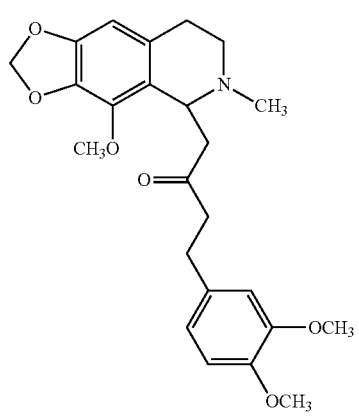

Table of Series-B Compounds

5009

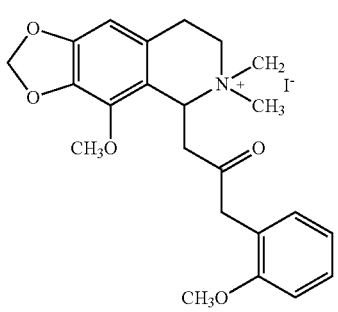

6810

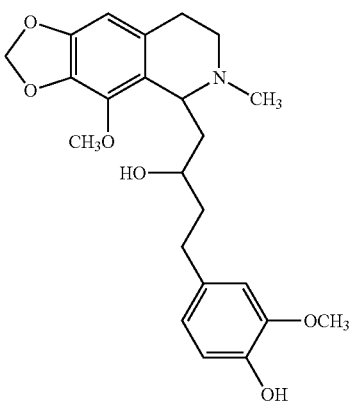

An illustrative synthetic scheme is shown below for preparation of Series-C (both C-1 and C-2) compounds that contain various substituents and ring atoms. That scheme can be readily adapted for the preparation of compounds containing two carbonyl linkages, and also one carbonyl and one sulfonyl linkage in the opposite configurations from those shown. Ethanolamine or thioethanolamine can be replaced by ethylenediamine or N-methylethylene-diamine to prepare the corresponding dinitrogen compounds. Similar replacement with 2-aminoacetamide or an N-substituted acetamide or propionamide provides the corresponding aminoamido-containing ring system.

Scheme 3
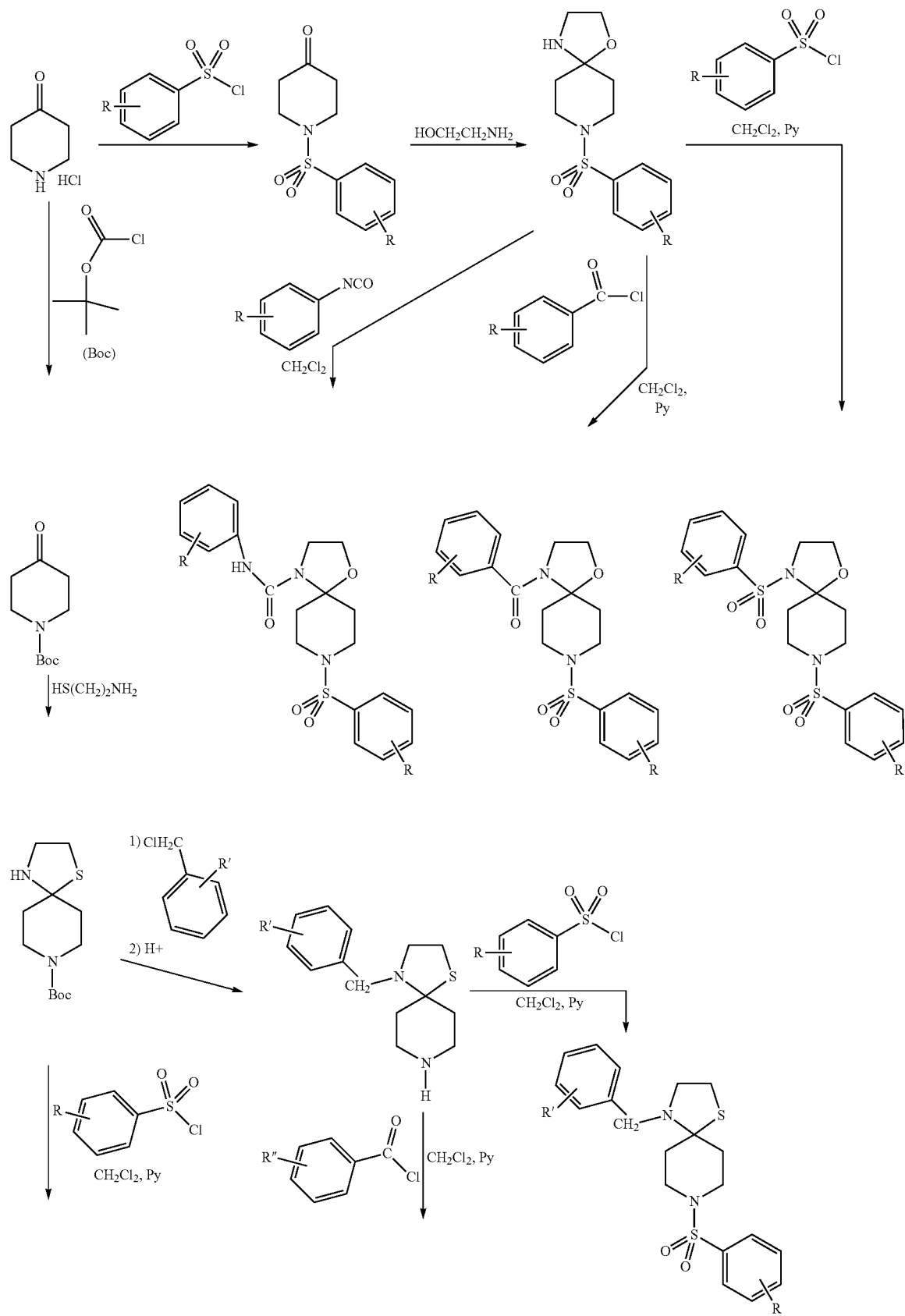

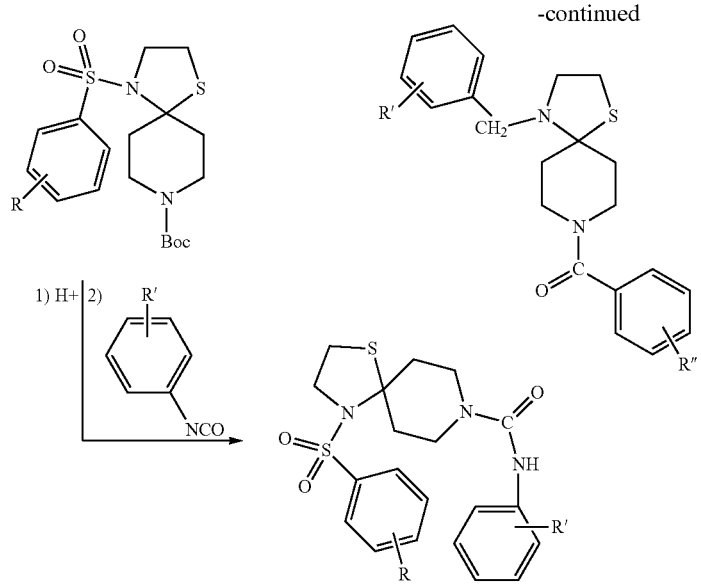
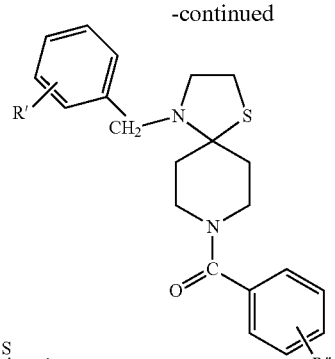
Table of Series-C-1 Compounds
7866
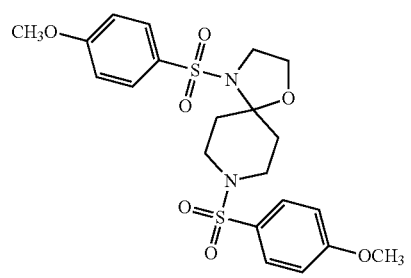
C0001
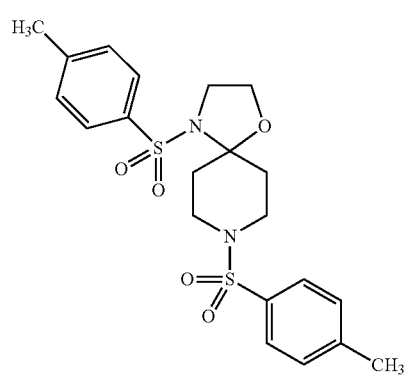
-continued
Table of Series-C-1 Compounds
C0002
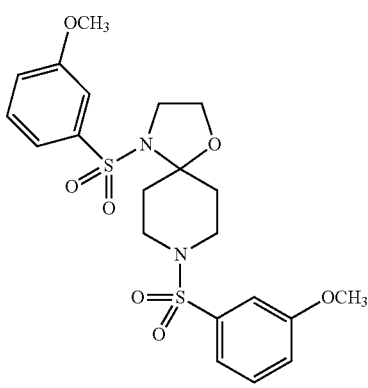 [SMILES: COc1cccc(S(=O)(=O)N2CCC3(CC2)OCCN3S(=O)(=O)c2cccc(OC)c2)c1]
C0003
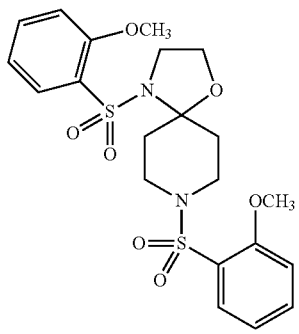 [SMILES: COc1ccccc1S(=O)(=O)N1CCC2(CC1)OCCN2S(=O)(=O)c1ccccc1OC]

Table of Series-C-1 Compounds
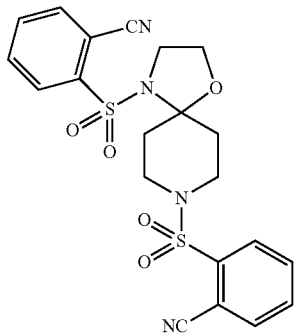 [SMILES: N#Cc1ccccc1S(=O)(=O)N1CCC2(CC1)OCCN2S(=O)(=O)c1ccccc1C#N]
C0004
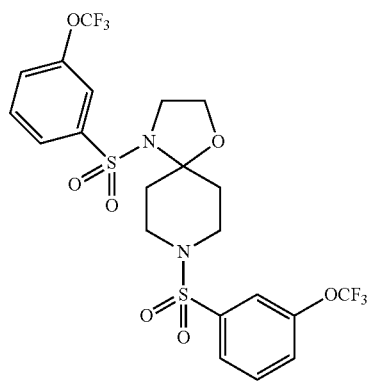 [SMILES: O=S(=O)(c1cccc(OC(F)(F)F)c1)N1CCC2(CC1)OCCN2S(=O)(=O)c1cccc(OC(F)(F)F)c1]
C0005
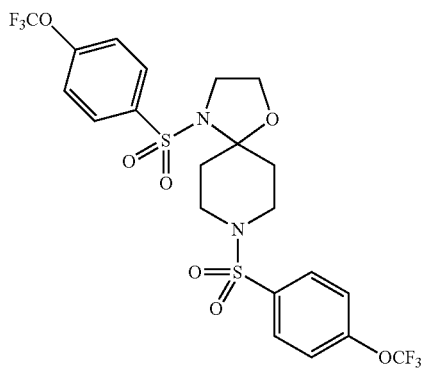 [SMILES: O=S(=O)(c1ccc(OC(F)(F)F)cc1)N1CCC2(CC1)OCCN2S(=O)(=O)c1ccc(OC(F)(F)F)cc1]
C0006
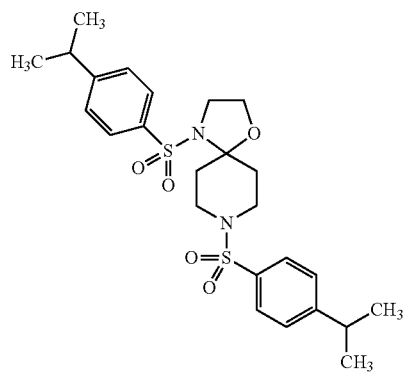 [SMILES: CC(C)c1ccc(S(=O)(=O)N2CCC3(CC2)OCCN3S(=O)(=O)c2ccc(C(C)C)cc2)cc1]
C0007
Table of Series-C-1 Compounds
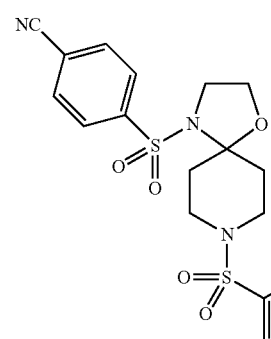
C0008
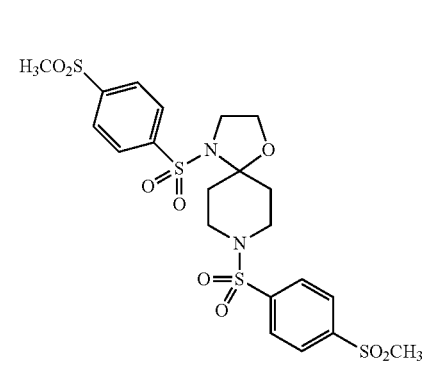
C0009
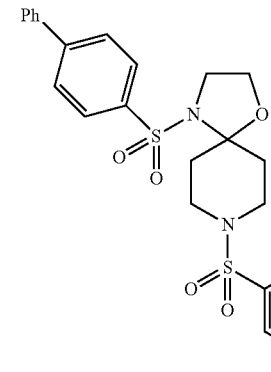
C0010
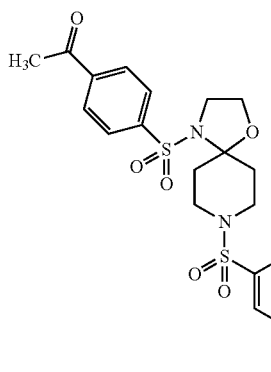
C0011

Table of Series-C-1 Compounds
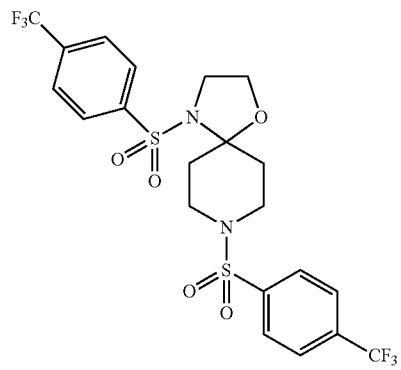 [SMILES: O=S(=O)(c1ccc(C(F)(F)F)cc1)N1CCC2(CC1)OCCN2S(=O)(=O)c1ccc(C(F)(F)F)cc1]
C0012
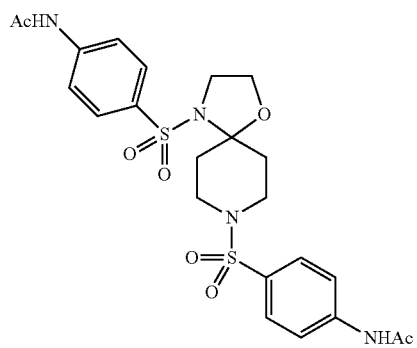 [SMILES: CC(=O)Nc1ccc(S(=O)(=O)N2CCC3(CC2)OCCN3S(=O)(=O)c2ccc(NC(C)=O)cc2)cc1]
C0013
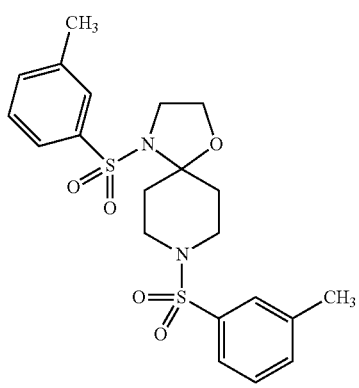 [SMILES: Cc1cccc(S(=O)(=O)N2CCC3(CC2)OCCN3S(=O)(=O)c2cccc(C)c2)c1]
C0014
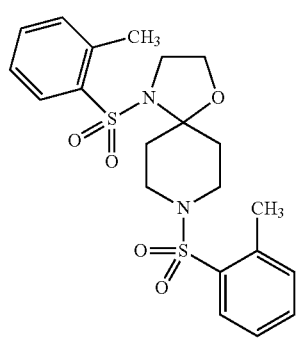 [SMILES: Cc1ccccc1S(=O)(=O)N1CCC2(CC1)OCCN2S(=O)(=O)c1ccccc1C]
C0015
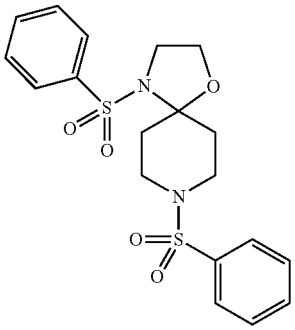 [SMILES: O=S(=O)(c1ccccc1)N1CCC2(CC1)OCCN2S(=O)(=O)c1ccccc1]
C0016
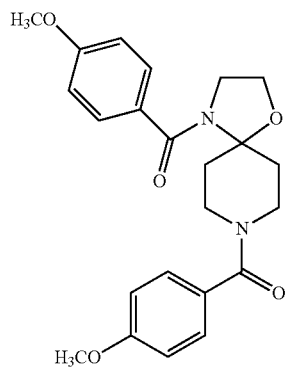 [SMILES: COc1ccc(C(=O)N2CCC3(CC2)OCCN3C(=O)c2ccc(OC)cc2)cc1]
C0017
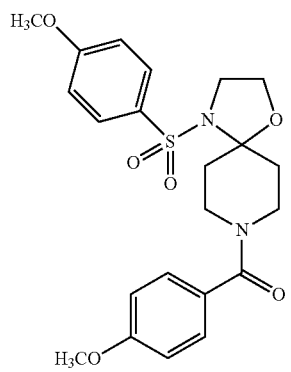 [SMILES: COc1ccc(C(=O)N2CCC3(CC2)OCCN3S(=O)(=O)c2ccc(OC)cc2)cc1]
C0018
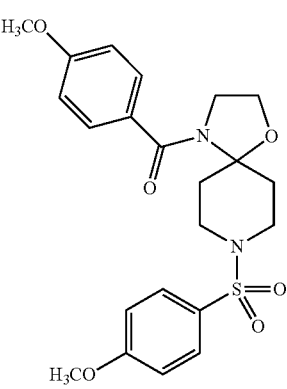
C0019

Table of Series-C-1 Compounds
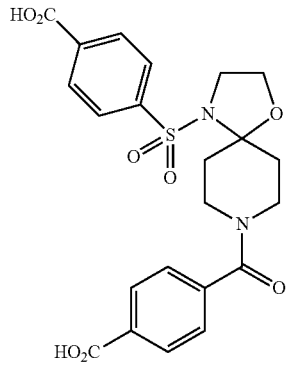 [SMILES: O=C(O)c1ccc(C(=O)N2CCC3(CC2)OCCN3S(=O)(=O)c2ccc(C(=O)O)cc2)cc1]
C0021
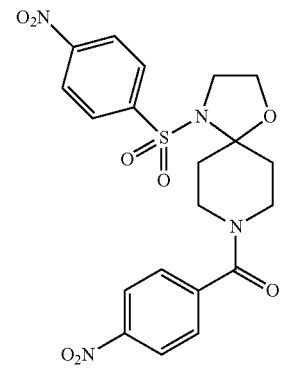 [SMILES: O=C(c1ccc([N+](=O)[O-])cc1)N1CCC2(CC1)OCCN2S(=O)(=O)c1ccc([N+](=O)[O-])cc1]
C0022
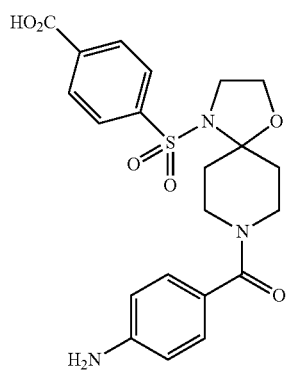 [SMILES: Nc1ccc(C(=O)N2CCC3(CC2)OCCN3S(=O)(=O)c2ccc(C(=O)O)cc2)cc1]
C0023
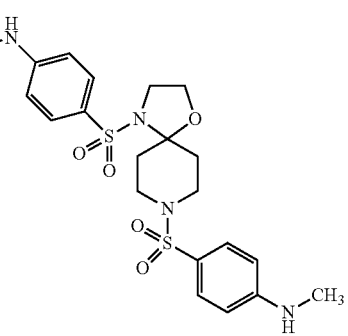
C0024
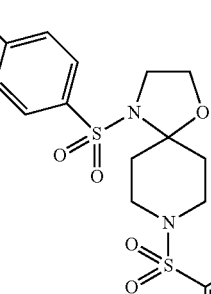
C0025
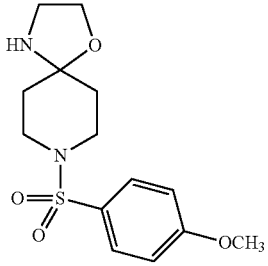 [SMILES: COc1ccc(S(=O)(=O)N2CCC3(CC2)NCCO3)cc1]
C0026
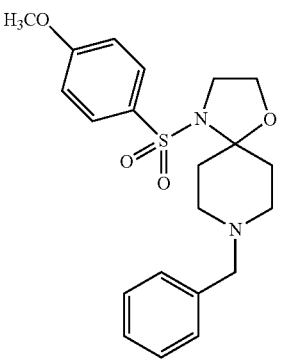 [SMILES: COc1ccc(S(=O)(=O)N2CCOC23CCN(Cc2ccccc2)CC3)cc1]
C0027-1
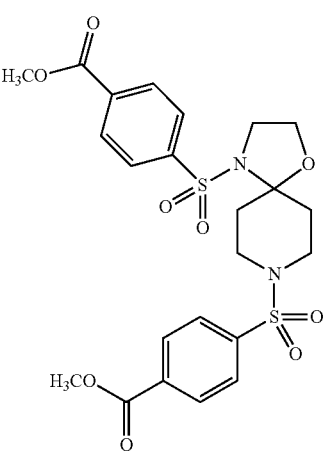 [SMILES: COC(=O)c1ccc(S(=O)(=O)N2CCC3(CC2)OCCN3S(=O)(=O)c2ccc(C(=O)OC)cc2)cc1]
C0028

Table of Series-C-1 Compounds
C0029
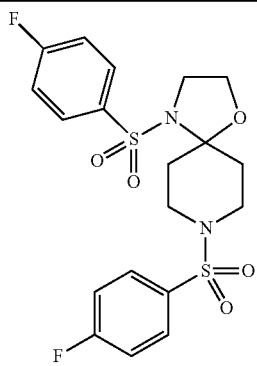
C0030
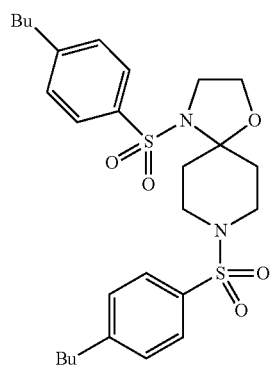
C0031
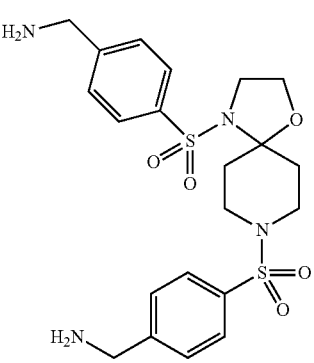 [SMILES: NCc1ccc(S(=O)(=O)N2CCC3(CC2)OCCN3S(=O)(=O)c2ccc(CN)cc2)cc1]
C0032
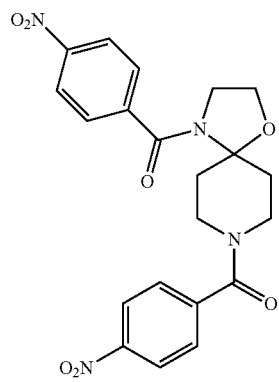 [SMILES: O=C(c1ccc([N+](=O)[O-])cc1)N1CCC2(CC1)OCCN2C(=O)c1ccc([N+](=O)[O-])cc1]
Table of Series-C-1 Compounds
C0033
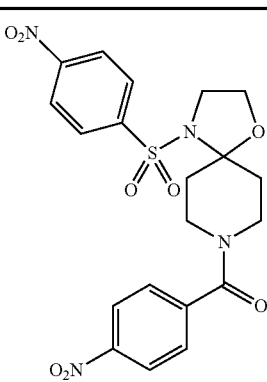
C0034
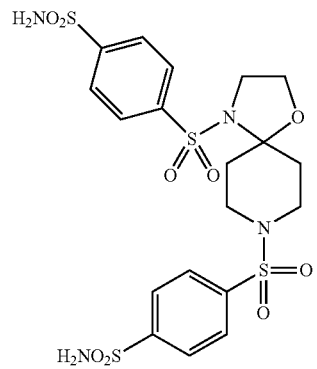 [SMILES: NS(=O)(=O)c1ccc(S(=O)(=O)N2CCC3(CC2)OCCN3S(=O)(=O)c2ccc(S(N)(=O)=O)cc2)cc1]
C0034-3
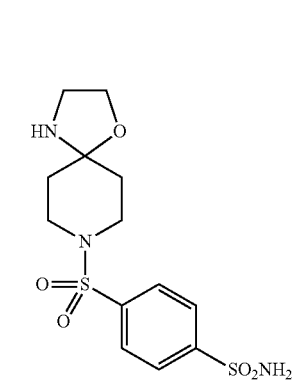 [SMILES: NS(=O)(=O)c1ccc(S(=O)(=O)N2CCC3(CC2)NCCO3)cc1]
C0037-2
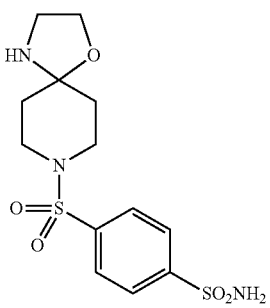

Table of Series-C-1 Compounds
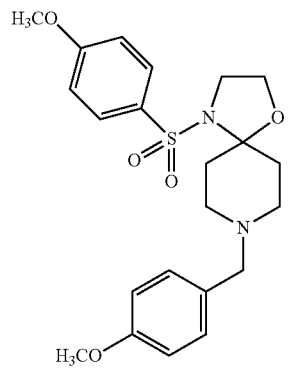 [SMILES: COc1ccc(CN2CCC3(CC2)OCCN3S(=O)(=O)c2ccc(OC)cc2)cc1]
C0038
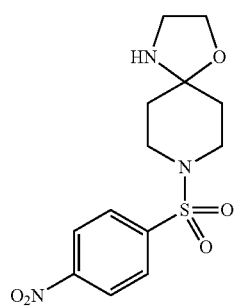 [SMILES: O=[N+]([O-])c1ccc(S(=O)(=O)N2CCC3(CC2)NCCO3)cc1]
C0040
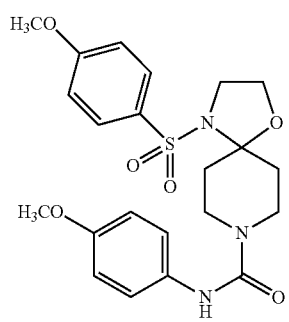 [SMILES: COc1ccc(NC(=O)N2CCC3(CC2)OCCN3S(=O)(=O)c2ccc(OC)cc2)cc1]
C0041
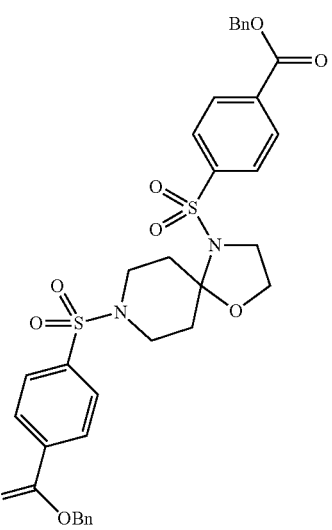
C0042
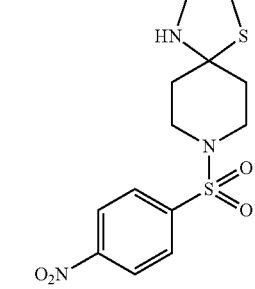
C0044
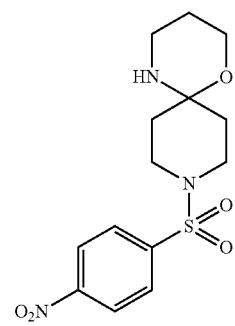 [SMILES: O=[N+]([O-])c1ccc(S(=O)(=O)N2CCC3(CC2)NCCCO3)cc1]
C0045
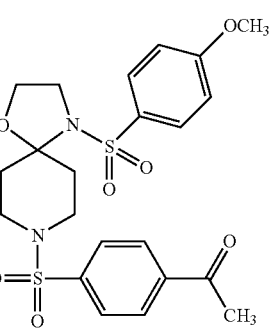
C0047
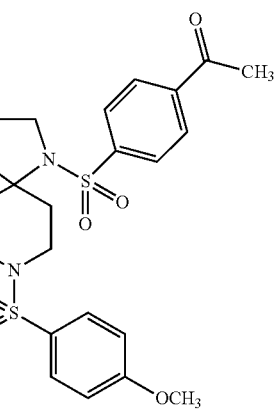
C0048

Table of Series-C-1 Compounds
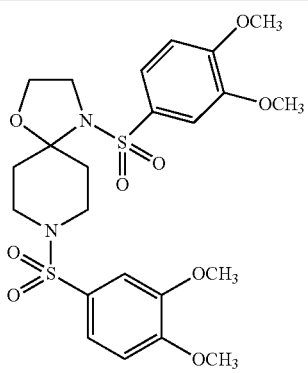 [SMILES: COc1ccc(S(=O)(=O)N2CCC3(CC2)OCCN3S(=O)(=O)c2ccc(OC)c(OC)c2)cc1OC]
C0049
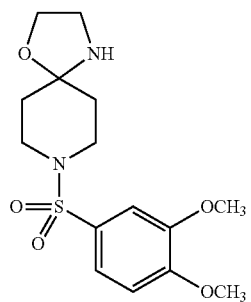 [SMILES: COc1ccc(S(=O)(=O)N2CCC3(CC2)NCCO3)cc1OC]
C0049-2
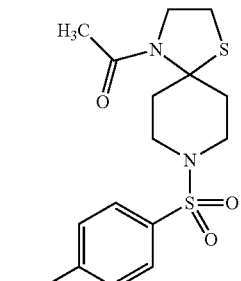
C0050
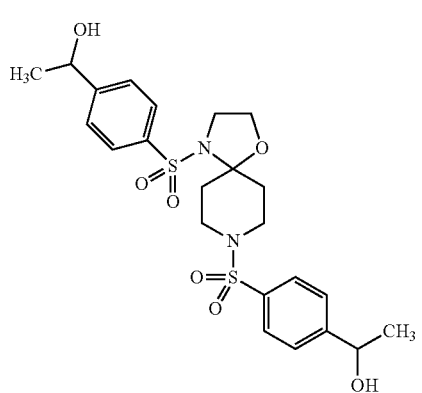 [SMILES: CC(O)c1ccc(S(=O)(=O)N2CCC3(CC2)OCCN3S(=O)(=O)c2ccc(C(C)O)cc2)cc1]
C0051
Table of Series-C-1 Compounds
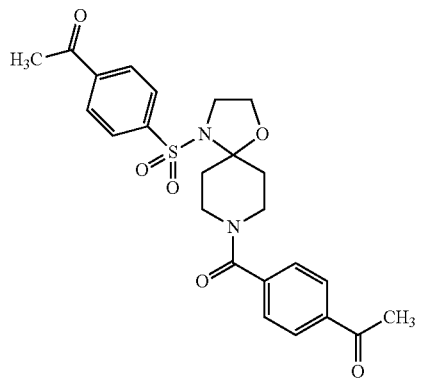 [SMILES: CC(=O)c1ccc(C(=O)N2CCC3(CC2)OCCN3S(=O)(=O)c2ccc(C(C)=O)cc2)cc1]
C0052
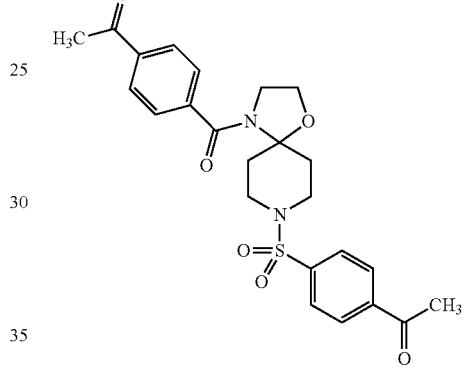
C0053
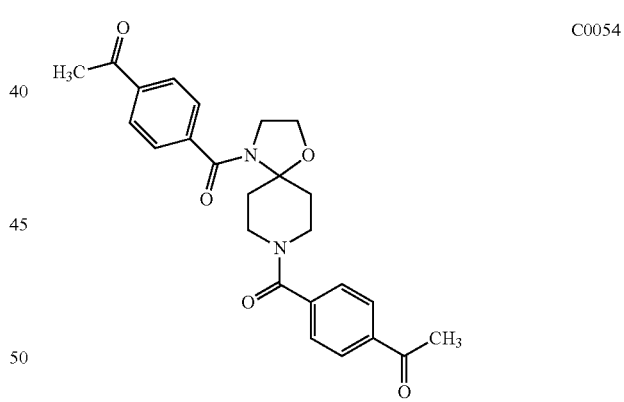
C0054
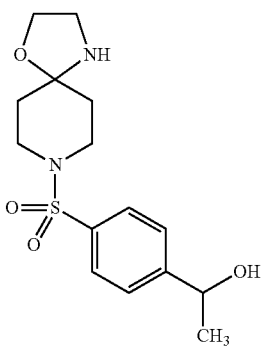 [SMILES: CC(O)c1ccc(S(=O)(=O)N2CCC3(CC2)NCCO3)cc1]
C0055-4

Table of Series-C-1 Compounds
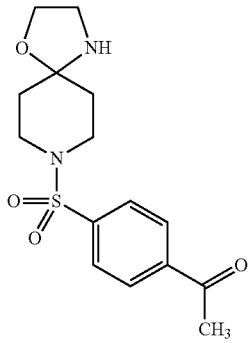 [SMILES: CC(=O)c1ccc(S(=O)(=O)N2CCC3(CC2)NCCO3)cc1]
C0055
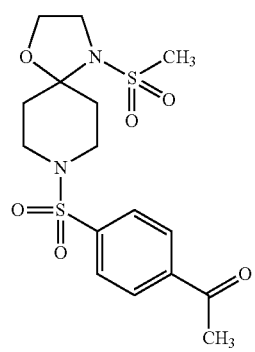 [SMILES: CC(=O)c1ccc(S(=O)(=O)N2CCC3(CC2)OCCN3S(C)(=O)=O)cc1]
C0056
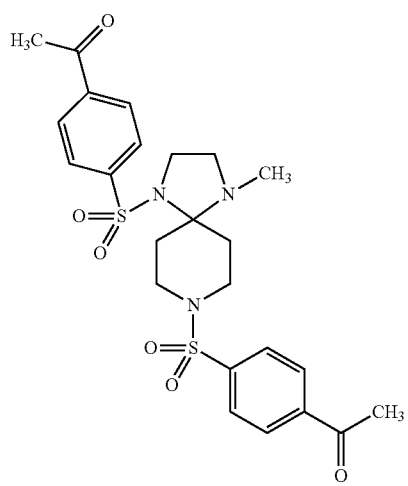 [SMILES: CC(=O)c1ccc(S(=O)(=O)N2CCC3(CC2)N(C)CCN3S(=O)(=O)c2ccc(C(C)=O)cc2)cc1]
C0057
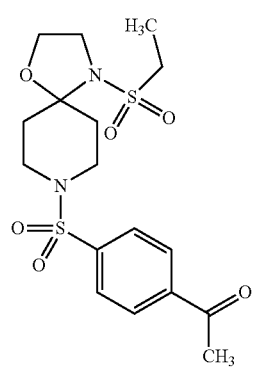 [SMILES: CCS(=O)(=O)N1CCOC12CCN(S(=O)(=O)c1ccc(C(C)=O)cc1)CC2]
C0058
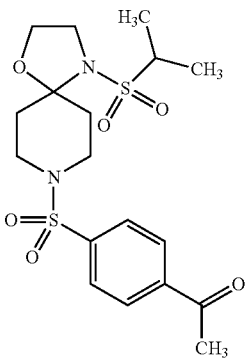 [SMILES: CC(=O)c1ccc(S(=O)(=O)N2CCC3(CC2)OCCN3S(=O)(=O)C(C)C)cc1]
C0059
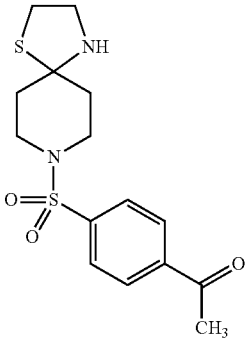
C0060
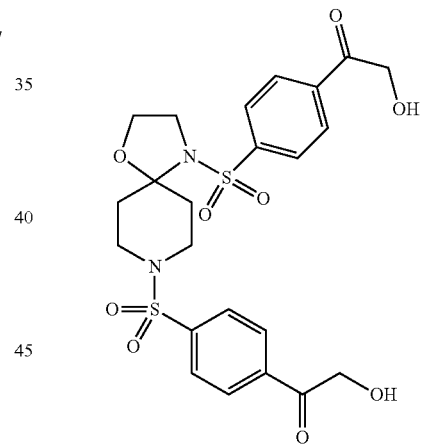
C0061
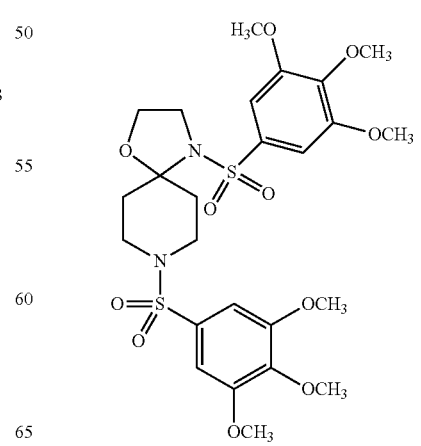
C0062

Table of Series-C-1 Compounds
C0064
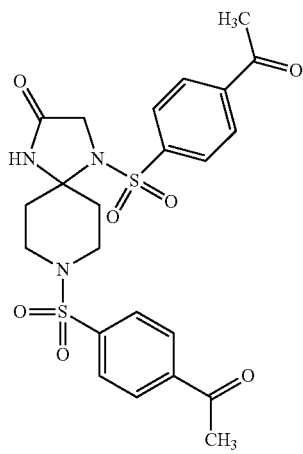 [SMILES: CC(=O)c1ccc(S(=O)(=O)N2CCC3(CC2)NC(=O)CN3S(=O)(=O)c2ccc(C(C)=O)cc2)cc1]
C0065
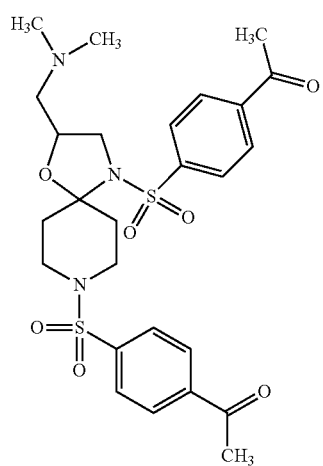 [SMILES: CC(=O)c1ccc(S(=O)(=O)N2CCC3(CC2)OC(CN(C)C)CN3S(=O)(=O)c2ccc(C(C)=O)cc2)cc1]
C0066
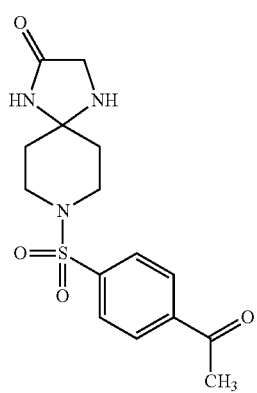 [SMILES: CC(=O)c1ccc(S(=O)(=O)N2CCC3(CC2)NCC(=O)N3)cc1]
Table of Series-C-1 Compounds
C0067
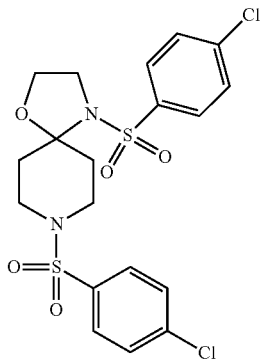 [SMILES: O=S(=O)(c1ccc(Cl)cc1)N1CCC2(CC1)OCCN2S(=O)(=O)c1ccc(Cl)cc1]
C0068
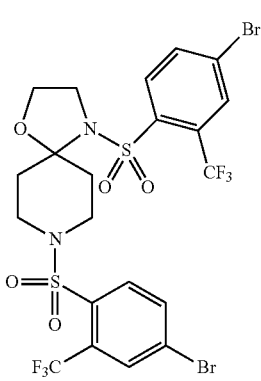 [SMILES: O=S(=O)(c1ccc(Br)cc1C(F)(F)F)N1CCC2(CC1)OCCN2S(=O)(=O)c1ccc(Br)cc1C(F)(F)F]
C0068-2
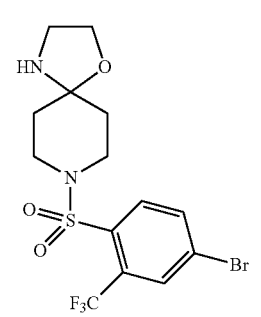 [SMILES: O=S(=O)(c1ccc(Br)cc1C(F)(F)F)N1CCC2(CC1)NCCO2]
C0069
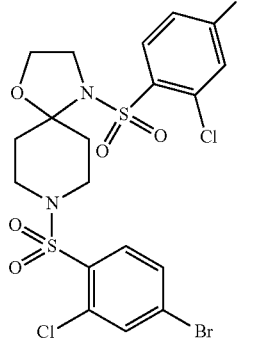

Table of Series-C-1 Compounds
C0070
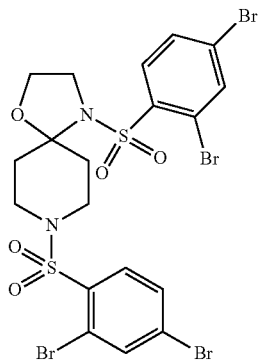 [SMILES: O=S(=O)(c1ccc(Br)cc1Br)N1CCC2(CC1)OCCN2S(=O)(=O)c1ccc(Br)cc1Br]
C0071
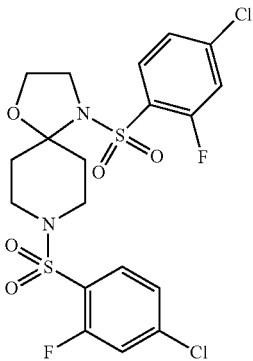
C0071-2
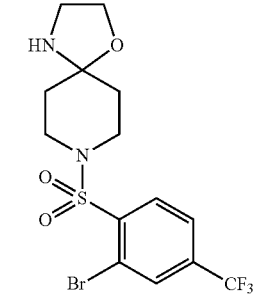
C0072
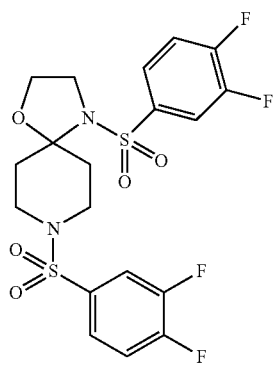 [SMILES: O=S(=O)(c1ccc(F)c(F)c1)N1CCC2(CC1)OCCN2S(=O)(=O)c1ccc(F)c(F)c1]
Table of Series-C-1 Compounds
C0073
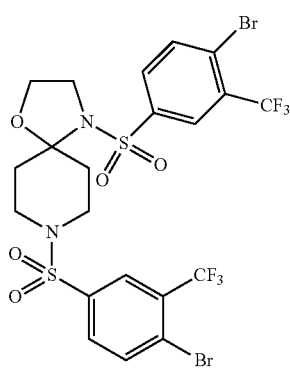 [SMILES: O=S(=O)(c1ccc(Br)c(C(F)(F)F)c1)N1CCC2(CC1)OCCN2S(=O)(=O)c1ccc(Br)c(C(F)(F)F)c1]
C0077
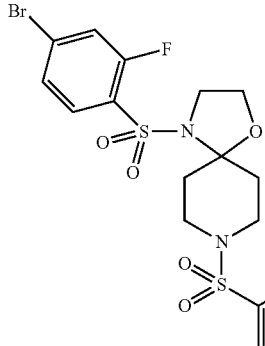
C0078
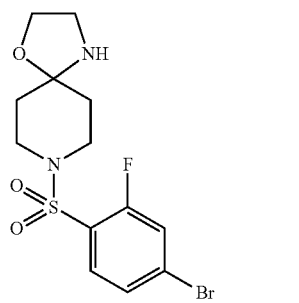 [SMILES: O=S(=O)(c1ccc(Br)cc1F)N1CCC2(CC1)NCCO2]
C0078-2

Table of Series-C-1 Compounds
C0080
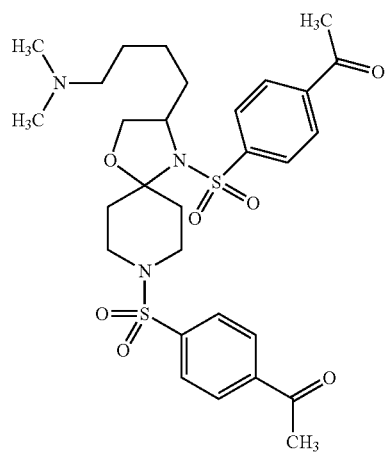 [SMILES: CC(=O)c1ccc(S(=O)(=O)N2CCC3(CC2)OCC(CCCCN(C)C)N3S(=O)(=O)c2ccc(C(C)=O)cc2)cc1]
C0082M
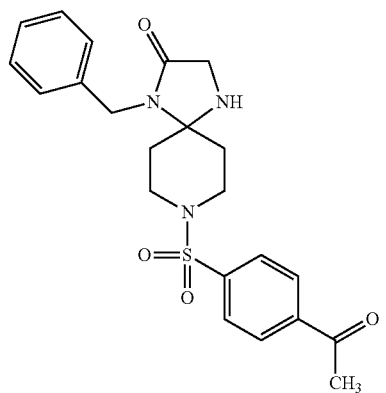 [SMILES: CC(=O)c1ccc(S(=O)(=O)N2CCC3(CC2)NCC(=O)N3Cc2ccccc2)cc1]
C0083M
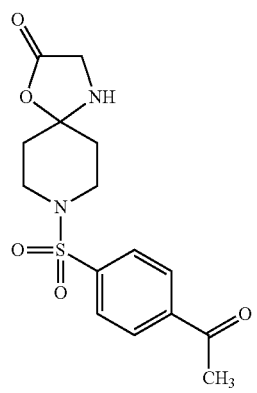 [SMILES: CC(=O)c1ccc(S(=O)(=O)N2CCC3(CC2)NCC(=O)O3)cc1]
Table of Series-C-1 Compounds
C0084M
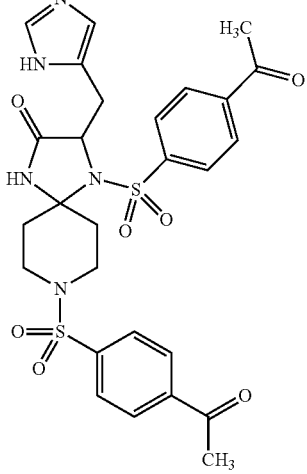
C0085M
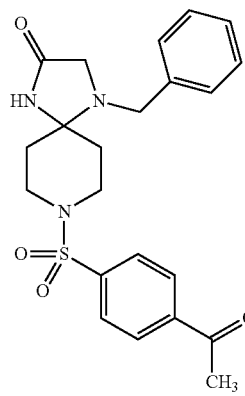
C0087M
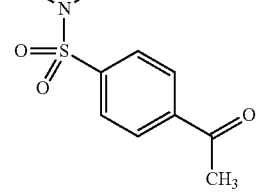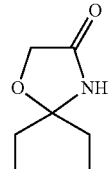
C0136M(P5)
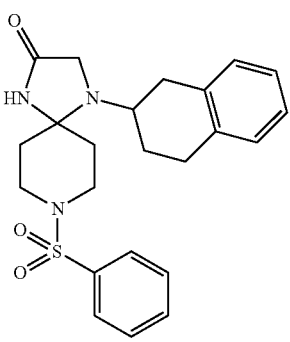 [SMILES: O=C1CN(C2CCc3ccccc3C2)C2(CCN(S(=O)(=O)c3ccccc3)CC2)N1]

Table of Series-C-1 Compounds
C0138M
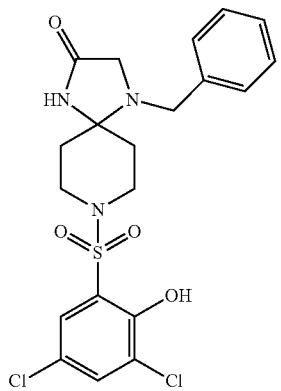 [SMILES: O=C1CN(Cc2ccccc2)C2(CCN(S(=O)(=O)c3cc(Cl)cc(Cl)c3O)CC2)N1]
C0139M
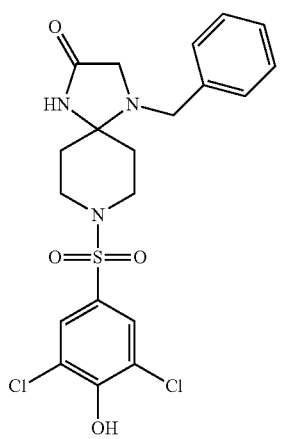 [SMILES: O=C1CN(Cc2ccccc2)C2(CCN(S(=O)(=O)c3cc(Cl)c(O)c(Cl)c3)CC2)N1]
C0140M
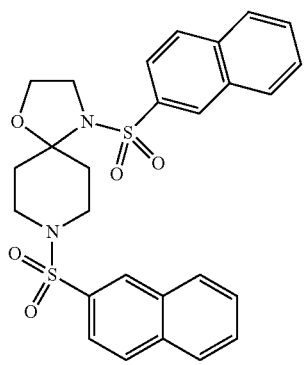 [SMILES: O=S(=O)(c1ccc2ccccc2c1)N1CCC2(CC1)OCCN2S(=O)(=O)c1ccc2ccccc2c1]
C0141M
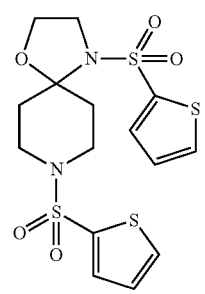 [SMILES: O=S(=O)(c1cccs1)N1CCC2(CC1)OCCN2S(=O)(=O)c1cccs1]
Table of Series-C-1 Compounds
C0141M-2
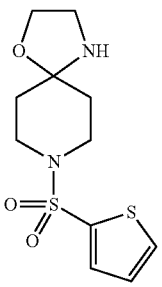 [SMILES: O=S(=O)(c1cccs1)N1CCC2(CC1)NCCO2]
C0142M
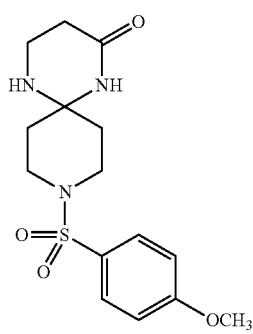 [SMILES: COc1ccc(S(=O)(=O)N2CCC3(CC2)NCCC(=O)N3)cc1]
C0143M-2
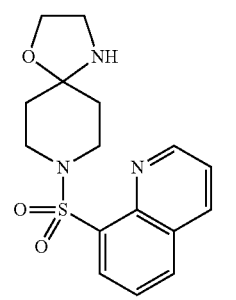 [SMILES: O=S(=O)(c1cccc2cccnc12)N1CCC2(CC1)NCCO2]
C0143M
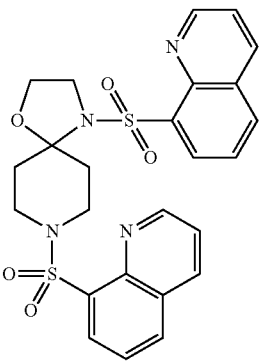 [SMILES: O=S(=O)(c1cccc2cccnc12)N1CCC2(CC1)OCCN2S(=O)(=O)c1cccc2cccnc12]
C0143M-2
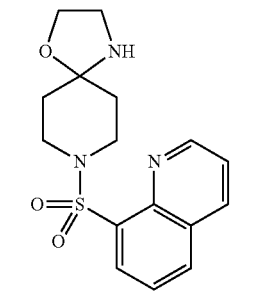 [SMILES: O=S(=O)(c1cccc2cccnc12)N1CCC2(CC1)NCCO2]

Table of Series-C-1 Compounds
C0144M
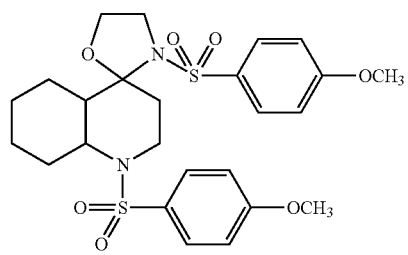 [SMILES: COc1ccc(S(=O)(=O)N2CCC3(OCCN3S(=O)(=O)c3ccc(OC)cc3)C3CCCCC32)cc1]
C0144M-2
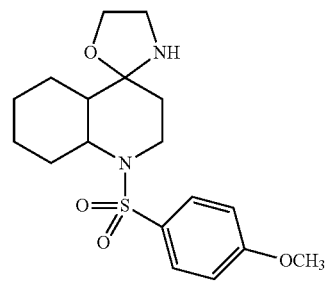 [SMILES: COc1ccc(S(=O)(=O)N2CCC3(NCCO3)C3CCCCC32)cc1]
C0145M
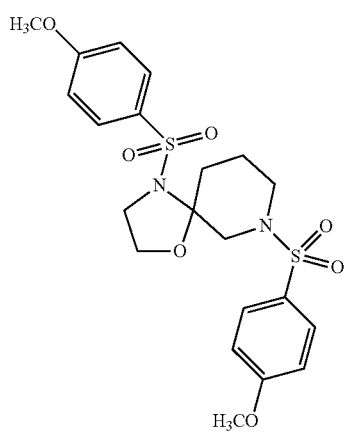 [SMILES: COc1ccc(S(=O)(=O)N2CCCC3(C2)OCCN3S(=O)(=O)c2ccc(OC)cc2)cc1]
C0146M
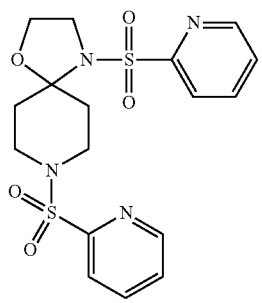 [SMILES: O=S(=O)(c1ccccn1)N1CCC2(CC1)OCCN2S(=O)(=O)c1ccccn1]
Table of Series-C-1 Compounds
C0147M A2
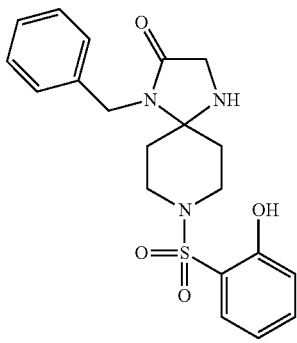 [SMILES: O=C1CNC2(CCN(S(=O)(=O)c3ccccc3O)CC2)N1Cc1ccccc1]
C0148M
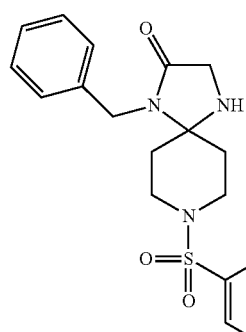
C0149M-2
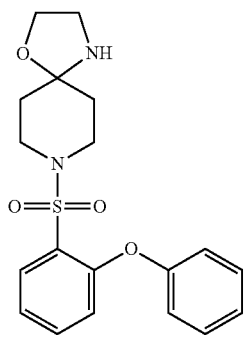 [SMILES: O=S(=O)(c1ccccc1Oc1ccccc1)N1CCC2(CC1)NCCO2]
C0149M
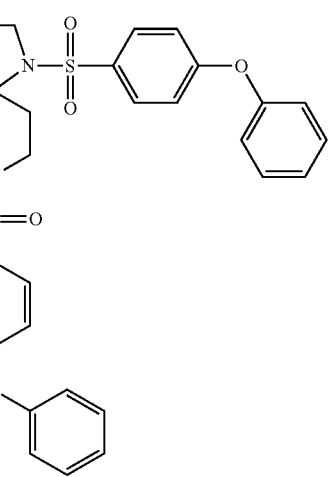

Table of Series-C-1 Compounds
C0150M
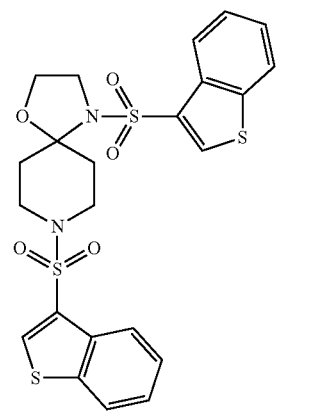 [SMILES: O=S(=O)(c1csc2ccccc12)N1CCC2(CC1)OCCN2S(=O)(=O)c1csc2ccccc12]
C0151M
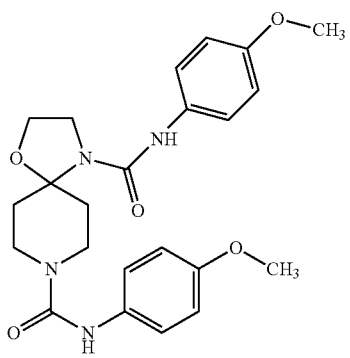 [SMILES: COc1ccc(NC(=O)N2CCC3(CC2)OCCN3C(=O)Nc2ccc(OC)cc2)cc1]
C0151M-2
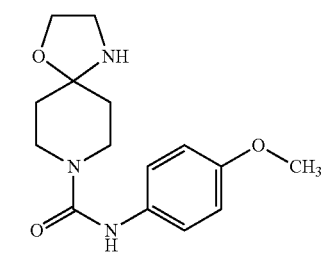 [SMILES: COc1ccc(NC(=O)N2CCC3(CC2)NCCO3)cc1]
C0152M-4
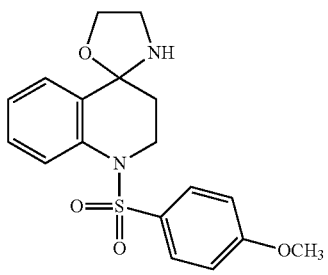 [SMILES: COc1ccc(S(=O)(=O)N2CCC3(NCCO3)c3ccccc32)cc1]
Compound A
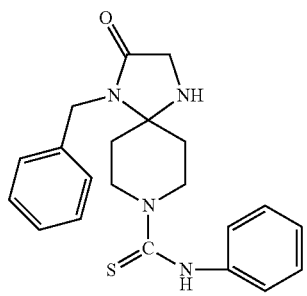 [SMILES: O=C1CNC2(CCN(C(=S)Nc3ccccc3)CC2)N1Cc1ccccc1]
Table of Series-C-1 Compounds
Compound B
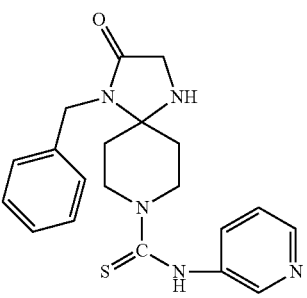 [SMILES: O=C1CNC2(CCN(C(=S)Nc3cccnc3)CC2)N1Cc1ccccc1]
Compound C
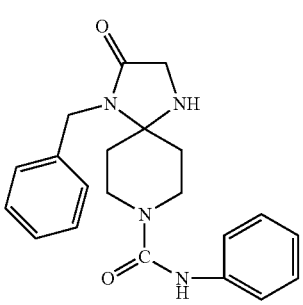
Preparation of Compounds A, B and C
Compound A
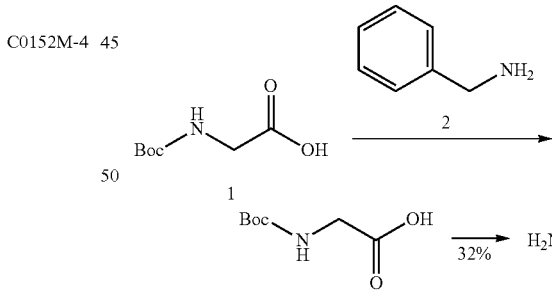
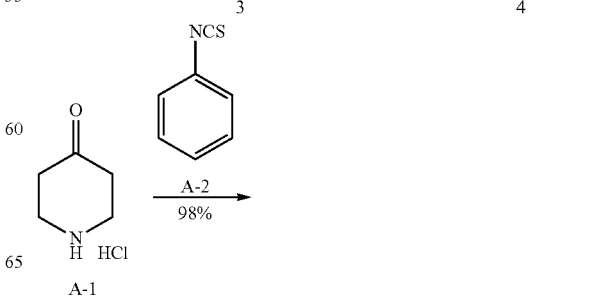

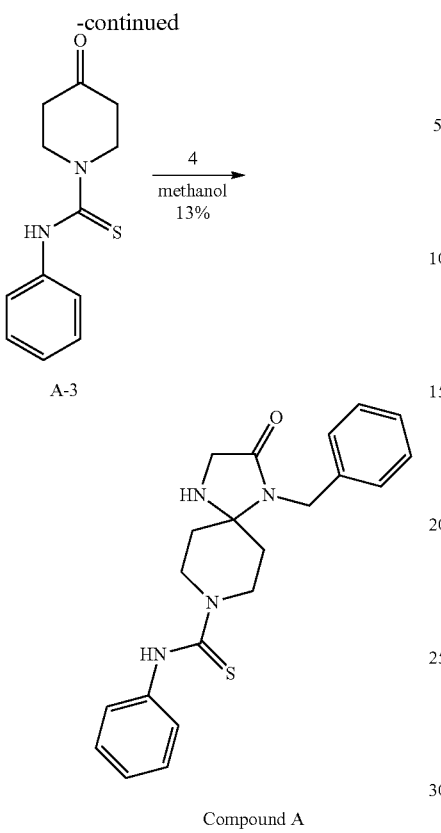

Compound A 3.52 (s, 2H); 4.42 (s, 2H); 4.47 (s, 2H); 7.06 (t, J=7.6 Hz, 2H); 7.14 (t, J=7.6 Hz, 1H); 7.24~7.33 (m, 9H). MS (ESI) calcd for $C_{21}H_{24}N_4OS$ (m/z): 380.17, found: 381.2 $[M+1]^+$.

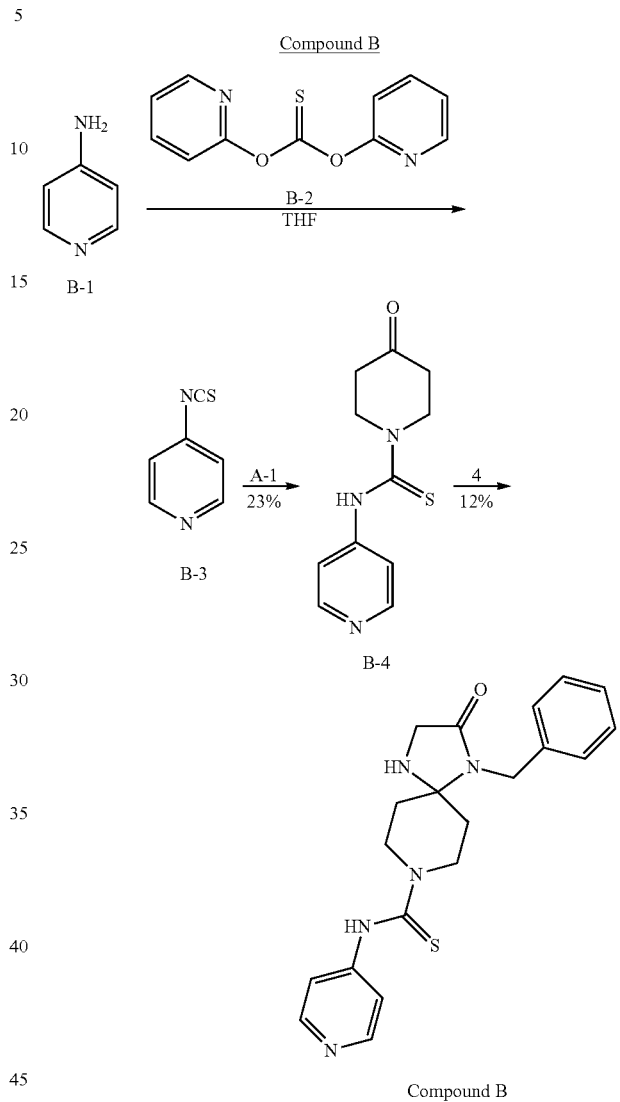

Compound B

Compound 4

To a solution of Compound 1 (10 g, 57 mmol) in THF (100 mL) was added 1,1'-carbonyldiimidazole (CDI) (11.1 g, 68.5 mmol) at room temperature, and the mixture was stirred for 30 minutes. Compound 2 (7.34 g, 68.5 mmol) was then added and stirred overnight (about 18 hours). The solvent was evaporated and the residue was dissolved in ethyl acetate (EA; 400 mL) to which was added 4M HCl/MeOH (50 mL), and the resulting admixture was stirred overnight (about 18 hours). The resulting white solid was filtered and suspended in EA, washed with aq.$NaHCO_3$ and concentrated to afford product as white solid (3.2 g, 34% yield, as confirmed by NMR).

1H-NMR (400 MHz, $CDCl_3$): 3.41 (s, 3H); 4.48 (d, J=6.0 Hz, 2H); 7.26-7.36 (m, 5H); 7.57 (br, s, 1H).

Compound A-3

A mixture of Compound A-1 (3.75 g, 24 mmol), A-2 (1.5 g, 11 mmol) and triethylamine (TEA) (4.5 g, 44.38 mmol) in dichloromethane (DCM) (50 mL) was stirred at room temperature overnight (about 18 hours) The reaction mixture was washed with water, dried over $Na_2SO_4$ and concentrated to afford product as white solid (2.55 g, 98% yield, confirmed by NMR).

1H-NMR (400 MHz, $CDCl_3$): 2.53 (t, J=6.4 Hz, 4H); 4.01 (t, J=6.4 Hz, 4H); 7.10~7.30 (m, 5H).

Compound A

A mixture of Compound A-3 (400 mg, 1.7 mmol) and Compound 4 (280 mg, 1.7 mmol) in methanol (60 mL) was heated to reflux overnight (about 18 hours) under argon. The mixture was concentrated and purified by pre-TLC to get product as pale white solid (84 mg, 13% yield, NMR and MS confirmed, 98% by HPLC).

1H-NMR (400 MHz, $CDCl_3$): 1.42 (d, J=12.4 Hz, 2H); 1.92 (dt, J=4.4, 13.2 Hz, 2H); 3.32 (dt, J=2.0, 12.8 Hz, 2H);

Compound B-4

To a solution of pyridin-4-amine (400 mg, 4.25 mmol) in THF (35 mL) was added 60% NaH (340 mg, 8.5 mmol) in an ice bath, and the mixture was stirred for 1 hour. Compound B-2 (0.99 g, 4.25 mmol) was added and the mixture was permitted to gradually to reach room temperature and stirred for 3 hours. Compound A-1 (0.78 g, 5.1 mmol) and N,N-diisopropyl-ethylamine (DIEA; 1 mL) was added and the mixture was stirred at room temperature overnight (about 18 hours). Water was added and the resulting composition was extracted with EA, washed with brine, dried over $Na_2SO_4$, concentrated and purified by column chromatography to afford oil (0.23 g, 23% yield, NMR was not pure but the major component was title compound).

1H-NMR (400 MHz, $CDCl_3$): 2.66 (t, J=6.4 Hz, 4H); 4.12 (t, J=6.4 Hz, 4H); 7.11~7.12 (d, J=4.8 Hz, 2H); 8.50~8.52 (d, J=5.6 Hz, 2H).

Compound B

A solution of Compound B-4 (230 mg, 1.7 mmol) and Compound 4 (225 mg, 1.37 mmol) in methanol (25 mL) was heated to reflux overnight (about 18 hours) under argon. The mixture was concentrated and purified by pre-TLC to get product as yellow solid (45 mg, 12% yield, NMR and MS confirmed, 96% by HPLC).

1H-NMR (400 MHz, CDCl$_3$): 1.47 (d, J=13.2 Hz, 2H); 1.92~1.98 (m, 2H); 3.41 (t, J=13.2 Hz, 2H); 3.54 (s, 2H); 4.44 (s, 4H); 6.95 (d, J=4.4 Hz, 2H); 7.26~7.31 (m, 5H); 8.45 (d, J=4.0 Hz, 2H). MS (ESI) calcd for C$_{20}$H$_{23}$N$_5$OS (m/z): 381.16, found: 382.4 [M+1]$^+$.

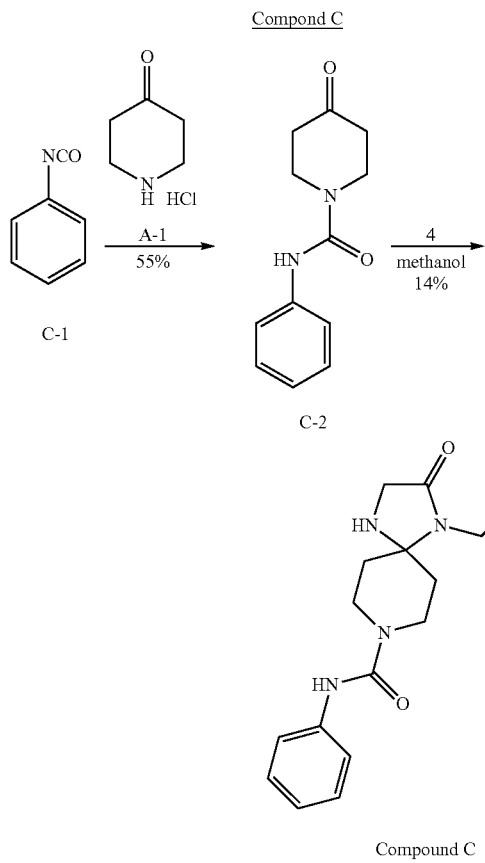

Compound C-2

A mixture of Compound C-1 (1.0 g, 8.39 mmol), Compound A-1 (2.83 g, 18.45 mmol) and potassium carbonate (4.64 g, 33.6 mmol) in DCM (50 mL) was stirred at ambient temperature for 18 hours. The mixture was washed with water, 1N HCl (aqueous), dried over Na$_2$SO$_4$ and concentrated. The residue was purified by column chromatography (PE/EA=3:1) to afford product as white solid (1.0 g, 55% yield, NMR confirmed the title compound)

1H-NMR (400 MHz, CDCl$_3$): 2.56 (t, J=6.4 Hz, 4H); 3.81 (t, J=6.4 Hz, 4H); 6.50 (brs, 1H); 7.07 (t, J=7.2 Hz, 4H); 7.28~7.37 (m, 4H).

Compound C

A mixture of Compound C-2 (400 mg, 1.84 mmol) and Compound 4 (400 mg, 2.44 mmol) in methanol (40 mL) was heated to reflux overnight (about 18 hours) under argon. The mixture was concentrated and purified by pre-TLC to provide the product as white solid (96 mg, 14% yield, NMR and MS confirmed, 98% by HPLC).

1H-NMR (400 MHz, CDCl$_3$): 1.45 (d, J=12.0 Hz, 2H); 1.85 (dt, J=4.4, 13.2 Hz, 2H); 3.19 (dt, J=2.0, 13.2 Hz, 2H); 3.55 (s, 2H); 3.96 (dt, J=13.6, 2.0 Hz, 2H); 4.44 (s, 2H); 6.29 (s, 1H); 7.02~7.06 (m, 1H); 7.22~7.33 (m, 10H). MS (ESI) calcd for C$_{21}$H$_{24}$N$_4$O$_2$ (m/z): 364.19, found: 365.2 [M+1].

Table of Series C-2 Compounds

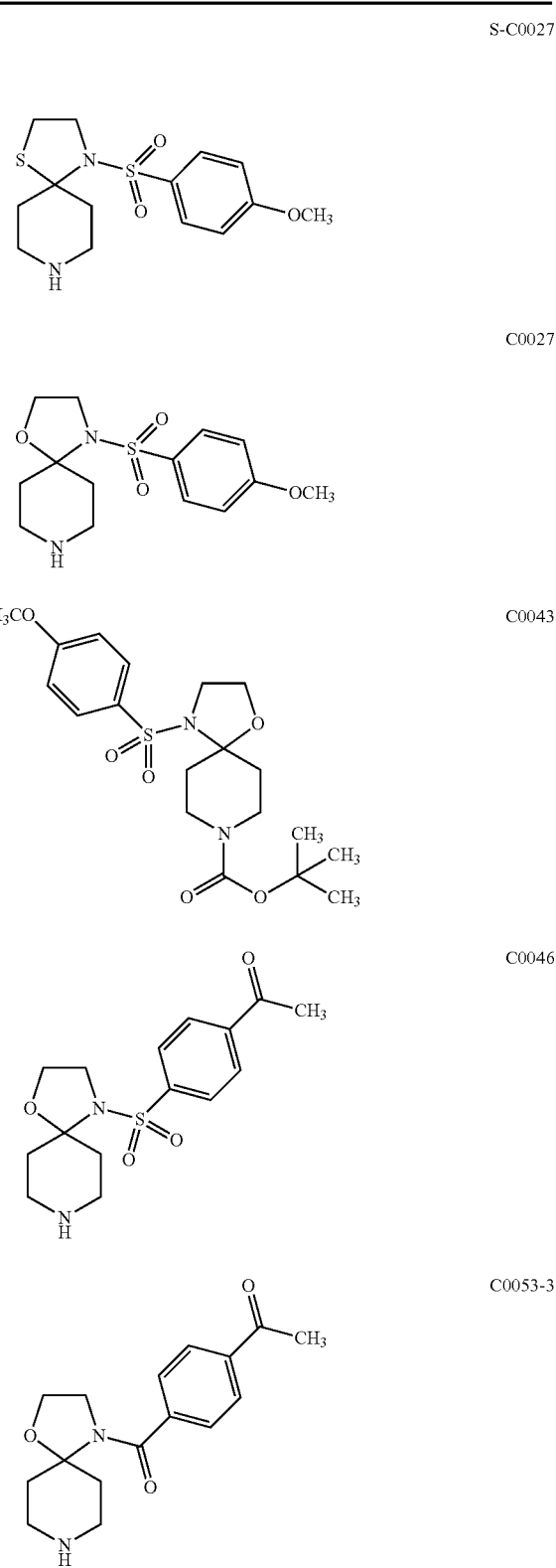

Table of Series C-2 Compounds
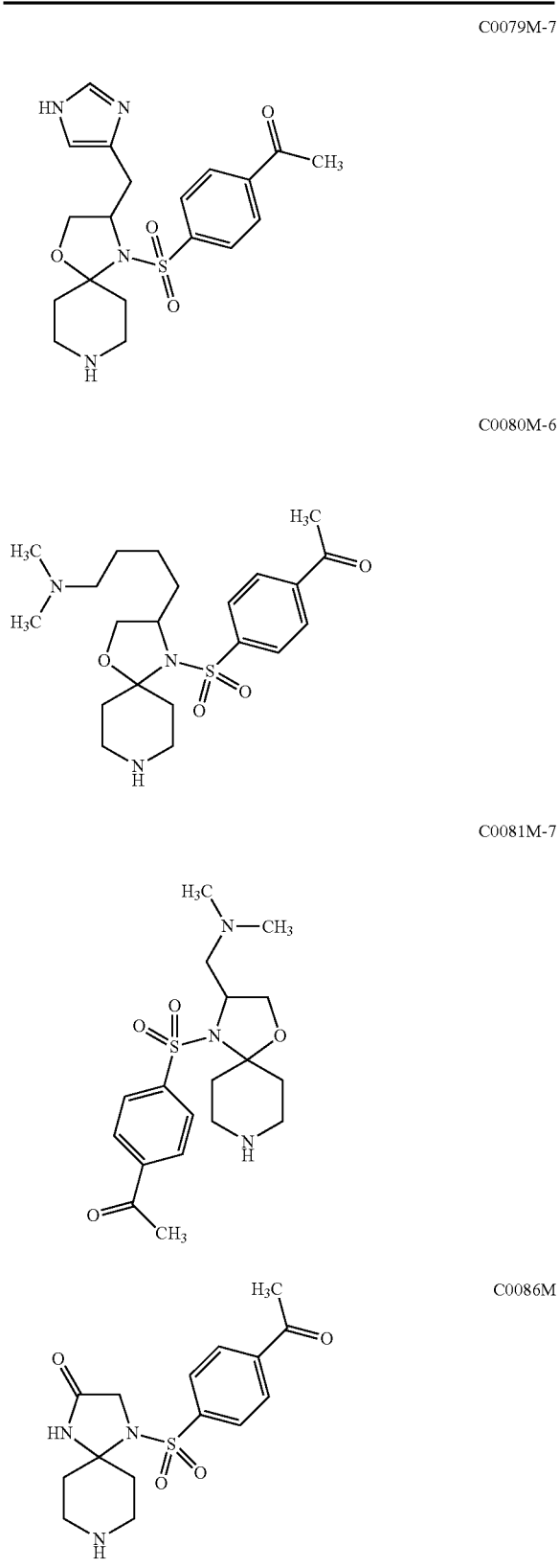
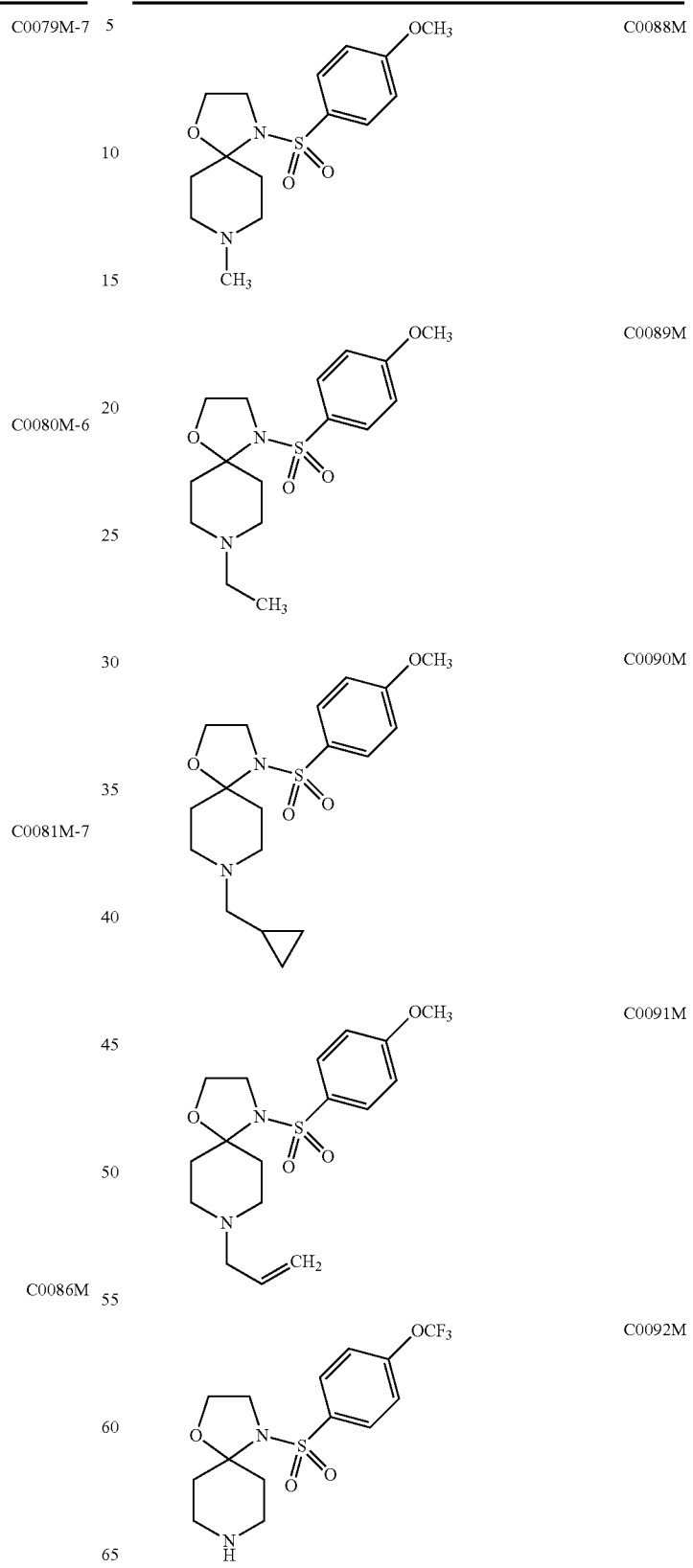

Table of Series C-2 Compounds
C0093M
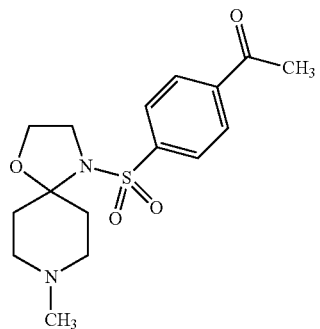 [SMILES: CC(=O)c1ccc(S(=O)(=O)N2CCOC23CCN(C)CC3)cc1]
C0094M
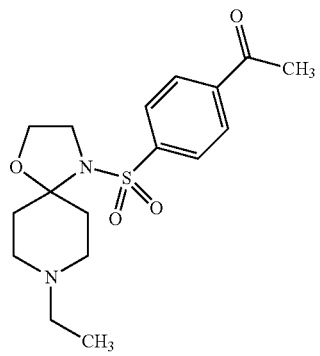 [SMILES: CCN1CCC2(CC1)OCCN2S(=O)(=O)c1ccc(C(C)=O)cc1]
C0095M
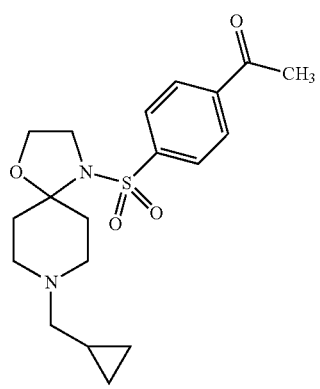 [SMILES: CC(=O)c1ccc(S(=O)(=O)N2CCOC23CCN(CC2CC2)CC3)cc1]
C0096M
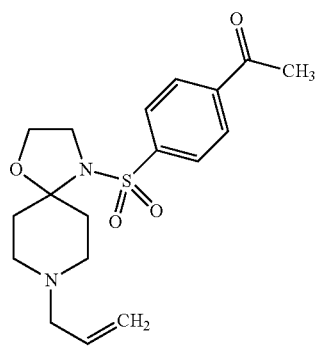 [SMILES: C=CCN1CCC2(CC1)OCCN2S(=O)(=O)c1ccc(C(C)=O)cc1]
Table of Series C-2 Compounds
C0097M
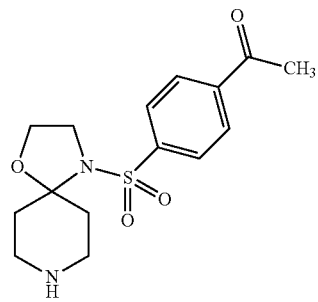 [SMILES: CC(=O)c1ccc(S(=O)(=O)N2CCOC23CCNCC3)cc1]
C0099M
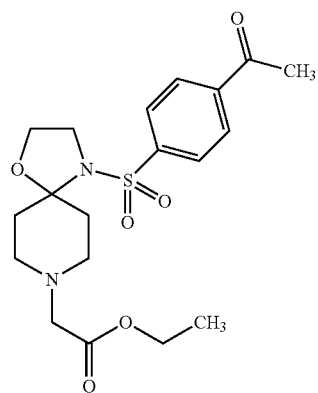 [SMILES: CCOC(=O)CN1CCC2(CC1)OCCN2S(=O)(=O)c1ccc(C(C)=O)cc1]
C0100M
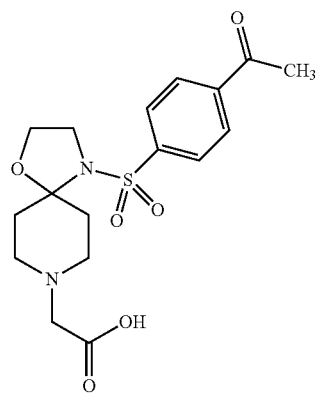 [SMILES: CC(=O)c1ccc(S(=O)(=O)N2CCOC23CCN(CC(=O)O)CC3)cc1]
C0101M
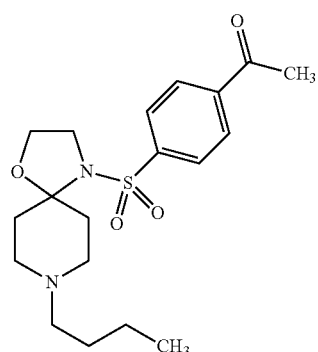

Table of Series C-2 Compounds
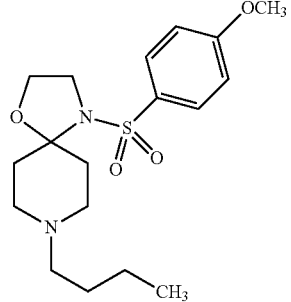 [SMILES: CCCCN1CCC2(CC1)OCCN2S(=O)(=O)c1ccc(OC)cc1]
C0102M
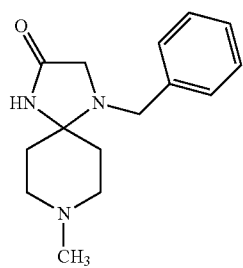 [SMILES: CN1CCC2(CC1)NC(=O)CN2Cc1ccccc1]
C0104M
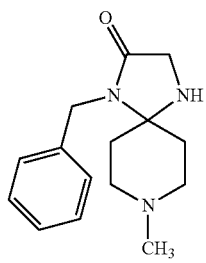 [SMILES: CN1CCC2(CC1)NCC(=O)N2Cc1ccccc1]
C0105M
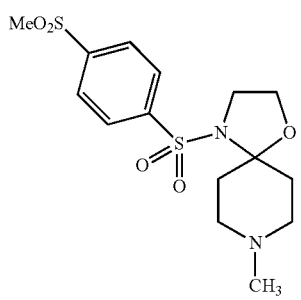
C0106M
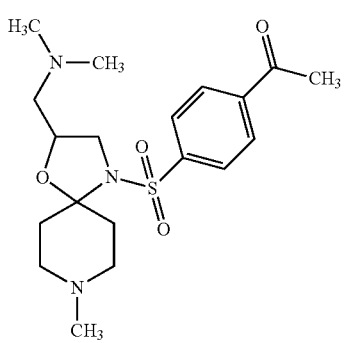 [SMILES: CC(=O)c1ccc(S(=O)(=O)N2CC(CN(C)C)OC23CCN(C)CC3)cc1]
C0108M
Table of Series C-2 Compounds
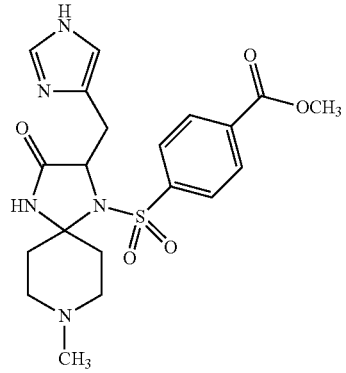 [SMILES: COC(=O)c1ccc(S(=O)(=O)N2C(Cc3c[nH]cn3)C(=O)NC23CCN(C)CC3)cc1]
C0109M
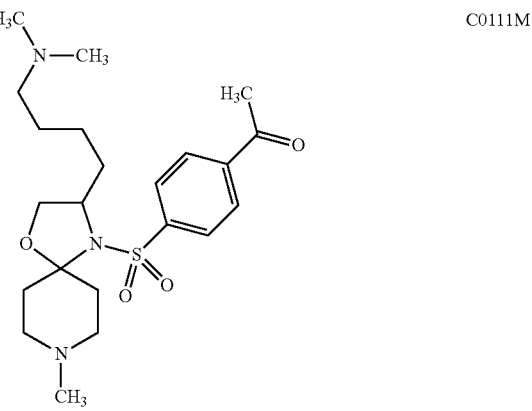
C0111M
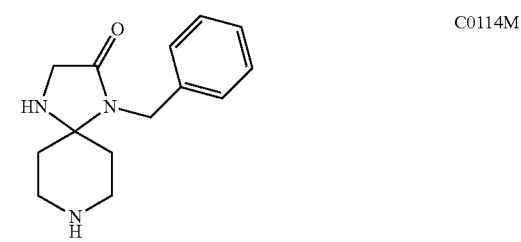
C0114M
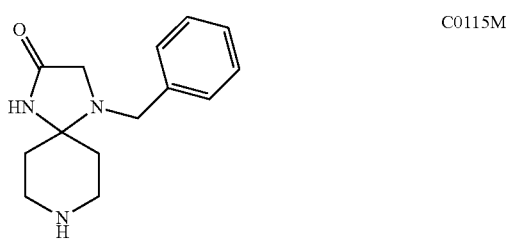
C0115M
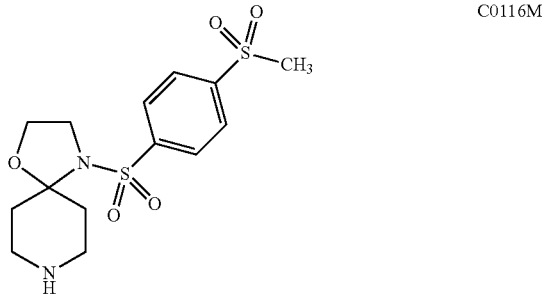
C0116M -continued
Table of Series C-2 Compounds
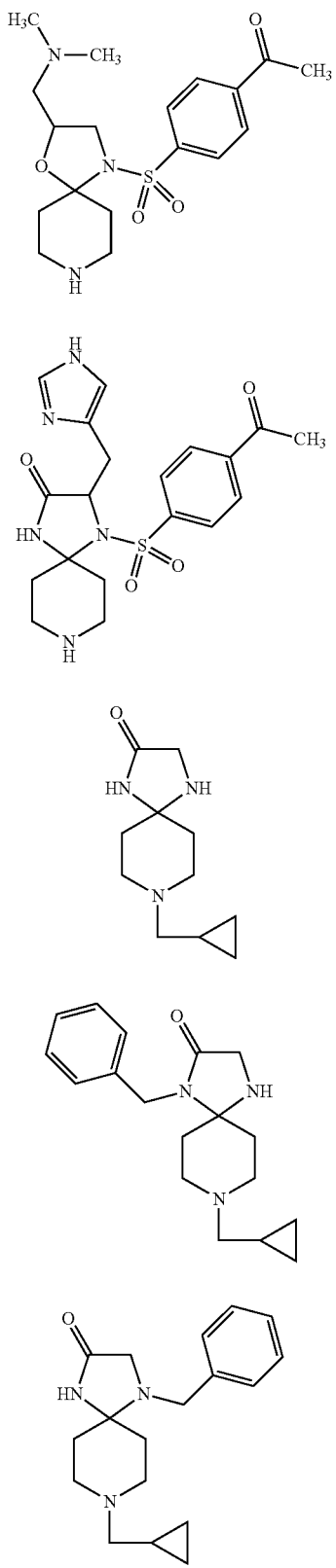
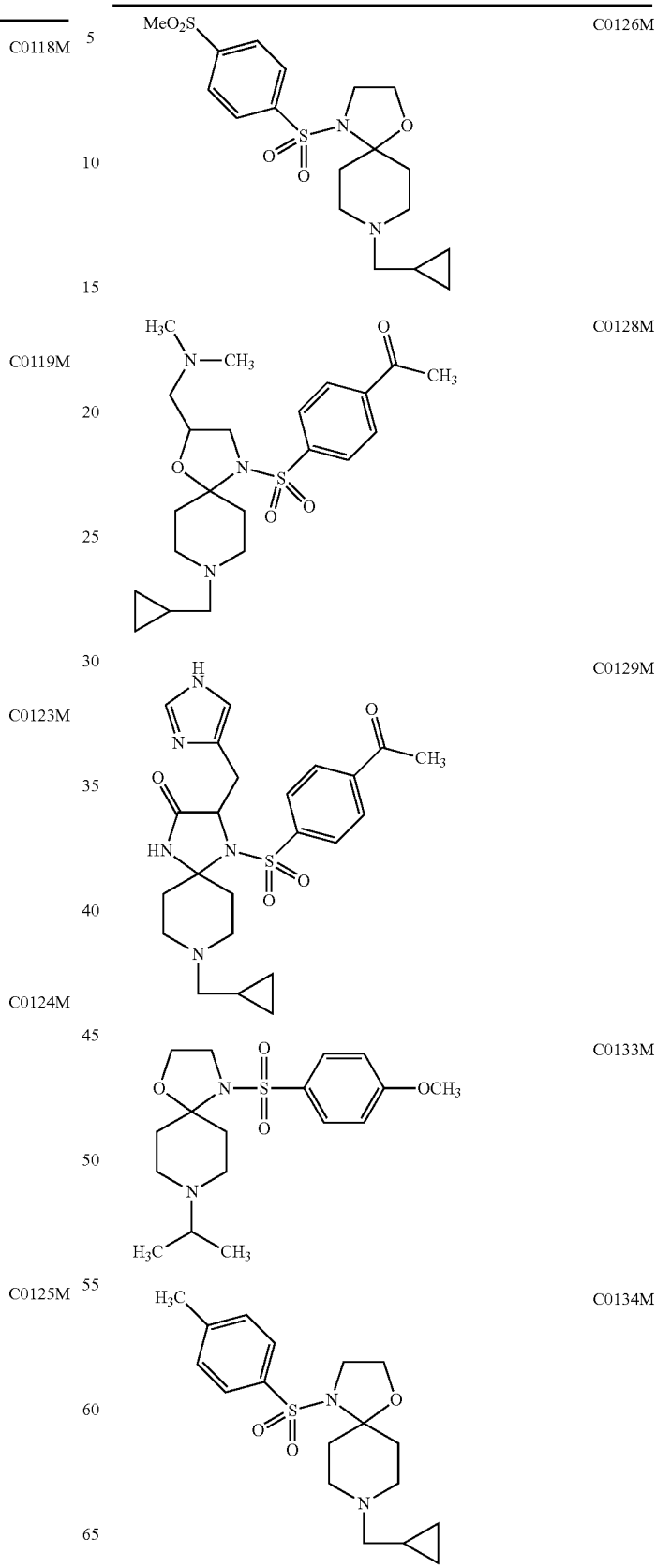

Table of Series C-2 Compounds

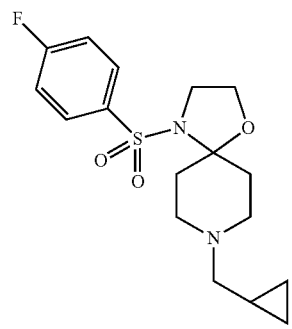 [SMILES: O=S(=O)(c1ccc(F)cc1)N1CCOC12CCN(CC1CC1)CC2]

F-C0134

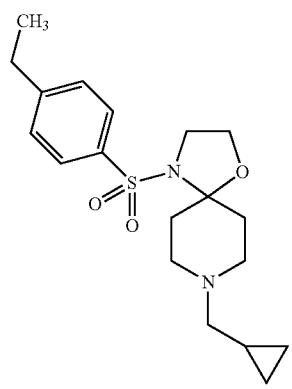 [SMILES: CCc1ccc(S(=O)(=O)N2CCOC23CCN(CC2CC2)CC3)cc1]

C0135M

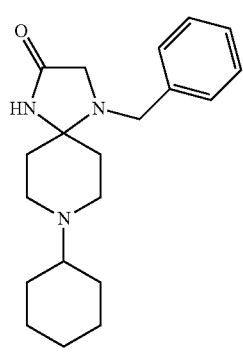 [SMILES: O=C1CN(Cc2ccccc2)C2(CCN(C3CCCCC3)CC2)N1]

C0137M P7

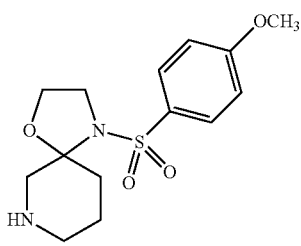 [SMILES: COc1ccc(S(=O)(=O)N2CCOC23CCCNC3)cc1]

C0145M-3

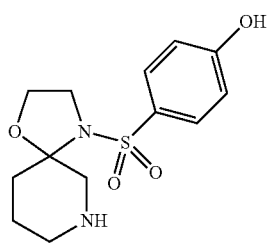 [SMILES: O=S(=O)(c1ccc(O)cc1)N1CCOC12CCCNC2]

C0153M-3

Table of Series C-2 Compounds

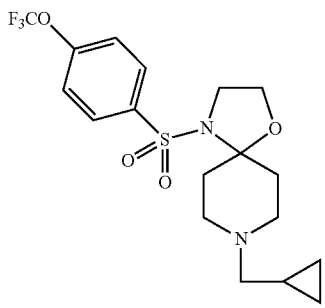 [SMILES: O=S(=O)(c1ccc(OC(F)(F)F)cc1)N1CCOC12CCN(CC1CC1)CC2]

Compound 4

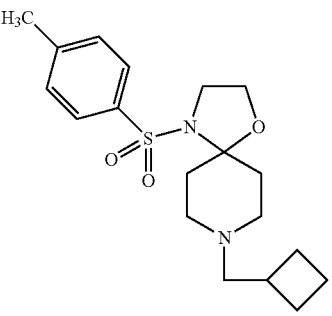 [SMILES: Cc1ccc(S(=O)(=O)N2CCOC23CCN(CC2CCC2)CC3)cc1]

Compound 9

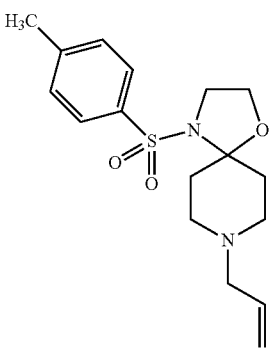 [SMILES: C=CCN1CCC2(CC1)OCCN2S(=O)(=O)c1ccc(C)cc1]

Compound 10

Preparation of Series C-2 Compounds 4, 9 and 10

These three compounds were prepared via a common intermediate designated 9-2 herein that was prepared during the synthesis of Compound C0116M in application Ser. No. 12/5610,091 (US Publication No. 20110105487 A1 dated May 5, 2011; WO 2010/051497), and referred to therein as Compound C0116M-1.

After preparation of Compound 9-2, the syntheses of Compounds 9 and 10 proceeded routinely by first adding the tosyl group in pyridine to the nitrogen of the five-membered ring, followed by removal of the t-BOC group with trifluoroacetic acid (TFA) in dichloromethane to form Compound 9-4 as shown below. Specifics of the syntheses are provided hereinafter.

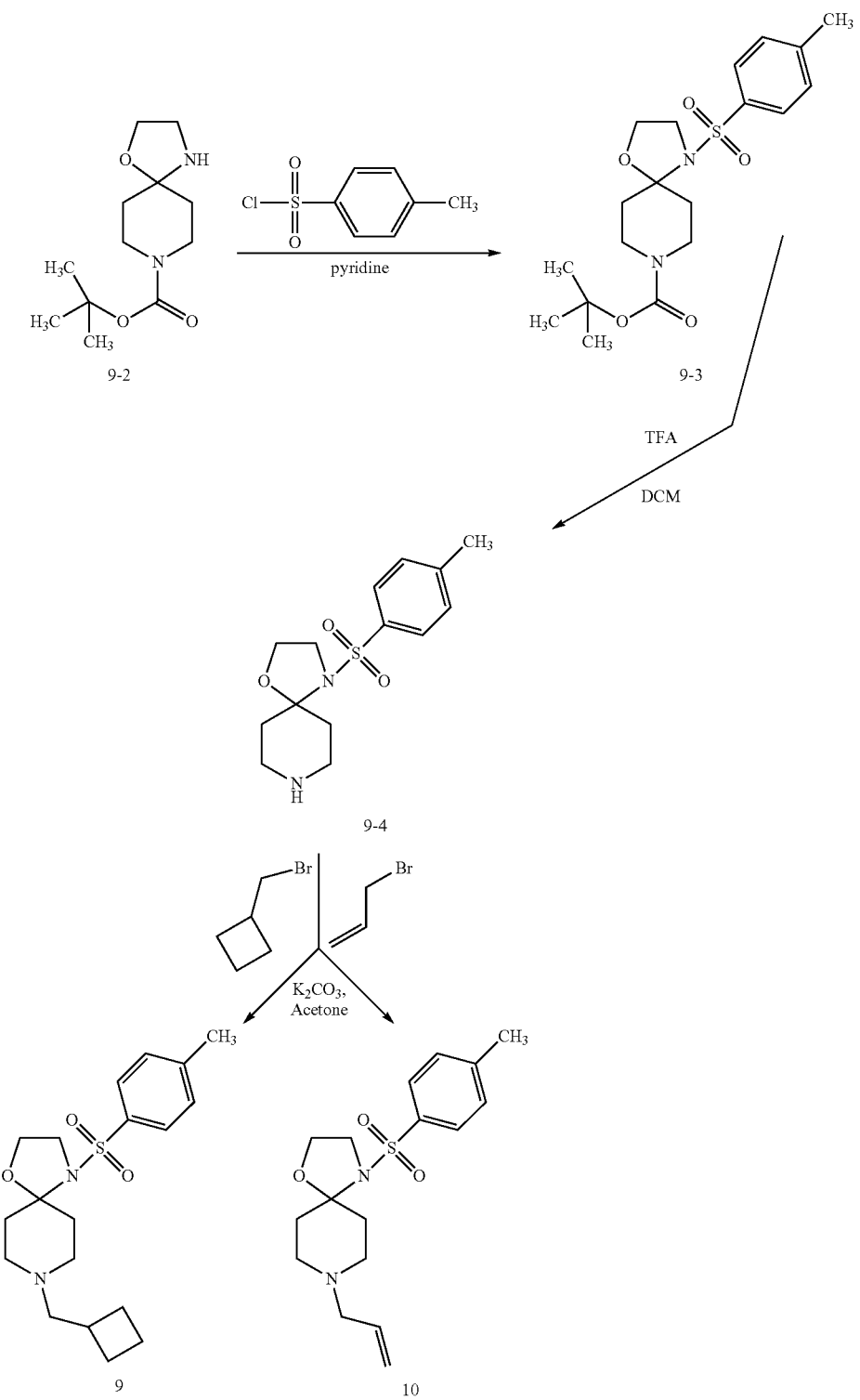

Compound 9-2 also served as the basis for preparation of Compound 4. Here, as shown below, 4-trifluoromethoxyphenyl sulfonylchloride was reacted in pyridine with the amine of the five-membered ring, and the t-BOC group removed in TFA/DCM as above to form Compound 4-1. The amine nitrogen of the six-membered ring of Compound 4-1 was then reacted with (bromomethyl)cyclopropane to form the N-alkylated product that is Compound 4.

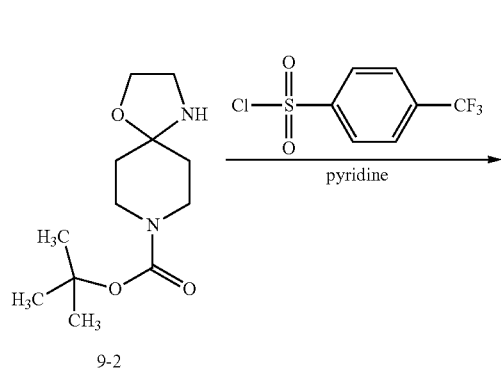
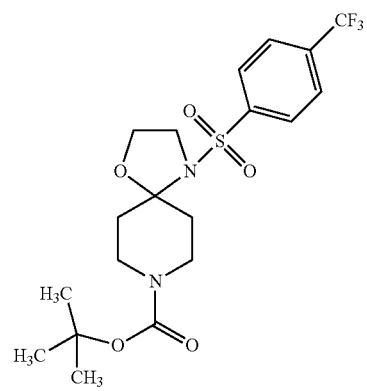
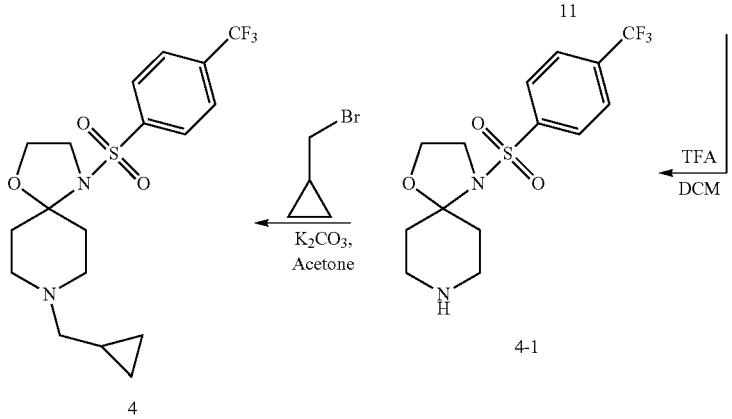

Preparation of Compound 9-2

To a solution of N-Boc-piperidin-4-one (50 g, 251 mmol) in ethanol (500 mL) was added 2-aminoethanol (46 g). The mixture was stirred at room temperature overnight (about 18 hours). Then the solvent was removed under reduced pressure. The residue was diluted with $CH_2Cl_2$ (DCM) and washed with saturated aqueous $Na_2CO_3$ (100 mL×6). The organic phase was dried over anhydrous $Na_2SO_4$, and concentrated to provide the product as a yellow oil (61 g, yield: 100%, confirmed by TLC).

Preparation of Compound 9-3

Toluenesulfonyl chloride (TsCl; 24.7 g, 130 mmol) was added to a solution of Compound 9-2 (31.2 g, 130 mmol) in pyridine (320 mL). The mixture was stirred overnight (about 18 hours) at room temperature. The reaction mixture was concentrated in vacuo to remove the pyridine and the residue was dissolved with DCM and washed with saturated $NaHCO_3$. The organic layer was dried over $Na_2SO_4$, concentrated and purified by column chromatography to provide the product as white solid (40 g, yield: 78%, confirmed by 1H NMR).

$^1$H NMR (400 MHz, $CDCl_3$): 7.74 (d, J=8.4 Hz, 2H); 7.31 (d, J=8.0 Hz, 2H); 4.13~4.03 (m, 4H); 3.56~3.50 (m, 2H); 2.89 (brs, 2H); 2.46 (s, 3H); 2.43~2.36 (m, 2H); 1.63 (brs, 2H); 1.47 (s, 9H).

Preparation of Compound 9-4

Trifluoroacetic acid ($CF_3COOH$; 60 mL) was added to a solution of Compound 9-3 (35.2 g, 88.7 mmol) in DCM (350 mL). The mixture was stirred at ice/water for 50 minutes. To the reaction mixture was added 200 mL of DCM, and the resulting composition washed with saturated $Na_2CO_3$. The organic layer was dried over $Na_2SO_4$, concentrated in vacuo to provide the crude product. The crude product was purified by column chromatography to provide the desired product as pale yellow oil (11.2 g, yield: 42%, confirmed by $^1$H NMR).

$^1$H NMR (400 MHz, $CDCl_3$): 7.75 (d, J=8.4 Hz, 2H); 7.29 (d, J=8.0 Hz, 2H); 3.95 (t, J=6.4 Hz, 2H); 3.75 (brs, 1H); 3.51~3.48 (t, J=5.6 Hz, 2H); 3.16~3.12 (dd, J=12.4, 4.0 Hz, 2H); 2.92~2.86 (td, J=12.8, 2.0 Hz, 2H); 2.48~2.44 (m, 2H); 2.41 (s, 3H); 1.65 (d, J=12.8 Hz, 2H).

Preparation of Compound 9

(Bromomethyl)cyclobutane (1.86 g, 12.5 mmol) was added to a mixture of Compound 9-4 (1.85 g, 6.25 mmol) and $K_2CO_3$ (3.39 g, 12.5 mmol) in acetone (40 mL), and the reaction mixture was stirred at reflux overnight (about 18 hours). After cooling, the mixture was filtered and concentrated, purified by chromatography with ethyl acetate (EA) to obtain crude product as pale yellow solid (1.6 g, yield: 70%, confirmed by LCMS, $^1$H NMR showed it was impure). The crude product was purified by further chromatography with EA to provide the desired product as white solid (1.15 g, yield: 50%, confirmed by LCMS and $^1$H NMR, HPLC: 99.3% @ 254 nm, 99.5 @ 214 nm).

$^1$H NMR (400 MHz, $CDCl_3$): 7.77 (d, J=8.0 Hz, 2H); 7.31 (d, J=8.0 Hz, 2H); 3.95 (t, J=6.0 Hz, 2H); 3.52 (t, J=6.4 Hz, 2H); 2.76~2.73 (d, J=10.0 Hz, 2H); 2.54~2.39 (m, 8H); 2.21~2.15 (t, J=11.6 Hz, 2H); 2.07~2.05 (m, 2H); 1.93~1.88 (m, 2H); 1.70~1.65 (m, 2H); 1.56~1.53 (d, J=12.4 Hz, 2H). MS (ESI) calcd for $C_{19}H_{28}N_2O_3S$ (m/z): 364.18, found: 365.1 $[M+1]^+$.

Preparation of Compound 10

To a mixture of Compound 9-4 (1.72 g, 5.8 mmol) and $K_2CO_3$ (1.6 g, 11.6 mmol) in acetone (30 mL) was added 3-bromoprop-1-ene (0.7 g, 5.8 mmol), and the reaction mixture was stirred at 40° C. for 2 hours. After cooling, the mixture was filtered and concentrated, purified by chromatography with EA to obtain the desired product as white solid (1.1 g, 56% yield, confirmed by LCMS and $^1$H NMR, HPLC: 98.8% @ 254 nm, 98.9 @ 214 nm).

$^1$H NMR (400 MHz, CDCl$_3$): 7.76~7.74 (d, J=8.0 Hz, 2H); 7.29~7.27 (d, J=8.0 Hz, 2H); 5.90~5.82 (m, 1H); 5.18~5.11 (m, 2H); 3.95~3.91 (t, J=6.0 Hz, 2H); 3.52~3.49 (t, J=6.0 Hz, 2H); 3.0~2.98 (d, J=6.4 Hz, 2H); 2.83~2.80 (dd, J=8.8, 2.4 Hz, 2H); 2.55~2.48 (td, J=13.2, 4.4 Hz, 2H); 2.41 (s, 3H); 2.19~2.14 (t, J=11.2 Hz, 2H); 1.58~1.55 (d, J=12.0 Hz, 2H). MS (ESI) calcd for C$_{17}$H$_{24}$N$_2$O$_3$S (m/z): 336.45, found: 337.1 [M+1]$^+$.

Preparation of Compound 11

To a solution of Compound 9-2 (14.6 g, 60 mmol) in pyridine (150 mL) was added 4-(trifluoro-methoxy)benzene-1-sulfonyl chloride (15.7 g, 60 mmol). The mixture was stirred overnight (about 18 hours) at room temperature. The reaction mixture was concentrated in vacuo to remove the pyridine and the residue was dissolved with DCM, washed with saturated NaHCO$_3$. The organic layer was dried over Na$_2$SO$_4$, concentrated and purified by column chromatography to give product as white solid (20 g, yield: 71%, confirmed by 1H NMR and LCMS).

$^1$H NMR (400 MHz, CDCl$_3$): 7.92~7.90 (d, J=8.4 Hz, 2H); 7.35~7.32 (d, J=8.4 Hz, 2H); 4.13~3.97 (m, 4H); 3.51 (brs, 2H); 2.90 (brs, 2H); 2.45~2.35 (m, 2H); 1.58 (brs, 2H); 1.47 (s, 9H). MS (ESI) calcd for C$_{19}$H$_{25}$F$_3$N$_2$O$_6$S (m/z): 466.14, found: 367.0 [M+1]$^+$.

Preparation of Compound 4-1

Trifluoroacetic acid (CF$_3$COOH; 20 mL) was added to a solution of Compound 11 (15 g, 32 mmol) in DCM (150 mL). The mixture was stirred at ice/water for 50 minutes. The reaction mixture was added to 200 mL of DCM, washed with saturated Na$_2$CO$_3$. The organic layer was dried over Na$_2$SO$_4$, concentrated in vacuo to provide the crude product. The crude product was purified by column chromatography to provide the desired product as pale yellow solid (5.9 g, yield: 50%, confirmed by 1H NMR).

$^1$H NMR (400 MHz, CDCl$_3$): 7.93~7.91 (d, J=8.4 Hz, 2H); 7.34~7.32 (d, J=8.0 Hz, 2H); 4.0~3.97 (t, J=5.6 Hz, 2H); 3.51~3.48 (t, J=6.0 Hz, 2H); 3.06~3.02 (dd, J=12.4, 4.0 Hz, 2H); 2.86~2.80 (t, J=13.2 Hz, 2H); 2.39~2.31 (td, J=12.8, 4.8 Hz, 2H); 2.48~2.44 (m, 2H); 1.64~1.62 (d, J=12.8 Hz, 2H).

Preparation of Compound 4

(Bromomethyl)cyclobutane (1.5 g, 4.1 mmol) was added to a mixture of Compound 4-1 (1.5 g, 4.1 mmol) and K$_2$CO$_3$ (1.13 g, 8.2 mmol) in acetone (15 mL), and the reaction mixture was stirred at reflux for 4 hours. After cooling, the mixture was filtered and concentrated, purified by chromatography with EA to provide the desired product as an off-white solid (1.05 g, yield: 61%, confirmed by LCMS and $^1$H NMR, HPLC: 96.9% @ 254 nm, 98.4 @ 214 nm).

$^1$H NMR (400 MHz, CDCl$_3$): 7.91~7.94 (d, J=8.8 Hz, 2H); 7.34~7.32 (d, J=8.0 Hz, 2H); 3.98~3.95 (t, J=6.0 Hz, 2H); 3.54~3.51 (t, J=6.4 Hz, 2H); 2.99~2.96 (dd, J=8.8, 2.0 Hz, 2H); 2.56~2.49 (td, J=12.8, 4.4 Hz, 2H); 2.26~2.17 (m, 4H); 1.60~1.57 (d, J=12.4 Hz, 2H); 0.87~0.84 (m, 1H); 0.52~0.48 (m, 2H); 0.10~0.07 (m, 2H). MS (ESI) calcd for C$_{18}$H$_{23}$F$_3$N$_2$O$_4$S (m/z): 420.13, found: 421.1 [M+1]$^+$.

Table of Series D Compounds

Compound A

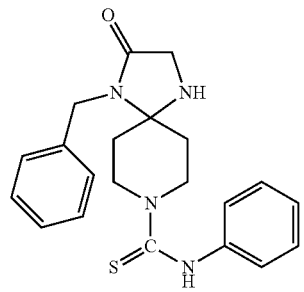

Compound B

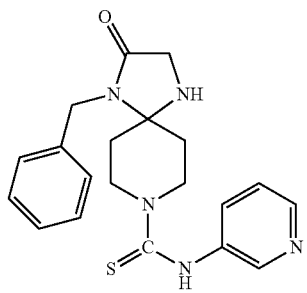 [SMILES: O=C1CNC2(CCN(C(=S)Nc3cccnc3)CC2)N1Cc1ccccc1]

Compound C

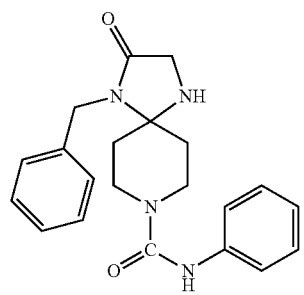 [SMILES: O=C(Nc1ccccc1)N1CCC2(CC1)NCC(=O)N2Cc1ccccc1]

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

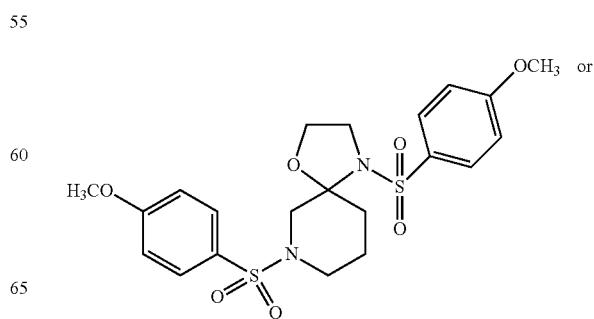

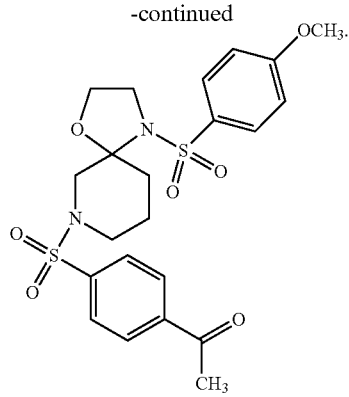

The invention claimed is:

1. A method of inhibiting the growth of cancerous cells that contain an enhanced amount of one or more of phosphorylated-mTOR, phosphorylated-Akt1, phosphorylated-ERK2 and serine2152-phosphorylated filamin A that comprises contacting said cancer cells with an FLNA-binding effective amount of a compound or a pharmaceutically acceptable salt thereof that binds to the pentapeptide of FLNA of SEQ ID NO: 1 and exhibits at least about 60 percent of the FITC-labeled naloxone binding amount when present at a 10 μM concentration, using unlabeled naloxone as the control inhibitor at the same concentration as said compound or salt, said pentapeptide of FLNA being biotinylated at its N-terminal valine residue and bound to a streptavidin-coated solid support, wherein said enhanced amount of phosphorylated-mTOR, phosphorylated-Akt1, phosphorylated-ERK2 and serine2152-phosphorylated filamin A being an amount that is greater by more than 1 standard deviation to three standard deviations than the amount present in a non-cancerous cell of the same type, wherein said compound is a compound of Series C-1 that corresponds in structure to Formula I below:

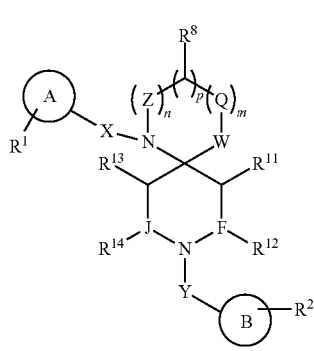

I wherein
X and Y are the same or different and are $SO_2$, C(O), $CH_2$, $CD_2$ (where D is deuterium), NHC(NH), OC(O), NHC(S) or NHC(O);
W is $NR^7$, $CH_2$, S or O, where $R^7$ is H, $C_1$-$C_{12}$ hydrocarbyl, or $C_1$-$C_{12}$ hydrocarboyl (acyl);
Q is $CHR^9$ or C(O);
Z is $CHR^{10}$ or C(O);
J and F are the same or different and are CH or CD (where D is deuterium);
each of m, n and p is zero or one and the sum of m+n+p is 2 or 3; and
circles A and B are the same or different aromatic or heteroaromatic ring systems that contain one ring or two fused rings;
$R^1$ and $R^2$ are the same or different and each can be hydrogen or represent up to three substituents other than hydrogen that themselves can be the same or different ($R^{1a}$, $R^{1b}$, and $R^{1c}$, and $R^{2a}$, $R^{2b}$, and $R^{2c}$) each of those six groups, $R^{1a-c}$ and $R^{2a-c}$, is separately selected from the group consisting of H, $C_1$-$C_6$ hydrocarbyl, $C_1$-$C_6$ hydrocarbyloxy, trifluoromethyl, trifluoromethoxy, $C_1$-$C_7$ hydrocarboyl, hydroxy-, trifluoromethyl- or halogen-substituted $C_1$-$C_7$ hydrocarboyl, $C_1$-$C_6$ hydrocarbylsulfonyl, halogen, nitro, phenyl, cyano, carboxyl, $C_1$-$C_7$ hydrocarbyl carboxylate, carboxamide or sulfonamide
wherein the amido nitrogen of either group has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur,
MAr, where M is where M is —$CH_2$—, —O— or —N=N— and Ar is a single-ringed aryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur;
$R^8$, $R^9$, and $R^{10}$ are each H, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms;
$R^{11}$, $R^{12}$, $R^{13}$ and $R^{14}$ are all H, or $R^{11}$ and $R^{13}$ are H and $R^{12}$ and $R^{14}$ are H or D (where D is deuterium), or one of the pair $R^{11}$ and $R^{12}$ or the pair $R^{13}$ and $R^{14}$ together with the depicted ring form a saturated or unsaturated 6-membered ring, and the other pair are each H or they are H and D.

2. The method according to claim 1, wherein said cancer cells are solid tumor cancer cells.

3. The method according to claim 2, wherein said solid tumor cancer cells are selected from the group consisting of one or more of melanoma cells, glioblastoma cells, small cell lung carcinoma cells, breast cancer cells and pancreatic cancer cells.

4. The method according to claim 1, wherein said compound is a compound of Series C-1 that corresponds in structure to the Formula II below:

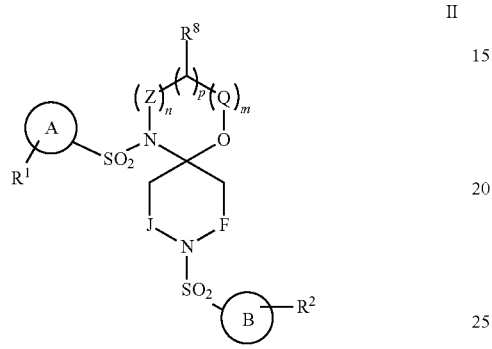

II wherein
Q is CHR$^9$ or C(O);
Z is CHR$^{10}$ or C(O);
each of m, n and p is zero or one and the sum of m+n+p is 2 or 3;
J and F are the same or different and are CH$_2$, CHD or CD$_2$ (where D is deuterium);
circles A and B are the same or different aromatic or heteroaromatic ring systems;
R$^1$ and R$^2$ are the same or different and each can be hydrogen or represent up to three substituents other than hydrogen that themselves can be the same or different (R$^{1a}$, R$^{1b}$, and R$^{1c}$, and R$^{2a}$, R$^{2b}$, and R$^{2c}$), each of those six groups, R$^{1a-c}$ and R$^{2a-c}$, is separately selected from the group consisting of H, C$_1$-C$_6$ hydrocarbyl, C$_1$-C$_6$ hydrocarbyloxy, C$_1$-C$_6$ hydrocarbyloxycarbonyl, trifluoromethyl, trifluoromethoxy, C$_1$-C$_7$ hydrocarboyl, hydroxy-, trifluoromethyl- or halogen-substituted C$_1$-C$_7$ hydrocarboyl, C$_1$-C$_6$ hydrocarbylsulfonyl, C$_1$-C$_6$ hydrocarbyloxysulfonyl, halogen, nitro, phenyl, cyano, carboxyl, C$_1$-C$_7$ hydrocarbyl carboxylate, carboxamide or sulfonamide,
wherein the amido nitrogen in either group has the formula NR$^3$R$^4$ wherein R$^3$ and R$^4$ are the same or different and are H, C$_1$-C$_4$ hydrocarbyl, or R$^3$ and R$^4$ together with the depicted nitrogen form a 5-7-membered ring that optionally contains 1 or 2 additional hetero atoms that independently are nitrogen, oxygen or sulfur,
MAr, where M is —CH$_2$—, —O— or —N═N— and Ar is a single-ringed aryl group, and NR$^5$R$^6$
wherein R$^5$ and R$^6$ are the same or different and are H, C$_1$-C$_4$ hydrocarbyl, C$_1$-C$_4$ acyl, C$_1$-C$_4$ hydrocarbylsulfonyl, or R$^5$ and R$^6$ together with the depicted nitrogen form a 5-7-membered ring that optionally contains 1 or 2 additional hetero atoms that independently are nitrogen, oxygen or sulfur.

5. The method according to claim 4, wherein said compound of Series C-1 corresponds in structure to a compound of Formula II in which W is O and is shown below:

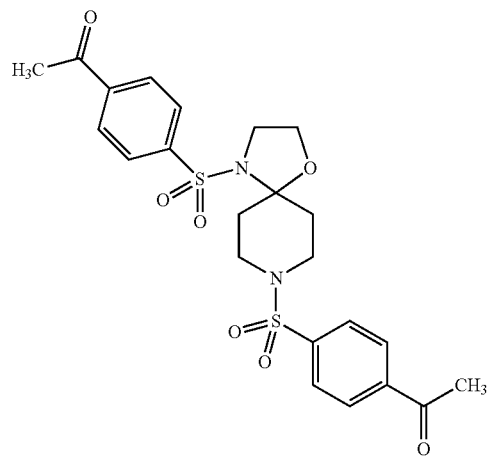

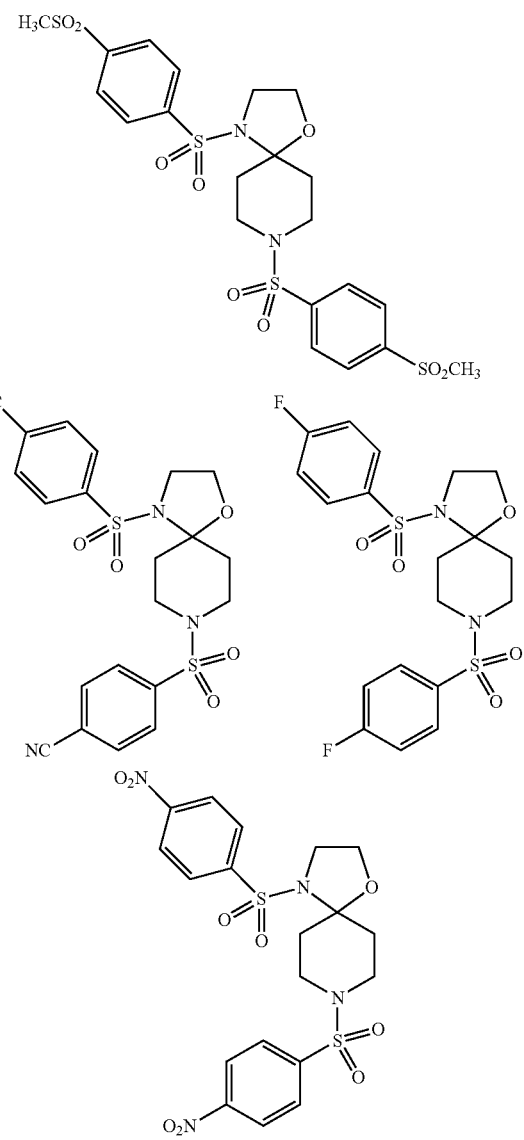

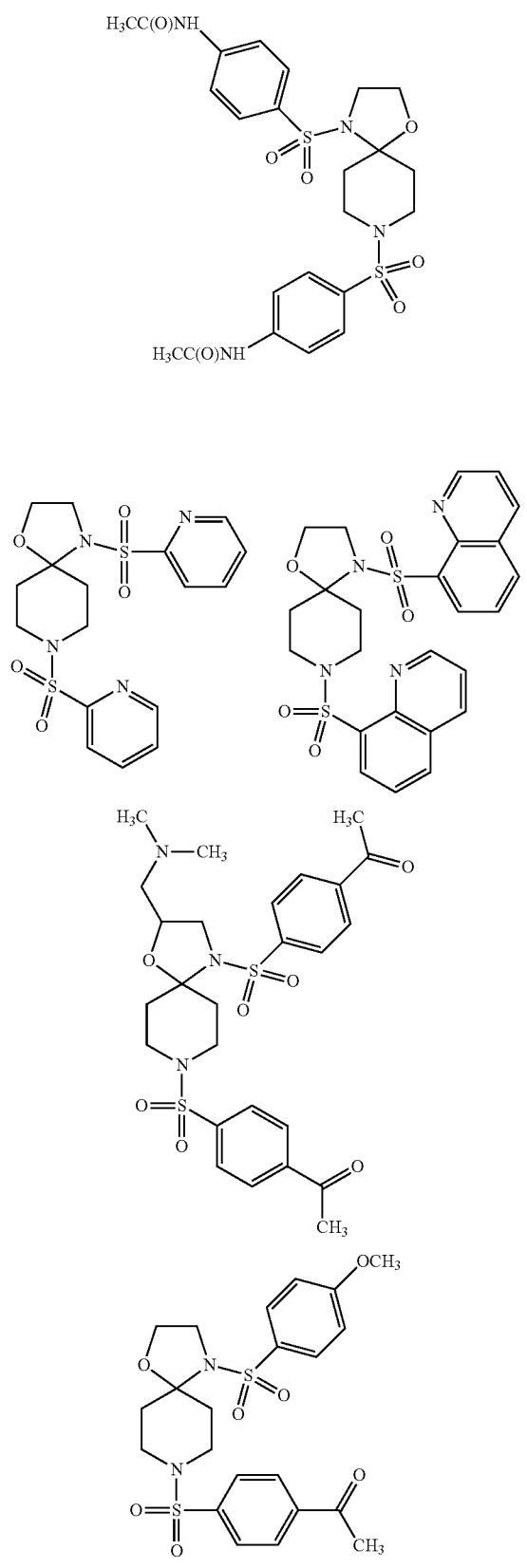
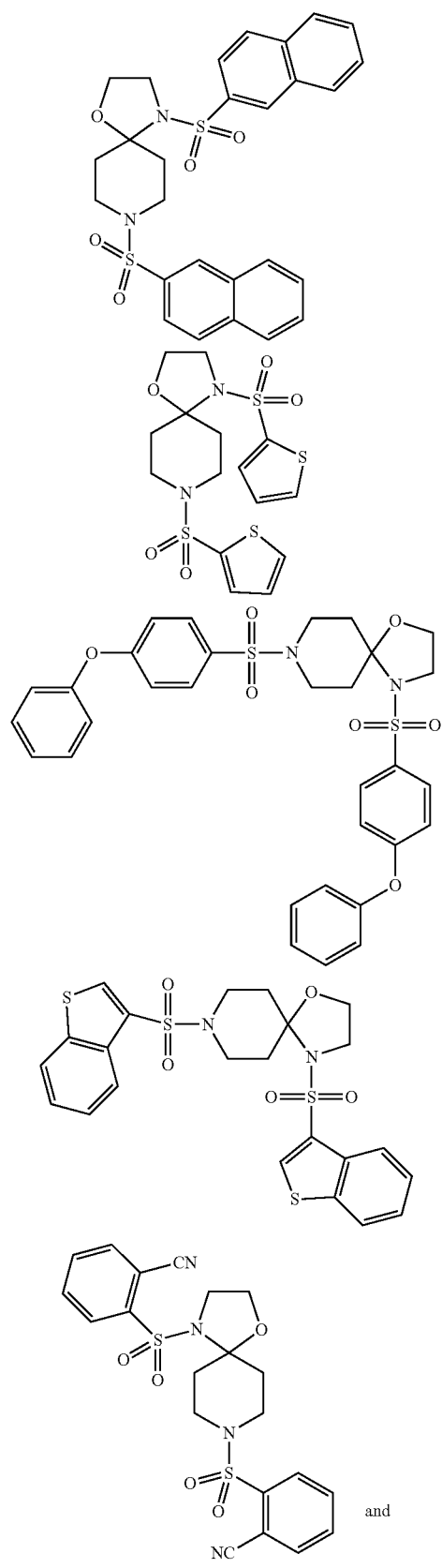

-continued

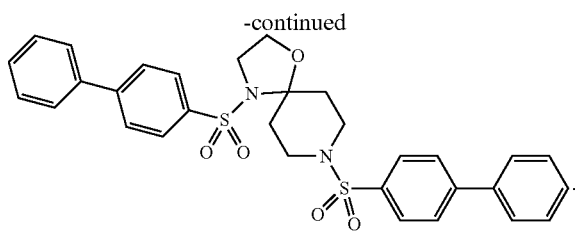

6. The method according to claim 1, wherein said compound is a compound of Series C-1 that corresponds in structure to the Formula III below:

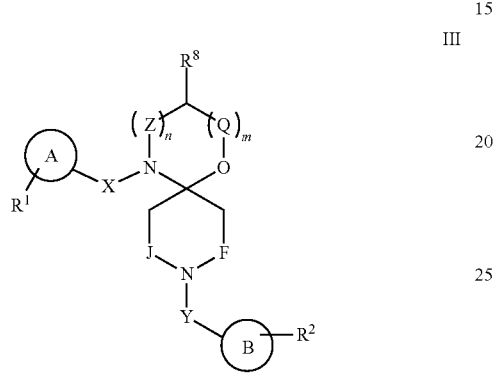

III wherein
Q is $CHR^9$ or $C(O)$;
Z is $CHR^{10}$ or $C(O)$;
each of m and n is zero or one and the sum of m+n is 1;
J and F are the same or different and are $CH_2$, CHD or $CD_2$ (where D is deuterium);
X and Y are both CO, or X and Y are different and are $SO_2$, C(O), $CH_2$, $CD_2$, NHC(NH), NHC(S) or NHC(O);
circles A and B are the same or different aromatic or heteroaromatic ring systems;
$R^1$ and $R^2$ are the same or different and each can be hydrogen or represent up to three substituents other than hydrogen that themselves can be the same or different ($R^{1a}$, $R^{1b}$, and $R^{1c}$, and $R^{2a}$, $R^{2b}$, and $R^{2c}$), each of those six groups, $R^{1a-c}$ and $R^{2a-c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl, hydroxy-, trifluoromethyl- or halogen-substituted $C_1$-$C_7$ hydrocarboyl, $C_1$-$C_6$ hydrocarbylsulfonyl, $C_1$-$C_6$ hydrocarbyloxysulfonyl, halogen, nitro, phenyl, cyano, carboxyl, $C_1$-$C_7$ hydrocarbyl carboxylate, carboxamide or sulfonamide,
  wherein the amido nitrogen in either group has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur,
MAr, where M is —$CH_2$—, —O— or —N=N— and Ar is a single-ringed aryl group, and $NR^5R^6$
  wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur.

7. The method according to claim 6, wherein said compound of Series C-1 corresponds in structure to a compound of Formula III in which W is O and is shown below:

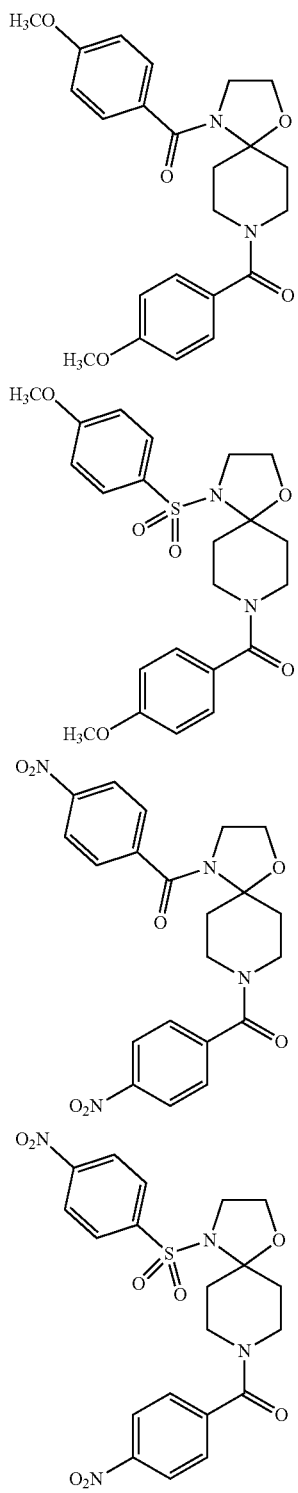

191
-continued

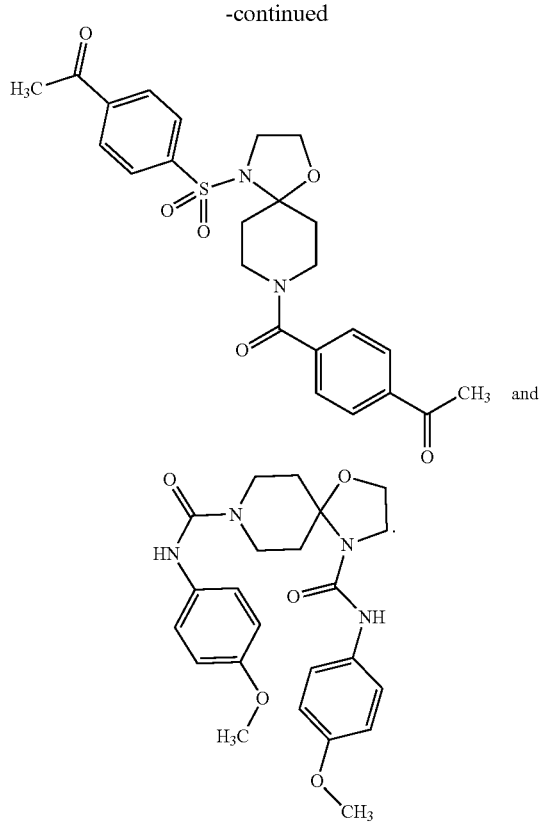

and

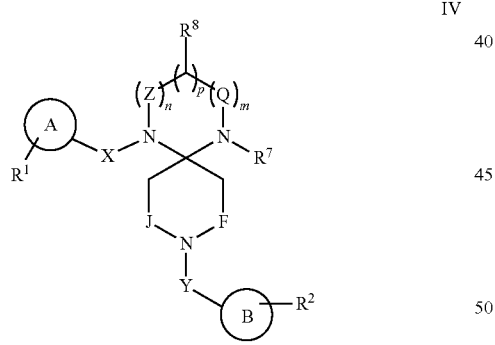

8. The method according to claim 1, wherein said compound is a compound of Series C-1 that corresponds in structure to the Formula IV below:

IV

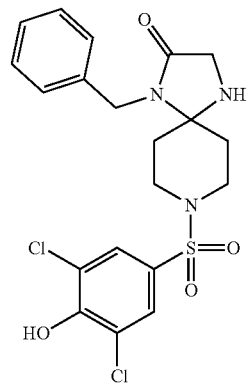

wherein
Q is CHR$^9$ or C(O);
Z is CHR$^{10}$ or C(O);
each of m, n and p is zero or one and the sum of m+n+p is 2 or 3;
J and F are the same or different and are CH$_2$, CHD or CD$_2$ (where D is deuterium);
X and Y are the same or different and are SO$_2$, C(O), CH$_2$, CD$_2$, OC(O), NHC(NH), NHC(S) or NHC(O);
circles A and B are the same or different aromatic or heteroaromatic ring systems;
R$^1$ and R$^2$ are the same or different and each can be hydrogen or represent up to three substituents other than hydrogen that themselves can be the same or different (R$^{1a}$, R$^{1b}$, and R$^{1c}$, and R$^{2a}$, R$^{2b}$, and, R$^{2c}$), each of those six groups, R$^{1a-c}$ and R$^{2a-c}$, is separately selected from the group consisting of H, C$_1$-C$_6$ hydrocarbyl, C$_1$-C$_6$ hydrocarbyloxy, C$_1$-C$_6$ hydrocarbyloxycarbonyl, trifluoromethyl, trifluoromethoxy, C$_1$-C$_7$ hydrocarboyl, hydroxy-, trifluoromethyl- or halogen-substituted C$_1$-C$_7$ hydrocarboyl, C$_1$-C$_6$ hydrocarbylsulfonyl, C$_1$-C$_6$ hydrocarbyloxysulfonyl, halogen, nitro, phenyl, cyano, carboxyl, C$_1$-C$_7$ hydrocarbyl carboxylate, carboxamide or sulfonamide,
wherein the amido nitrogen in either group has the formula NR$^3$R$^4$ wherein R$^3$ and R$^4$ are the same or different and are H, C$_1$-C$_4$ hydrocarbyl, or R$^3$ and R$^4$ together with the depicted nitrogen form a 5-7-membered ring that optionally contains 1 or 2 additional hetero atoms that independently are nitrogen, oxygen or sulfur,
MAr, where M is —CH$_2$—, —O— or —N═N— and Ar is a single-ringed aryl group, and NR$^5$R$^6$
wherein R$^5$ and R$^6$ are the same or different and are H, C$_1$-C$_4$ hydrocarbyl, C$_1$-C$_4$ acyl, C$_1$-C$_4$ hydrocarbylsulfonyl, or R$^5$ and R$^6$ together with the depicted nitrogen form a 5-7-membered ring that optionally contains 1 or 2 additional hetero atoms that independently are nitrogen, oxygen or sulfur.

9. The method according to claim 8, wherein said compound of Series C-1 corresponds in structure to a compound of Formula IV as is shown below:

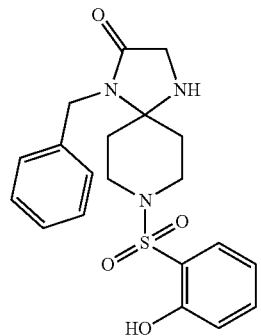

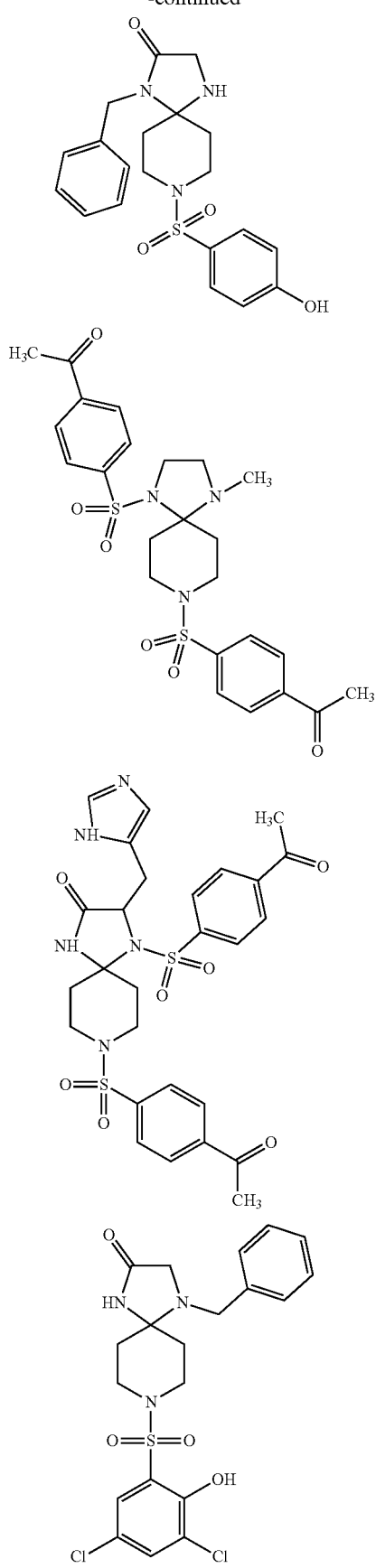
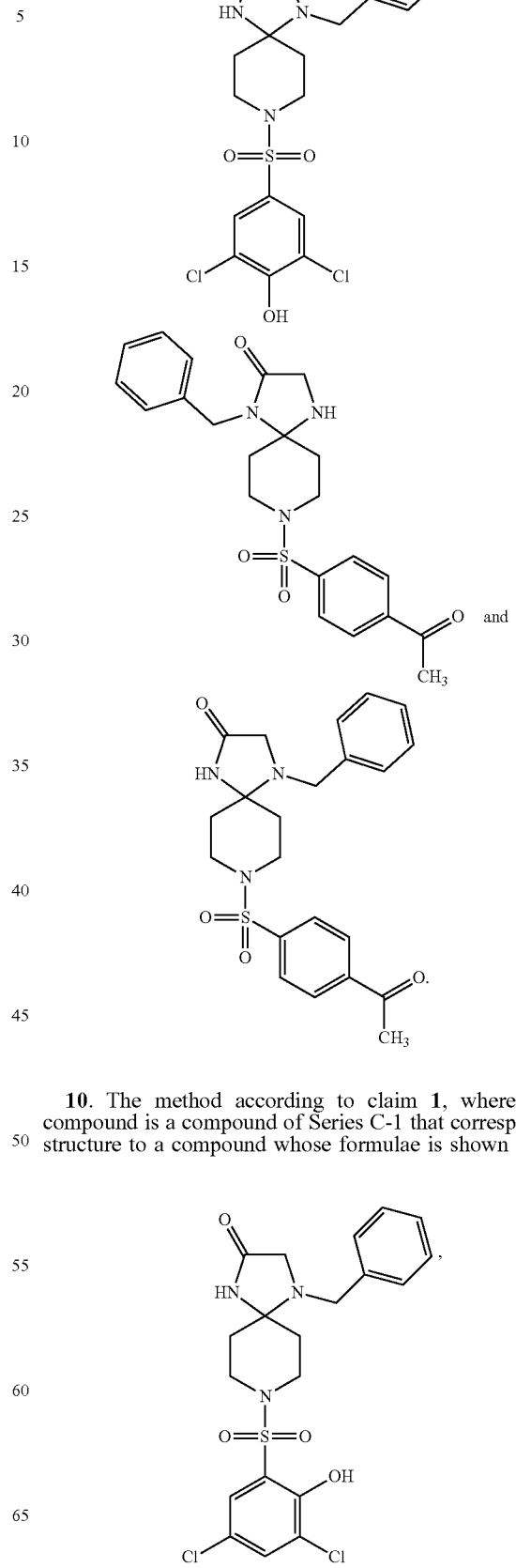
10. The method according to claim 1, wherein said compound is a compound of Series C-1 that corresponds in structure to a compound whose formulae is shown below:

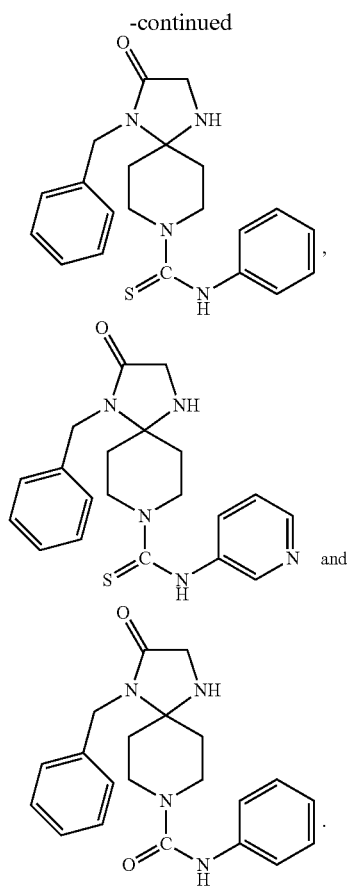

11. The method according to claim 1, wherein said administration is carried out a plurality of times.

12. The method according to claim 11, wherein said administration is carried out daily.

13. The method according to claim 11, wherein said administration is carried out multiple times daily.

14. The method according to claim 1, wherein said administration is carried out by contacting said cancer cells in vitro.

15. The method according to claim 1, wherein said administration is carried out by contacting said cancer cells in vivo.

16. The method according to claim 15, wherein said administration is carried out in the absence of a mu opioid receptor- (MOR-) binding effective amount of a separate MOR agonist or antagonist.

17. The method according to claim 1, wherein said compound or a pharmaceutically acceptable salt thereof is present dissolved or dispersed in a pharmaceutically acceptable diluent as a pharmaceutical composition when administered.

18. The method according to claim 1, wherein said cancer cells contain an elevated amount of serine2152-phosphorylated filamin A.

19. The method according to claim 18, wherein said cancer cells additionally contain an enhanced amount of one or more of phosphorylated-mTOR, phosphorylated-Akt1 and phosphorylated-ERK2.

20. The method according to claim 1, wherein said cancer cells are contacted a plurality of times with said compound or pharmaceutically acceptable salt thereof.

21. The method according to claim 1, wherein said compound of Series C-1 corresponds in structure to a compound shown below:

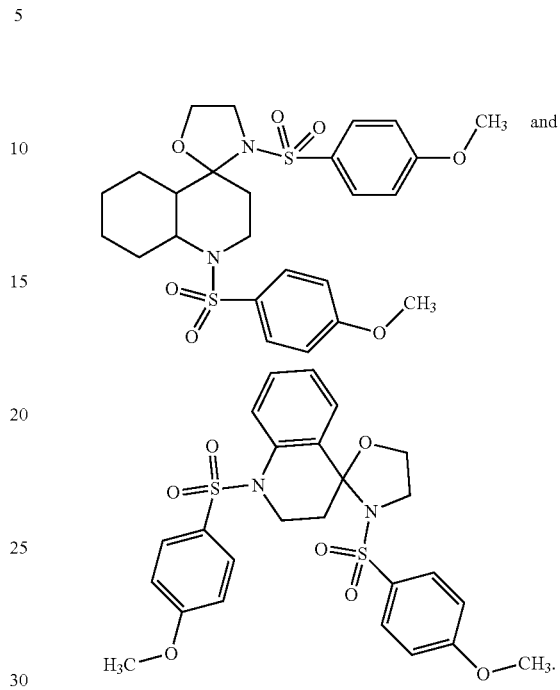

22. A method of inhibiting the growth of cancerous cells that contain an enhanced amount of one or more of phosphorylated-mTOR, phosphorylated-Akt1, phosphorylated-ERK2 and serine2152-phosphorylated filamin A that comprises contacting said cancer cells with an FLNA-binding effective amount of a compound or a pharmaceutically acceptable salt thereof that binds to the pentapeptide of FLNA of SEQ ID NO: 1 and exhibits at least about 60 percent of the FITC-labeled naloxone binding amount when present at a 10 µM concentration, using unlabeled naloxone as the control inhibitor at the same concentration as said compound or salt, said pentapeptide of FLNA being biotinylated at its N-terminal valine residue and bound to a streptavidin-coated solid support, wherein said enhanced amount of phosphorylated-mTOR, phosphorylated-Akt1, phosphorylated-ERK2 and serine2152-phosphorylated filamin A being an amount that is greater by more than 1 standard deviation to three standard deviations than the amount present in a non-cancerous cell of the same type, wherein said compound is a compound of Series C-1 that corresponds in structure to a compound shown below:

SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:

```
<223> OTHER INFORMATION: Chemically synthesized FLNA sequence that
      corresponds to amino acid residue positions 2561-2565 of the FLNA
      protein

<400> SEQUENCE: 1

Val Ala Lys Gly Leu
1               5

<210> SEQ ID NO 2
<211> LENGTH: 5
<212> TYPE: PRT
<213> ORGANISM: Artificial Sequence
<220> FEATURE:
<223> OTHER INFORMATION: Control peptide for the Seq. No. 1 peptide

<400> SEQUENCE: 2

Val Ala Ala Gly Leu
1               5
```